(12) United States Patent
Serrano-Wu et al.

(10) Patent No.: US 8,143,288 B2
(45) Date of Patent: Mar. 27, 2012

(54) INHIBITORS OF HCV REPLICATION

(75) Inventors: Michael Serrano-Wu, Belmont, MA (US); Makonen Belema, North Haven, CT (US); Lawrence B. Snyder, Killingworth, CT (US); Nicholas A. Meanwell, East Hampton, CT (US); Denis R. St. Laurent, Newington, CT (US); Ramesh Kakarla, South Glastonbury, CT (US); Van N. Nguyen, New Britain, CT (US); Yuping Qiu, Glastonbury, CT (US); Xuejie Yang, Cheshire, CT (US); John E. Leet, Madison, CT (US); Min Gao, Madison, CT (US); Donald R. O'Boyle, II, Killingworth, CT (US); Julie A. Lemm, Durham, CT (US); Fukang Yang, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 271 days.

(21) Appl. No.: 11/446,788

(22) Filed: Jun. 5, 2006

(65) Prior Publication Data

US 2006/0276511 A1 Dec. 7, 2006

Related U.S. Application Data

(60) Provisional application No. 60/687,760, filed on Jun. 6, 2005.

(51) Int. Cl.
*A61K 31/444* (2006.01)
*A61K 31/4439* (2006.01)
*A61K 31/42* (2006.01)
*A61K 31/416* (2006.01)
*A61K 31/4025* (2006.01)
*C07D 413/14* (2006.01)
*C07D 403/14* (2006.01)
*C07D 409/14* (2006.01)

(52) U.S. Cl. ........ 514/332; 514/343; 514/378; 514/397; 514/406; 514/422; 546/256; 546/277.1; 548/248; 548/311.1; 548/365.7; 548/465; 548/518

(58) Field of Classification Search .................. None
See application file for complete search history.

(56) References Cited

U.S. PATENT DOCUMENTS 5,654,451 A 8/1997 Kari

FOREIGN PATENT DOCUMENTS

WO WO 94/15909 7/1994

OTHER PUBLICATIONS

Yip et al., Bioorg Med Chem Let, 14, 2004, 5007-5011.*
http://www.apath.com/Directory/Licensing/Technology/HCV_Replicon.asp.*
http://www.mayoclinic.com/health/hepatitis-c/DS00097/DSECTION=8.*
STN ref, Matsuda et al., caplus an 2006:195963.*
HCV, 2011, http://hepatitiscresearchandnewsupdates.blogspot.com/2011/04/in-vitro-model-systems-to-study.html.*
Guha et al., Lab Animal, vol. 34, 2005, 39-47.*
http://www.apath.com/Directory/Licensing/Technology/HCV_Replicon.asp (2008).*
http:||www.mayoctinic.com|health|hepatitis-c|DSOOO971DSECTION=8(2008).*

* cited by examiner

*Primary Examiner* — Sun Jae Loewe
(74) *Attorney, Agent, or Firm* — Pamela A. Mingo

(57) ABSTRACT

Compounds having the structure of formula I are described.

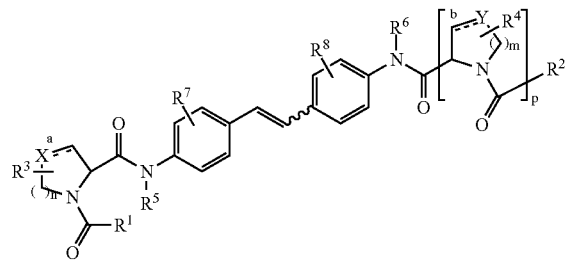

(I)

The compounds can inhibit hepatitis C virus (HCV) replication, and in particular can inhibit the function of the HCV NS5A protein.

21 Claims, No Drawings

INHIBITORS OF HCV REPLICATION

CROSS REFERENCE TO RELATED APPLICATION

This application claims priority from U.S. Provisional Application Ser. No. 60/687,760, filed Jun. 6, 2005.

FIELD OF THE INVENTION

The present invention is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

Presently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Among the compounds that have demonstrated efficacy in inhibiting HCV replication as selective HCV serine protease inhibitors are the peptide compounds disclosed in U.S. Pat. No. 6,323,180. NS5B polymerase inhibitors have also demonstrated activity. However, none of these compounds have, to date, progressed beyond clinical trials (De Clercq, E. *J Clin. Virol.* 2001, 22, 73-89).

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1-12; and in Park, K.-J.; Choi, S.-H, *J Biological Chemistry* 2003.

SUMMARY OF THE INVENTION

The present invention relates to compounds of formula (I)

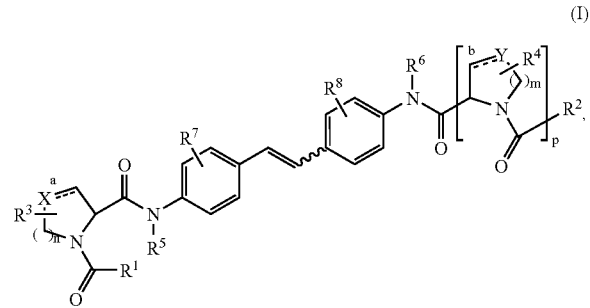

(I)

or pharmaceutically acceptable salts thereof, wherein $\overset{a}{-----}$ is a single or double bond;

$\overset{b}{-----}$ is a single or double bond;

when $\overset{a}{-----}$ is a single bond, X is selected from the group consisting of O, $CH_2$, and $CHR^3$;

when $\overset{a}{-----}$ is a double bond, X is selected from the group consisting of CH and $CR^3$;

when $\overset{b}{-----}$ is a single bond, Y is selected from the group consisting of O, $CH_2$, and $CHR^4$;

when $\overset{b}{-----}$ is a double bond, Y is selected from the group consisting of CH and $CR^4$;

n and m are independently 0, 1, 2, or 3;

p is 0 or 1;

$R^1$ and $R^2$ are independently selected from the group consisting of alkoxy, alkoxyalkoxyalkyl, alkoxyalkyl, alkyl, alkylsulfenylalkyl, alkylsulfinylalkyl, alkylsulfonylalkyl, aryl, arylalkoxy, arylalkoxyalkyl, arylalkyl, arylcarbonyl, aryloxy, aryloxyalkyl, arylsulfenylalkyl, arylsulfinylalkyl, arylsulfonylalkyl, carboxyalkyl, cycloalkenyl, cycloalkenylalkyl, cycloalkyl, cycloalkylalkyl, heterocyclyl, heterocyclylalkoxy, heterocyclylalkoxyalkyl, heterocyclylalkyl, heterocyclylcarbonyl, heterocyclyloxy, heterocyclyloxyalkyl, —NR$^a$R$^b$, and (NR$^a$R$^b$)alkyl;

R$^3$ and R$^4$ are independently selected from the group consisting of hydrogen, alkenyl, alkoxy, alkoxycarbonyloxy, alkyl, alkylsulfonyl, alkylsulfonyloxy, aryl, arylalkyl, azido, hydroxy, —NR$^a$R$^b$, (NR$^a$R$^b$)alkyl, and (NR$^a$R$^b$)carbonyloxy; wherein the alkenyl and the alkyl can optionally form a saturated or unsaturated cyclic structure, respectively, with an adjacent carbon atom;

R$^5$ and R$^6$ are independently selected from the group consisting of hydrogen, alkenyl, alkoxycarbonyl, alkyl, alkylcarbonyl, aryl, arylalkyl, heterocyclylalkylcarbonyl, and heterocyclylcarbonyl;

R$^7$ and R$^8$ are independently selected from the group consisting of hydrogen, alkenyl, alkoxy, alkyl, halo, and haloalkyl; and R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

The present invention also provides compositions comprising the compounds of the invention or pharmaceutically acceptable enantiomers, diastereomers, salts, or solvates thereof and a pharmaceutically acceptable carrier. In particular, the present invention provides pharmaceutical compositions useful for inhibiting the function of the HCV NS5A protein comprising a compound of the present invention, or a pharmaceutically acceptable enantiomer, diastereomer, salt, or solvate thereof, and a pharmaceutically acceptable carrier.

The present invention fuirther provides methods for treating patients infected with HCV comprising administering to the patient a therapeutically effective amount of a compound of the present invention, or a pharmaceutically acceptable enantiomer, diastereomer, salt, or solvate thereof. Additionally, the present invention provides methods of inhibiting the function of HCV NS5A protein by contacting the HCV NS5A protein with a compound of the present invention.

By virtue of the present invention, it is now possible to provide improved drugs comprising the compounds of the invention which can be effective in the treatment of patients infected with HCV. Specifically, the present invention provides compounds that can inhibit the function of the NS5A protein. Further, the present invention makes it possible to administer combination therapy to a patient whereby a compound in accordance with the present invention, which is effective to inhibit the HCV NS5A protein, can be administered with another compound having anti-HCV activity, e.g., a compound which is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5B protein, IMPDH, and a nucleoside analog for the treatment of an HCV infection.

DETAILED DESCRIPTION OF THE INVENTION

As used in the present specification the following terms have the meanings indicated:

The term "alkenyl," as used herein, refers to a straight or branched chain group of two to six carbon atoms containing at least one carbon-carbon double bond. Examples of alkenyl groups include, but are not limited to, ethenyl, 2-propenyl, and isobutenyl.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxyalkyl," as used herein, refers to an alkyl group substituted with one, two, or three alkoxyalkoxy groups.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkoxycarbonyloxy," as used herein, refers to an alkoxycarbonyl group attached to the parent molecular moiety through an oxygen atom.

The term "alkyl," as used herein, refers to a group derived from a straight or branched chain saturated hydrocarbon containing from one to six carbon atoms. Examples of alkyl groups include, but are not limited to, methyl, ethyl, isopropyl, and tert-butyl.

The term "alkylcarbonyl," as used herein, refers to an alkyl group attached to the parent molecular moiety through a carbonyl group.

The term "alkylsulfenyl," as used herein, refers to an alkyl group attached to the parent molecular moiety through a sulfur atom.

The term "alkylsulfenylalkyl," as used herein, refers to an alkyl group substituted with one, two, or three alkylsulfenyl groups.

The term "alkylsulfinyl," as used herein, refers to an alkyl group attached to the parent molecular moiety through a sulfinyl group.

The term "alkylsulfinylalkyl," as used herein, refers to an alkyl group substituted with one, two, or three alkylsulfinyl groups.

The term "alkylsulfonyl," as used herein, refers to an alkyl group attached to the parent molecular moiety through a sulfonyl group.

The term "alkylsulfonylalkyl," as used herein, refers to an alkyl group substituted with one, two, or three alkylsulfonyl groups.

The term "alkylsulfonyloxy," as used herein, refers to an alkylsulfonyl group attached to the parent molecular moiety through an oxygen atom.

The term "alkynyl," as used herein, refers to a straight or branched chain hydrocarbon of two to six carbon atoms containing at least one carbon-carbon triple bond. Examples of alkynyl groups include, but are not limited to, ethynyl, propynyl, and 4-methyl-1-pentynyl.

The term "aryl," as used herein, refers to a phenyl group, or a bicyclic or tricyclic fused ring system wherein one or more of the rings is a phenyl group. Bicyclic fused ring systems consist of a phenyl group fused to a monocyclic cycloalkenyl group, a monocyclic cycloalkyl group, or another phenyl group. Tricyclic fused ring systems consist of a bicyclic fused ring system fused to a monocyclic cycloalkenyl group, a monocyclic cycloalkyl group, or another phenyl group. The aryl groups of the present invention can be attached to the parent molecular moiety through any substitutable carbon atom in the group. Representative examples of aryl groups include, but are not limited to, anthracenyl, azulenyl, bicyclooctatrienyl, fluorenyl, indanyl, indenyl, naphthyl, phenyl, and tetrahydronaphthyl. Preferred aryl groups of the present invention are bicyclooctatrienyl, fluorenyl, naphthyl, and phenyl. The aryl groups of the present invention can be optionally substituted with one, two, three, four, or five substituents independently selected from the group consisting of alkenyl, alkoxy, alkoxycarbonyl, alkyl, alkylcarbonyl, alkylsulfenyl, alkylsulfonyl, alkynyl, a second aryl group, arylalkoxy, arylalkyl, arylcarbonyl, aryloxy, arylsulfenyl, arylsulfonyl, azido, cyano, cycloalkenyl, cycloalkenylalkyl, cycloalkyl, cycloalkylalkyl, halo, haloalkoxy, haloalkyl, heterocyclyl, heterocyclylalkoxy, heterocyclylalkyl, heterocyclylcarbonyl, heterocyclyloxy, —NR$^c$R$^d$, (NR$^c$R$^d$)alkyl, (NR$^c$R$^d$)carbonyl, and oxo; wherein the aryloxy, the arylsulfenyl, and the arylsulfonyl, the cycloalkenyl, the cycloalkenyl part of the cycloalkenylalkyl, the cycloalkyl, the cycloalkyl part of the cycloalkylalkyl, the heterocyclyl, and the heterocyclyl part of the heterocyclylalkoxy, the heterocyclylalkyl, the heterocyclylcarbonyl, and the heterocyclyloxy can be fuirther heterocyclylalkyl, the heterocyclylcarbonyl, and the heterocyclyloxy can be further selected from the group consisting of alkoxy, alkyl, cyano, halo, haloalkoxy, haloalkyl, and oxo; and wherein Rc and Rd are each independently selected from the haloalkyl, and oxo; and wherein R$^c$ and R$^d$ are each independently selected from the unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkyl," as used herein, refers to an alkyl group substituted with one, two, or three aryl groups. The alkyl part of the arylalkyl can be optionally substituted with one or two additional groups selected from the group consisting of alkenyl, alkoxy, alkynyl, arylalkoxy, aryloxy, heterocyclyl, heterocyclylalkoxy, heterocyclyloxy, hydroxy, and —NR$^c$R$^d$; wherein R$^c$ and R$^d$ are independently selected from the group consisting of hydrogen, alkoxyalkyl, alkoxycarbonyl, alkyl, alkylcarbonyl, unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "arylsulfenyl," as used herein, refers to an aryl group attached to the parent molecular moiety through a sulfur atom.

The term "arylsulfenylalkyl," as used herein, refers to an alkyl group substituted with one, two, or three arylsulfenyl groups.

The term "arylsulfinyl," as used herein, refers to an aryl group attached to the parent molecular moiety through a sulfinyl group.

The term "arylsulfinylalkyl," as used herein, refers to an alkyl group substituted with one, two, or three arylsulfinyl groups.

The term "arylsulfonyl," as used herein, refers to an aryl group attached to the parent molecular moiety through a sulfonyl group.

The term "arylsulfonylalkyl," as used herein, refers to an alkyl group substituted with one, two, or three arylsulfonyl groups.

The term "azido," as used herein, refers to —N$_3$.

The term "carbonyl," as used herein, refers to —C(O)—.

The term "carboxy," as used herein, refers to —CO$_2$H.

The term "carboxyalkyl," as used herein, refers to an alkyl group substituted with one, two, or three carboxy groups.

The term "cyano," as used herein, refers to —CN.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl. A preferred cycloalkenyl of the present invention is cyclopentenyl. The cycloalkenyl groups of the present invention can be optionally substituted with one, two, three, four, or five substituents independently selected from the group consisting of alkenyl, alkoxy, alkoxycarbonyl, alkyl, alkylcarbonyl, cyano, halo, haloalkoxy, haloalkyl, —NR$^c$R$^d$, (NR$^c$R$^d$)alkyl, (NR$^c$R$^d$)carbonyl, and oxo; wherein R$^c$ and R$^d$ are each independently selected from the group consisting of hydrogen, alkoxyalkyl, alkoxycarbonyl, alkyl, alkylcarbonyl, unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "cycloalkenylalkyl," as used herein, refers to an alkyl group substituted with one, two, or three cycloalkenyl groups.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, adamantyl, bicyclo[3.1.1]heptyl, cyclobutyl, cyclopentyl, and cyclopropyl. Preferred cycloalkyl groups of the present invention are cyclobutyl, cyclopentyl, and cyclopropyl. The cycloalkyl groups of the present invention can be optionally substituted with one, two, three, four, or five substituents independently selected from the group consisting of alkenyl, alkoxy, alkoxycarbonyl, alkyl, alkylcarbonyl, cyano, halo, haloalkoxy, haloalkyl, —NR$^c$R$^d$, (NR$^c$R$^d$)alkyl, (NR$^c$R$^d$)carbonyl, and oxo; wherein R$^c$ and R$^d$ are each independently selected from the group consisting of hydrogen, alkoxyalkyl, alkoxycarbonyl, alkyl, alkylcarbonyl, unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "cycloalkylalkyl," as used herein, refers to an alkyl group substituted with one, two, or three cycloalkyl groups.

The terms "halo," and "halogen," as used herein, refer to Br, Cl, F, or I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "heterocyclyl," as used herein, refers to a three-, four-, five-, six-, or seven-membered ring containing one, two, or three heteroatoms independently selected from the group consisting of nitrogen, oxygen, and sulfur. The three- and four-membered rings have zero or one double bond. The five-membered ring has zero to two double bonds and the sixand seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group; and tricyclic groups in which a bicyclic system is fused to a phenyl group, a monocyclic cycloalkenyl group, a monocyclic cycloalkyl group, or another monocyclic heterocyclyl group. The heterocyclyl groups of the present invention can be attached to the parent molecular moiety through a carbon atom or a nitrogen atom in the group. Examples of heterocyclyl groups include, but are not limited to, azetidinyl, benzimidazolyl, benzothienyl, diazirenyl, furyl, hexahydrothienoimidazolyl, imidazolyl, imidazopyridinyl, imidazothiazolyl, indolinyl, indolyl, isothiazolyl, isoxazolyl, morpholinyl, oxazolyl, piperazinyl, piperidinyl, pyrazinyl, pyrazolyl, pyridinyl, pyrrolidinyl, pyrrolopyridinyl, pyrrolyl, tetrahydrofuryl, thiadiazolyl, thiazolyl, thienyl, and thiomorpholinyl. Preferred heterocyclyl groups of the present invention are azetidinyl, benzimidazolyl, diazirenyl, furyl, hexahydrothienoimidazolyl, imidazolyl, imidazopyridinyl, imidazothiazolyl, indolinyl, indolyl, isothiazolyl, morpholinyl, oxazolyl, piperidinyl, pyrazinyl, pyrazolyl, pyridinyl, tetrahydrofuryl, thiadiazolyl, and thienyl. The heterocyclyl groups of the present invention can be optionally substituted with one, two, three, four, or five substituents independently selected from the group consisting of alkenyl, alkoxy, alkoxycarbonyl, alkyl, alkylcarbonyl, alkylsulfenyl, alkylsulfonyl, alkynyl, aryl, arylalkoxy, arylalkyl, arylcarbonyl, aryloxy, arylsulfenyl, arylsulfonyl, azido, cyano, cycloalkenyl, cycloalkenylalkyl, cycloalkyl, cycloalkylalkyl, halo, haloalkoxy, haloalkyl, a second heterocyclyl group, heterocyclylalkoxy, heterocyclylalkyl, heterocyclylcarbonyl, heterocyclyloxy, —NR$^c$R$^d$, (NR$^c$R$^d$)alkyl, (NR$^c$R$^d$)carbonyl, and oxo, wherein the aryl, the aryl part of the arylalkoxy, the arylalkyl, the arylcarbonyl, the aryloxy, the arylsulfenyl, and the arylsulfonyl, the cycloalkenyl, the cycloalkenyl part of the cycloalkenylalkyl, the cycloalkyl, the cycloalkyl part of the cycloalkylalkyl, the second heterocyclyl group, and the heterocyclyl part of the heterocyclylalkoxy, the heterocyclylalkyl, the heterocyclylcarbonyl, and the heterocyclyloxy can be further optionally substituted with one, two, three, four, or five substituents independently selected from the group consisting of alkoxy, alkyl, cyano, halo, haloalkoxy, haloalkyl, and oxo; and wherein R$^c$ and R$^d$ are each independently selected from the group consisting of hydrogen, alkoxyalkyl, alkoxycarbonyl, alkyl, alkylcarbonyl, unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "heterocyclylalkoxy," as used herein, refers to a heterocyclyl group attached to the parent molecular moiety through an alkoxy group.

The term "heterocyclylalkoxyalkyl," as used herein, refers to an alkyl group substituted with one, two, or three heterocyclylalkoxy groups.

The term "heterocyclylalkyl," as used herein, refers to an alkyl group substituted with one, two, or three heterocyclyl groups. The alkyl part of the heterocyclylalkyl can be optionally substituted with one or two additional groups selected from the group consisting of alkenyl, alkoxy, alkynyl, arylalkoxy, aryloxy, heterocyclylalkoxy, heterocyclyloxy, hydroxy, and —NR$^c$R$^d$; wherein R$^c$ and R$^d$ are independently selected from the group consisting of hydrogen, alkoxyalkyl, alkoxycarbonyl, alkyl, alkylcarbonyl, unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "hydroxy," as used herein, refers to —H.

The term "—NR$^a$R$^b$," as used herein, refers to two groups, R$^a$ and R$^b$, which are attached to the parent molecular moiety through a nitrogen atom. R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

The term "(NR$^a$R$^b$)alkyl," as used herein, refers to an alkyl group substituted with one, two, or three —NR$^a$R$^b$ groups. R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

The term "(NR$^a$R$^b$)carbonyl," as used herein, refers to an —NR$^a$R$^b$ group attached to the parent molecular moiety through a carbonyl group. R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, The term "(NR$^a$R$^b$)carbonyloxy," as used herein, refers to an (NR$^a$R$^b$)carbonyl group attached to the parent molecular moiety through an oxygen atom.

The term "—NR$^c$R$^d$," as used herein, refers to two groups, R$^c$ and R$^d$, which are attached to the parent molecular moiety through a nitrogen atom. R$^c$ and R$^d$ are independently selected from the group consisting of hydrogen, alkoxyalkyl, alkoxycarbonyl, alkyl, alkylcarbonyl, unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "(NR$^c$R$^d$)alkyl," as used herein, refers to an alkyl group substituted with one, two, or three —NR$^c$R$^d$ groups. R$^c$ and R$^d$ are each independently selected from the group consisting of hydrogen, alkoxyalkyl, alkoxycarbonyl, alkyl, alkylcarbonyl, unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "(NR$^c$R$^d$)carbonyl," as used herein, refers to an —NR$^c$R$^d$ group attached to the parent molecular moiety through a carbonyl group. R$^c$ and R$^d$ are each independently selected from the group consisting of hydrogen, alkoxyalkyl, alkoxycarbonyl, alkyl, alkylcarbonyl, unsubstituted aryl, unsubstituted arylalkyl, unsubstituted cycloalkyl, unsubstituted cycloalkylalkyl, unsubstituted heterocyclyl, and unsubstituted heterocyclylalkyl.

The term "oxo," as used herein, refers to =O.

The term "sulfinyl," as used herein, refers to —S(O)—.

The term "sulfonyl," as used herein, refers to —SO$_2$—.

Asymmetric centers exist in the compounds of the present invention. These centers are designated by the symbols "R" or "S", depending on the configuration of substituents around the chiral carbon atom. In the compounds of the present invention at least one of the proline moieties is in the L configuration. Preferably, the compounds of the invention contain two L-proline moieties. It should be understood that the invention encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Because carbon-carbon double bonds exist in the present compounds, the invention contemplates various geometric isomers and mixtures thereof resulting from the arrangement of substituents around these carbon-carbon double bonds. It is well known in the art that stilbenes isomerize under a variety of reaction conditions (see, for Example WO02/50007). It should be understood that the invention encompasses both isomeric forms, and mixtures thereof, which possess the ability to inhibit NS5A. The symbol "∿∿" is used to indicate that the compound can be the "E" isomer, the "Z" isomer, or a mixture of both. The term "E" represents higher order substituents on opposite sides of the carbon-carbon double bond, and the term "Z" represents higher order substituents on the same side of the carbon-carbon double bond.

The term "compounds of the invention", and equivalent expressions, are meant to embrace compounds of formula I, and pharmaceutically acceptable enantiomers, diastereomers, salts, solvates, e.g. hydrates, thereof. Similarly, references to intermediates are meant to embrace their salts and solvates where the context so permits. The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The term "solvate" encompasses both solution-phase and isolable solvates. Exemplary solvates include hydrates, ethanolates, methanolates, and the like. In addition, compounds of the present invention, or salts or solvates thereof, may exhibit polymorphism. The present invention also encompasses any such polymorphic form.

The compounds of the present invention can exist as pharmaceutically acceptable salts. The term "pharmaceutically acceptable salt," as used herein, represents salts or zwitterionic forms of the compounds of the present invention which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent (s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the invention are typical in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The present invention provides a compound of formula (I)

or a pharmaceutically acceptable salt thereof, wherein $\overset{a}{-----}$ is a single or double bond;

$\overset{b}{-----}$ is a single or double bond;

when $\overset{a}{-----}$ is a single bond, X is selected from the group consisting of O, $CH_2$, and $CHR^3$;

when $\overset{a}{-----}$ is a double bond, X is selected from the group consisting of CH and $CR^3$;

when $\overset{b}{-----}$ is a single bond, Y is selected from the group consisting of O, $CH_2$, and $CHR^4$;

when $\overset{b}{-----}$ is a double bond, Y is selected from the group consisting of CH and $CR^4$;

n and m are independently 0, 1, 2, or 3;

p is 0 or 1;

$R^1$ and $R^2$ are independently selected from the group consisting of alkoxy, alkoxyalkoxyalkyl, alkoxyalkyl, alkyl, alkylsulfenylalkyl, alkylsulfinylalkyl, alkylsulfonylalkyl, aryl, arylalkoxy, arylalkoxyalkyl, arylalkyl, arylcarbonyl, aryloxy, aryloxyalkyl, arylsulfenylalkyl, arylsulfinylalkyl, arylsulfonylalkyl, carboxyalkyl, cycloalkenyl, cycloalkenylalkyl, cycloalkyl, cycloalkylalkyl, heterocyclyl, heterocyclylalkoxy, heterocyclylalkoxyalkyl, heterocyclylalkyl, heterocyclylcarbonyl, heterocyclyloxy, heterocyclyloxyalkyl, —$NR^aR^b$, and $(NR^aR^b)$alkyl;

$R^3$ and $R^4$ are independently selected from the group consisting of hydrogen, alkenyl, alkoxy, alkoxycarbonyloxy, alkyl, alkylsulfonyl, alkylsulfonyloxy, aryl, arylalkyl, azido, hydroxy, —$NR^aR^b$, $(NR^aR^b)$alkyl, and $(NR^aR^b)$carbonyloxy; wherein the alkenyl and the alkyl can optionally form a saturated or unsaturated cyclic structure, respectively, with an adjacent carbon atom;

$R^5$ and $R^6$ are independently selected from the group consisting of hydrogen, alkenyl, alkoxycarbonyl, alkyl, alkylcarbonyl, aryl, arylalkyl, heterocyclylalkylcarbonyl, and heterocyclylcarbonyl;

$R^7$ and $R^8$ are independently selected from the group consisting of hydrogen, alkenyl, alkoxy, alkyl, halo, and haloalkyl; and $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

In a preferred aspect of the invention, the compounds have the structure of formula (I), wherein at least one of $R^1$ and $R^2$ is selected from the group consisting of arylalkyl and heterocyclylalkyl, wherein the alkyl part of the arylalkyl and the heterocyclyl are substituted with one or two additional substituents independently selected from the group consisting of alkenyl, alkoxy, alkynyl, arylalkoxy, aryloxy, heterocyclyl, heterocyclylalkoxy, heterocyclyloxy, hydroxy, and —NR$^c$R$^d$.

In another preferred aspect of the invention, the compounds have the structure of formula (I), wherein at least one of $R^1$ and $R^2$ is heterocyclyl, wherein the heterocyclyl is optionally substituted with one, two, or three substituents independently selected from the group consisting of alkoxy, alkyl, aryloxy, halo, —NR$^c$R$^d$, and (NR$^c$R$^d$)alkyl. More preferably the heterocyclyl is isoquinolinyl.

In another preferred aspect of the invention, the compounds have the structure of formula (II)

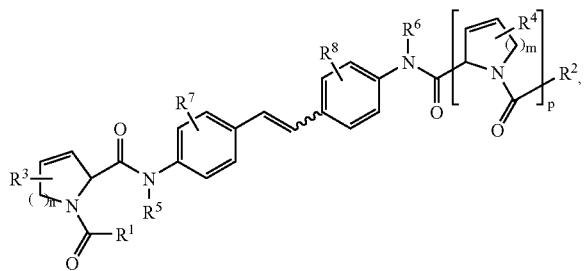

(II)

or a pharmaceutically acceptable salt thereof, wherein
n and m are independently 1 or 2;
p is 0 or 1;

$R^1$ and $R^2$ are independently selected from the group consisting of alkoxy, alkoxyalkoxyalkyl, alkoxyalkyl, alkyl, alkylsulfenylalkyl, alkylsulfinylalkyl, alkylsulfonylalkyl, aryl, arylalkoxy, arylalkoxyalkyl, arylalkyl, arylcarbonyl, aryloxy, aryloxyalkyl, arylsulfenylalkyl, arylsulfinylalkyl, arylsulfonylalkyl, carboxyalkyl, cycloalkenyl, cycloalkenylalkyl, cycloalkyl, cycloalkylalkyl, heterocyclyl, heterocyclylalkoxy, heterocyclylalkoxyalkyl, heterocyclylalkyl, heterocyclylcarbonyl, heterocyclyloxy, heterocyclyloxyalkyl, —NR$^a$R$^b$, and (NR$^a$R$^b$)alkyl;

$R^3$ and $R^4$ are independently selected from the group consisting of hydrogen, alkenyl, alkoxy, alkoxycarbonyloxy, alkyl, alkylsulfonyl, alkylsulfonyloxy, aryl, arylalkyl, azido, hydroxy, —NR$^a$R$^b$, (NR$^a$R$^b$)alkyl, and (NR$^a$R$^b$)carbonyloxy; wherein the alkenyl and the alkyl can optionally form a saturated or unsaturated cyclic structure, respectively, with an adjacent carbon atom;

$R^5$ and $R^6$ are independently selected from the group consisting of hydrogen, alkenyl, alkoxycarbonyl, alkyl, alkylcarbonyl, aryl, arylalkyl, heterocyclylalkylcarbonyl, and heterocyclylcarbonyl;

$R^7$ and $R^8$ are independently selected from the group consisting of hydrogen, alkenyl, alkoxy, alkyl, halo, and haloalkyl; and $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

In another preferred aspect of the invention, the compounds have the structure of formula (II), wherein
n and m are independently 1 or 2;
p is 0 or 1;

$R^1$ and $R^2$ are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —NR$^a$R$^b$, and (NR$^a$R$^b$)alkyl;

$R^3$ and $R^4$ are independently selected from the group consisting of hydrogen, alkoxy, alkylsulfonyloxy, azido, hydroxy, —NR$^a$R$^b$, and (NR$^a$R$^b$)carbonyloxy;

$R^5$ and $R^6$ are independently selected from the group consisting of hydrogen, alkoxycarbonyl, alkyl, and heterocyclylcarbonyl;

$R^7$ and $R^8$ are independently selected from the group consisting of hydrogen, alkyl, and halo; and $R^a$ and $R^b$ are independently selected from the group consisting of hydrogen, alkyl, alkylcarbonyl, arylalkyl, arylalkylcarbonyl, and cycloalkyl.

In another preferred aspect of the invention, the compounds have the structure of formula (II), wherein
n and m are 1;
p is 1;

$R^1$ and $R^2$ are independently selected from the group consisting of alkyl, aryl, arylalkyl, cycloalkyl, cycloalkylalkyl, heterocyclyl, and heterocyclylalkyl; and $R^3$, $R^4$, $R^5$, $R^6$, $R^7$, and $R^8$ are hydrogen.

In another preferred aspect of the invention, the compounds have the structure of formula (II), wherein
n and m are 1;
p is 1;

$R^1$ and $R^2$ are independently selected from the group consisting of alkyl, cycloalkyl, and heterocyclylalkyl; and $R^3$, $R^4$, $R^5$, $R^6$, $R^7$, and $R^8$ are hydrogen.

In another preferred aspect of the invention, the compounds have the structure of formula (III)

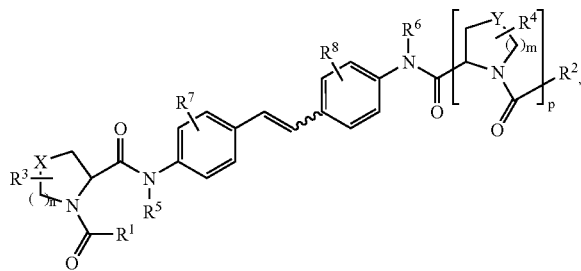

(III)

or a pharmaceutically acceptable salt thereof, wherein
X is selected from the group consisting of O, $CH_2$, and $CHR^3$;

Y is selected from the group consisting of O, $CH_2$, and $CHR^4$;

n and m are independently 0, 1, or 2;
p is 0 or 1;

$R^1$ and $R^2$ are independently selected from the group consisting of alkoxy, alkoxyalkoxyalkyl, alkoxyalkyl, alkyl, alkylsulfenylalkyl, alkylsulfinylalkyl, alkylsulfonylalkyl, aryl, arylalkoxy, arylalkoxyalkyl, arylalkyl, arylcarbonyl, aryloxy, aryloxyalkyl, arylsulfenylalkyl, arylsulfinylalkyl, arylsulfonylalkyl, carboxyalkyl, cycloalkenyl, cycloalkenylalkyl, cycloalkyl, cycloalkylalkyl, heterocyclyl, heterocyclylalkoxy, heterocyclylalkoxyalkyl, heterocyclylalkyl, heterocyclylcarbonyl, heterocyclyloxy, heterocyclyloxyalkyl, —NR$^a$R$^b$, and (NR$^a$R$^b$)alkyl;

R$^3$ and R$^4$ are independently selected from the group consisting of hydrogen, alkenyl, alkoxy, alkoxycarbonyloxy, alkyl, alkylsulfonyl, alkylsulfonyloxy, aryl, arylalkyl, azido, hydroxy, —NR$^a$R$^b$, (NR$^a$R$^b$)alkyl, and (NR$^a$R$^b$)carbonyloxy; wherein the alkenyl and the alkyl can optionally form a saturated or unsaturated cyclic structure, respectively, with an adjacent carbon atom;

R$^5$ and R$^6$ are independently selected from the group consisting of hydrogen, alkenyl, alkoxycarbonyl, alkyl, alkylcarbonyl, aryl, arylalkyl, heterocyclylalkylcarbonyl, and heterocyclylcarbonyl;

R$^7$ and R$^8$ are independently selected from the group consisting of hydrogen, alkenyl, alkoxy, alkyl, halo, and haloalkyl; and R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

In another preferred aspect of the invention, the compounds have the structure of formula (III) wherein
X is selected from the group consisting of O, CH$_2$, and CHR$^3$;
Y is selected from the group consisting of O, CH$_2$, and CHR$^4$;
n and m are independently 0, 1, or 2;
p is 0 or 1;
R$^1$ and R$^2$ are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —NR$^a$R$^b$, and (NR$^a$R$^b$)alkyl;
R$^3$ and R$^4$ are independently selected from the group consisting of hydrogen, alkenyl, alkoxy, alkylsulfonyloxy, azido, hydroxy, —NR$^a$R$^b$, (NR$^a$R$^b$)carbonyloxy; wherein the alkenyl can optionally form a saturated cyclic structure with an adjacent carbon atom;
R$^5$ and R$^6$ are independently selected from the group consisting of hydrogen, alkoxycarbonyl, alkyl, and heterocyclylcarbonyl;
R$^7$ and R$^8$ are independently selected from the group consisting of hydrogen, alkyl, and halo; and
R$^a$ and R$^b$ are independently selected from the group consisting of hydrogen, alkyl, alkylcarbonyl, arylalkyl, arylalkylcarbonyl, and cycloalkyl.

In another preferred aspect of the invention, the compounds have the structure of formula (III) wherein
X is CHR$^3$;
Y is CHR$^4$;
n and m are 1;
p is 0 or 1;
R$^1$ and R$^2$ are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —NR$^a$R$^b$, and (NR$^a$R$^b$)alkyl;
R$^3$ and R$^4$ are independently selected from the group consisting of hydrogen, alkenyl, alkoxy, alkylsulfonyloxy, azido, hydroxy, —NR$^a$R$^b$, (NR$^a$R$^b$)carbonyloxy; wherein the alkenyl can optionally form a saturated cyclic structure with an adjacent carbon atom;
R$^5$ and R$^6$ are independently selected from the group consisting of hydrogen, alkoxycarbonyl, alkyl, and heterocyclylcarbonyl;
R$^7$ and R$^8$ are independently selected from the group consisting of hydrogen, alkyl, and halo; and
R$^a$ and R$^b$ are independently selected from the group consisting of hydrogen, alkyl, alkylcarbonyl, arylalkyl, arylalkylcarbonyl, and cycloalkyl.

In another preferred aspect of the invention, the compounds have the structure of formula (III) wherein
X is CHR$^3$;
Y is CHR$^4$;
n and m are 1;
p is 1;
R$^1$ and R$^2$ are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —NR$^a$R$^b$, and (NR$^a$R$^b$)alkyl;
R$^3$ and R$^4$ are independently selected from the group consisting of hydrogen, alkenyl, alkoxy, alkylsulfonyloxy, azido, hydroxy, —NR$^a$R$^b$, (NR$^a$R$^b$)carbonyloxy; wherein the alkenyl can optionally form a saturated cyclic structure with an adjacent carbon atom;
R$^5$ and R$^6$ are independently selected from the group consisting of hydrogen, alkoxycarbonyl, alkyl, and heterocyclylcarbonyl;
R$^7$ and R$^8$ are independently selected from the group consisting of hydrogen, alkyl, and halo; and
R$^a$ and R$^b$ are independently selected from the group consisting of hydrogen, alkyl, alkylcarbonyl, arylalkyl, arylalkylcarbonyl, and cycloalkyl.

In another preferred aspect of the invention, the compounds have the structure of formula (III) wherein
X is CH$_2$;
Y is CH$_2$;
n and m are 1;
p is 1;
R$^1$ and R$^2$ are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —NR$^a$R$^b$, and (NR$^a$R$^b$)alkyl;
R$^5$, R$^6$, R$^7$, and R$^8$ are hydrogen; and
R$^a$ and R$^b$ are independently selected from the group consisting of hydrogen, alkyl, alkylcarbonyl, arylalkyl, arylalkylcarbonyl, and cycloalkyl.

Preferred compounds of the present invention are selected from the group consisting of

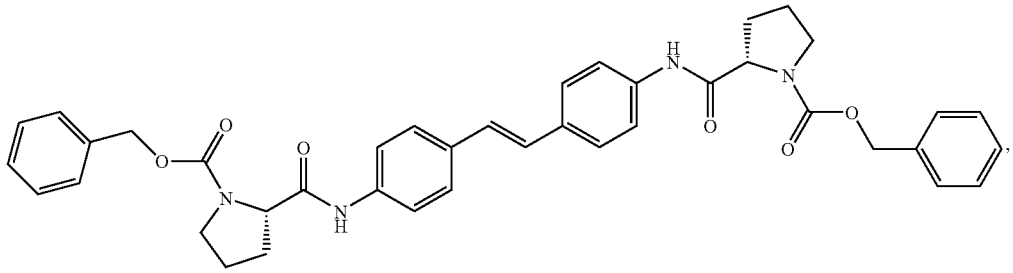

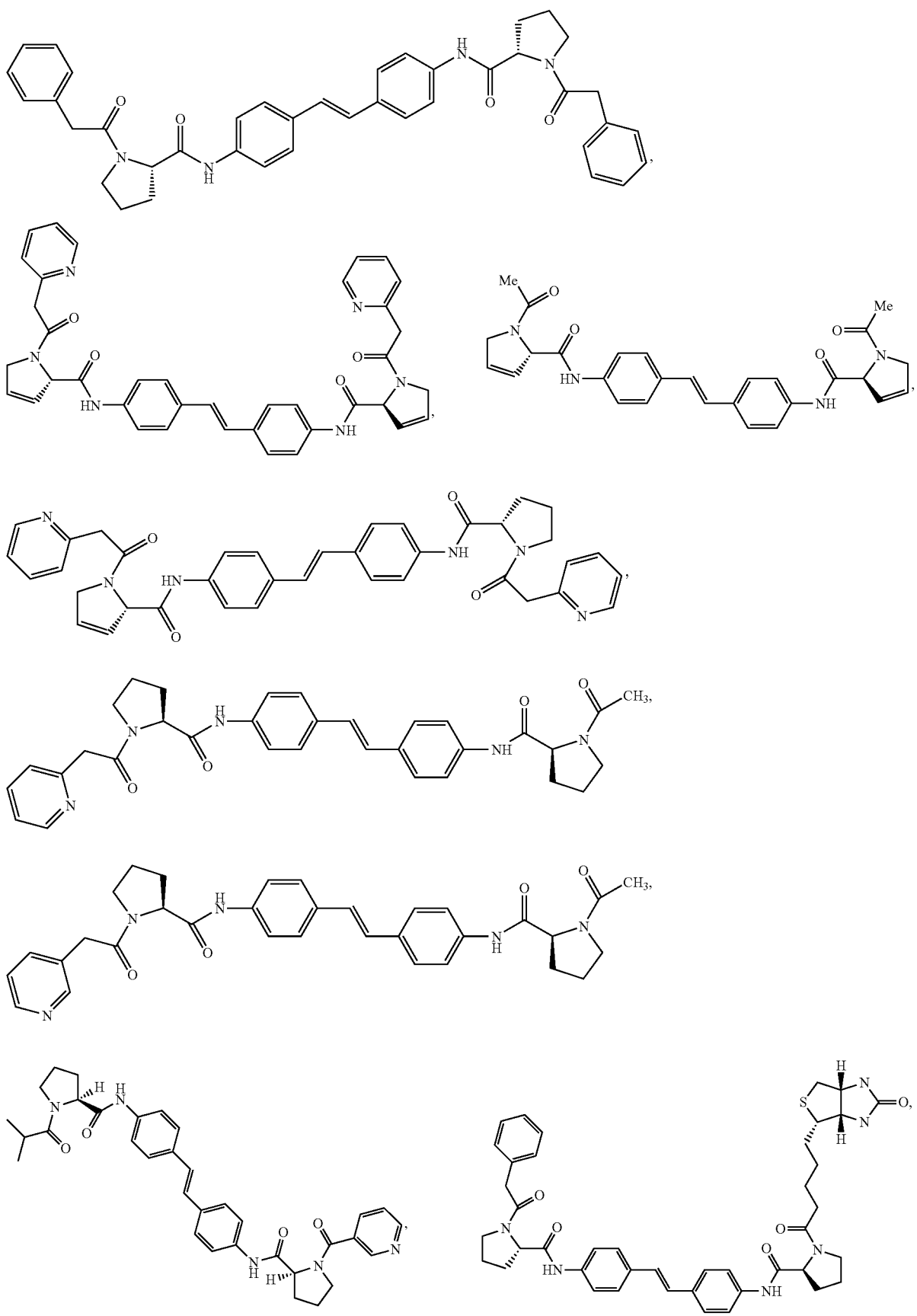

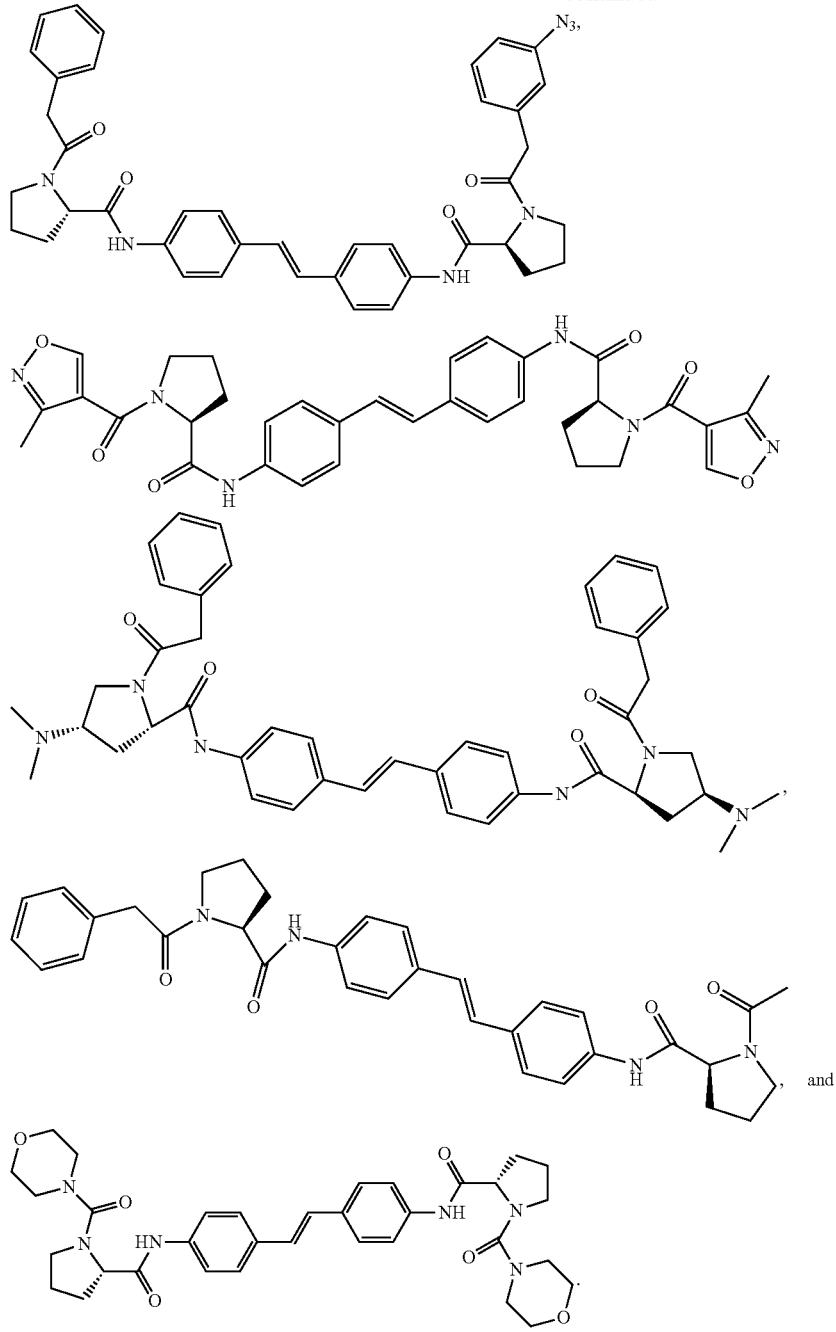

In another aspect of the invention, there is provided a composition comprising the compound of formula (I) and a pharmaceutically acceptable carrier. Preferably, the composition further comprises a compound having anti-HCV activity. As used herein, the term "anti-HCV activity" means the compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, HCV NS5B protein, IMPDH, and a nucleoside analog for the treatment of an HCV infection. Often, the other compound having anti-HCV activity is effective to inhibit the function of target in the HCV life cycle other than the HCV NS5A protein.

In one preferred aspect, the compound having anti-HCV activity is an interferon. Preferably, the interferon is selected from the group consisting of interferon alpha 2B, pegylated interferon alpha, consensus interferon, interferon alpha 2A, and lymphoblastoid interferon tau.

In another aspect of the invention, the compound having anti-HCV activity is a cyclosporin. In a preferred aspect, the cyclosporin is cyclosporin A.

In another aspect of the invention, the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In one preferred aspect of the invention, the composition comprises a compound of the invention, an interferon, and ribavirin.

In another preferred aspect of the invention, the compound having anti-HCV activity is a small molecule compound. As used herein, the term "small molecule compound" means a compound having a molecular weight of less than 1,500 daltons, preferably less than 1000 daltons. Preferably, the small molecule compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5B protein, inosine monophosphate dehydrogenase ("IMPDH"), and a nucleoside analog for the treatment of an HCV infection.

Certain illustrative HCV inhibitor compounds which can be administered with the compounds of the present invention include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000, WO 02/08198, published Jan. 31, 2002, WO 02/08187, published Jan. 31, 2002, WO 02/08244, published Jan. 31, 2002, WO 02/08251, published Jan. 31, 2002, WO 02/08256, published Jan. 31, 2002, WO 03/062228, published Jul. 31, 2003, WO 03/062265, published Jul. 31, 2003, WO 01/77113, published Oct. 18, 2001, WO 02/48172, published Jun. 20, 2002, WO 01/81325, published Nov. 1, 2001, and WO 01/58929, published Aug. 16, 2001.

The compounds of the present invention can also be administered with a cyclosporin, preferably cyclosporin A. Cyclosporin A has been shown to be active against HCV in clinical trials (*Hepatology* 2003, 38, 1282; *Biochem. Biophys. Res. Commun.* 2004, 313, 42; *J Gastroenterol.* 2003, 38, 567).

Table 1 below lists some illustrative examples of compounds that can be administered with the compounds of this invention. The compounds of the invention can be administered with other anti-HCV activity compounds in combination therapy, either jointly or separately, or by combining the compounds into a composition.

TABLE 1

| Brand Name | Type of Inhibitor or Target | Source Company |
| --- | --- | --- |
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Pharnaceuticals Inc., New York, NY |
| JTK-003 | RdRp inhibitor | Japan Tobacco Inc., Tokyo, Japan |
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ |

TABLE 1-continued

| Brand Name | Type of Inhibitor or Target | Source Company |
| --- | --- | --- |
| | | SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tabulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

When these compounds or their pharmaceutically acceptable enantiomers, diastereomers, salts, or solvates are formulated together with a pharmaceutically acceptable carrier, the resulting composition may be administered in vivo to mammals, such as man, to inhibit HCV NS5A or to treat or prevent HCV virus infection.

Accordingly, another aspect of this invention provides methods of inhibiting HCV replicon. Preferably, the compounds of the present invention inhibit the HCV NS5A protein.

In another aspect of the invention, there is provided a method of inhibiting the function of the HCV replicon comprising contacting the HCV replicon with a compound of the invention. In another aspect of the invention, there is provided a method of inhibiting HCV NS5A protein comprising contacting the HCV NS5A protein with a compound of the invention. In another aspect, there is provided a method of treating an HCV infection in a patient, comprising administering to the patient a therapeutically effective amount of the compound of the invention, or a pharmaceutically acceptable enantiomer, diastereomer, solvate, or salt thereof.

Preferably, the method of administering the compound is effective to inhibit the function of the HCV NS5A protein. In a preferred aspect, the method further comprises administering another compound having anti-HCV activity (as described above) prior to, after, or concurrently with a compound of the invention.

The compounds of the invention may also be used as laboratory reagents. Compounds may be instrumental in providing research tools for designing viral replication assays, validation of animal assay systems, and structural biology studies to further enhance knowledge of the HCV disease mechanisms. Further, the compounds of the present invention are useful in establishing or determining the binding site of other antiviral compounds, for example, by competitive inhibition.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

Further, the compounds and compositions of the invention can be used for the manufacture of a medicament for treating HCV infection in a patient.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of m, n, p, X, Y, and $R^1$-$R^8$ to successfully complete the syntheses below. The groups m, n, p, X, Y, and $R^1$-$R^8$ are as defined above unless otherwise noted below.

Abbreviations used within the schemes and examples are as follows: EEDQ for 2-ethoxy-1-ethoxycarbonyl-1,2-dihydroquinoline; EDCI for 1-(3-dimethylaminopropyl)-3-ethylcarbodiimide hydrochloride; HATU for O-(7-azabenzotriazol-1-yl)-N,N,N',N'-tetramethyluronium hexafluorophosphate; HBTU for O-benzotriazol-1-yl-N,N,N',N'-tetramethyluronium hexafluorophosphate; TBTU for O-benzotriazol-1-yl-N,N,N',N'-tetramethyluronium tetrafluoroborate; PPh₃ for triphenylphosphine; BOC for tert-butoxycarbonyl; DMSO for dimethylsulfoxide; TFA for trifluoroacetic acid; DMF for N,N-dimethylformamide; THF for tetrahydrofuran; DIC for diisopropylcarbodiimide; DCC for 1,3-dicyclohexylcarbodiimide; OAc for acetate; ACN for acetonitrile; FMOC for 9-fluorenylmethoxycarbonyl; PyBOP for benzotriazol-1-yloxytripyrrolidinophosphonium hexafluorophosphate; and CBZ for carbobenzyloxy.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme I

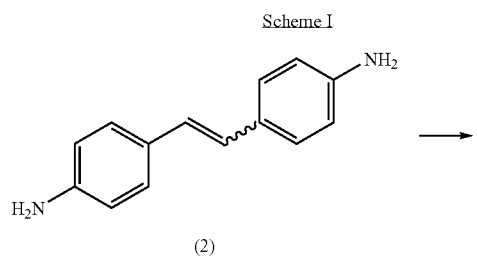

(2)

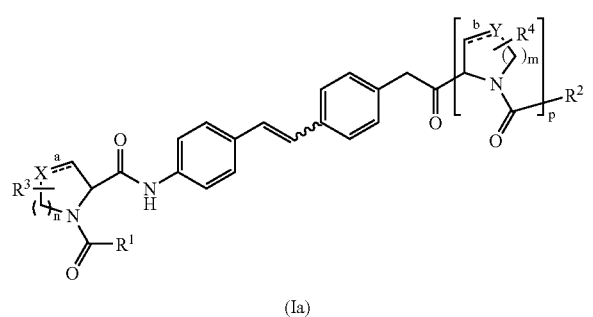

(Ia)

As shown in Scheme I, compounds of formula (2) can be reacted with an appropriately substituted amino acid to provide compounds of formula (Ia). If two equivalents of the same amino acid are used, symmetrical compounds are formed. If two different amino acids are used, asymmetrical compounds of formula (Ia) can be isolated after separation of the mixture of compounds that is formed. Representative examples of coupling reagents used in these reactions include EEDQ, EDCI, HATU, and other reagents known to those of ordinary skill in the art.

Scheme II

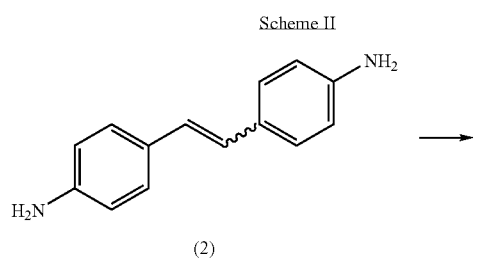

(2)

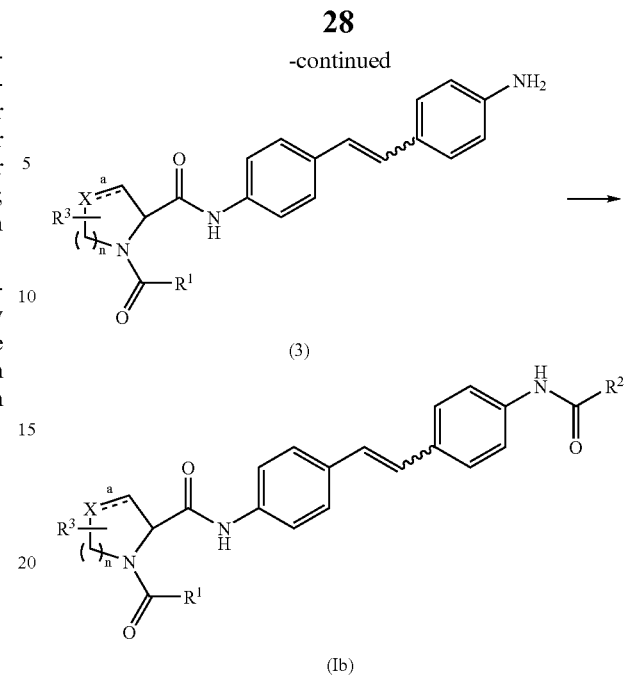

(3)

(Ib)

Scheme II shows the synthesis of compounds of formula (Ib). Compounds of formula (2) can be coupled to an appropriately substituted carboxylic acid under the conditions described in Scheme I to provide compounds of formula (3), which can be reacted with an isocyanate, carbamoyl chloride, acid chloride, or an amino acid in the presence of a base to provide compounds of formula (Ib). Representative bases include pyridine, diisopropylethylamine, and triethylamine. Examples of coupling reagents used with amino acids include HATU, HBTU, and TBTU.

Scheme III

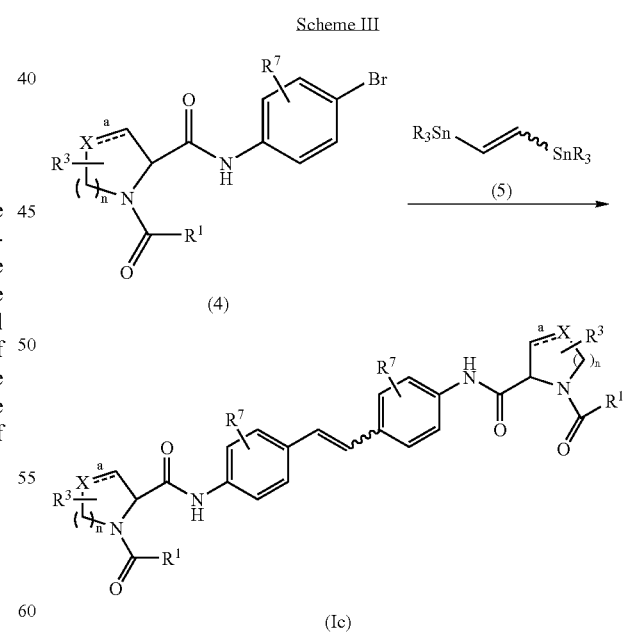

(4)

(Ic)

As shown in Scheme III, compounds of formula (4) can be coupled with bis(stannane) (5) (R is an alkyl or aryl group) in the presence of a palladium catalyst such as Pd(PPh₃)₄ or Pd(PPh₃)₂Cl₂ to provide compounds of formula (Ic) (compounds of formula (I) which are symmetrical).

Scheme IV

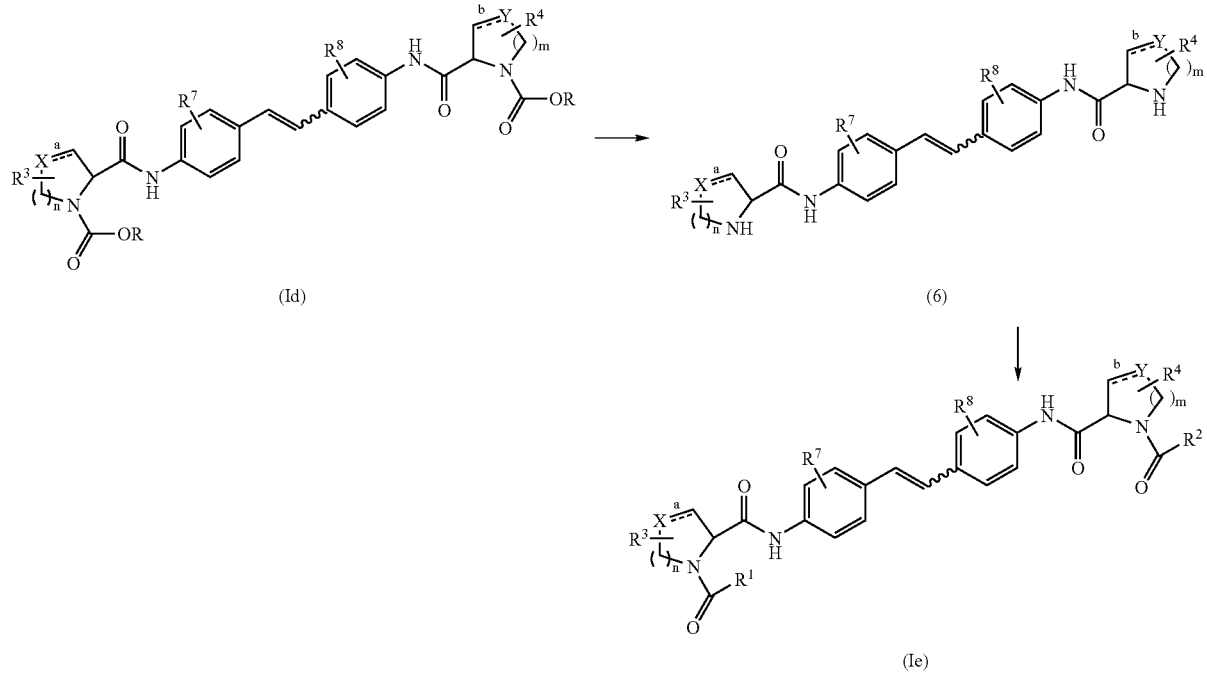

Scheme IV shows the synthesis of compounds of formula (Ie). Compounds of formula (Id) where R is alkyl (prepared by the methods shown in Schemes I-III) can be converted to compounds of formula (6) under conditions known to those of ordinary skill in the art (conditions which vary depending on the nature of R). Compounds of formula (6) can be treated with two equivalents of an appropriately substituted amino acid (in the presence of a coupling agent such as EDCI, HATU, or HBTU), carbamoyl chloride, or isocyanate to provide compounds of formula (Ie) where $R^1$ and $R^2$ are the same. Alternatively, if two different coupling partners are used, compounds of formula (Ie) where $R^1$ and $R^2$ are different can be isolated after separation of the mixture of products that is initially formed.

Scheme V

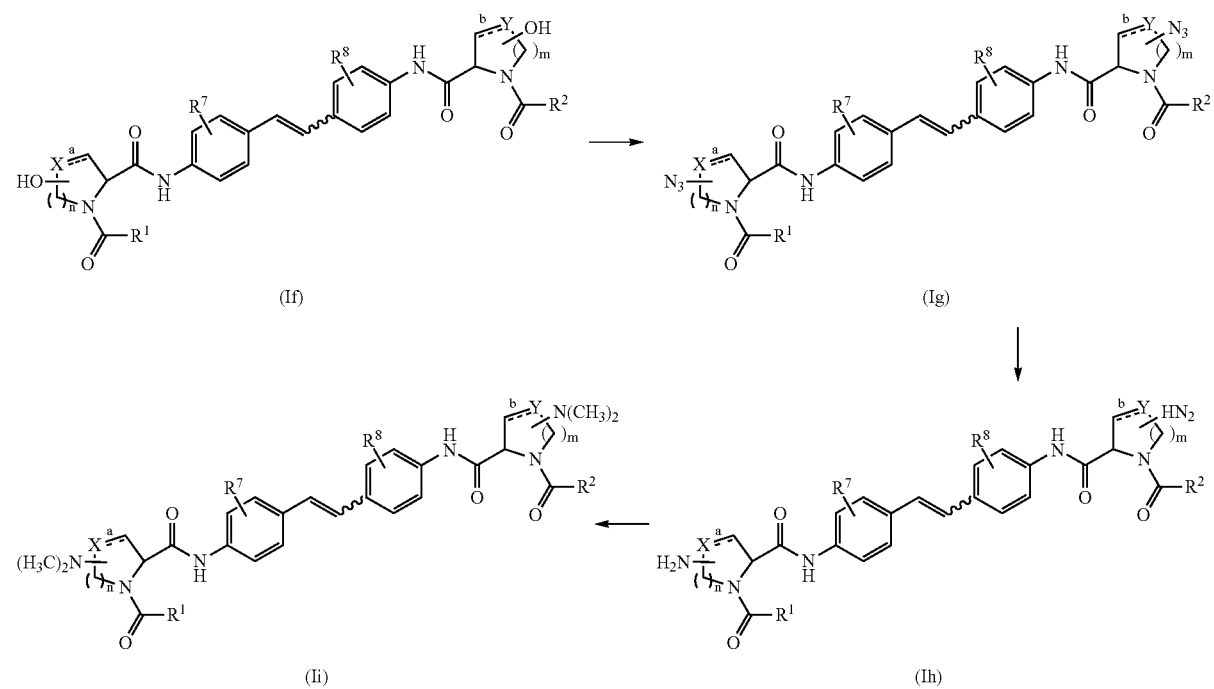

The synthesis of compounds of formula (Ii) is shown in Scheme V. The hydroxy groups in compounds of formula (If) (prepared by the methods described in Schemes I-IV) can be converted to a leaving group, such as a trifluoromethanesulfonyl group or a methanesulfonyl group, by methods known to those of ordinary skill in the art, then reacted with sodium azide to provide compounds of formula (Ig). Reduction of the azide under standard conditions (for example, tin(II) chloride) provides the free amine (Ig) which can be reacted with paraformaldehyde and sodium cyanoborohydride to provide compounds of formula (Ii).

Alternatively, the hydroxy groups in compounds of formula (If) can be converted to esters, carbonates, or carbamates by treatment with an appropriately substituted carbamyl chloride, acid halide, chloroformate, or isocyanate.

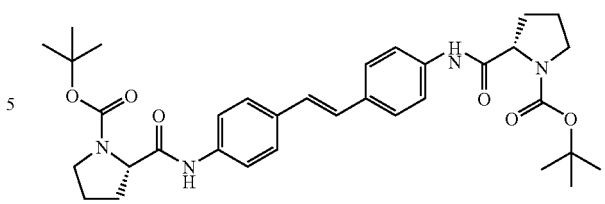

Example 1

2-Ethoxy-1-ethoxycarbonyl-1,2-dihydroquinoline (EEDQ, 22.58 g, 91.3 mmol) was added in one portion to a

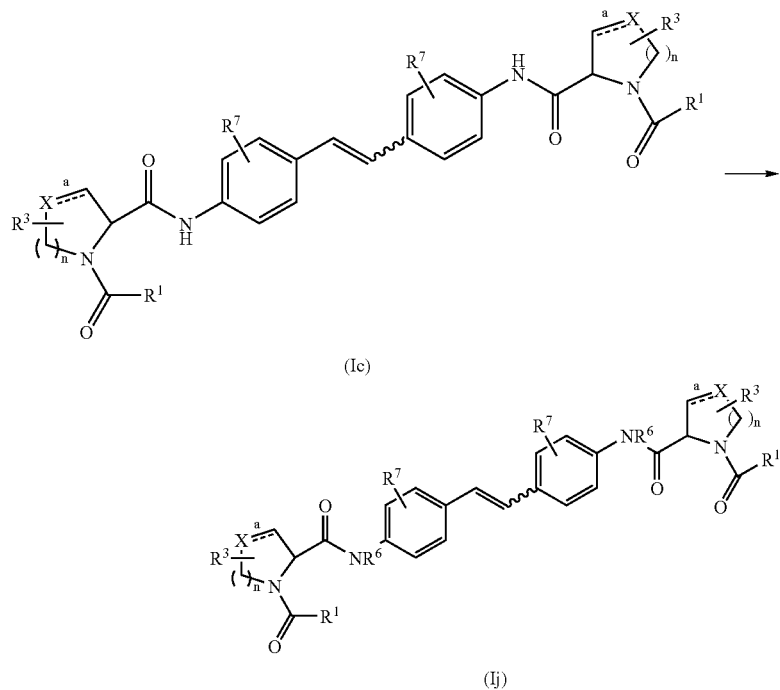

As shown in Scheme VI, compounds of formula (Ic) can be converted to compounds of formula (Ij) by treatment with a base such as sodium hydride or lithium hexamethyldisilazide followed by an alkylating or acylating agent.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

stirred suspension of 4,4'-diaminostilbene (8.0 g, 38.05 mmol) and N-BOC-L-proline (18.83 g, 87.5 mmol) in dry dichloromethane (250 mL) under nitrogen at room temperature. After 15 minutes the suspension became homogeneous and was stirred further for 16 hours before nearly all of the dichloromethane was removed in vacuo. The residue was then triturated with ethyl acetate and diethyl ether and filtered to provide the desired product (94% pure, 21.62 g, 94% yield) as an off-white solid: $^1$H NMR (DMSO-$d_6$, 400 MHz) δ 10.04 (s, 2H), 7.61 (d, J=8.8 Hz, 4H), 7.51 (d, J=8.4 Hz, 4H), 7.09 (s, 2H), 4.30-4.17 (2m, 2H), 3.45-3.34 (2m, 4H), 2.25-2.12 (m, 2H), 1.95-1.72 (2m, 6H), 1.40 and 1.27 (2s, 18H); LCMS ($R_t$=2.56 min, m/z 605.4).

Following the procedure described in Example 1 and substituting the appropriate reagents, the following compounds were prepared:

| Example | Structure | HPLC (min/method*) | (M + H)+ |
|---|---|---|---|
| 2 | 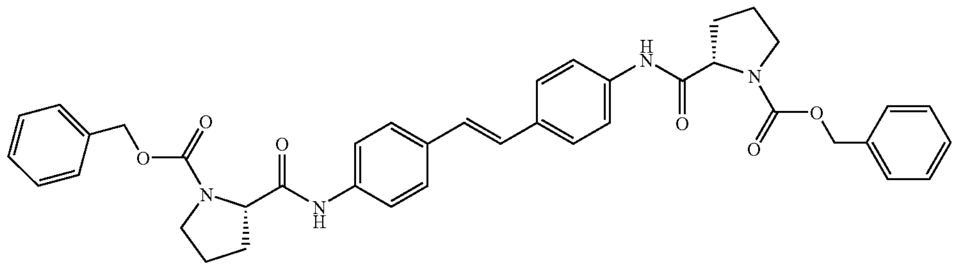 | 1.82/A | 673.4 |
| 3 | 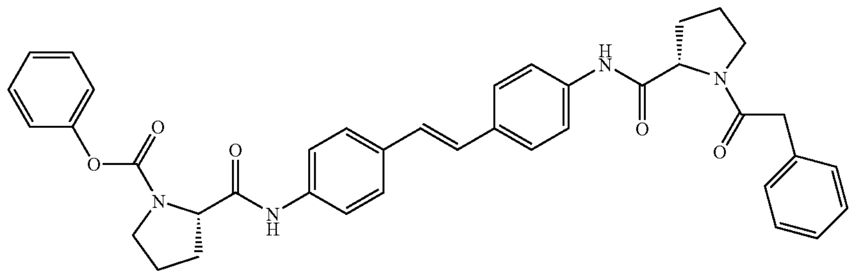 | 1.73/A | 641.5 |
| 4 | 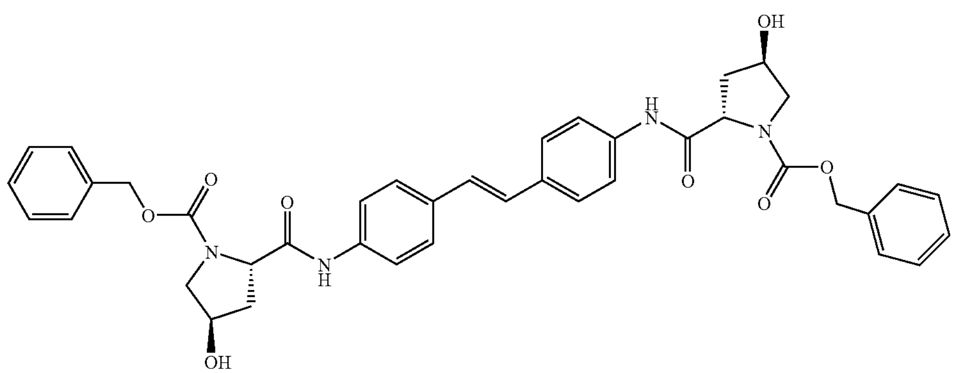 | 1.56/A | 705.4 |
| 5 | 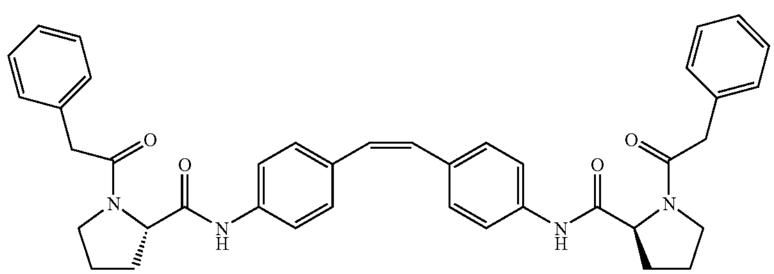 | 12.2/C | 641.5 |
| 6 | 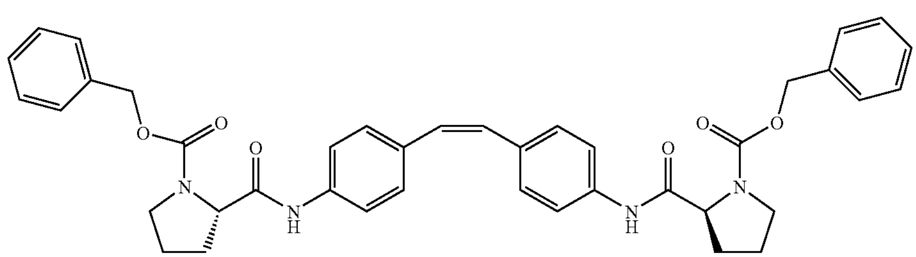 | 1.85/A | 673.5 |

-continued

| Example | Structure | HPLC (min/method*) | (M + H)+ |
|---|---|---|---|
| 7 | 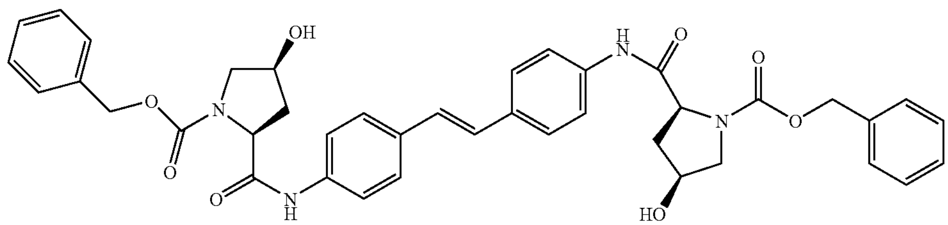 | 2.34/B | 705.4 |
| 8 | 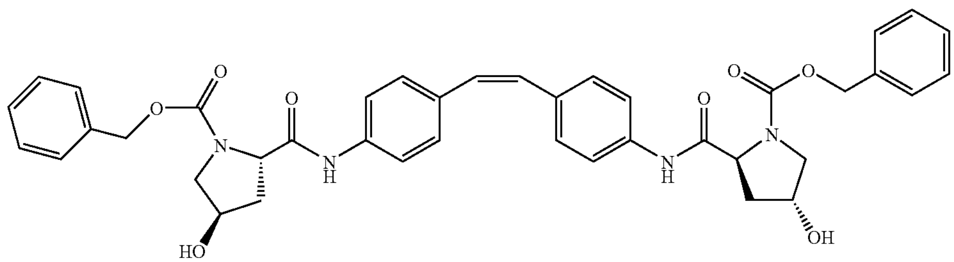 | 1.73/A | 705.4 |
| 9 | 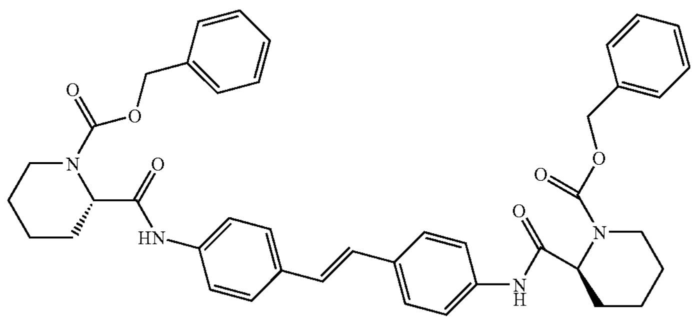 | 2.85/B | 701.3 |
| 10 | 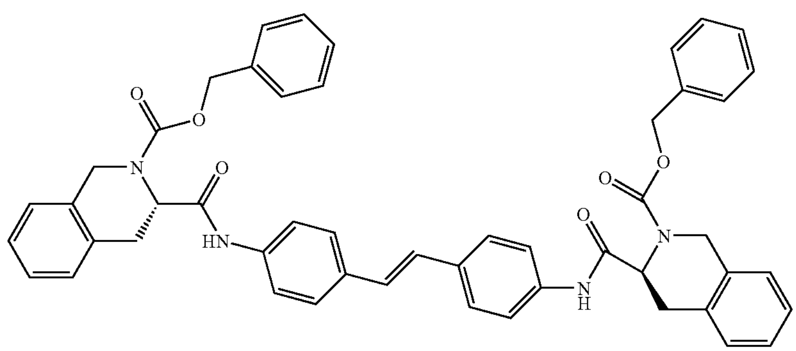 | 2.84/B | 797.3 |
| 11 | 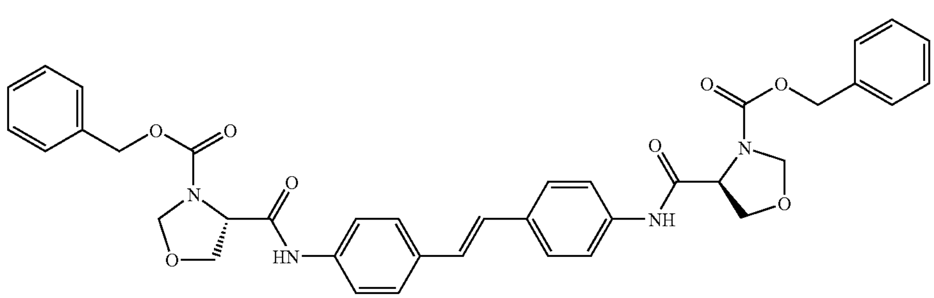 | 2.46/B | 677.2 |

-continued

| Example | Structure | HPLC (min/method*) | (M + H)+ |
|---|---|---|---|
| 12 | 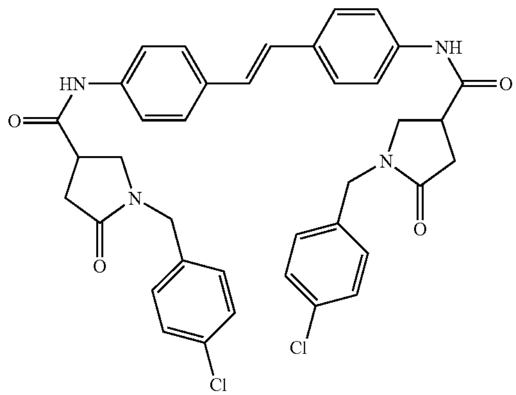 | 2.66/B | 681.2 |
| 13 | 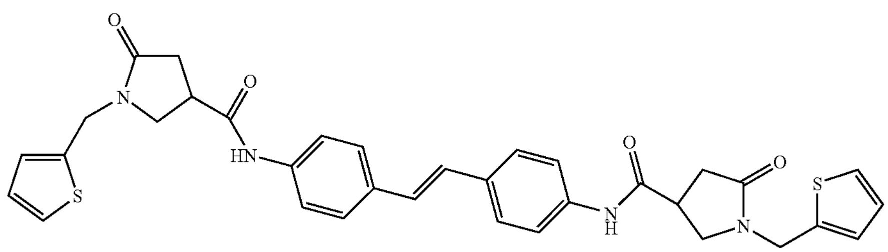 | 2.34/B | 625.3 |
| 14 | 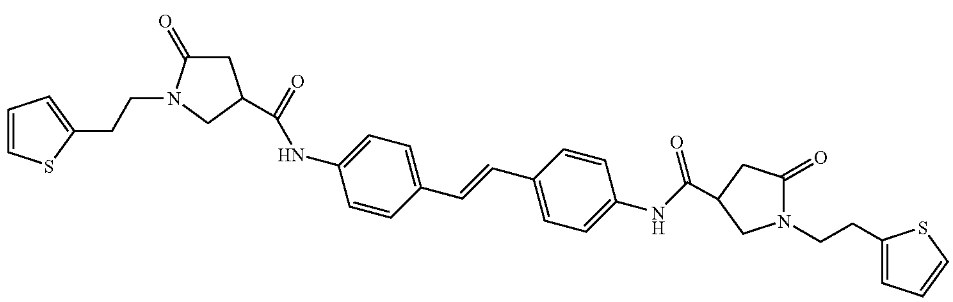 | 2.45/B | 653.2 |
| 15 | 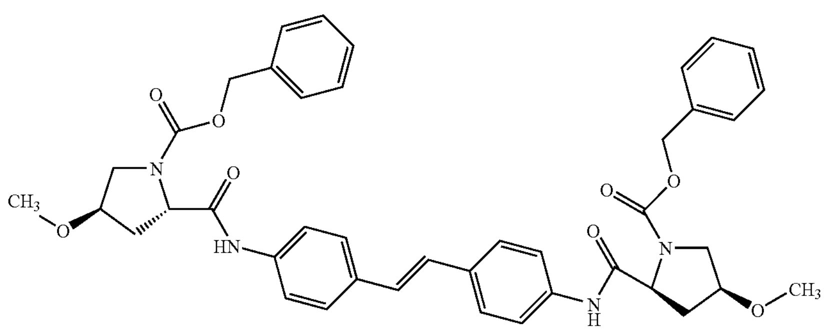 | 2.47/B | 733.5 |

-continued

| Example | Structure | HPLC (min/method*) | (M + H)+ |
|---|---|---|---|
| 16 | 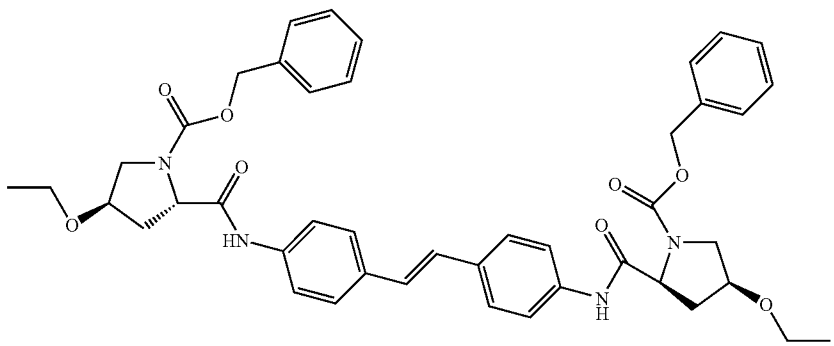 | 2.63/B | 761.5 |
| 17 | 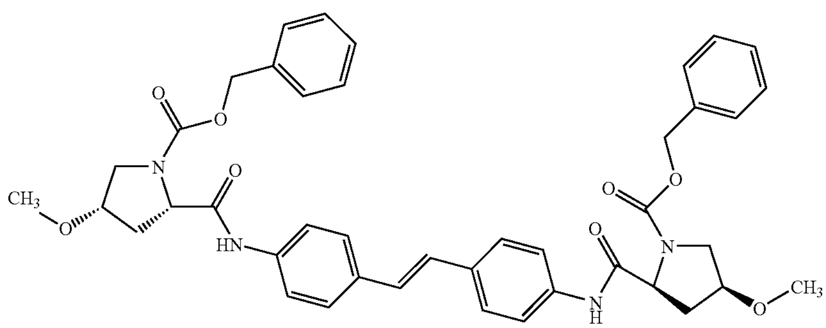 | 2.50/B | 733.5 |
| 18 | 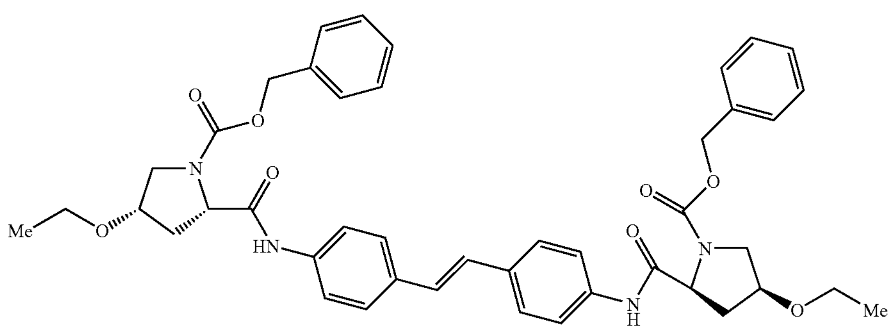 | 2.63/B | 761.5 |
| 19 | 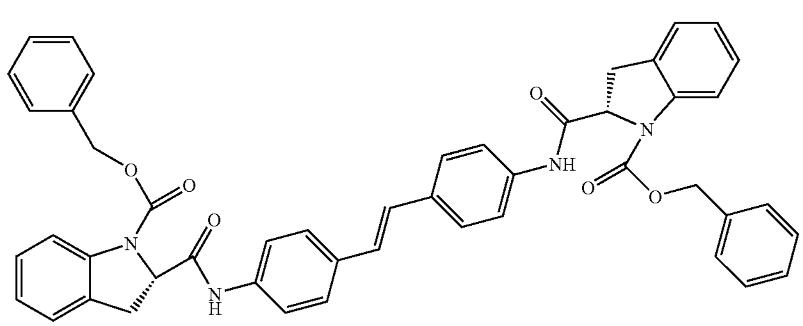 | 14.01/B | 769.3 |

| Example | Structure | HPLC (min/method*) | (M+H)+ |
|---|---|---|---|
| 20 | 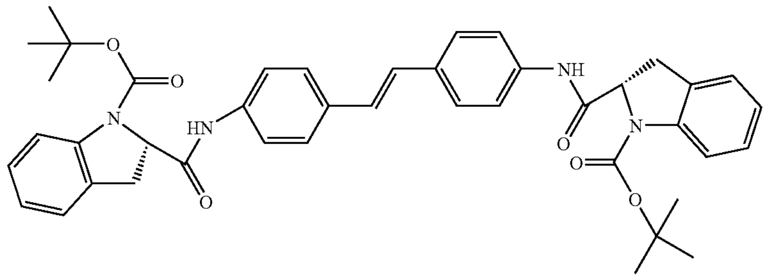 | 2.79/B | 701.3 |
| 21 | 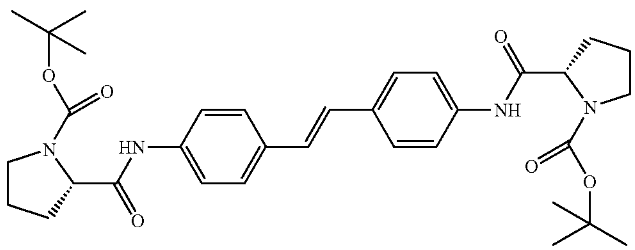 | 4.03/G | 605.41 |
| 22 | 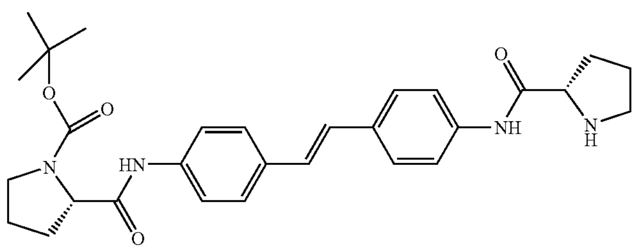 | 2.47/G | 505.31 |

Example 23A

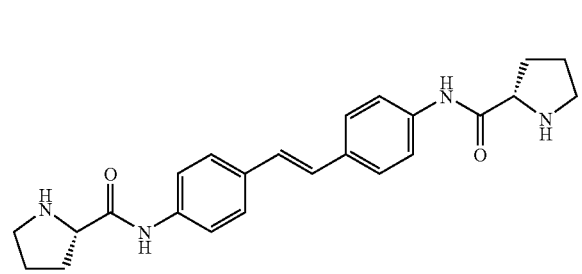

A suspension of Example 1 (21.6 g, 35.72 mmol) in dry dichloromethane (500 mL) was treated with trifluoroacetic acid (50 mL) at room temperature under nitrogen. The mixture was stirred for 3 hours before additional TFA (20 mL) was added. After stirring for an additional 4 hours at room temperature, the mixture was concentrated in vacuo. The residue was dissolved in ethyl acetate, washed with 1N sodium hydroxide solution and brine, and evaporated to ¼ of its original volume to provide the desired product (11.21 g, 77.6%) as a white solid: $^1$H NMR (DMSO-$d_6$, 500 MHz) δ 9.99 (s, 2H), 7.66 (d, J=8.5 Hz, 4H), 7.51 (d, J=8.5 Hz, 4H), 7.10 (s, 2H), 3.68 (dd, J=8.8, 6.0 Hz, 2H), 3.05 (br s, 2H), 2.89 (t, J=7.0 Hz, 4H), 2.07-2.01 (m, 2H), 1.80-1.75 (m, 2H), 1.68-1.64 (m, 4); LCMS ($R_t$=1.20 min, m/z 405.43).

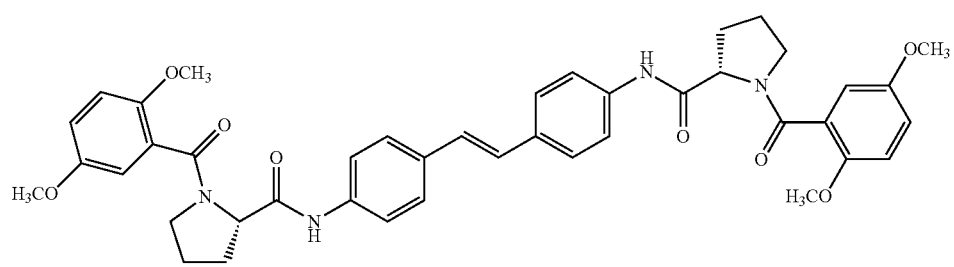

Example 23B

O-(7-Azabenzotriazol-1-yl)-N,N,N',N'-tetramethyluronium hexafluorophosphate (HATU, 108 mg, 0.28 mmol) was added in one portion to a solution of Example 23A (50 mg, 0.123 mmol), 2,5-dimethoxybenzoic acid (49.5 mg, 0.27 mmol) and diisopropylethylamine (80 µL, 0.49 mmol) in anhydrous DMF (1 mL). The mixture was stirred at room temperature for 3 hours before it was purified by reverse-phase preparative HPLC to provide the desired product (63.8 mg, 70.8%) as a white solid: $^1$H NMR (DMSO-d$_6$, 500 MHz) δ 10.08 and 9.63 (2s, 2H), 7.65-7.37 (series of m, 8H), 7.13 and 6.59 (series of m, 8H), 4.57-4.54 and 4.18-4.16 (2m, 2H 3.77 and 3.71 (2s, 6H), 3.73-3.48 (series of m, 8H), 3.36-3.22 (m, 2H), 2.29-2.17 (m, 2H), 2.01-1.75 (2m, 6H); LCMS (R$_t$=2.29 min, m/z 733.4).

Following the procedure described in Examples 23A and 23B and substituting the appropriate reagents, the following compounds were prepared. Unsymmetrical analogs were prepared in identical fashion to Example 23 except that 1.0 equivalent of each acid was used and the statistical mixture of products formed was separated by preparative HPLC.

| Example | Structure | HPLC (min/method*) | (M + H)$^+$ |
|---|---|---|---|
| 24 | 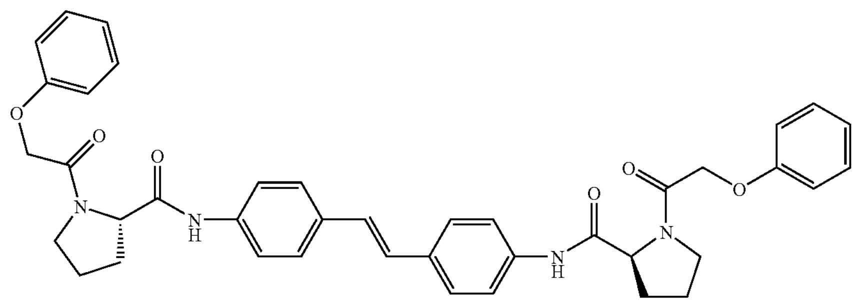 | 1.76/G | 697.34 |
| 25 | 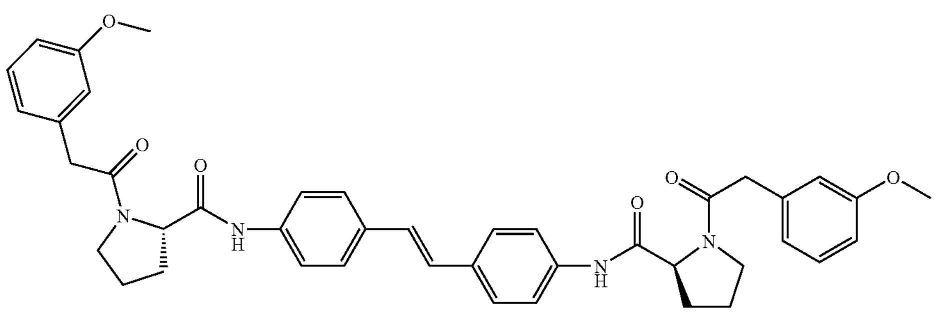 | 1.81/G | 723.39 |
| 26 | 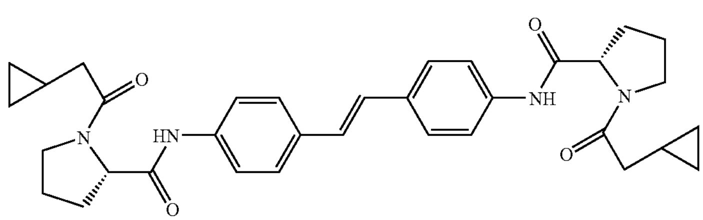 | 1.64/G | 569.32 |
| 27 | 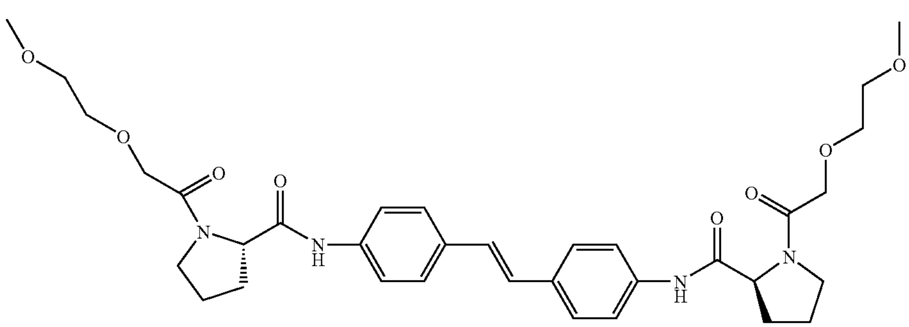 | 1.40/G | 637.34 |

-continued

| Example | Structure | HPLC (min/method*) | (M + H)+ |
|---|---|---|---|
| 28 | 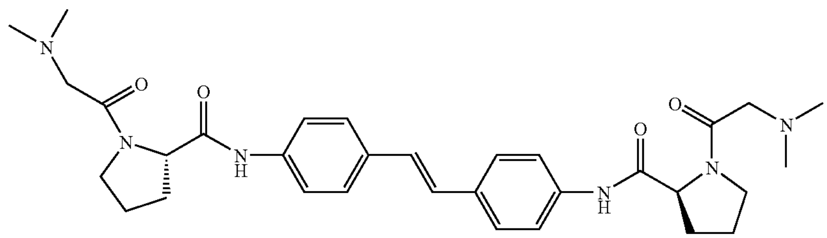 | 1.12/G | 575.34 |
| 29 | 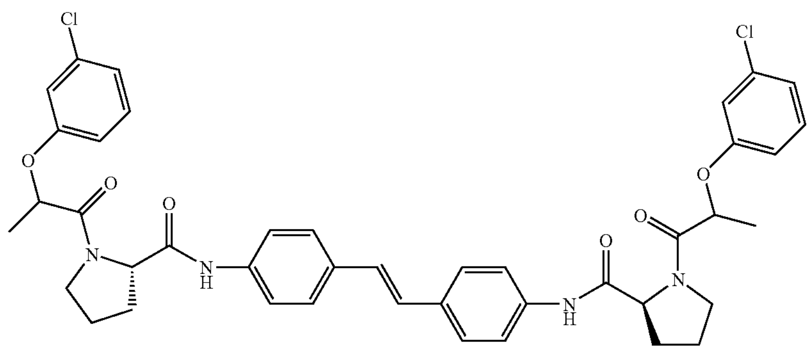 | 1.98/G | 769.23 |
| 30 | 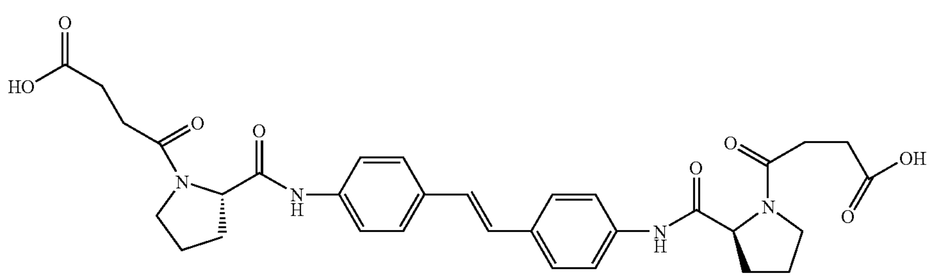 | 1.63/G | 627.24 |
| 31 | 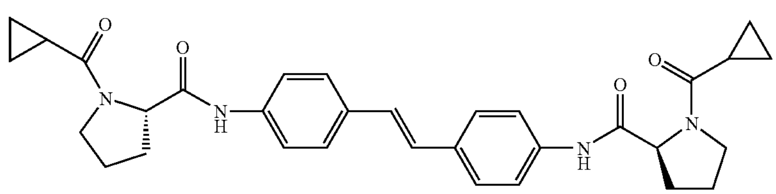 | 2.68/G | 541.26 |
| 32 | 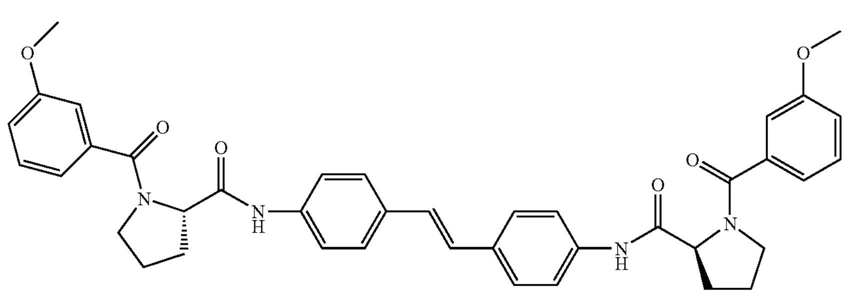 | 1.78/G | 695.27 |

-continued

| Example | Structure | HPLC (min/method*) | (M + H)+ |
|---|---|---|---|
| 33 | 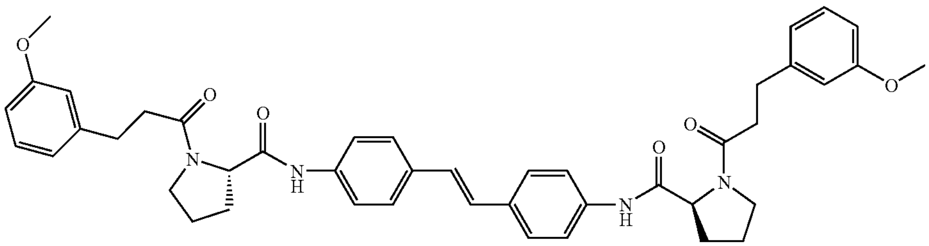 | 1.92/G | 729.28 |
| 34 | 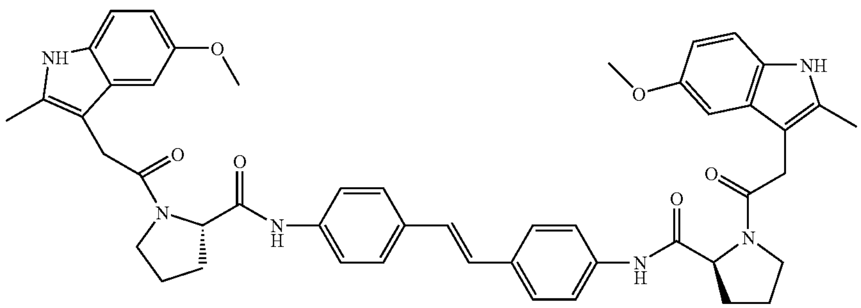 | 1.80/G | 807.36 |
| 35 | 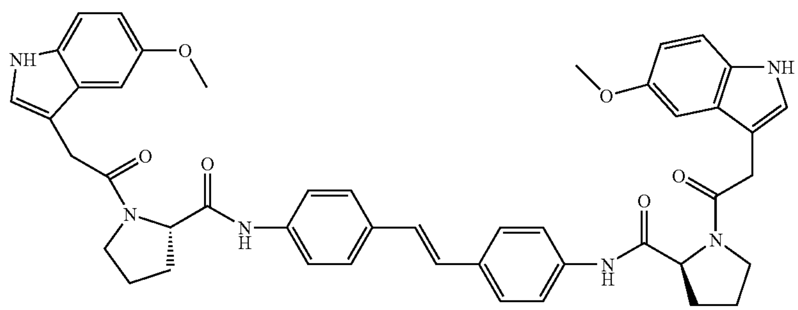 | 1.74/G | 779.35 |
| 36 | 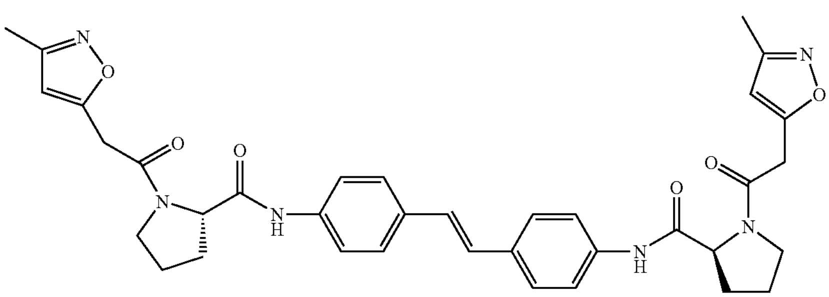 | 1.48/G | 651.24 |
| 37 | 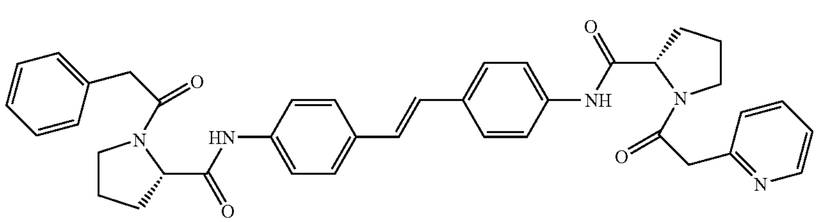 | 1.15/G | 643.28 |

-continued

| Example | Structure | HPLC (min/ method*) | (M + H)+ |
|---|---|---|---|
| 38 | 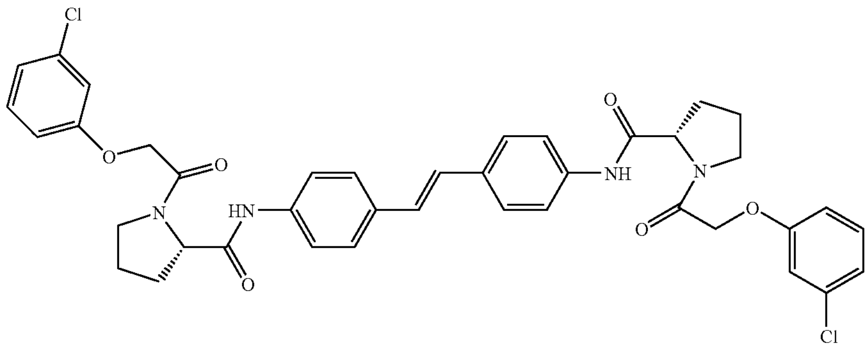 | 1.91/G | 763.14 |
| 39 | 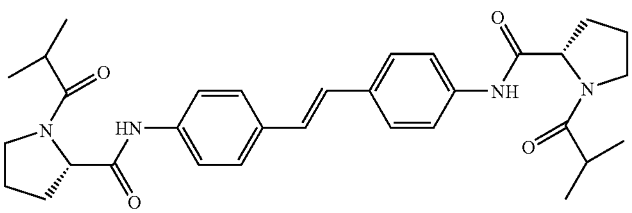 | 1.61/G | 567.33 |
| 40 | 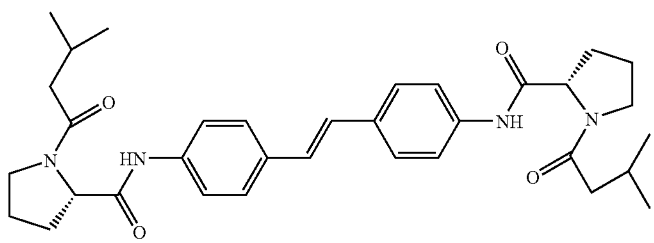 | 1.75/G | 573.39 |
| 41 | 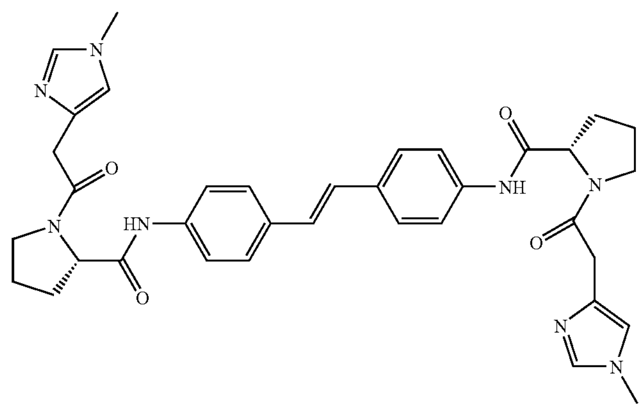 | 1.95/G | 649.37 |
| 42 | 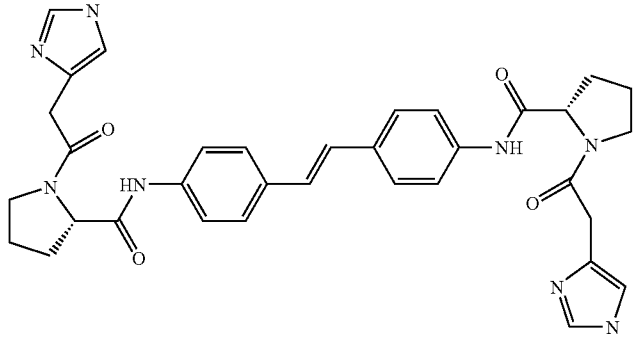 | 1.94/G | 621.30 |

-continued

| Example | Structure | HPLC (min/method*) | (M + H)+ |
|---|---|---|---|
| 43 | 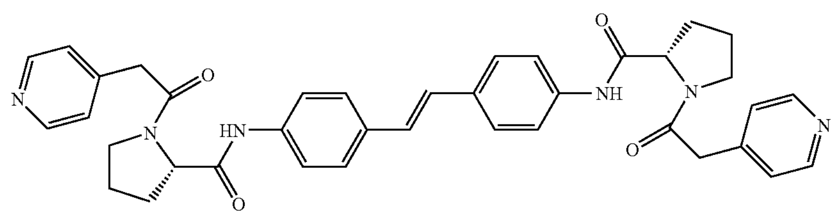 | 1.93/G | 643.35 |
| 44 | 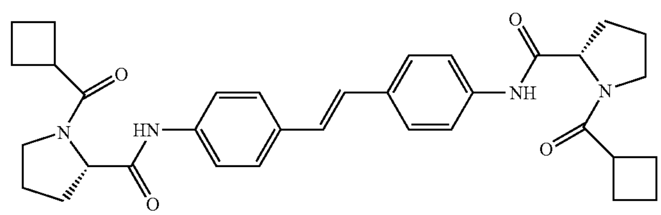 | 1.66/G | 569.34 |
| 45 | 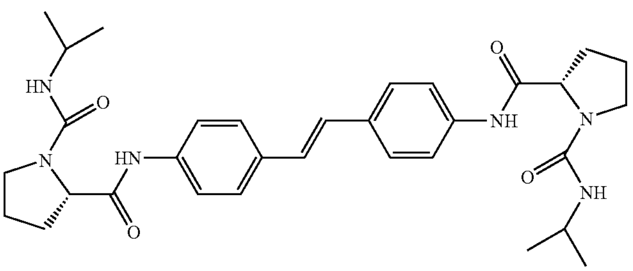 | 1.54/G | 575.36 |
| 46 | 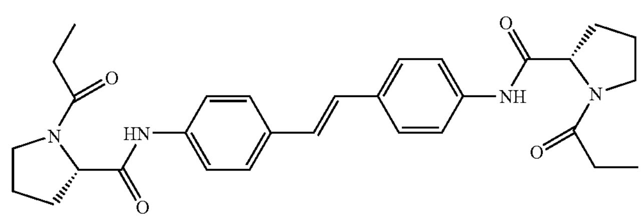 | 2.64/G | 517.28 |
| 47 | 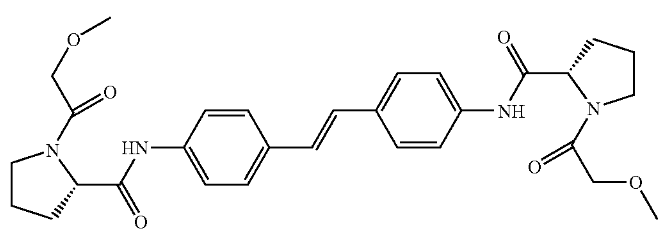 | 2.31/G | 549.28 |
| 48 | 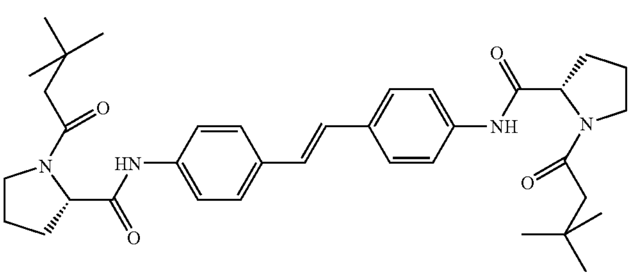 | 3.39/G | 601.39 |

-continued

| Example | Structure | HPLC (min/method*) | (M + H)+ |
|---|---|---|---|
| 49 | 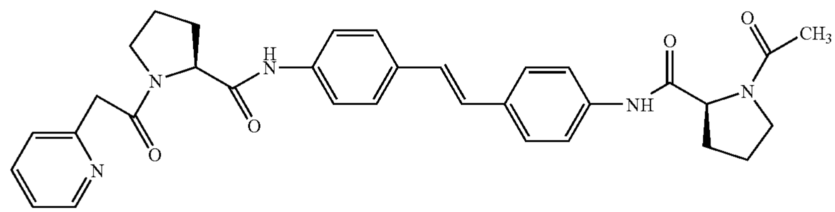 | 1.65/B | 566.3 |
| 50 | 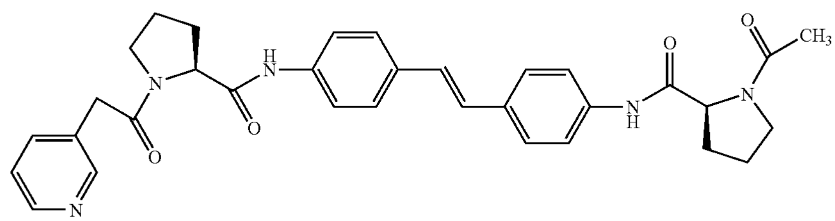 | 1.65/B | 566.3 |
| 51 | 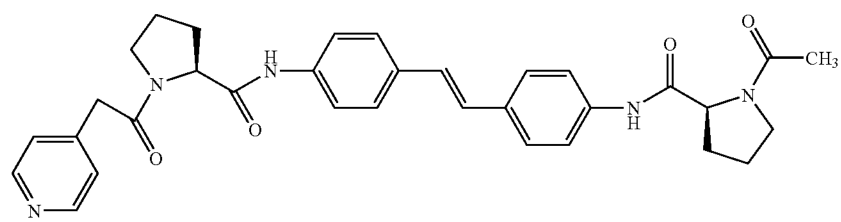 | 1.65/B | 566.3 |
| 52 | 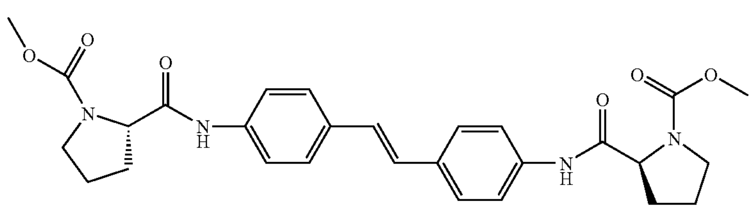 | 2.64/G | 521.23 |
| 53 | 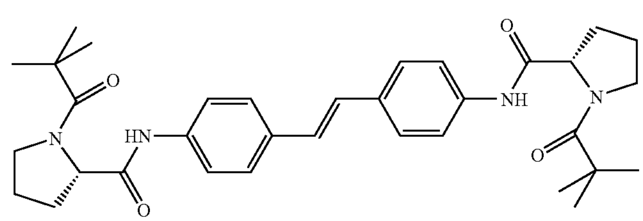 | 2.85/G | 573.26 |
| 54 | 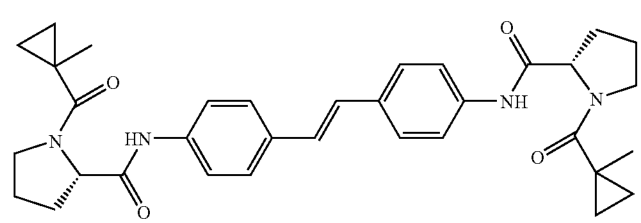 | 2.89/G | 581.30 |

-continued

| Example | Structure | HPLC (min/method*) | (M + H)+ |
|---|---|---|---|
| 55 | 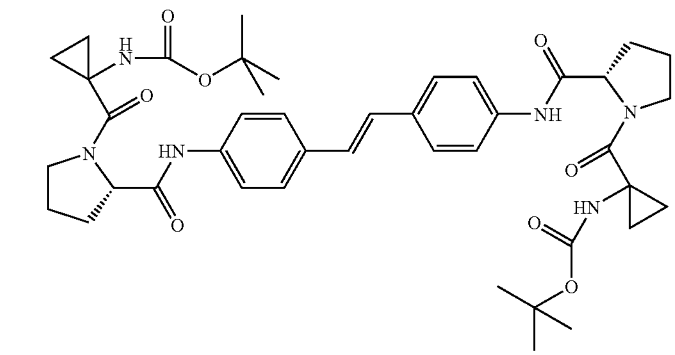 | 3.32/G | 793.55 |
| 56 | 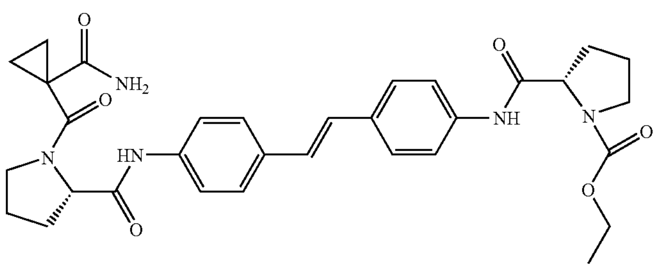 | 2.60/G | 588.33 |
| 57 | 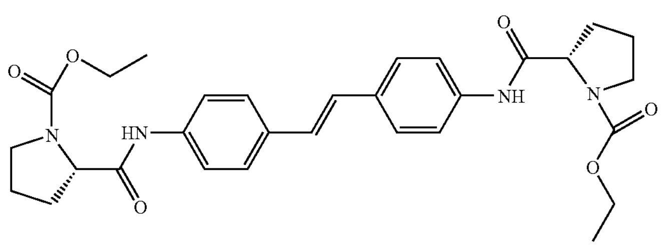 | 2.85/G | 571.31 |
| 58 | 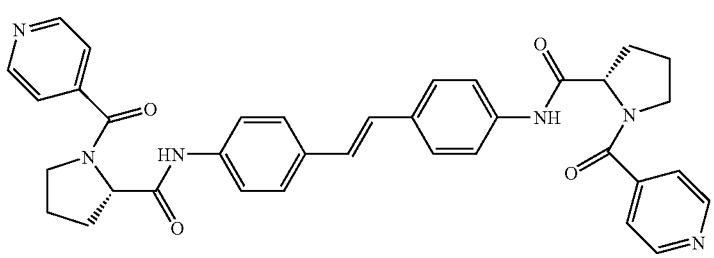 | 2.29/G | 616.31 |
| 59 | 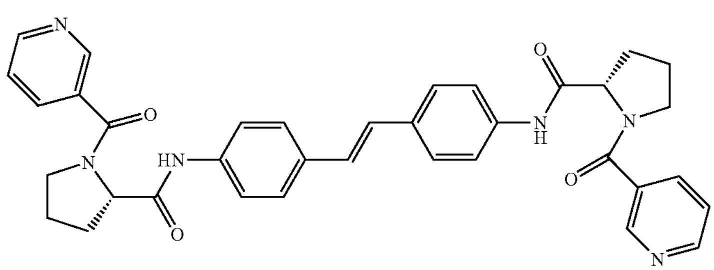 | 2.04/G | 615.33 |

-continued

| Example | Structure | HPLC (min/method*) | (M + H)+ |
|---|---|---|---|
| 60 | 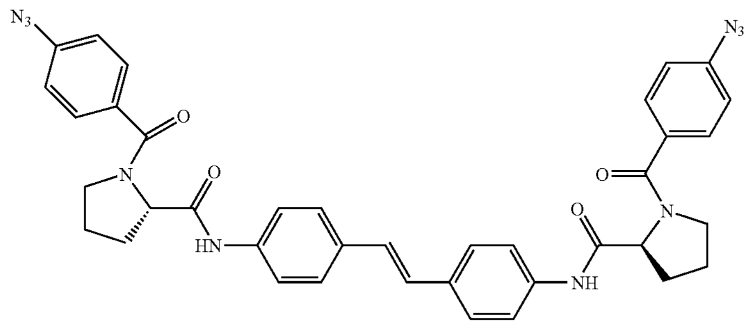 | 1.70/A | 695.3 |
| 61 | 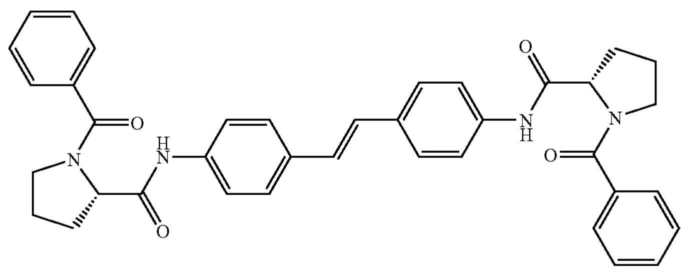 | 2.91/G | 635.32 |
| 62 | 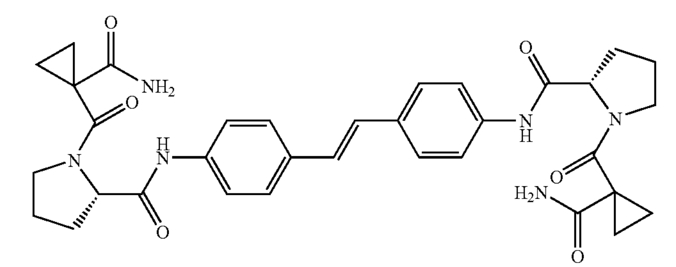 | 2.34/G | 627.35 |
| 63 | 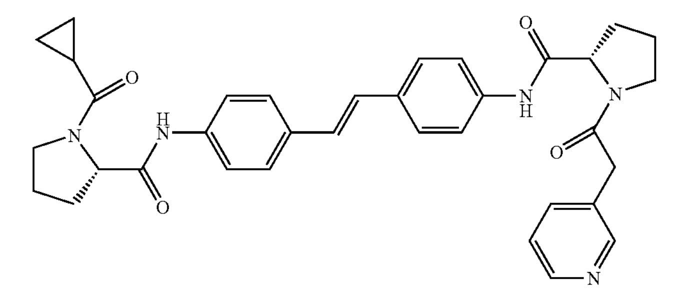 | 2.29/G | 592.32 |
| 64 | 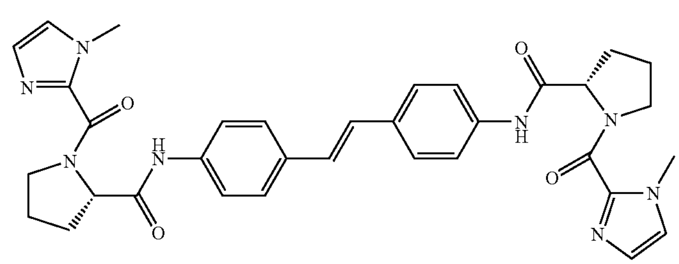 | 2.06/G | 621.33 |

-continued

| Example | Structure | HPLC (min/method*) | (M + H)+ |
|---|---|---|---|
| 65 | 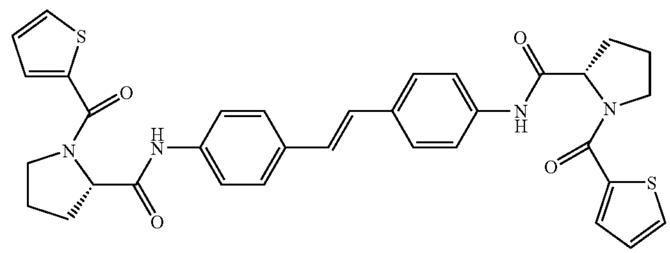 | 2.87/G | 649.26 |
| 66 | 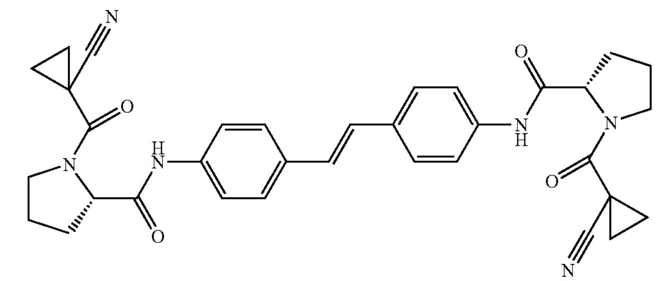 | 2.61/G | 591.34 |
| 67 | 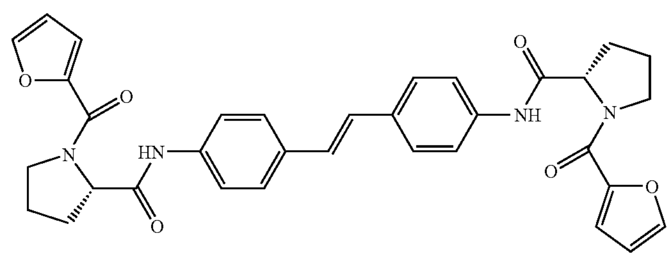 | 2.67/G | 593.32 |
| 68 | 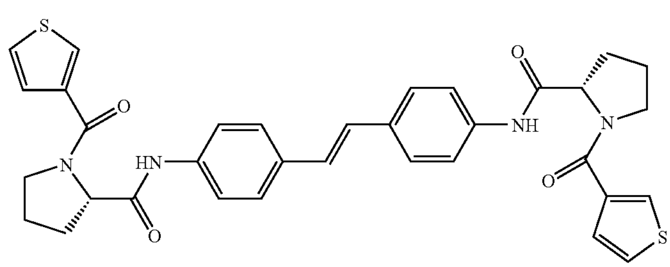 | 2.85/G | 647.26 |
| 69 | 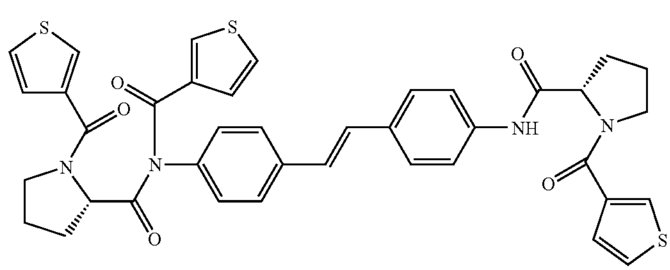 | 3.23/G | 743.23 |

-continued

| Example | Structure | HPLC (min/method*) | (M + H)+ |
|---|---|---|---|
| 70 | 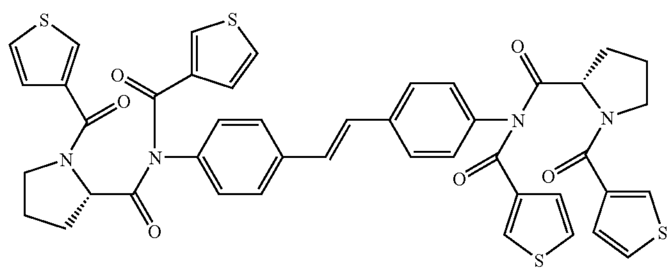 | 3.47/G | 847.30 |
| 71 | 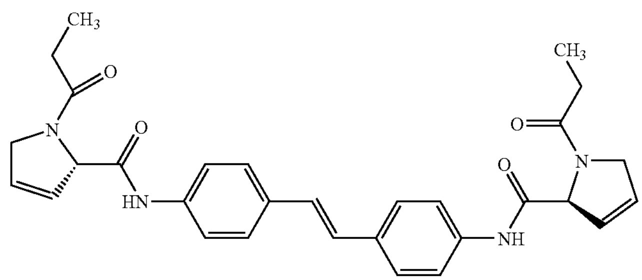 | 1.38/A | 513.2 |
| 72 | 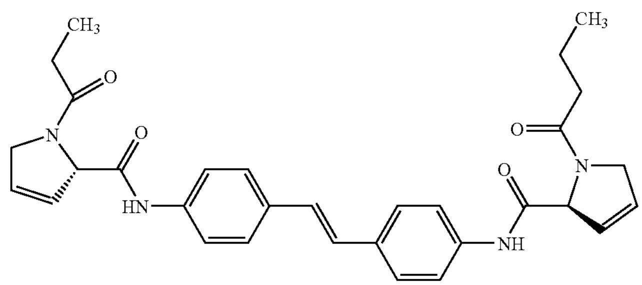 | 10.9/C | 541.3 |
| 73 | 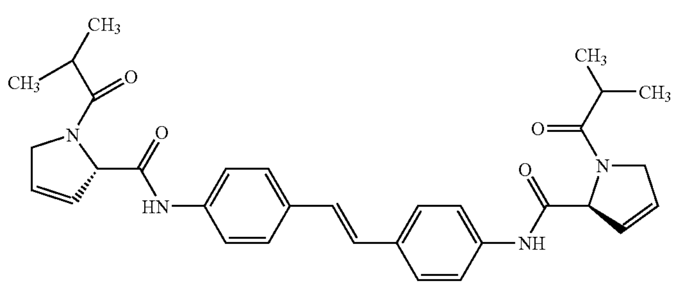 | 10.6/C | 541.3 |
| 74 | 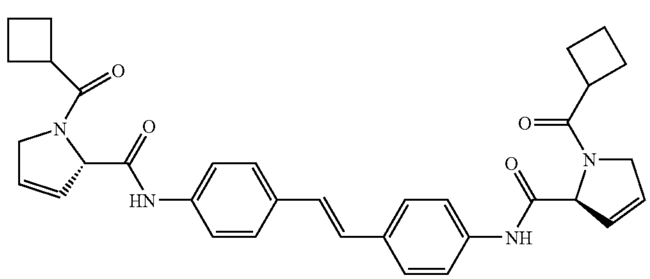 | 1.51/A | 565.2 |

| Example | Structure | HPLC (min/ method*) | (M + H)+ |
|---|---|---|---|
| 75 | 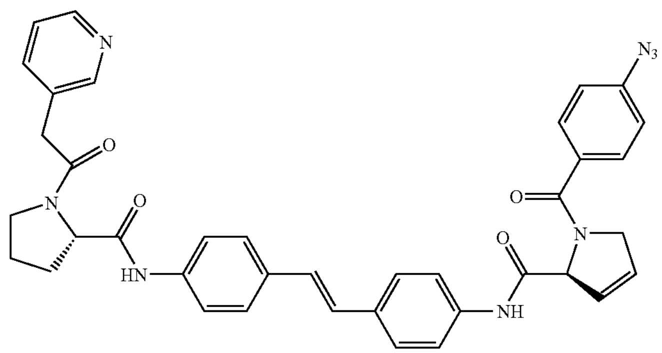 | 1.43/A | 669.2 |
| 76 | 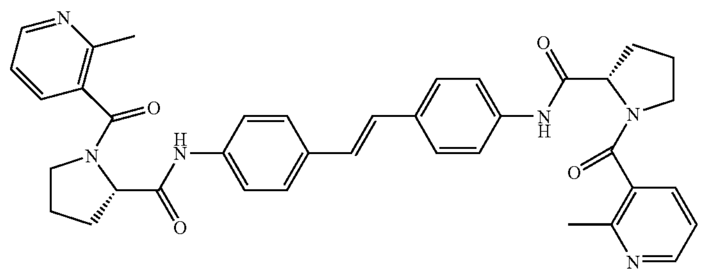 | 1.96/G | 644.28 |
| 77 | 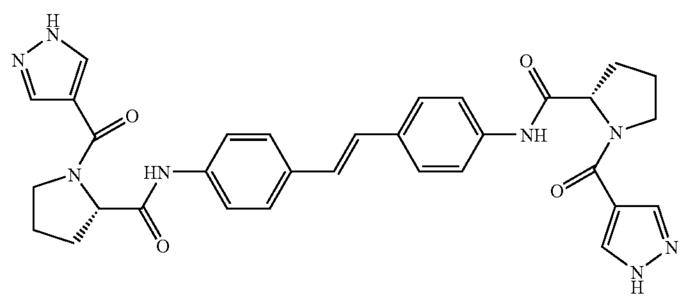 | 2.30/G | 615.24 |
| 78 | 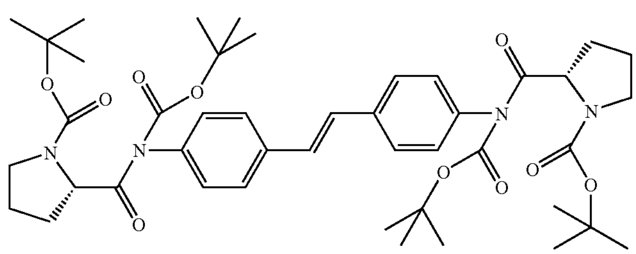 | 3.26/G | 807.81 |
| 79 | 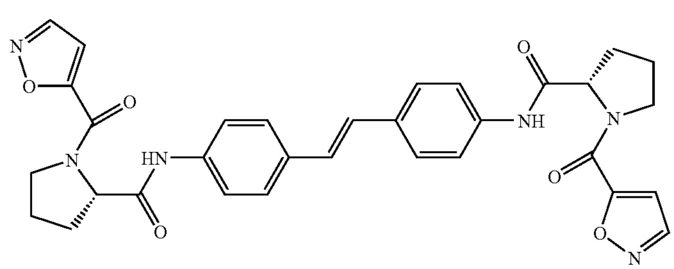 | 2.45/G | 595.19 |

| Example | Structure | HPLC (min/method*) | (M + H)+ |
|---|---|---|---|
| 80 | 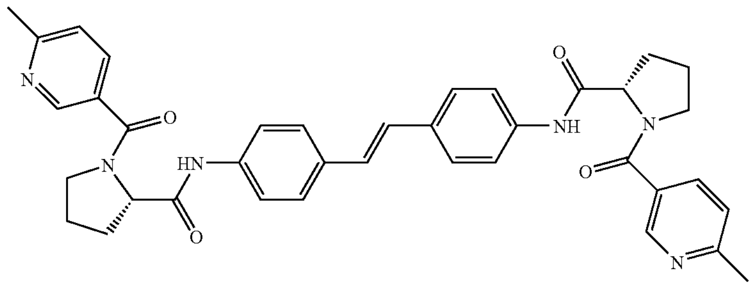 | 1.92/G | 643.37 |
| 81 | 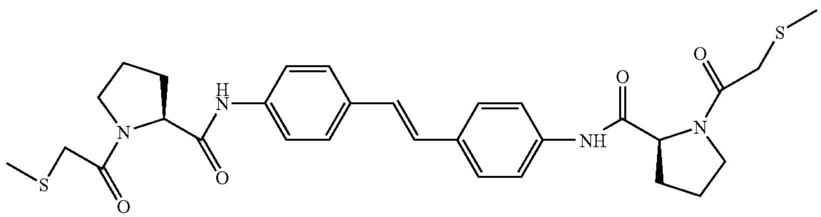 | 2.08/B | 581.2 |
| 82 | 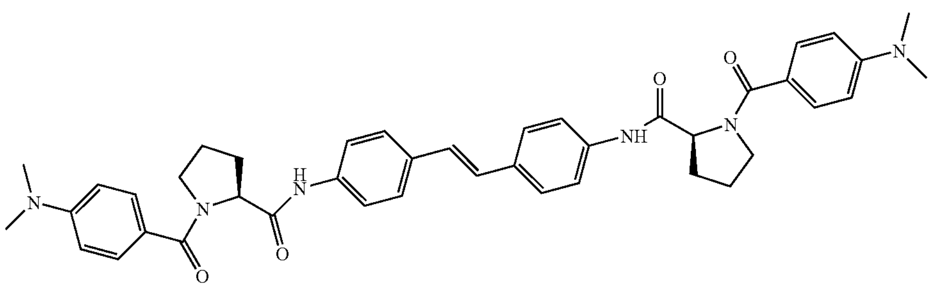 | 1.97/B | 699.5 |
| 83 | 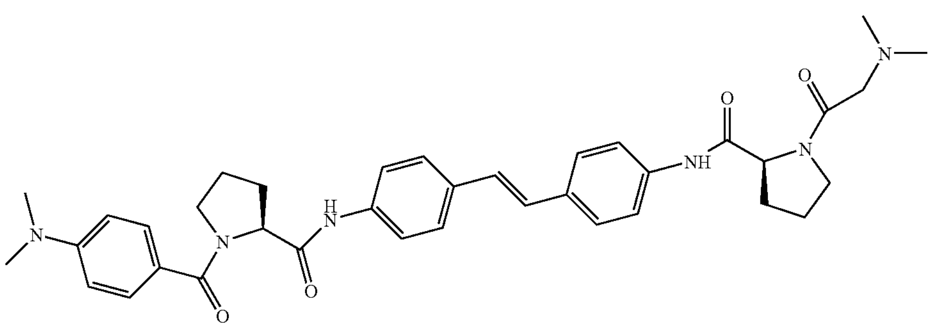 | 1.68/B | 637.4 |
| 84 | 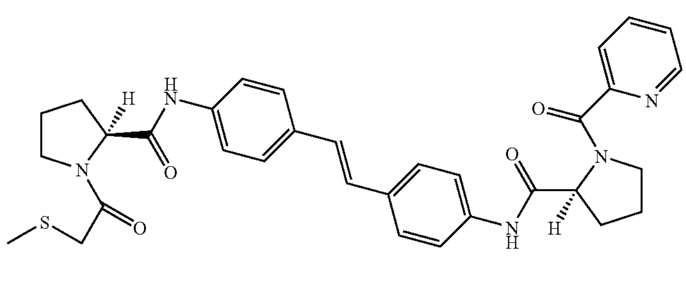 | 2.01/B | 598.2 |

-continued

| Example | Structure | HPLC (min/method*) | (M + H)+ |
|---|---|---|---|
| 85 | 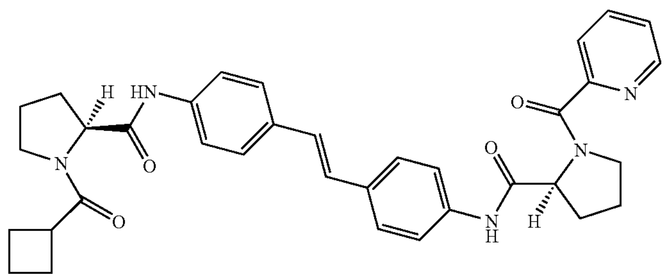 | 2.09/B | 592.3 |
| 86 | 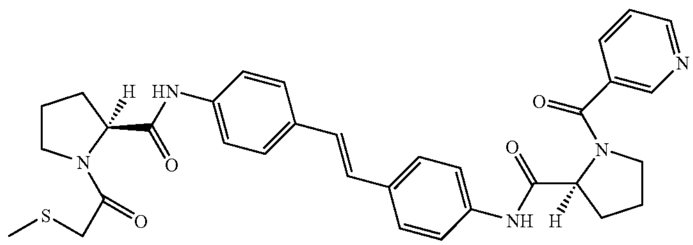 | 1.84/B | 598.2 |
| 87 | 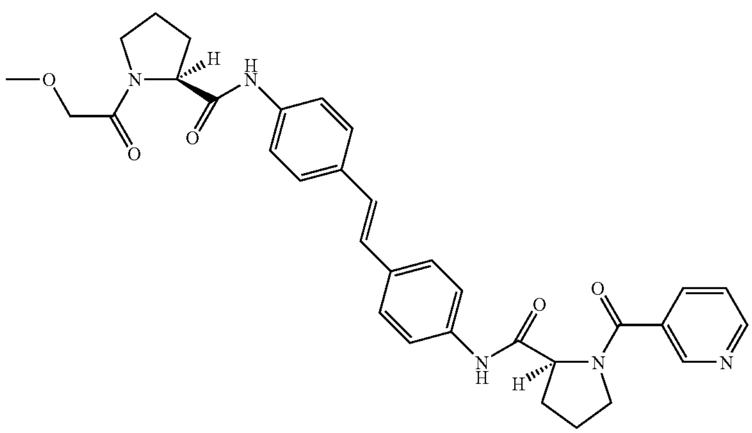 | 1.71/B | 582.3 |
| 88 | 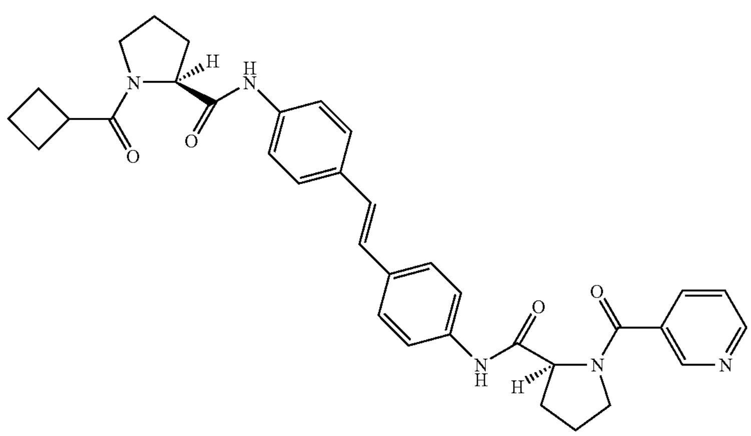 | 1.93/B | 592.3 |

-continued

| Example | Structure | HPLC (min/method*) | (M + H)+ |
|---|---|---|---|
| 89 | 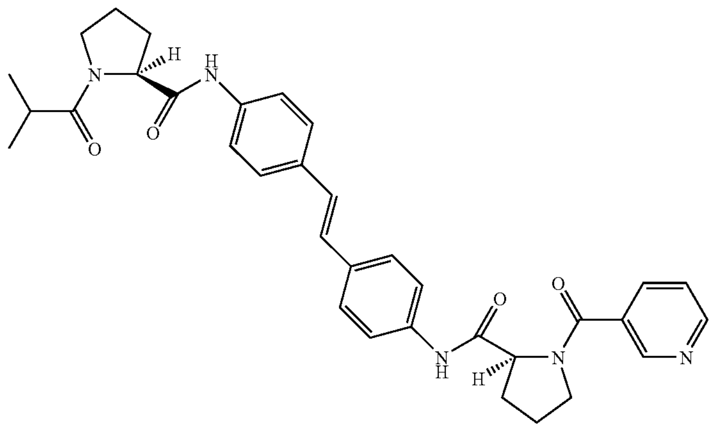 | 1.86/B | 580.3 |
| 90 | 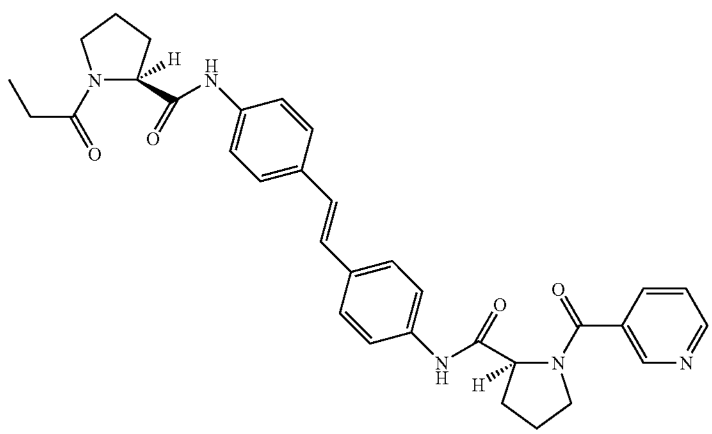 | 1.78/B | 566.3 |
| 91 | 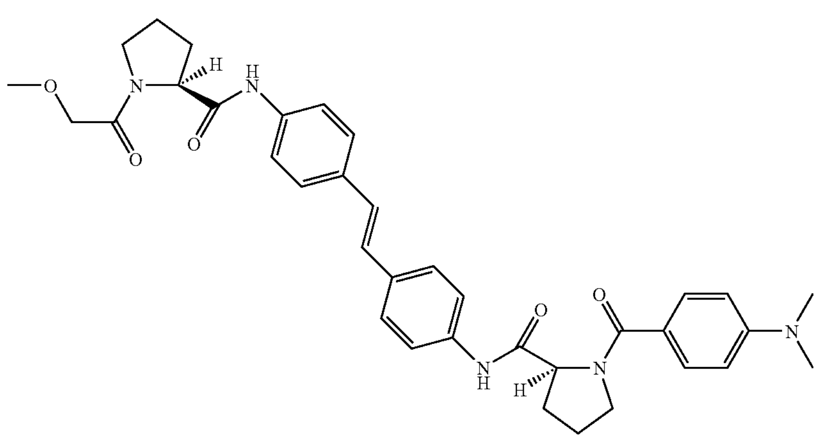 | 1.85/B | 624.3 |

-continued

| Example | Structure | HPLC (min/ method*) | (M + H)+ |
|---|---|---|---|
| 92 | 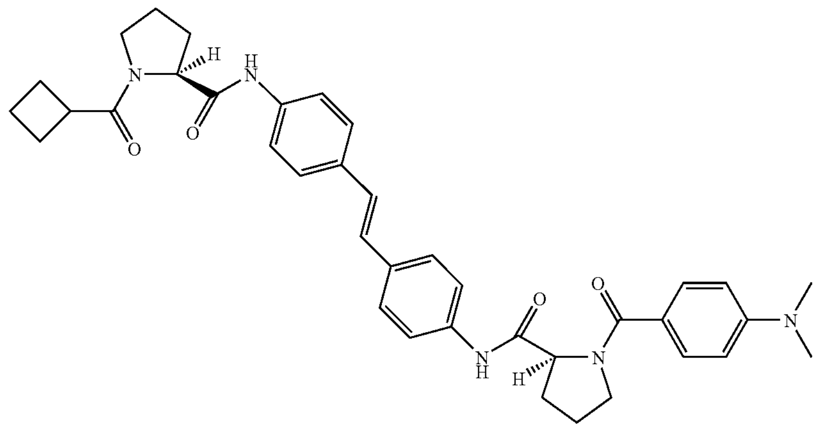 | 2.11/B | 634.4 |
| 93 | 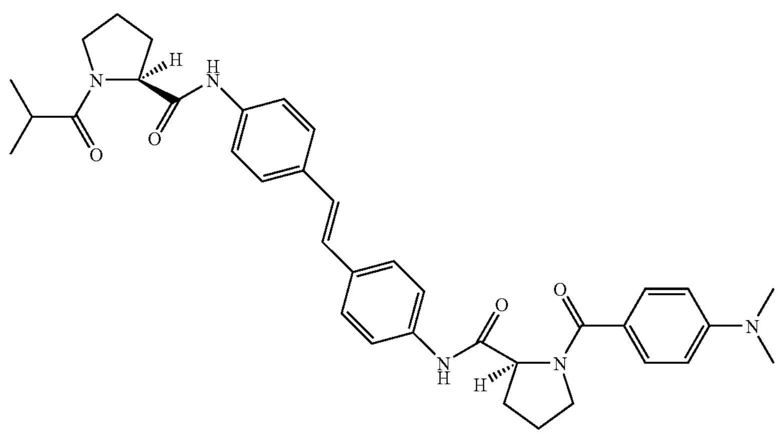 | 2.00/B | 622.4 |
| 94 | 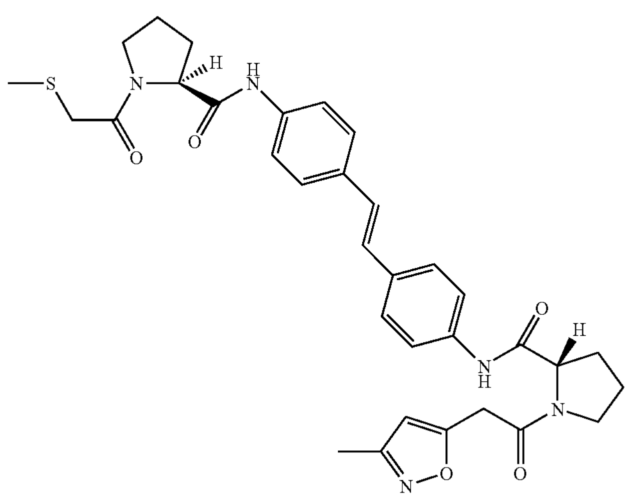 | 1.99/B | 616.3 |

| Example | Structure | HPLC (min/method*) | (M + H)+ |
|---|---|---|---|
| 95 | 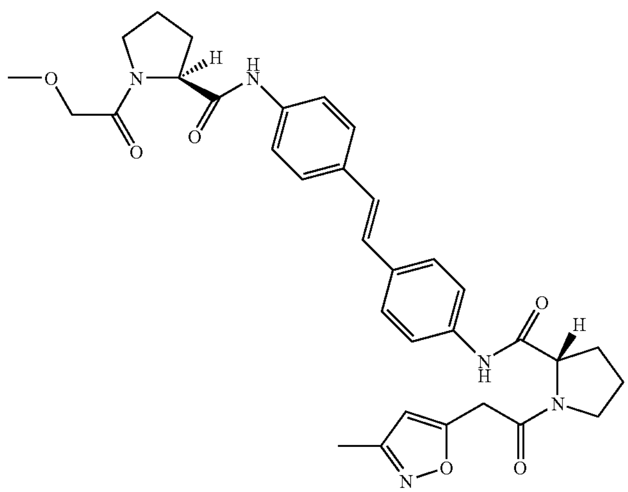 | 1.87/B | 600.3 |
| 96 | 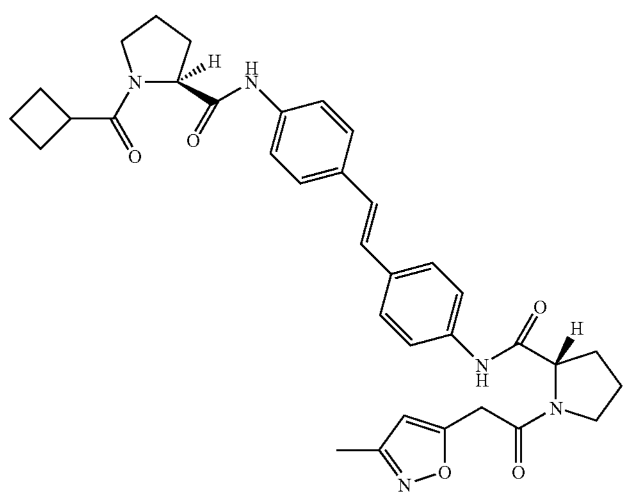 | 2.09/B | 610.3 |
| 97 | 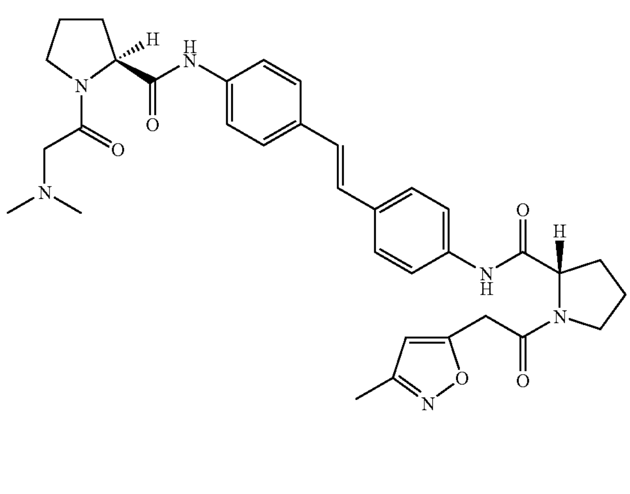 | 1.69/B | 613.4 |

| Example | Structure | HPLC (min/method*) | (M + H)+ |
|---|---|---|---|
| 98 | 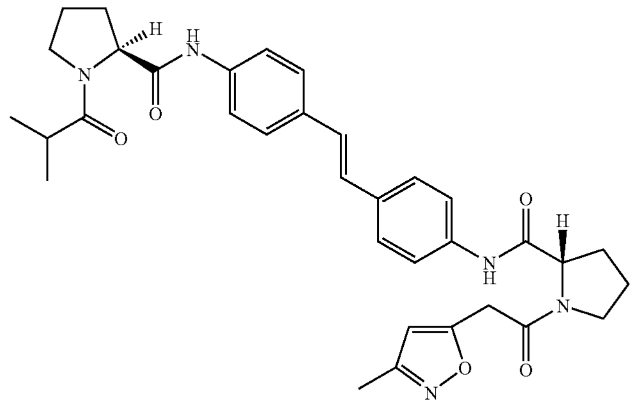 | 2.06/B | 598.3 |
| 99 | 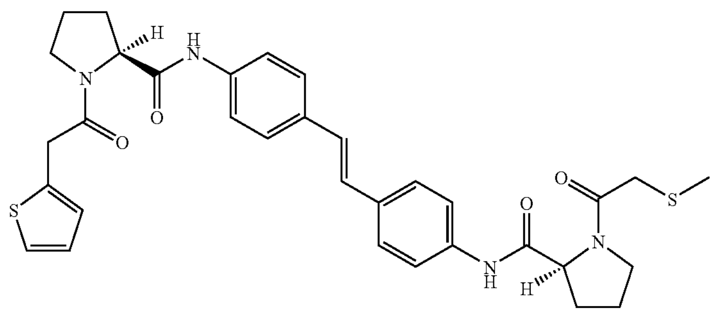 | 2.17/B | 617.3 |
| 100 | 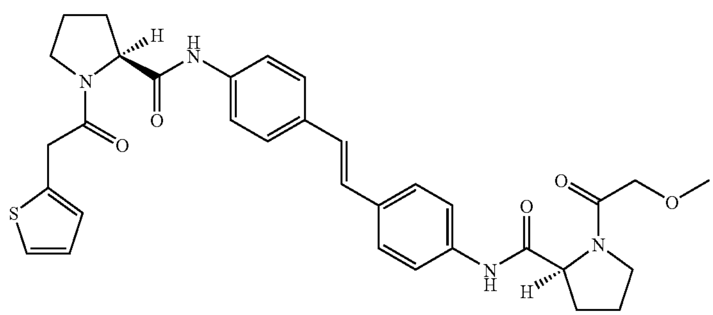 | 2.05/B | 601.3 |
| 101 | 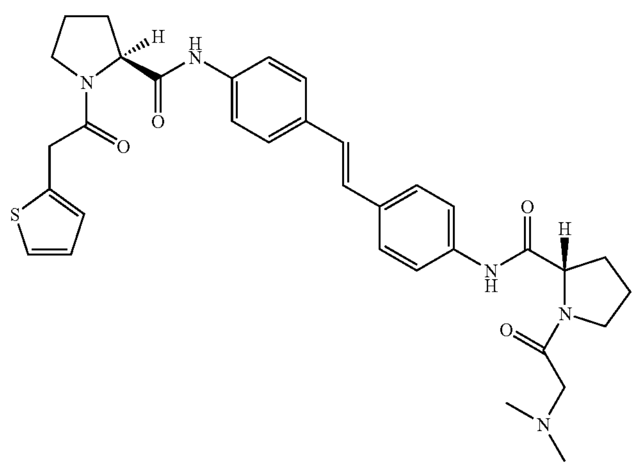 | 1.86/B | 614.3 |

-continued
| Example | Structure | HPLC (min/method*) | (M + H)+ |
|---|---|---|---|
| 102 | 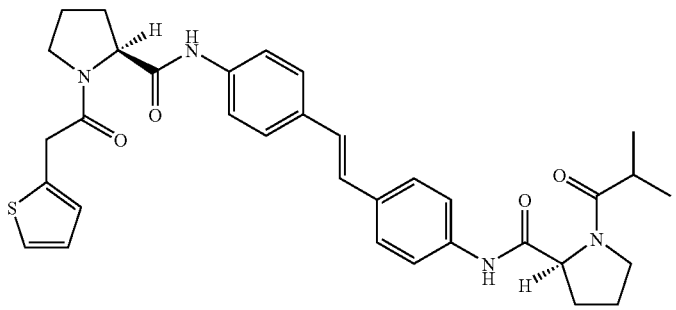 | 2.21/B | 599.3 |
| 103 | 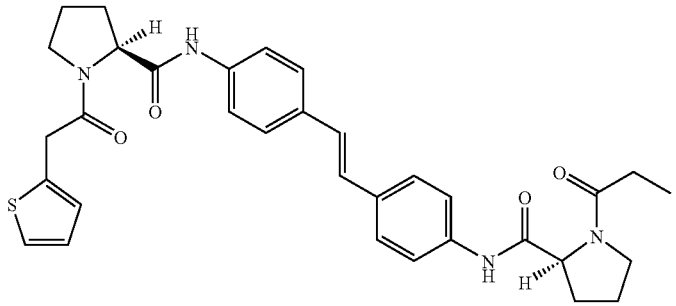 | 2.14/B | 585.3 |
| 104 | 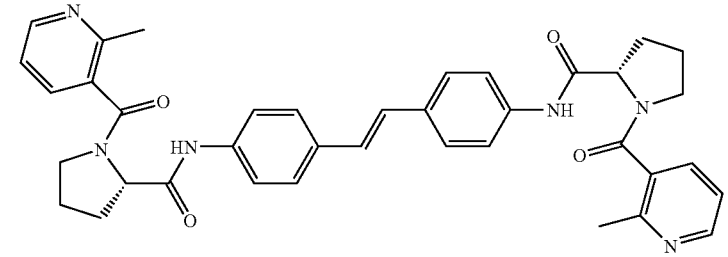 | 1.99/G | 644.21 |
| 105 | 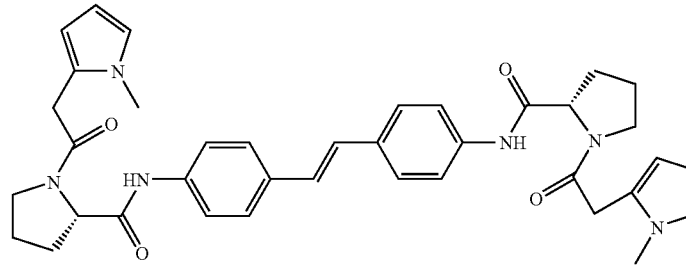 | 4.16/G | 647.98 |
| 106 | 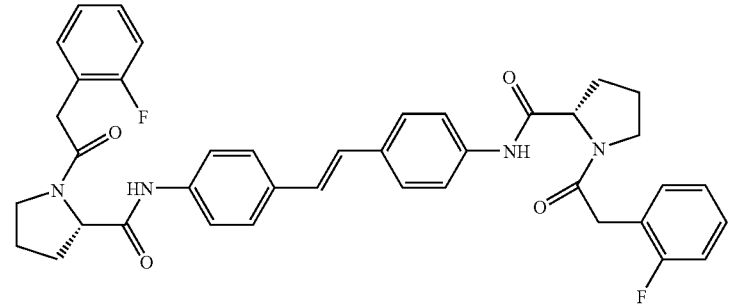 | 3.23/G | 677.25 |

| Example | Structure | HPLC (min/method*) | (M + H)+ |
|---|---|---|---|
| 107 | 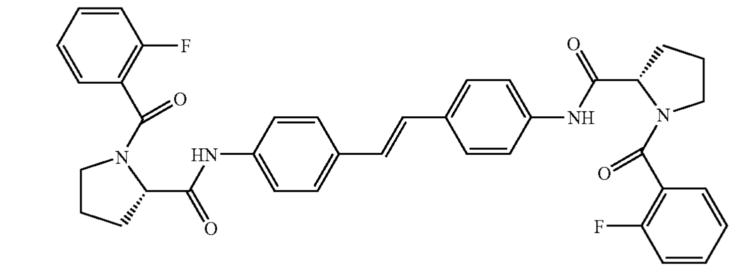 | 2.91/G | 649.21 |
| 108 | 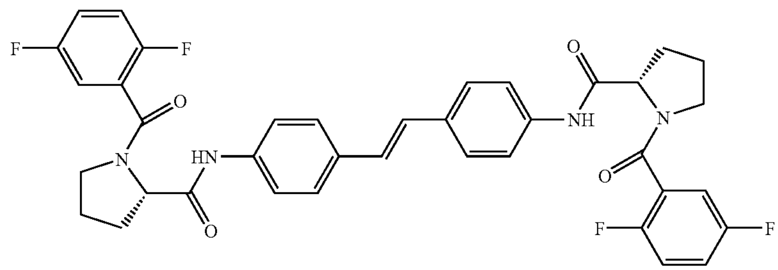 | 3.02/G | 685.19 |
| 109 | 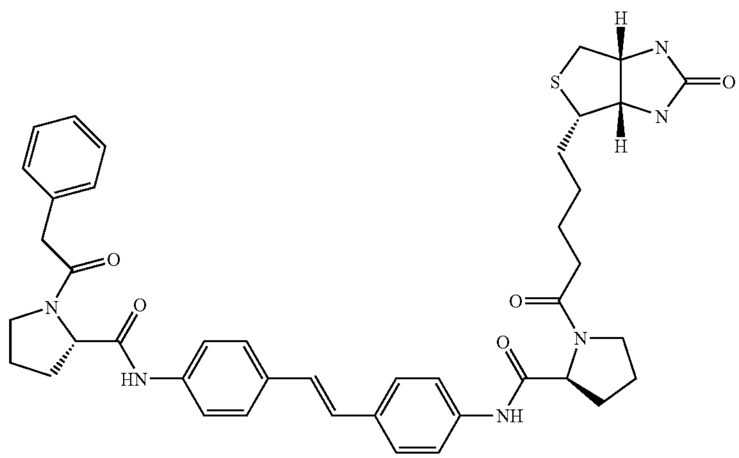 | 1.60/A | 749.3 |
| 110 | 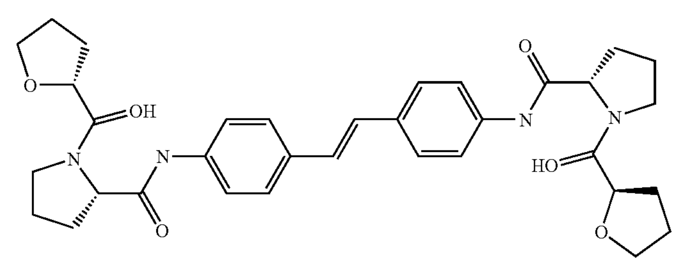 | 2.51/G | 601.38 |
| 111 | 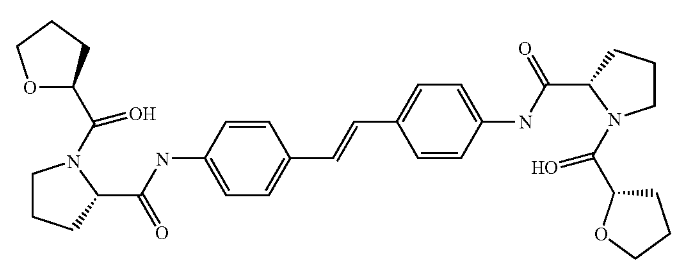 | 2.59/G | 623.36 |

| Example | Structure | HPLC (min/method*) | (M + H)+ |
|---|---|---|---|
| 112 | 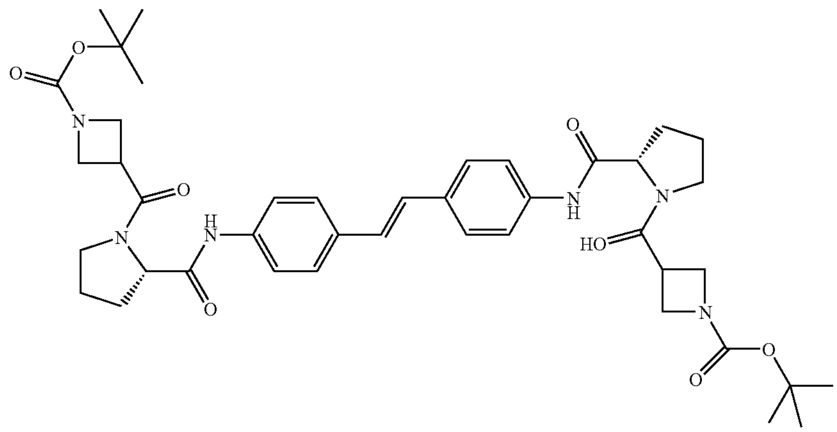 | 3.24/G | 793.33 |
| 113 | 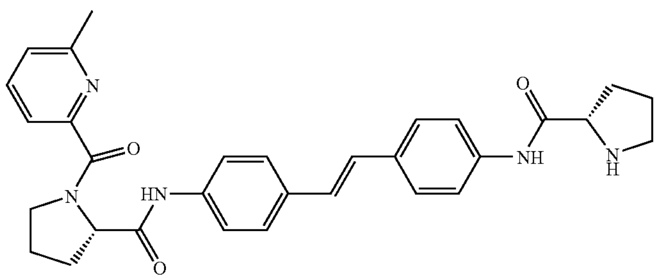 | 2.13/G | 524.41 |
| 114 | 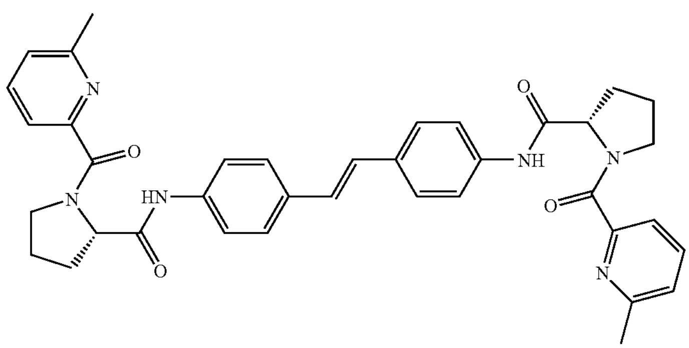 | 2.64/G | 643.39 |
| 115 | 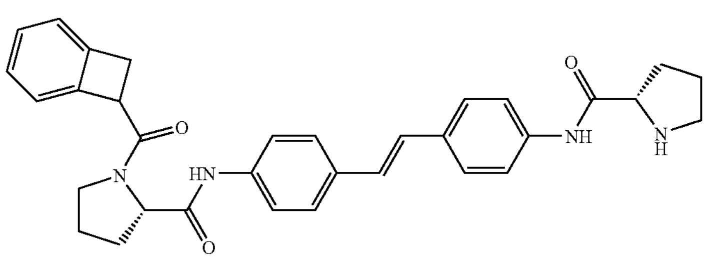 | 2.51/G | 535.48 |

-continued

| Example | Structure | HPLC (min/method*) | (M + H)+ |
|---|---|---|---|
| 116 | 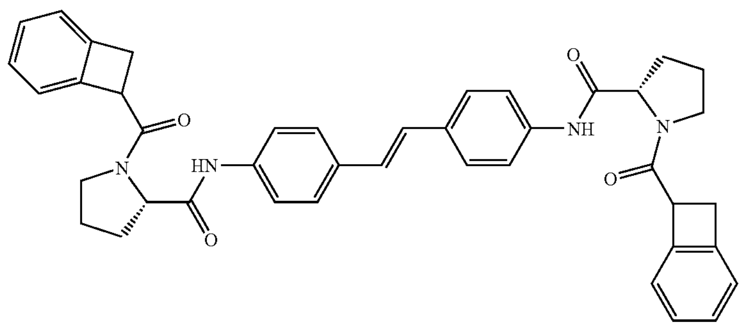 | 3.38/G | 665.36 |
| 117 | 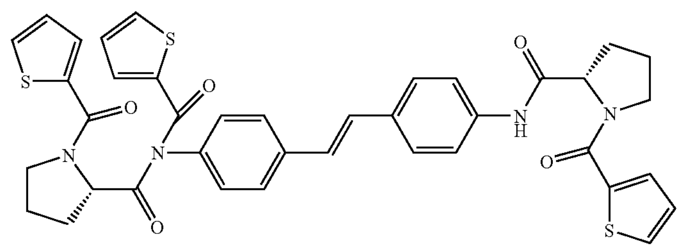 | 3.22/G | 757.27 |
| 118 | 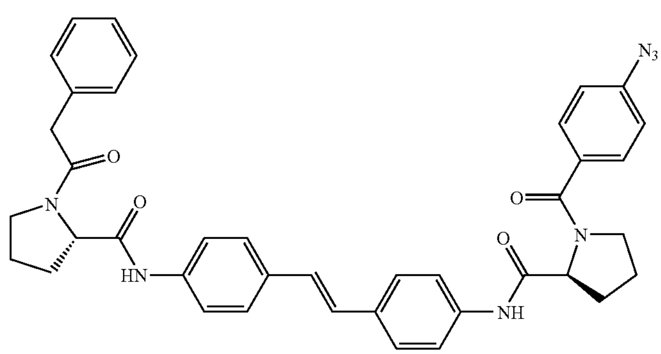 | 1.70/A | 668.2 |
| 119 | 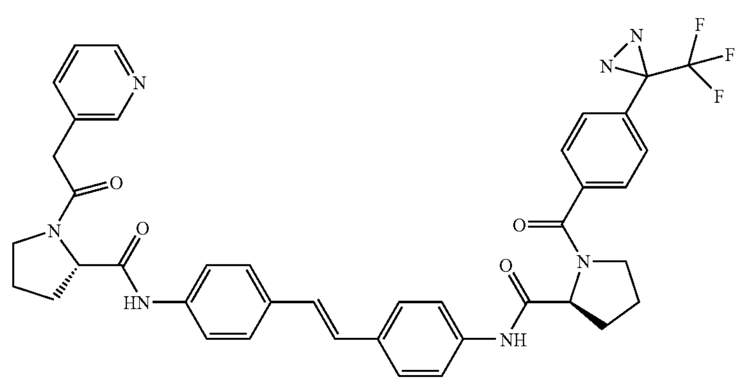 | 1.55/A | 736.2 |

| Example | Structure | HPLC (min/method*) | (M + H)+ |
|---|---|---|---|
| 120 | 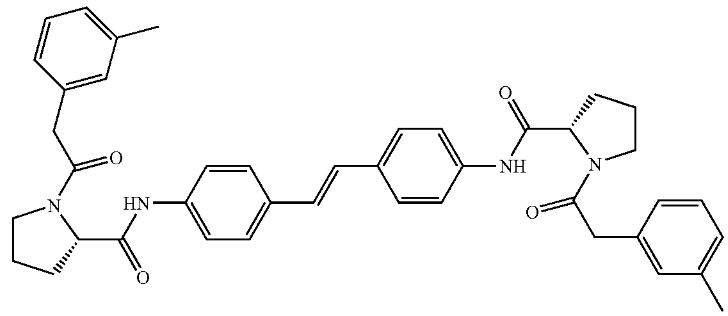 | 3.44/G | 668.46 |
| 121 | 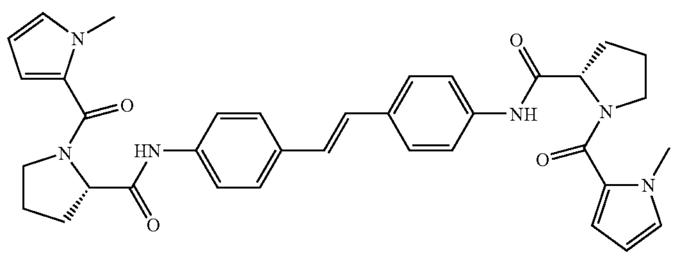 | 2.93/G | 641.43 |
| 122 | 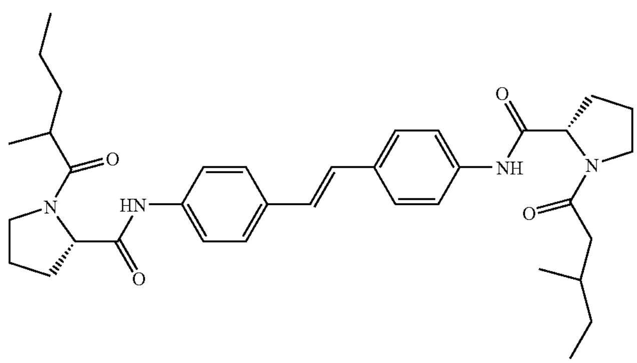 | 3.40/G | 600.49 |
| 123 | 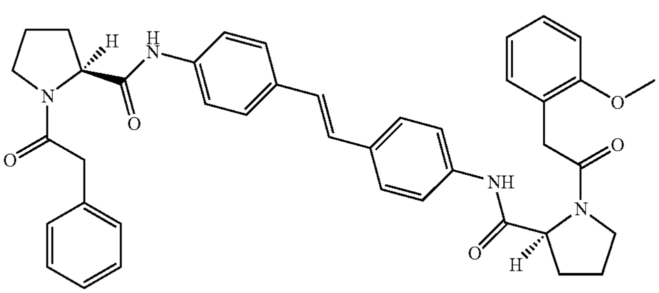 | 3.13/G | 701.00 |
| 124 | 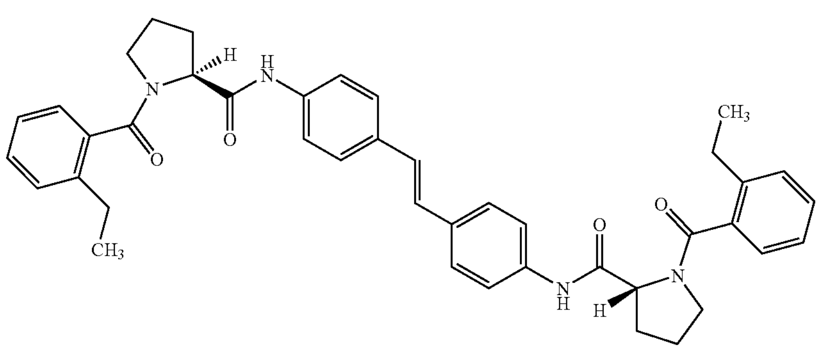 | 2.63/B | 669.3 |

-continued

| Example | Structure | HPLC (min/method*) | (M + H)+ |
|---|---|---|---|
| 125 | 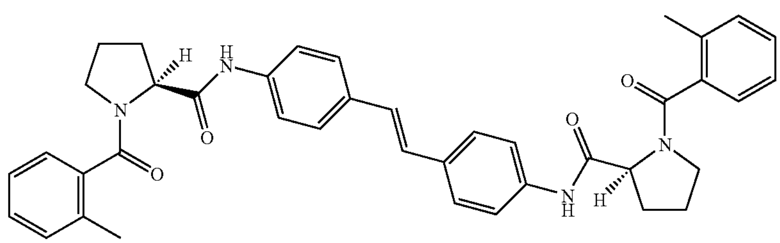 | 3.19/G | 641.00 |
| 126 | 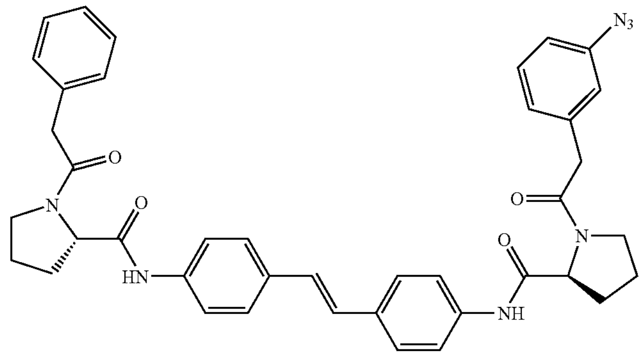 | 1.76/A | 682.2 |
| 127 | 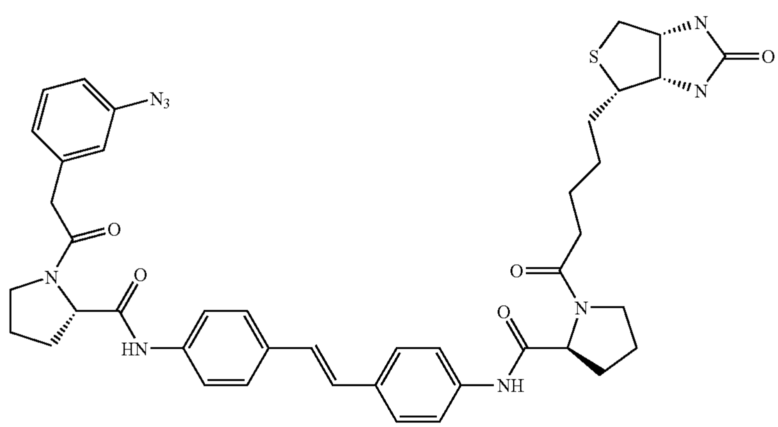 | 10.57/C | 790.3 |
| 128 | 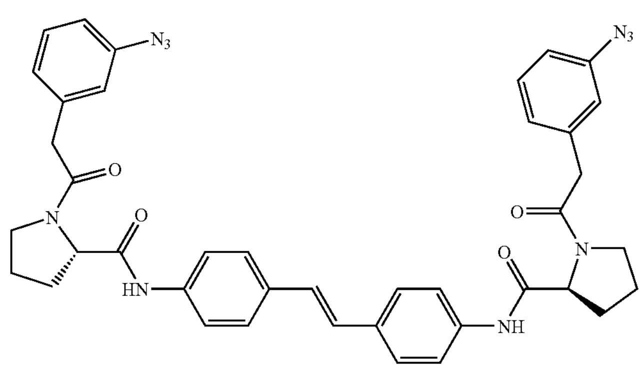 | 14.38/C | 723.3 |

-continued

| Example | Structure | HPLC (min/method*) | (M + H)+ |
|---|---|---|---|
| 129 | 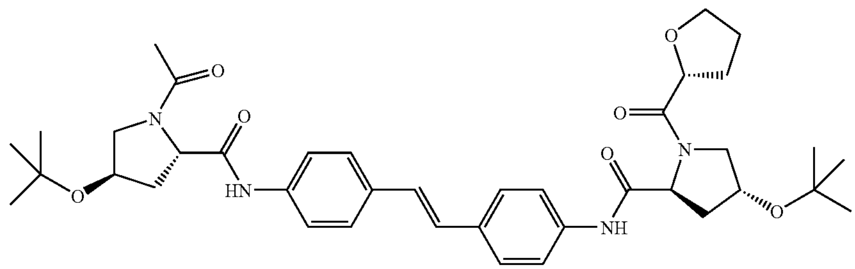 | 10.7/D | 689.5 |
| 130 | 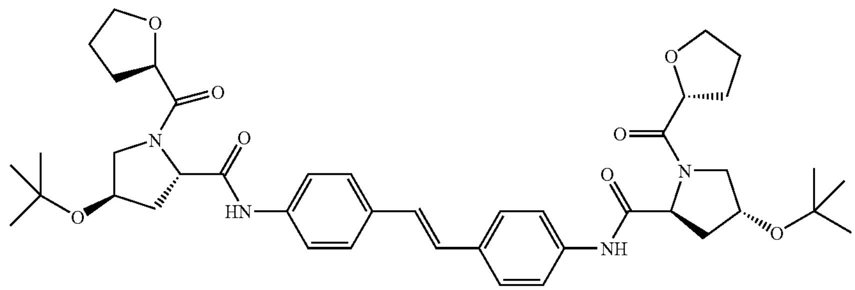 | 1.75/A | 745.4 |
| 131 | 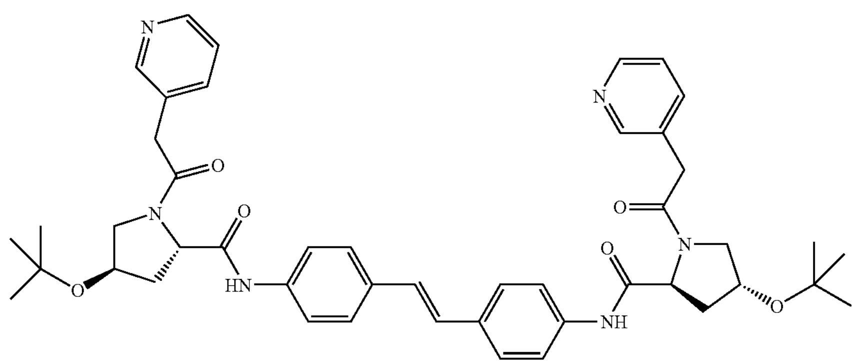 | 1.61/A | 787.3 |
| 132 | 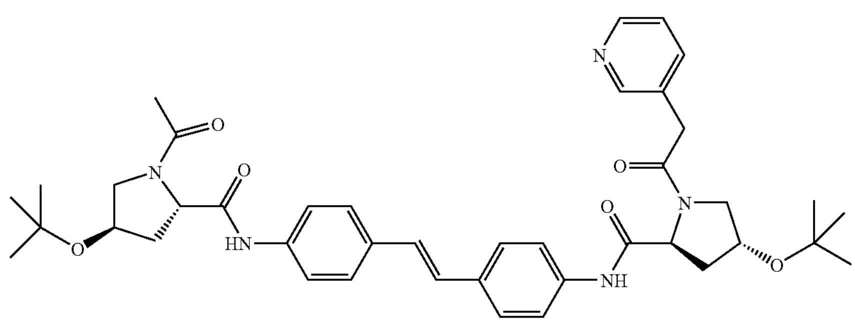 | 10.15/D | 710.5 |
| 133 | 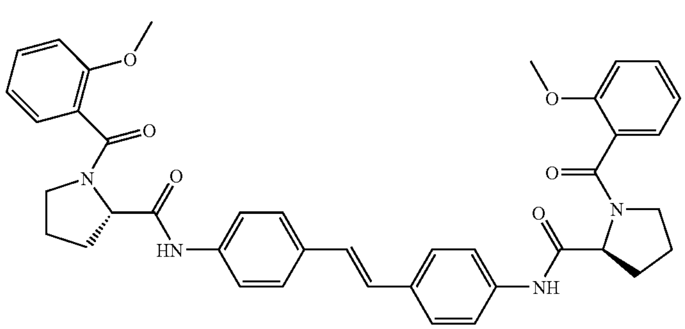 | 1.59/A | 673.4 |

-continued

| Example | Structure | HPLC (min/method*) | (M + H)+ |
|---|---|---|---|
| 134 | 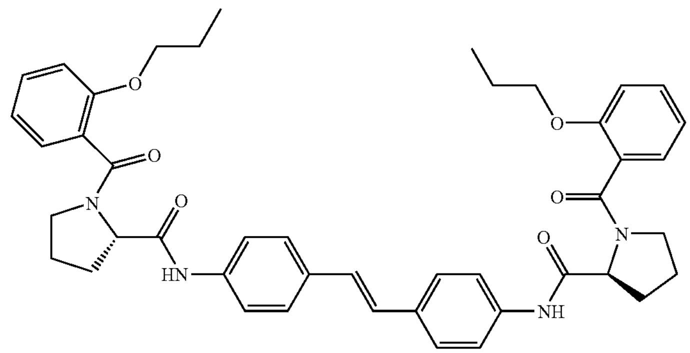 | 1.82/A | 729.4 |
| 135 | 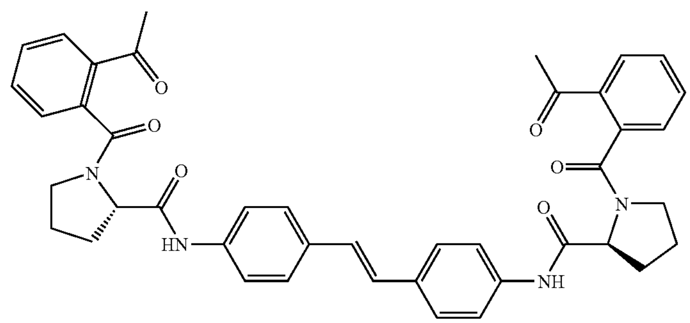 | 1.80/A | 697.2 |
| 136 | 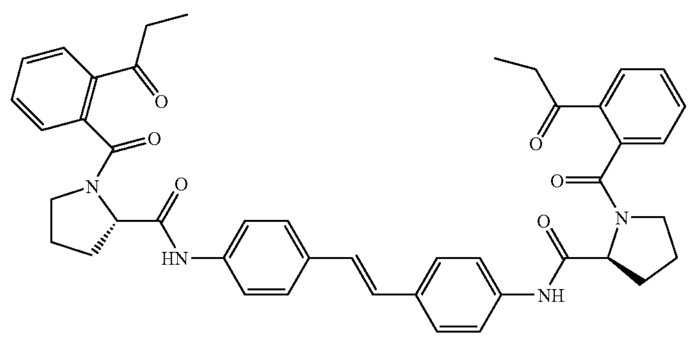 | 1.94/A | 725.3 |
| 137 | 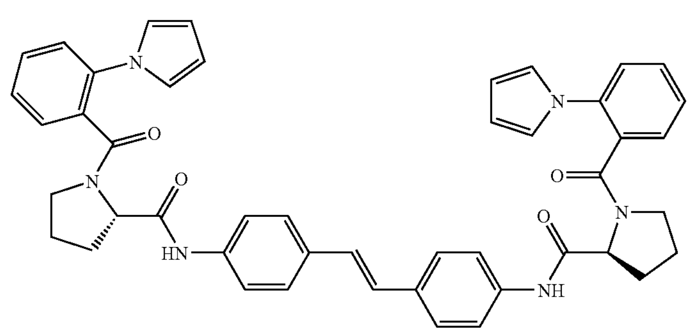 | 2.02/A | 743.3 |

-continued

| Example | Structure | HPLC (min/method*) | (M + H)+ |
|---|---|---|---|
| 138 | 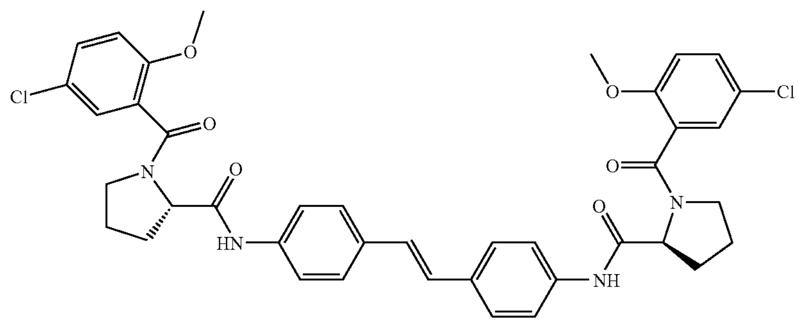 | 1.90/A | 741.2 |
| 139 | 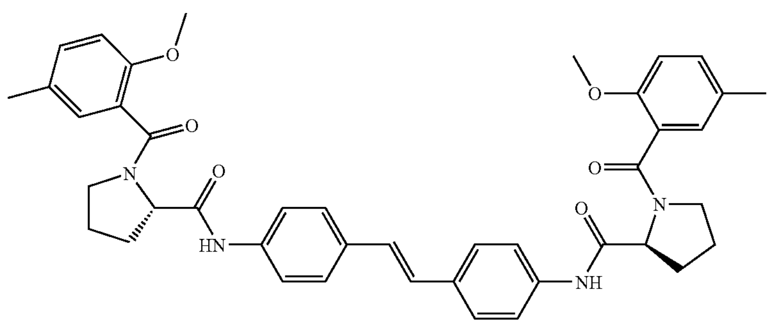 | 1.86/A | 701.3 |
| 140 | 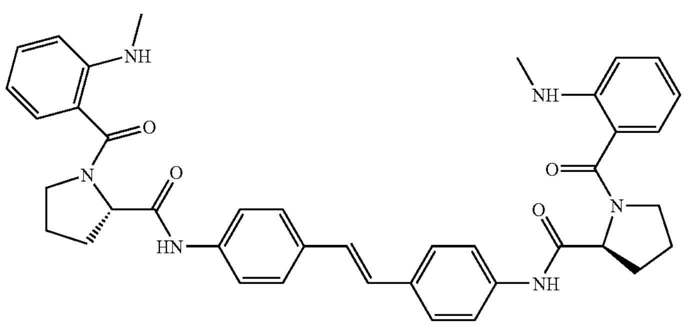 | 1.83/A | 671.2 |
| 141 | 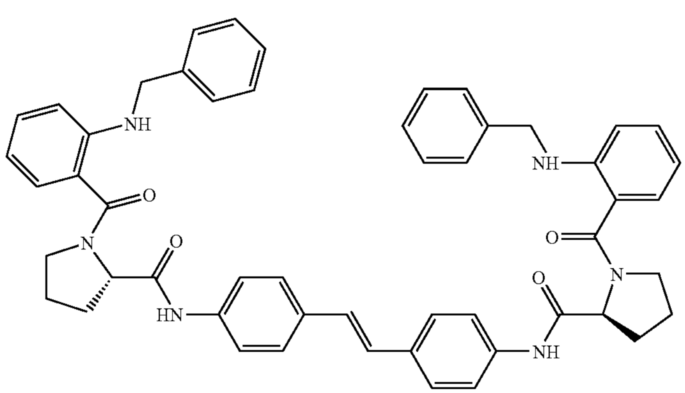 | 2.19/A | 823.4 |

-continued

| Example | Structure | HPLC (min/method*) | (M + H)+ |
|---|---|---|---|
| 142 | 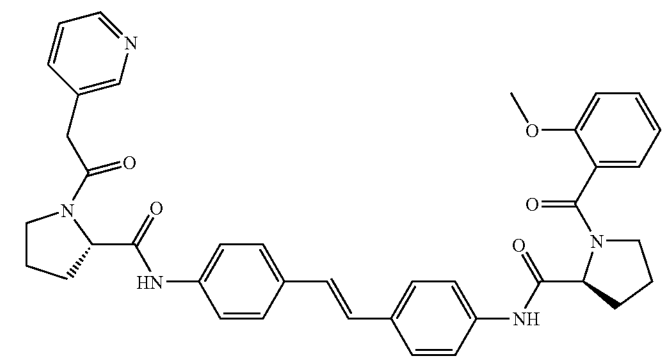 | 1.53/A | 658.2 |
| 143 | 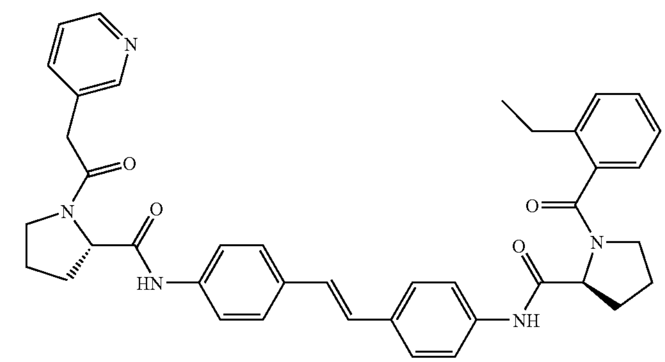 | 1.66/A | 656.2 |
| 144 | 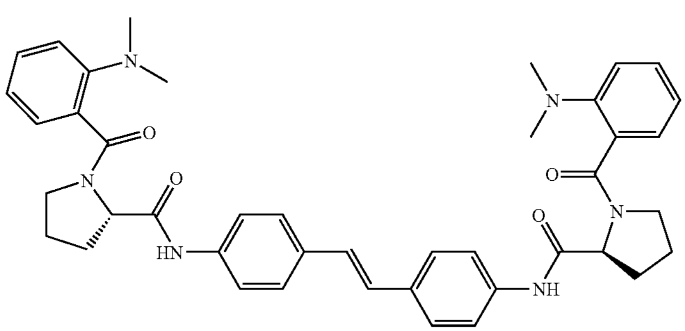 | 1.38/A | 699.3 |
| 145 | 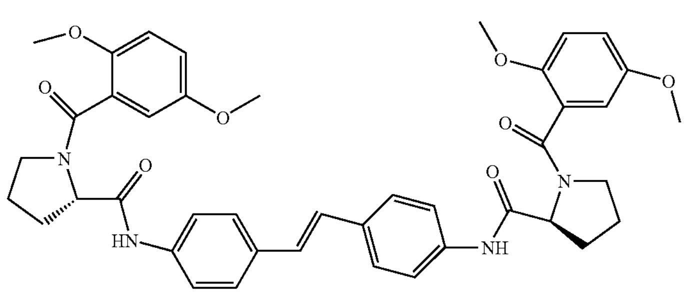 | 2.29/A | 733.4 |

| Example | Structure | HPLC (min/method*) | (M + H)+ |
|---|---|---|---|
| 146 | 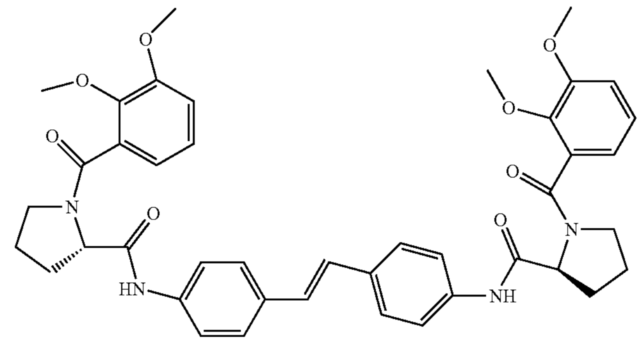 | 2.31/B | 733.4 |
| 147 | 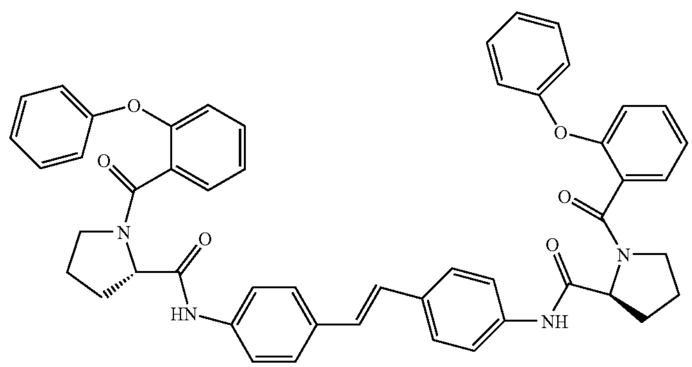 | 2.72/B | 797.5 |
| 148 | 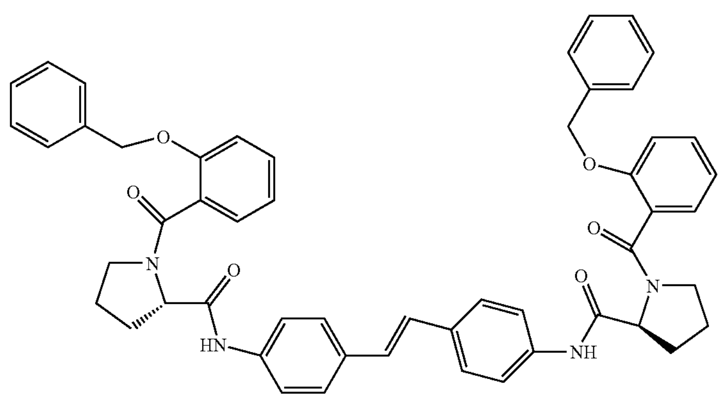 | 2.73/B | 825.5 |
| 149 | 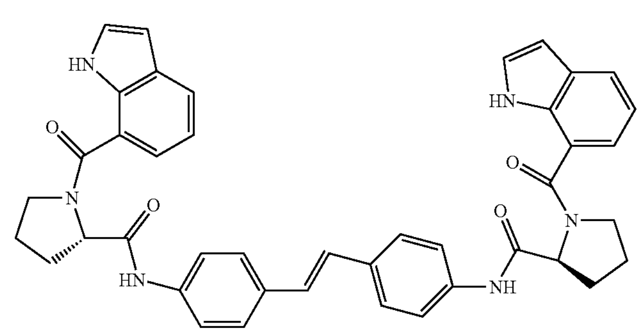 | 2.56/B | 691.3 |

-continued
| Example | Structure | HPLC (min/ method*) | (M + H)+ |
|---|---|---|---|
| 150 | 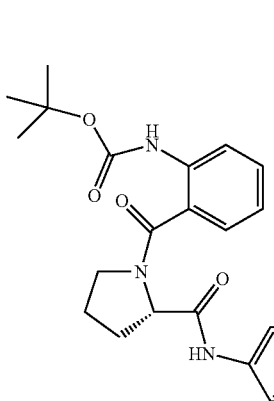 | 2.83/B | 843.5 |
| 151 | 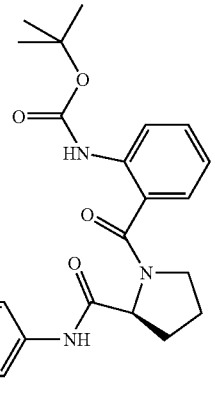 | 2.41/B | 733.5 |
| 152 | 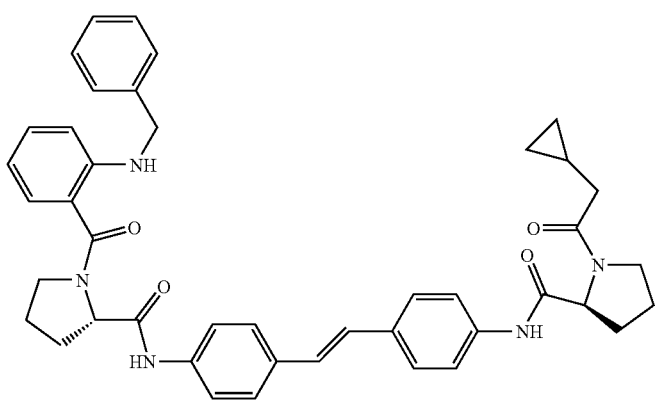 | 2.71/B | 696.4 |

-continued

| Example | Structure | HPLC (min/method*) | (M + H)+ |
|---|---|---|---|
| 153 | 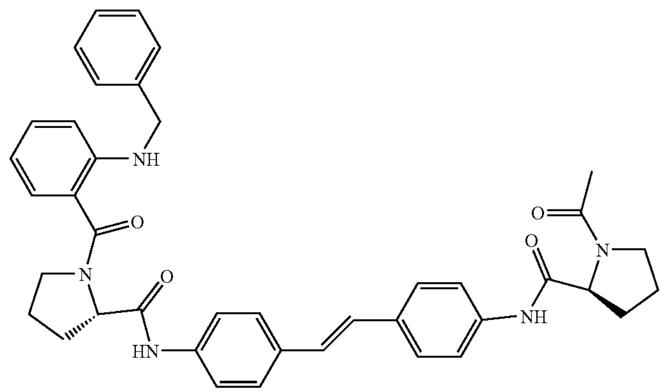 | 2.58/B | 656.4 |
| 154 | 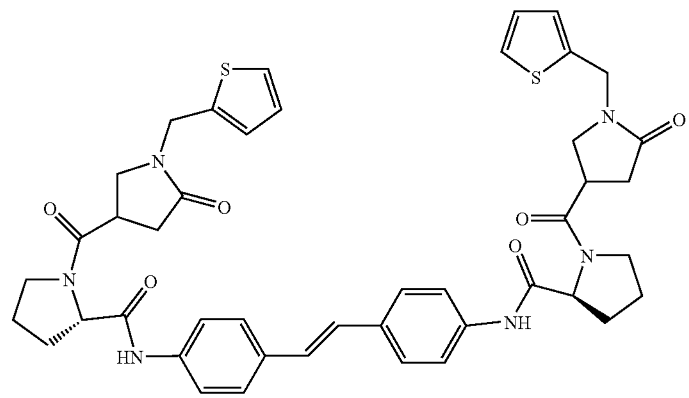 | 2.19/B | 819.4 |
| 155 | 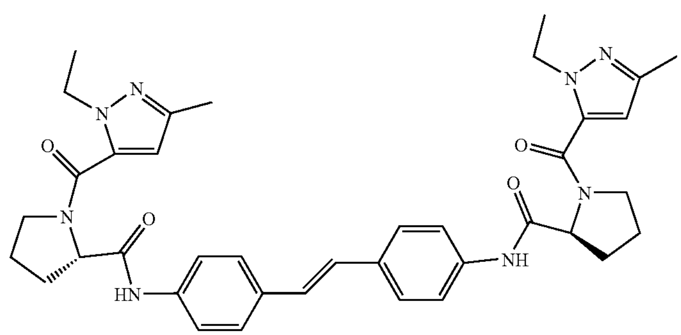 | 2.18/B | 677.4 |
| 156 | 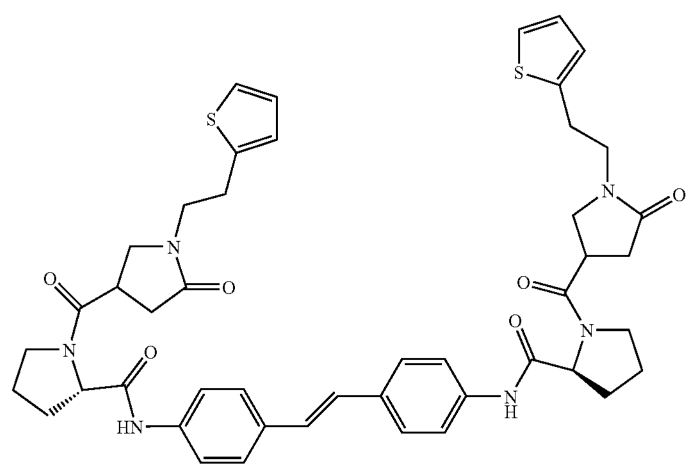 | 2.28/B | 847.4 |

-continued

| Example | Structure | HPLC (min/method*) | (M + H)+ |
|---|---|---|---|
| 157 | 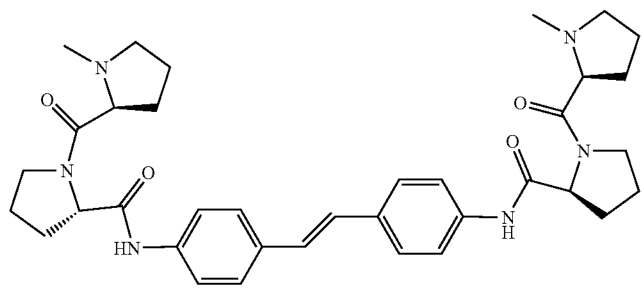 | 1.48/B | 627.2 |
| 158 | 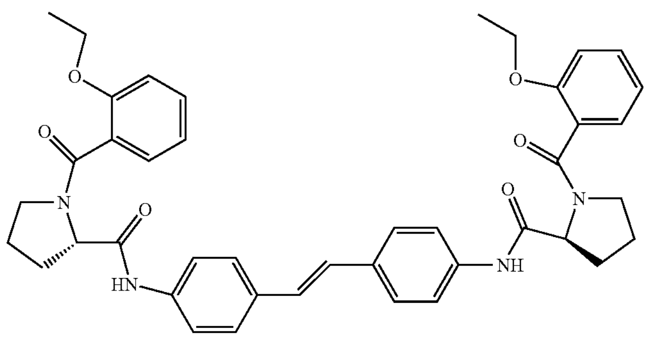 | 2.46/B | 701.5 |
| 159 | 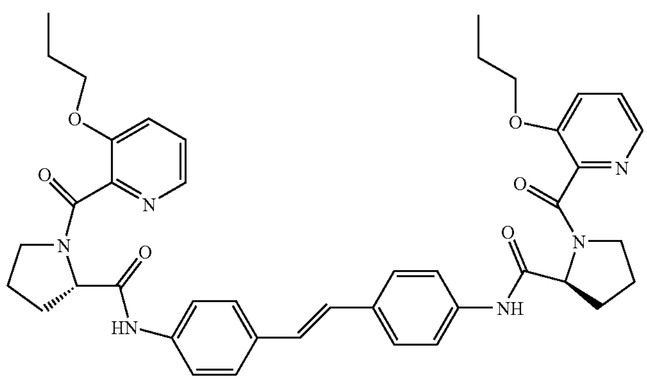 | 2.32/B | 731.5 |
| 160 | 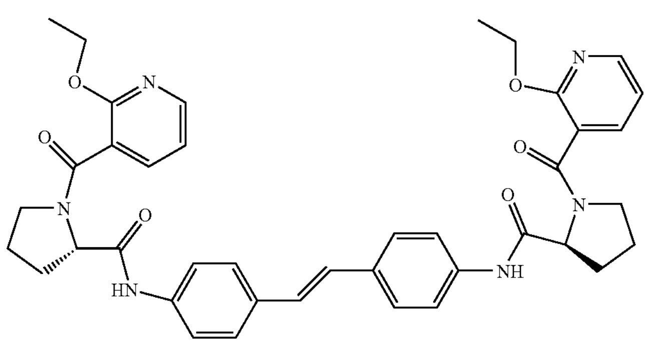 | 2.34/B | 703.5 |

-continued

| Example | Structure | HPLC (min/method*) | (M + H)+ |
|---|---|---|---|
| 161 | 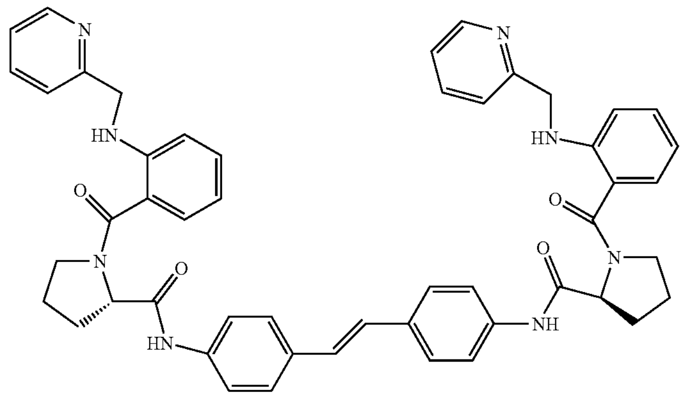 | 1.83/B | 825.4 |
| 162 | 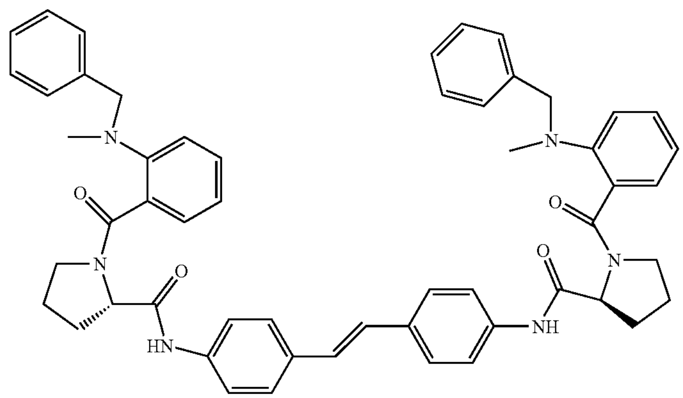 | 2.50/B | 851.4 |
| 163 | 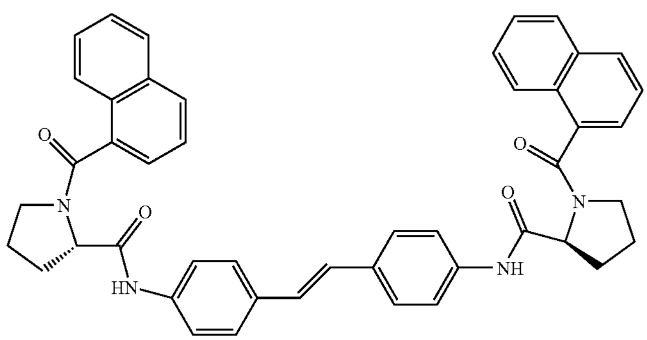 | 2.68/B | 713.3 |
| 164 | 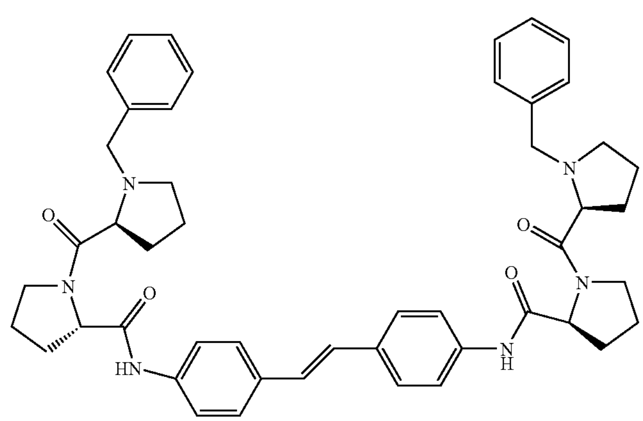 | 1.80/B | 779.8 |

| Example | Structure | HPLC (min/method*) | (M + H)+ |
|---|---|---|---|
| 165 | 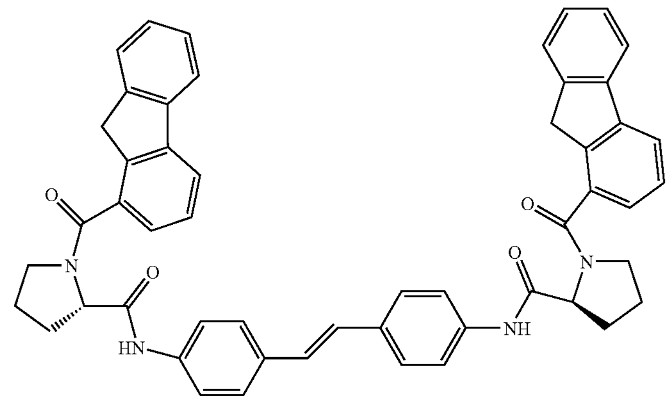 | 2.42/B | 789.5 |
| 166 | 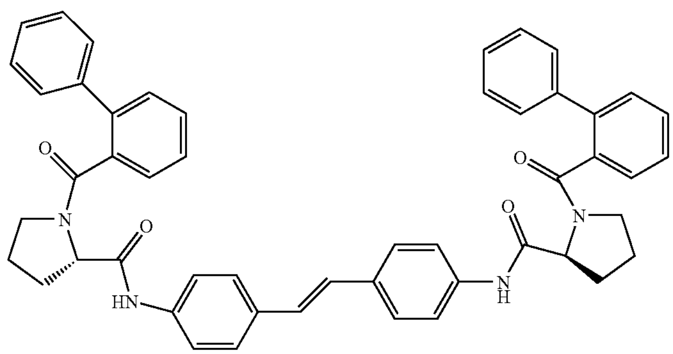 | 2.24/B | 765.5 |
| 167 | 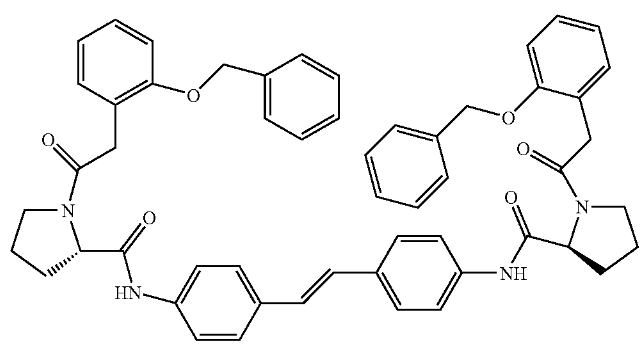 | 2.64/B | 853.5 |
| 168 | 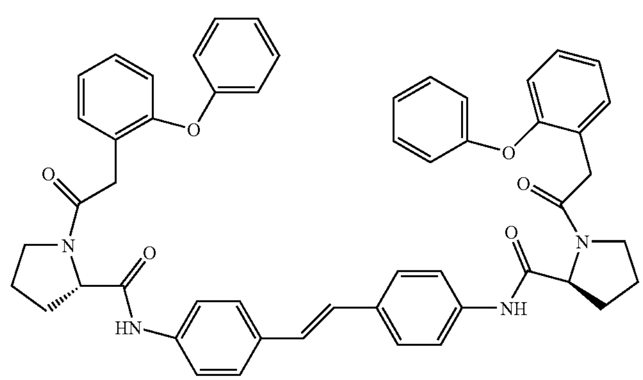 | 2.59/B | 825.5 |

-continued

| Example | Structure | HPLC (min/method*) | (M + H)+ |
|---|---|---|---|
| 169 | 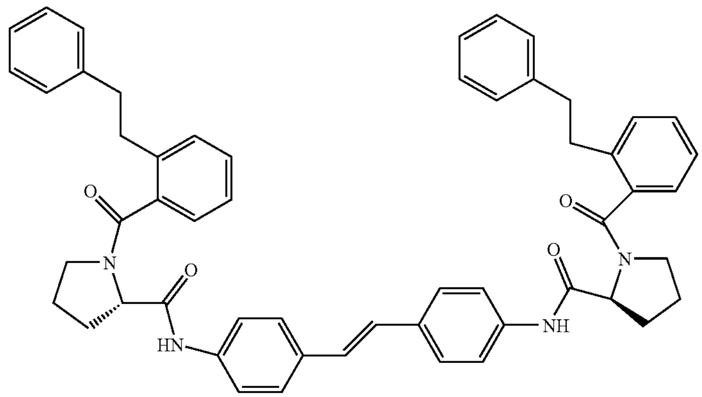 | 3.06/B | 821.6 |
| 170 | 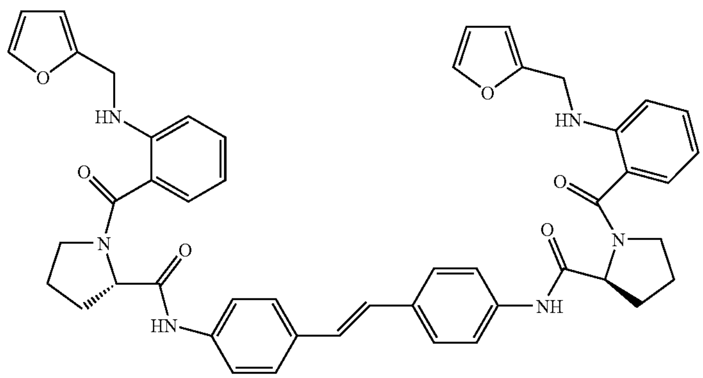 | 2.37/B | 803.5 |
| 171 | 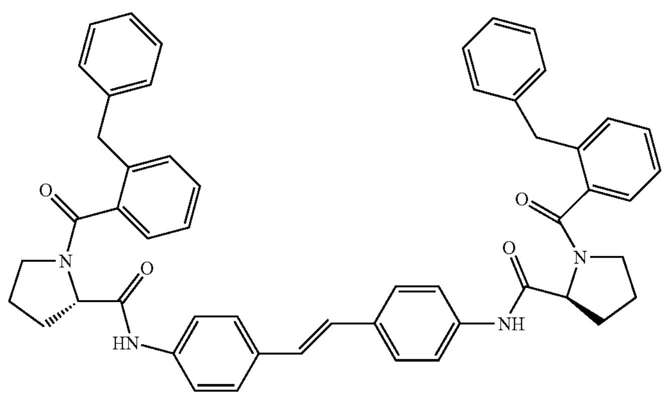 | 1.76/B | 793.7 |
| 172 | 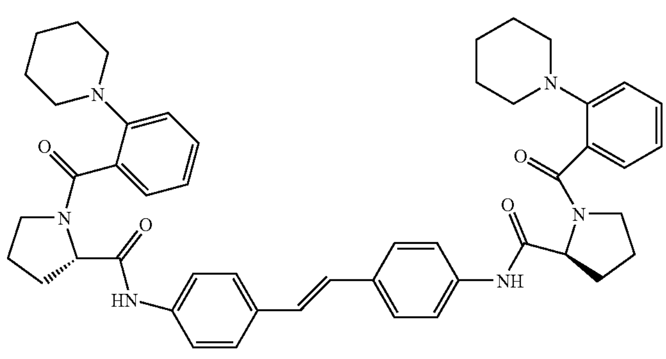 | 2.08/B | 779.8 |

-continued

| Example | Structure | HPLC (min/method*) | (M + H)+ |
|---|---|---|---|
| 173 | 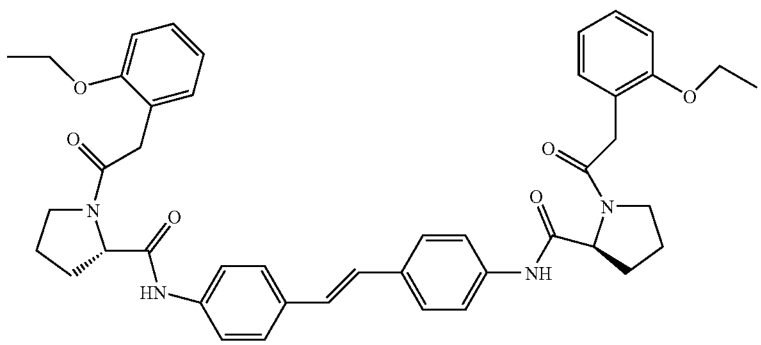 | 2.67/B | 729.6 |
| 174 | 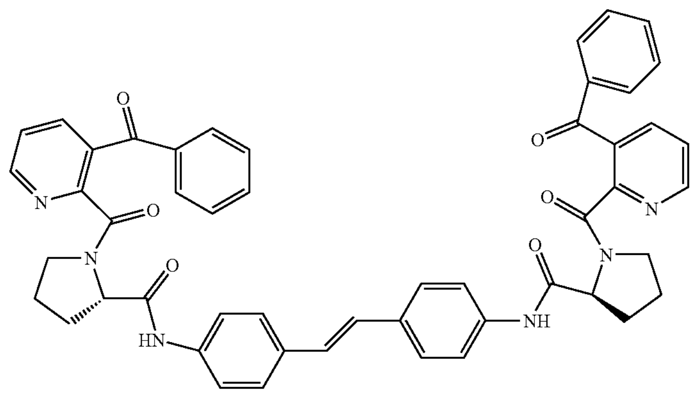 | 2.43/B | 823.8 |
| 175 | 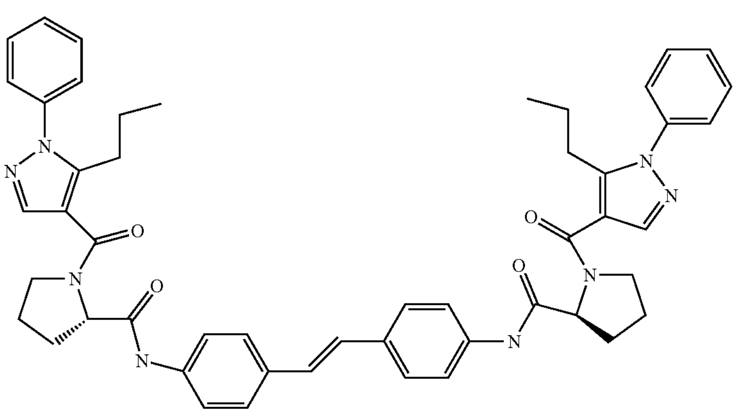 | 2.59/B | 829.7 |

-continued

| Example | Structure | HPLC (min/method*) | (M + H)+ |
|---|---|---|---|
| 176 | 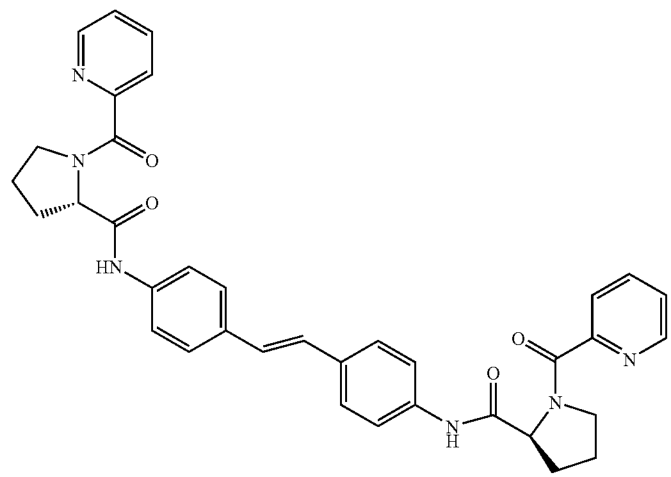 | 1.96/B | 615.5 |
| 177 | 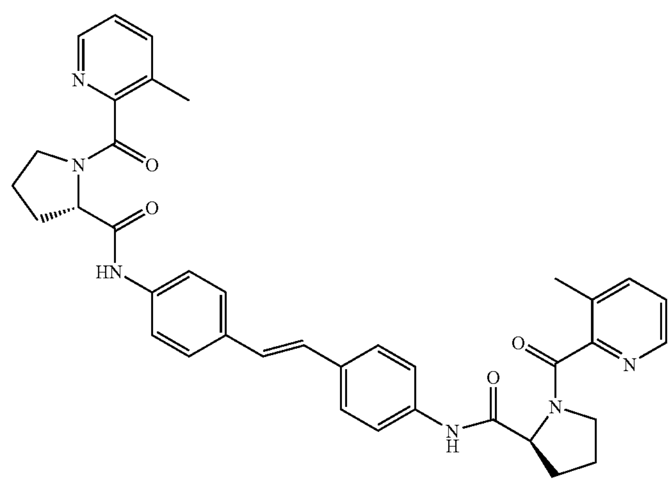 | 2.01/B | 643.6 |
| 178 | 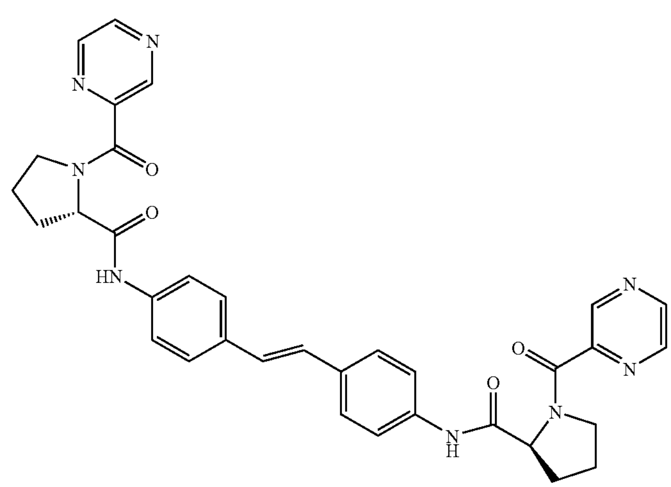 | 1.89/B | 617.5 |

-continued
| Example | Structure | HPLC (min/method*) | (M + H)+ |
|---|---|---|---|
| 179 | 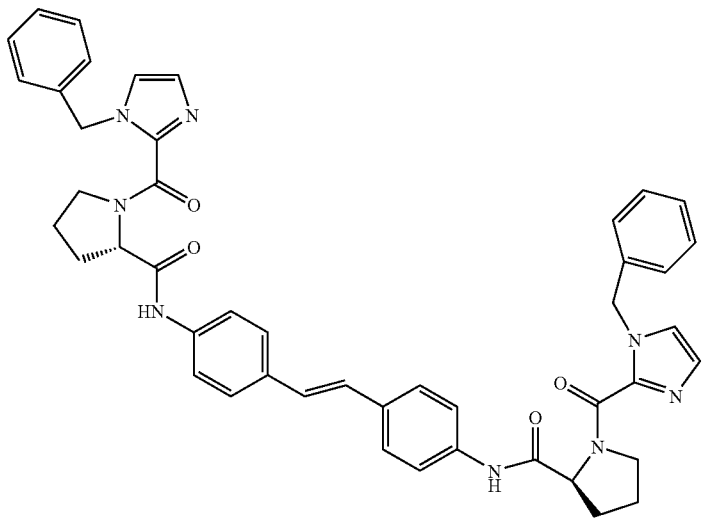 | 2.25/B | 773.7 |
| 180 | 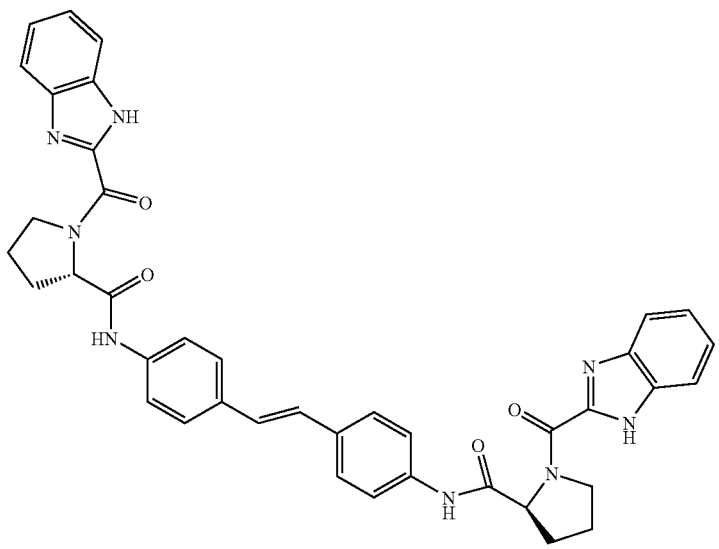 | 2.36/B | 693.5 |
| 181 | 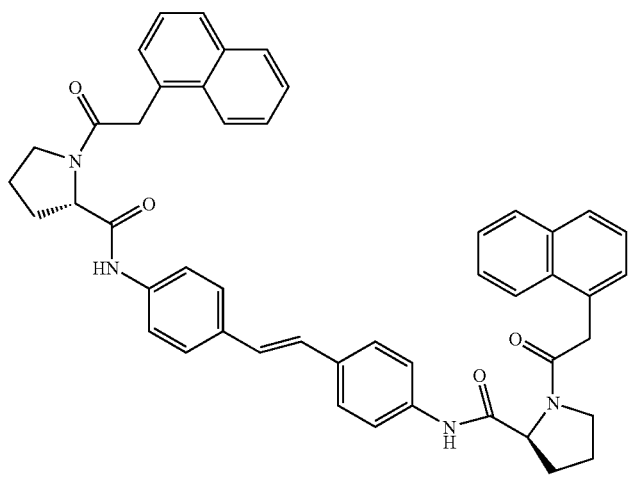 | 2.77/B | 741.5 |

| Example | Structure | HPLC (min/method*) | (M + H)⁺ |
|---|---|---|---|
| 182 | 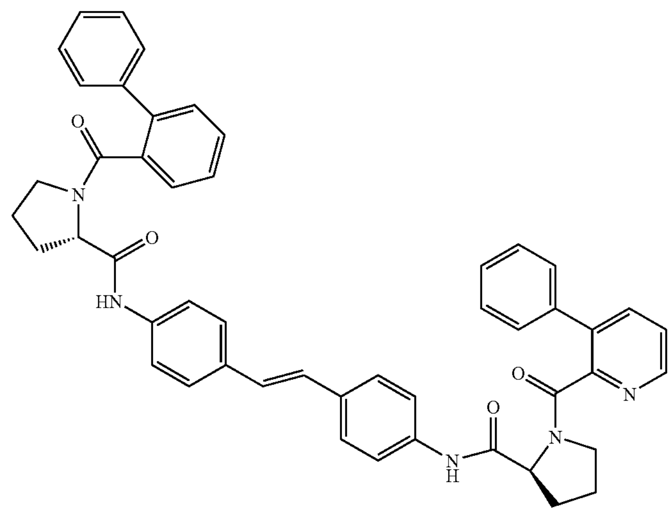 | 2.47/B | 767.6 |
| 183 | 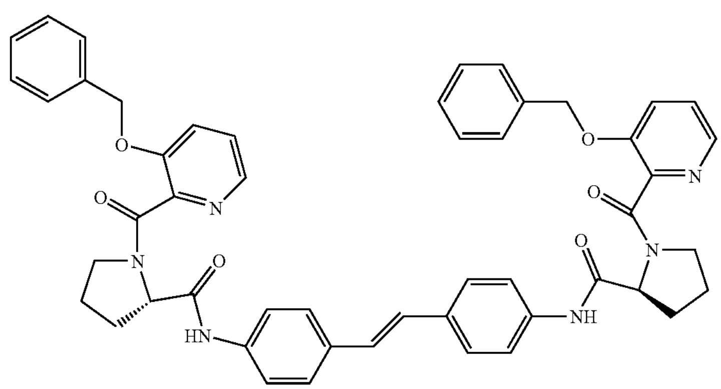 | 2.44/B | 827.7 |
| 184 | 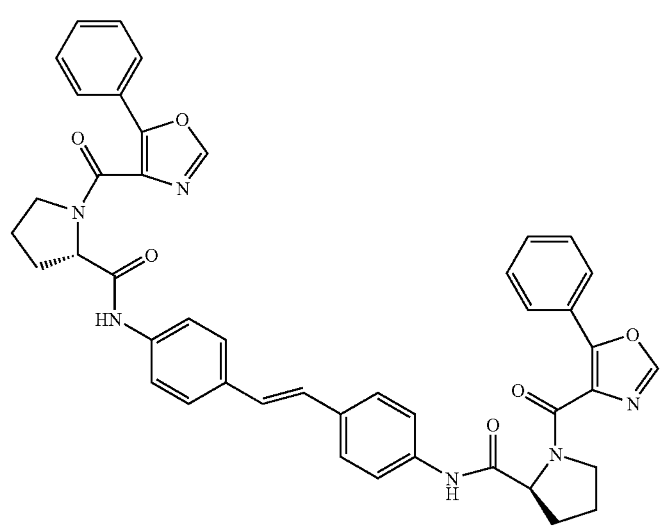 | 2.48/B | 747.3 |

-continued

| Example | Structure | HPLC (min/method*) | (M + H)+ |
|---|---|---|---|
| 185 | 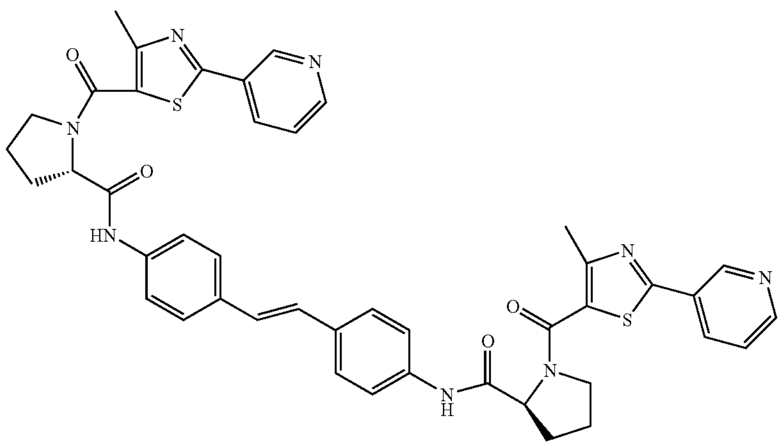 | 1.99/B | 809.3 |
| 186 | 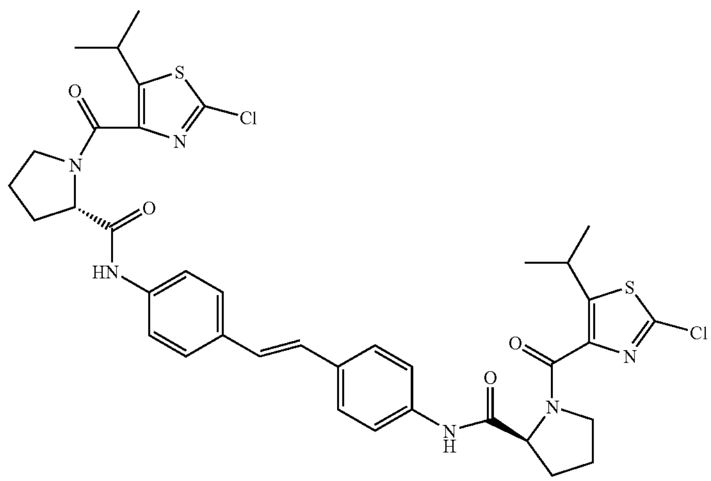 | 2.82/B | 779.1 |
| 187 | 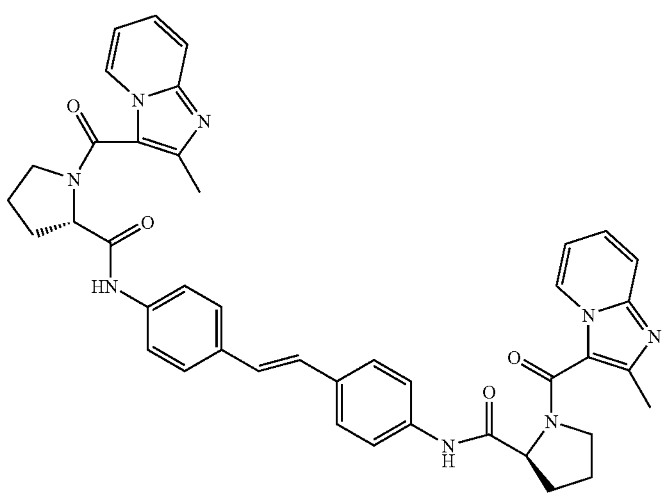 | 1.61/B | 721.2 |

-continued

| Example | Structure | HPLC (min/ method*) | (M + H)+ |
|---|---|---|---|
| 188 | 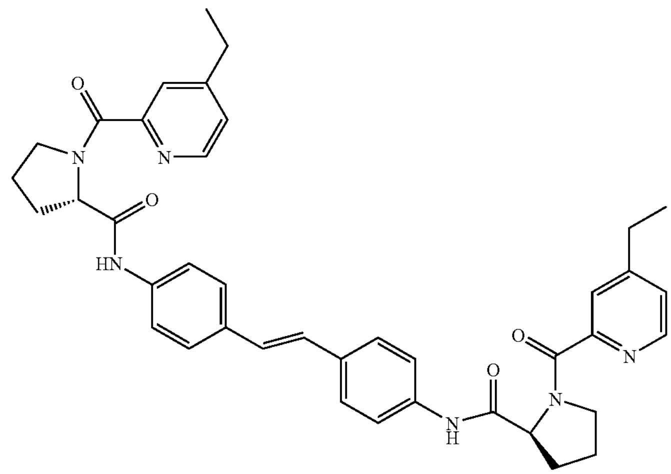 | 2.16/B | 671.4 |
| 189 | 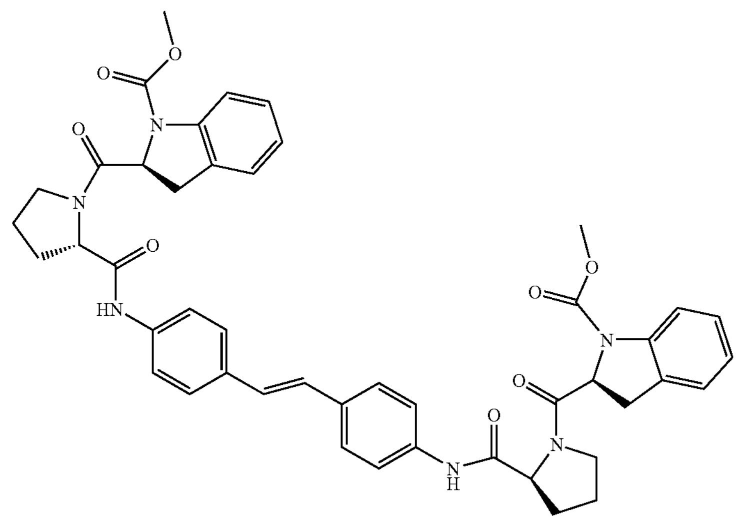 | 2.51/B | 811.5 |
| 190 | 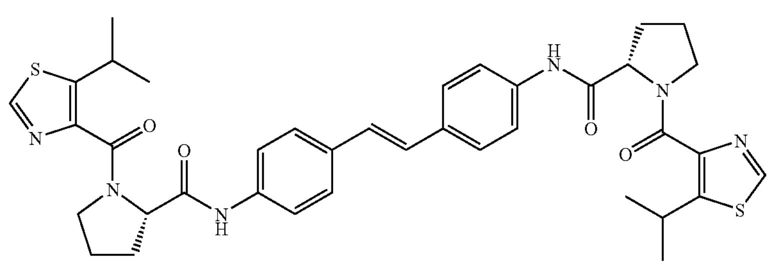 | 1.72/A | 711.3 |
| 191 | 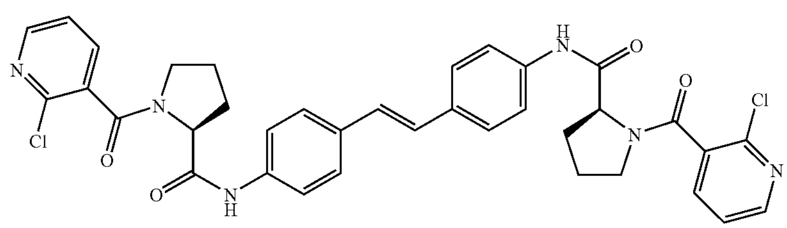 | 7.64/H | 683.2 |

-continued
| Example | Structure | HPLC (min/method*) | (M+H)+ |
|---|---|---|---|
| 192 | 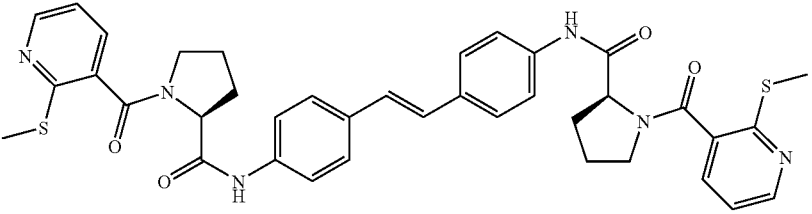 | 8.14/H | 707.2 |
| 193 | 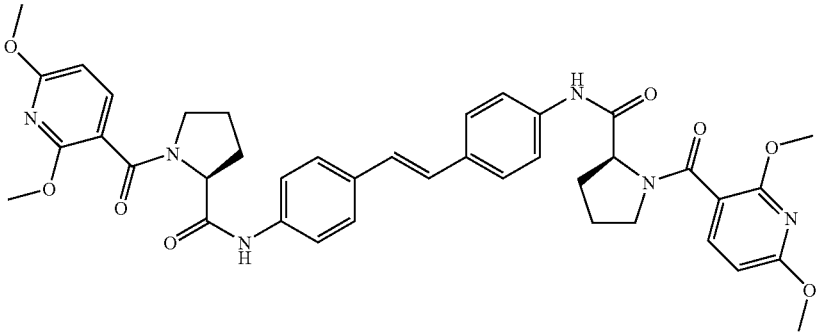 | 8.57/H | 735.5 |
| 194 | 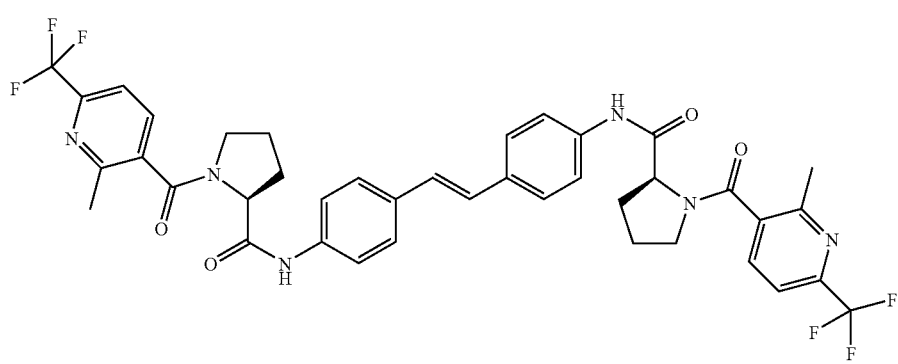 | 8.74/H | 779.3 |
| 195 | 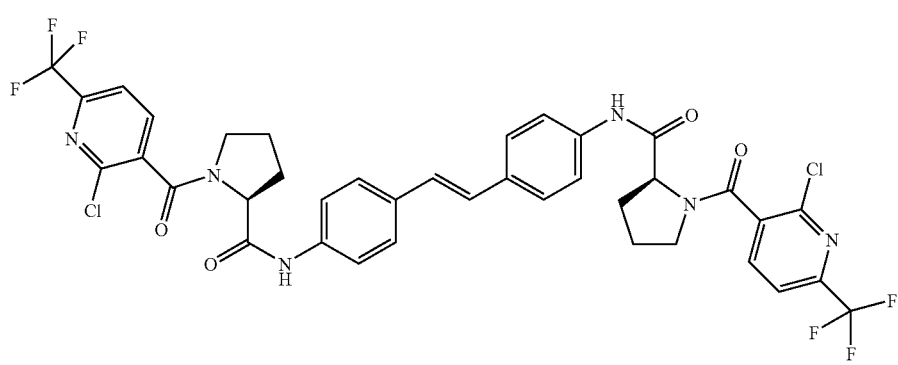 | 9.18/H | 819.1 |
| 196 | 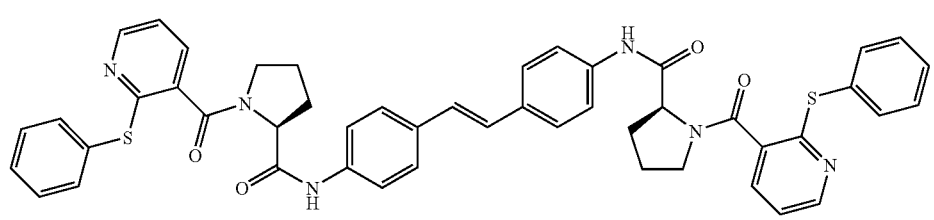 | 8.96/H | 831.2 |

-continued

| Example | Structure | HPLC (min/method*) | (M + H)+ |
|---|---|---|---|
| 197 | 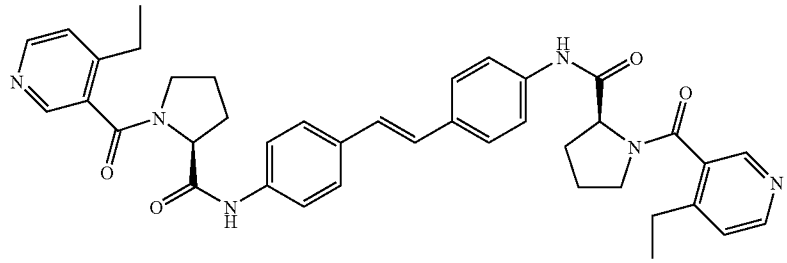 | 5.9/H | 671.4 |
| 198 | 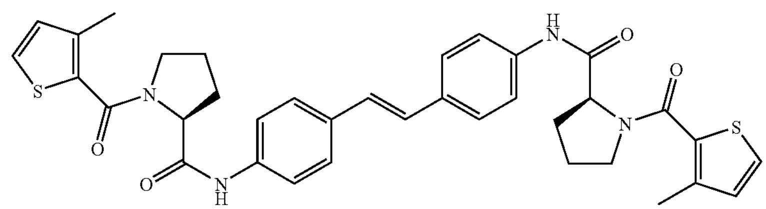 | 8.37/H | 653.2 |
| 199 | 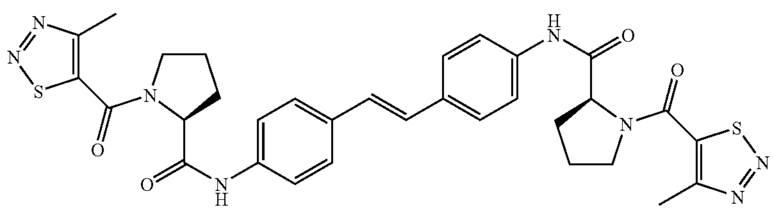 | 7.42/H | 657.2 |
| 200 | 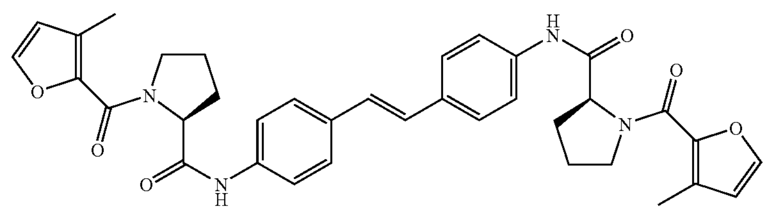 | 8.22/H | 621.2 |
| 201 | 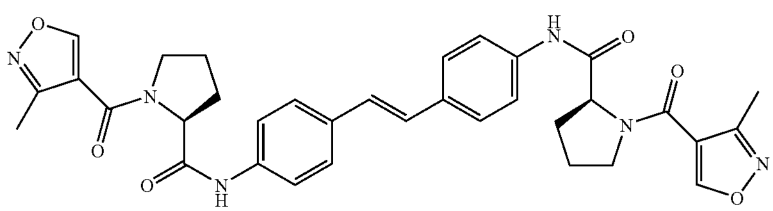 | 7.12/H | 623.2 |
| 202 | 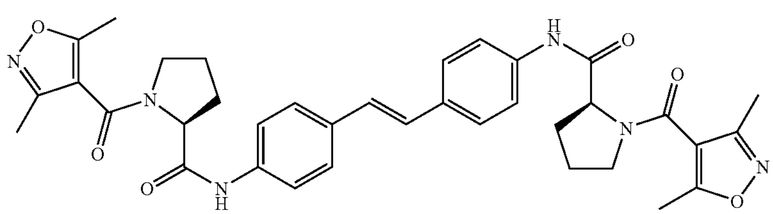 | 7.37/H | 651.3 |
| 203 | 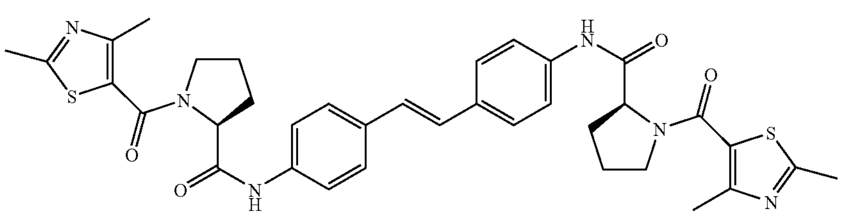 | 7.49/H | 683.3 |

-continued

| Example | Structure | HPLC (min/method*) | (M + H)+ |
|---|---|---|---|
| 204 | 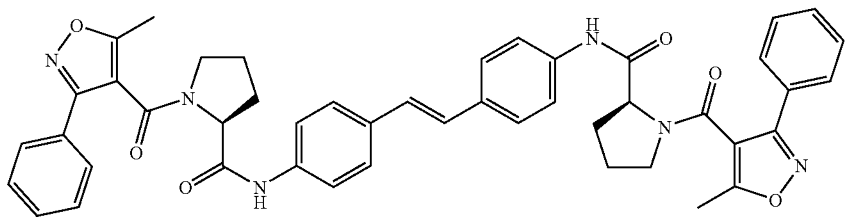 | 9.05/H | 775.3 |
| 205 | 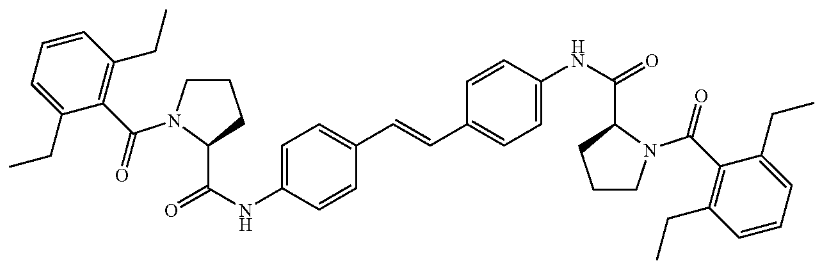 | 1.96/I | 725.5 |
| 206 | 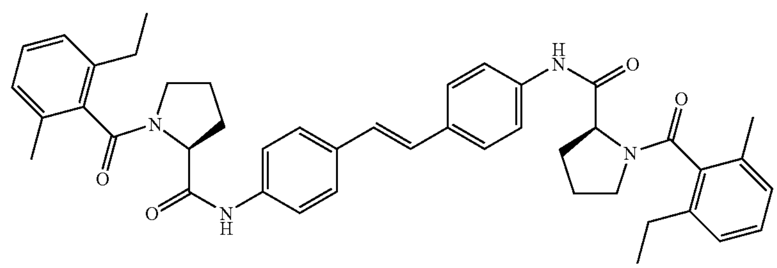 | 9.89/H | 696.3 |
| 207 | 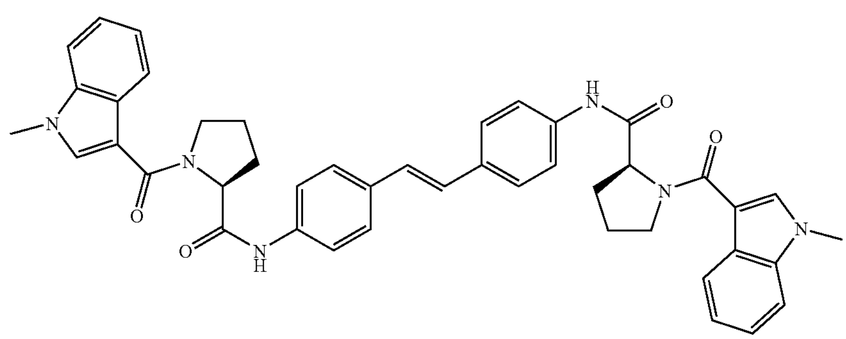 | 8.71/H | 719.6 |
| 208 | 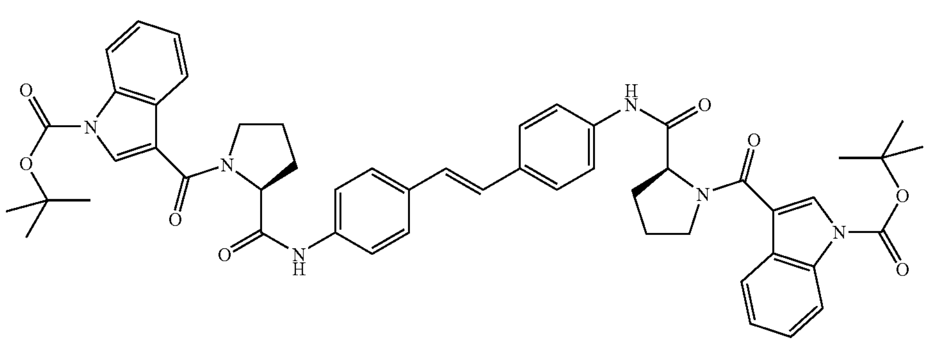 | 2.07/I | 891.8 |

-continued

| Example | Structure | HPLC (min/ method*) | (M + H)+ |
|---|---|---|---|
| 209 | 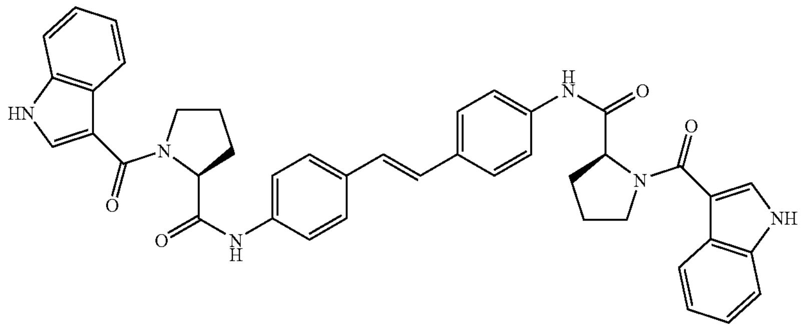 | 2.41/H | 691.4 |
| 210 | 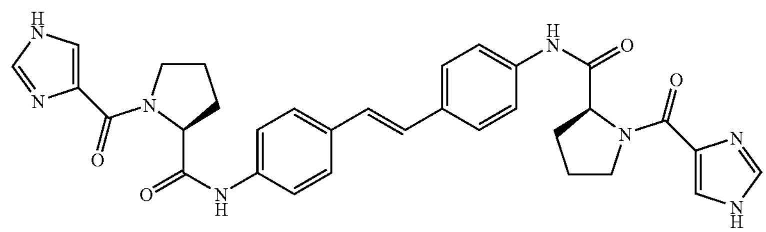 | 4.42/H | 593.5 |
| 211 | 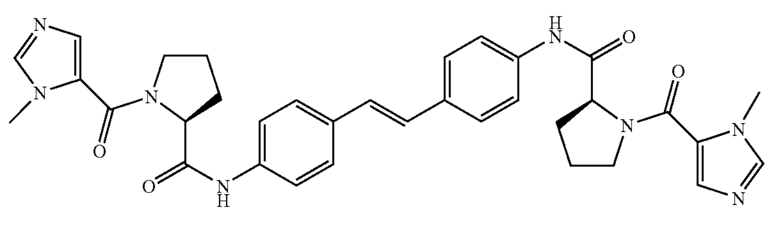 | 4.51/H | 621.5 |
| 212 | 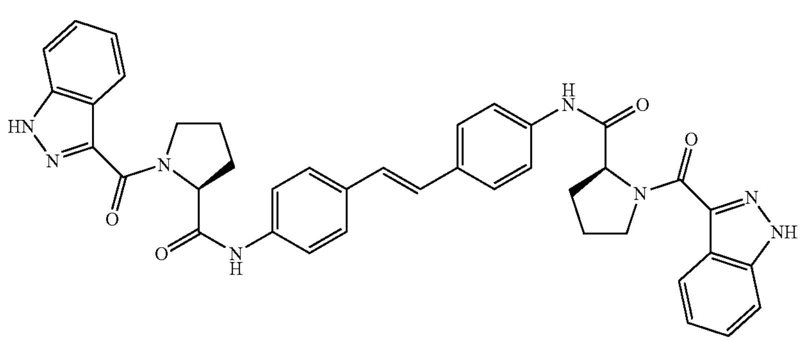 | 1.59/I | 693.4 |

| Example | Structure | HPLC (min/method*) | (M + H)+ |
|---|---|---|---|
| 213 | 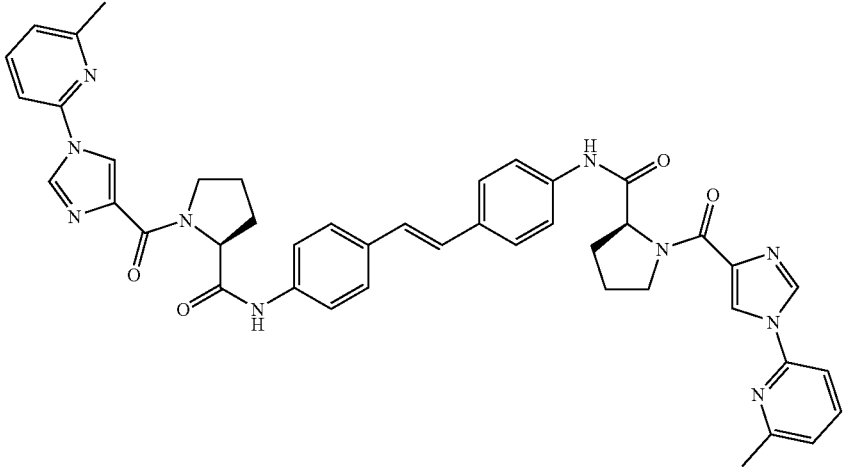 | 8.4/H | 775.7 |
| 214 | 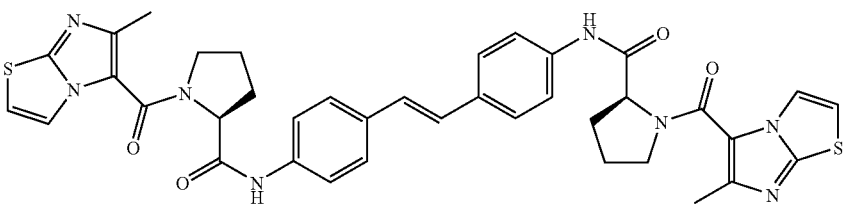 | 6.25/H | 733.4 |
| 215 | 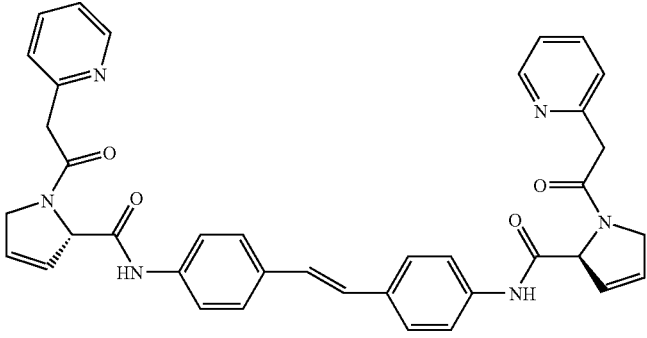 | 1.04/A | 639.3 |
| 216 | 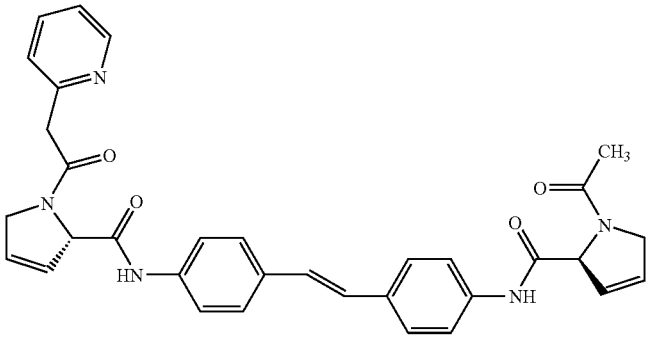 | 1.14/A | 562.3 |

-continued

| Example | Structure | HPLC (min/method*) | (M + H)+ |
|---|---|---|---|
| 217 | 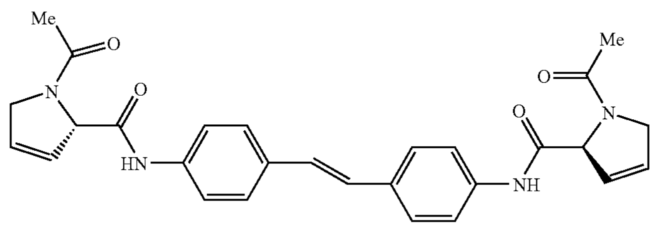 | 1.25/A | 485.3 |
| 218 | 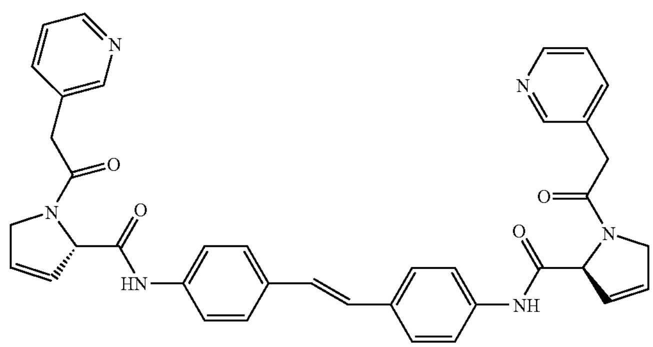 | 1.03/A | 639.3 |
| 219 | 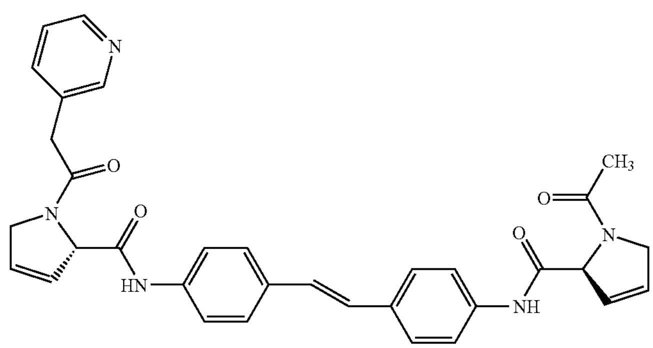 | 1.12/A | 562.3 |
| 220 | 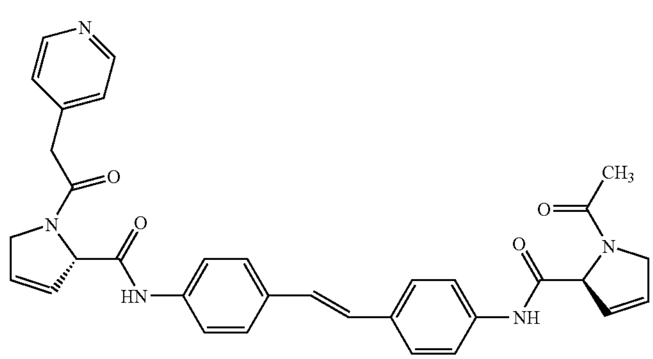 | 1.11/A | 562.2 |

| Example | Structure | HPLC (min/method*) | (M + H)+ |
|---|---|---|---|
| 221 | 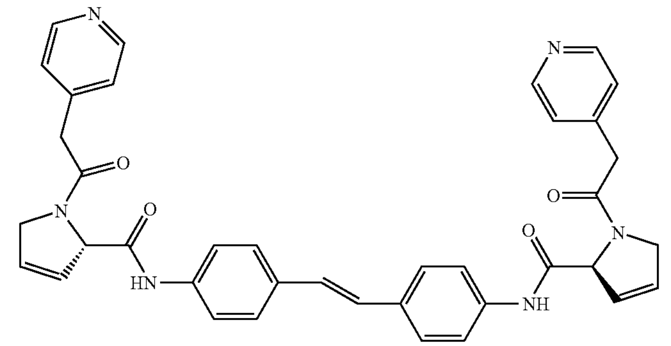 | 1.02/A | 639.3 |

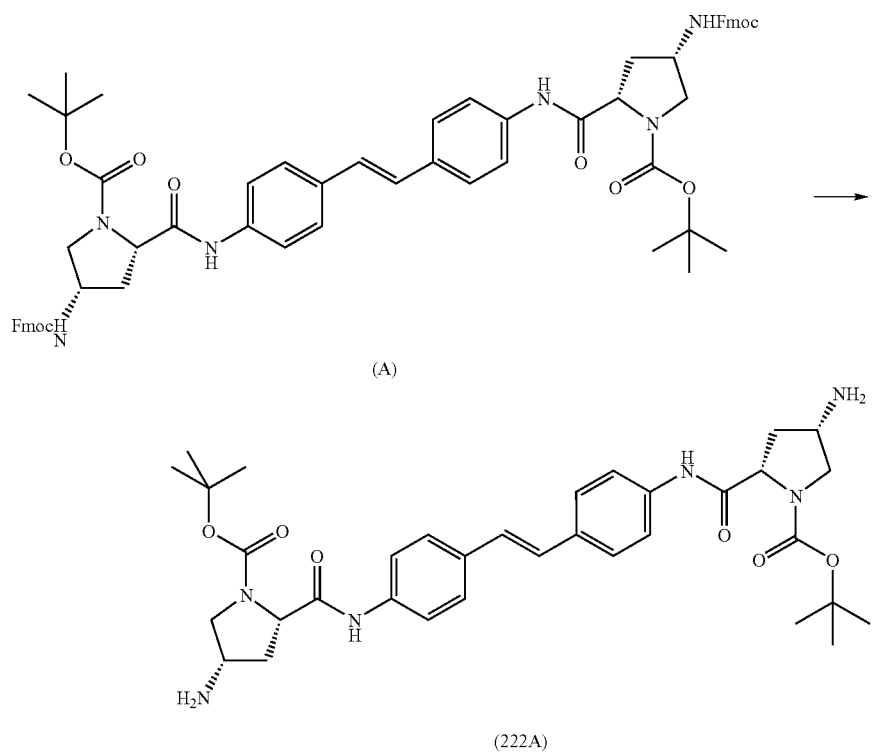

(A)

(222A)

Example 222A

Piperidine (4 mL) was added to a stirred solution of compound (A) (prepared by substituting the appropriate reagents in Example 1, 2.08 g, 1.93 mmol) in dry dichloromethane (20 mL) at room temperature under nitrogen. The mixture was stirred for 20 hours and collected by filtration to provide the desired product (0.80 g, 65%) as an off-white solid: $^1$H NMR (DMSO-d$_6$, 500 MHz) δ 10.54 and 10.42 (2s, 2H), 7.59 (d, J=9.0 Hz, 4H), 7.52 (d, J=8.5 Hz, 4H), 7.09 (s, 2H), 4.25-4.15 (m, 4H), 3.55-3.45 (2m, 4H), 3.19-3.15 (m, 2H), 2.40-2.36 (m, 2H), 1.75-1.70 (m, 2H), 1.55-1.51 (m, 2H), 1.40 and 1.27 (2s, 18H); LCMS (R$_t$=1.88 min, m/z 635.6).

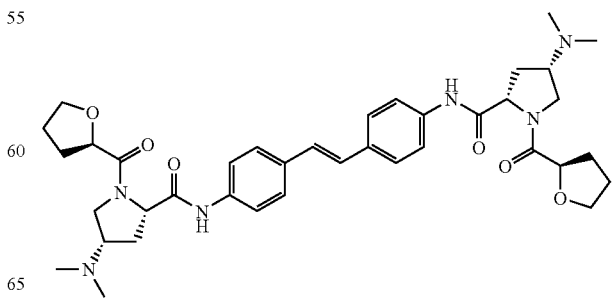

Example 222B

Sodium cyanoborohydride (146.5 mg, 2.33 mmol) was added to a stirred suspension of Example 222A (740 mg, 1.17 mmol), acetic acid (1.0 mL), and paraformaldehyde (900 mg) in anhydrous methanol (50 mL) at ambient temperature. The mixture was stirred for 16 hours, filtered through diatomaceous earth (Celite®), and concentrated. The residue was dissolved in ethyl acetate, washed with saturated NaHCO$_3$ and brine, dried (MgSO$_4$), filtered, and concentrated. The concentrate was dissolved in dry dioxane (2 mL) and methanol (1 mL) and treated with 4N HCl in dioxane (10 mL) at 0° C. in a sealed flask. The mixture was warmed to room temperature, stirred for 3 hours, diluted with diethyl ether, and collected by filtration to provide a light, tan, hygroscopic solid: LCMS (R$_f$=0.68 min, m/z 491.4). A solution of this solid (50 mg, 0.079 mmol), (2R)-2-tetrahydrofurancarboxylic acid (17 µL, 0.17 mmol), and diisopropylethylamine (112 µL, 0.63 mmol) in anhydrous DMF (1.5 mL) was treated with HATU (69 mg, 0.18 mmol), stirred at room temperature for 3 hours, and purified by HPLC to provide the desired product (40.8 mg, 45.4%) as a white solid: $^1$H NMR (CH$_3$OH-d$_4$, 500 MHz) δ 7.61-7.59 (m, 4H), 7.52-7.50 (m, 4H), 7.10-7.09 (m, 2H), 5.01-4.40 (3m, 4H), 4.25-4.17 (m, 2H), 4.13-4.10 (m, 2H), 3.99-3.85 (m, 6H), 3.03 and 2.98 (2s, 12H), 2.78-2.72 (m, 2H), 2.45-2.40 (m, 2H), 2.17-2.14 (m, 4H), 1.96-1.93 (m, 4H); LCMS (R$_f$=1.23 min, m/z 687.5).

Following the procedure described in Examples 222A and 222B and substituting the appropriate reagents, the following compounds were prepared.

| Example | Structure | HPLC (min/method*) | (M + H)$^+$ |
|---|---|---|---|
| 223 | 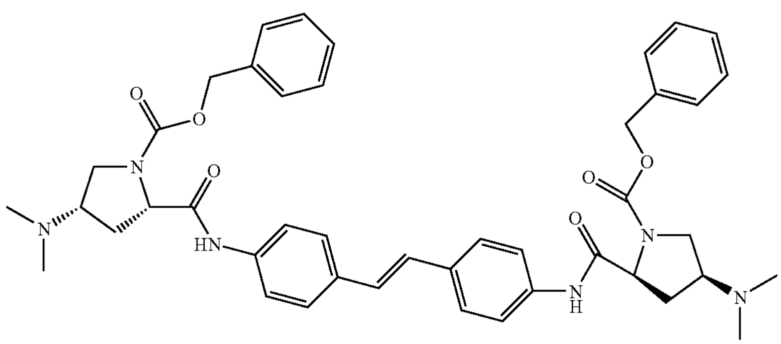 | 1.99/B | 759.9 |
| 224 | 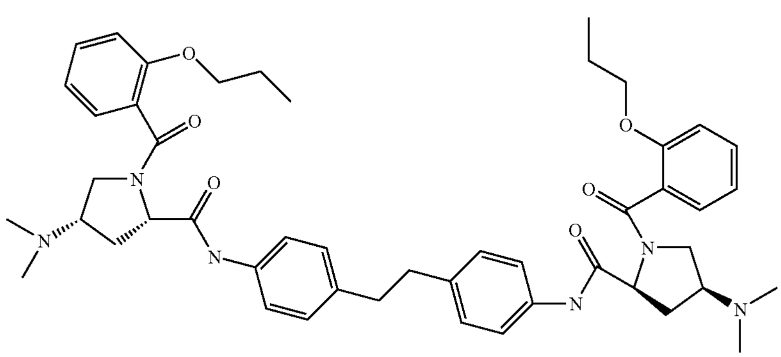 | 1.95/B | 817.5 |
| 225 | 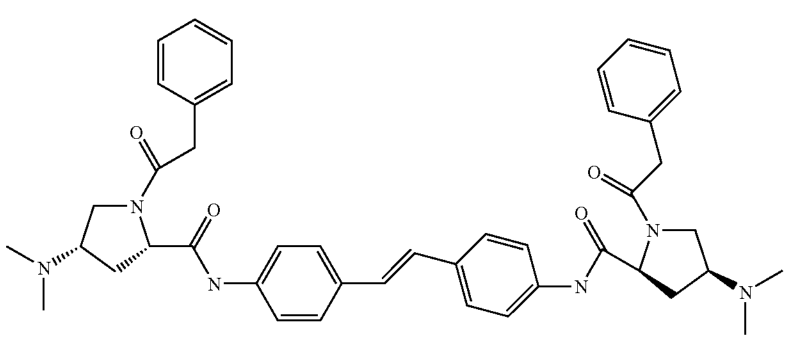 | 1.67/B | 727.6 |

-continued

| Example | Structure | HPLC (min/method*) | (M + H)+ |
|---|---|---|---|
| 226 | 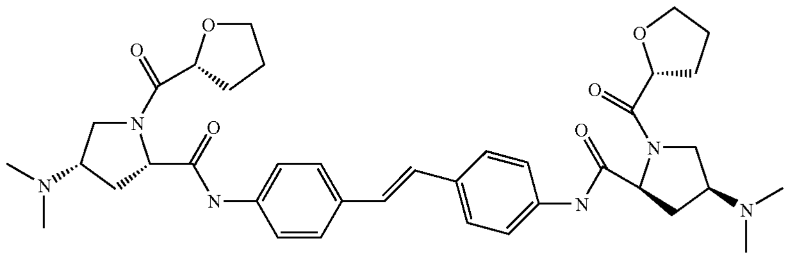 | 1.23/B | 687.5 |
| 227 | 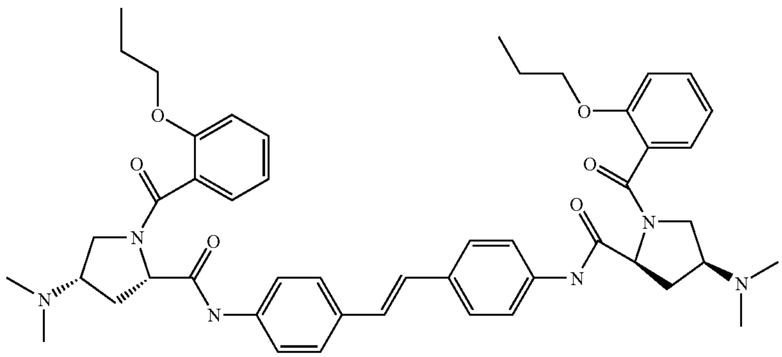 | 1.85/B | 815.7 |
| 228 | 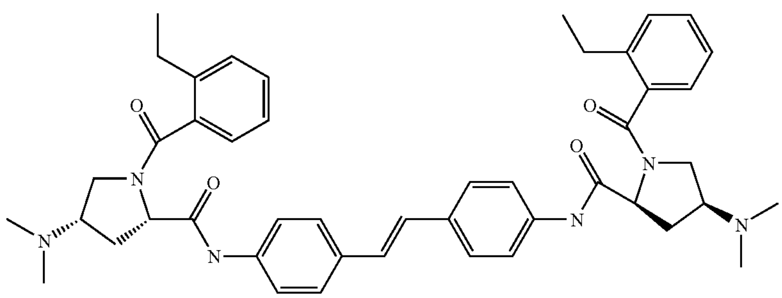 | 1.82/B | 755.5 |
| 229 | 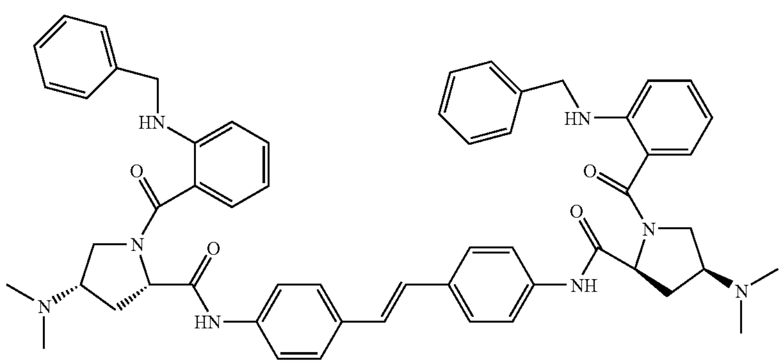 | 2.25/B | 909.6 |

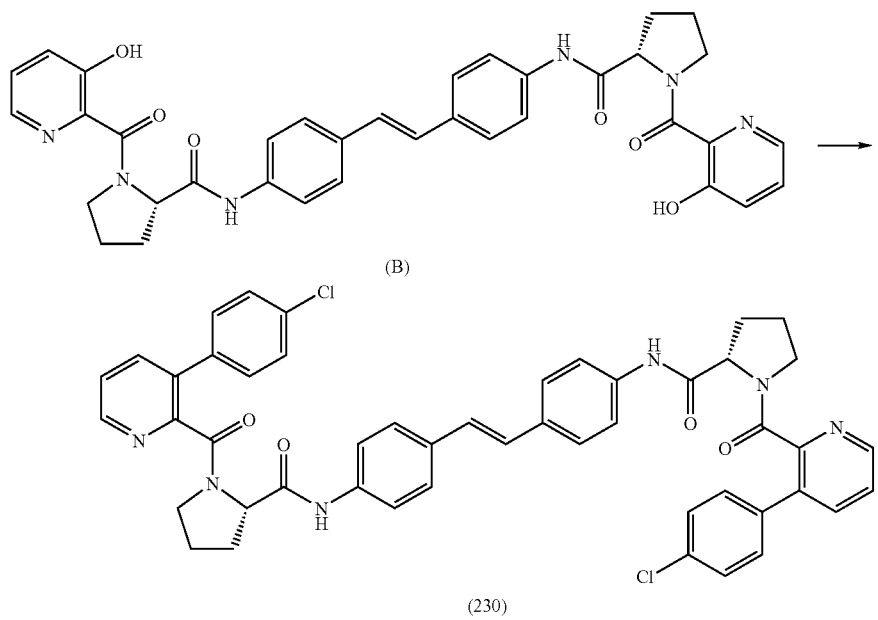

(B)

(230)

Example 230

4-Nitrophenyltrifluoromethanesulfonate (262.9 mg, 0.97 mmol) was added in one portion to a stirred suspension of compound (B) (prepared by substituting the appropriate reagents into Examples 23A and 23B, 285 mg, 0.44 mmol) and powdered potassium carbonate (133 mg, 0.97 mmol) in anhydrous dimethylformamide (4 mL) at room temperature. The mixture was stirred for 4 hours at room temperature, treated with additional 4-nitrophenyltrifluoromethylsulfonate (130 mg, 0.48 mmol) and powdered potassium carbonate (130 mg, 0.97 mmol), stirred for an additional 16 hours at room temperature, diluted with ethyl acetate, washed with 1N sodium hydroxide and brine, dried (MgSO$_4$), filtered, and concentrated. A portion of this sample (70.6 mg) was dissolved in anhydrous tetrahydrofuran (1 mL) and treated with potassium phosphate (50 mg, 0.23 mmol), [1,1'-bis(diphenylphosphino)ferrocene]dichloro palladium(II) dichloromethane complex (3 mg, 0.004 mmol) and 4-chlorophenylboronic acid (26 mg, 0.167 mmol). The vial was sealed and heated to 65° C. for 16 hours before the mixture was cooled to ambient temperature and concentrated to ½ of the original volume. DMSO (1 mL) and methanol (0.5 mL) were added and the resulting mixture was purified by HPLC to provide the desired product (5.8 mg) as an earth-colored solid: $^1$H NMR (DMSO-d$_6$, 500 MHz) δ 10.16 and 9.75 (2s, 2H), 8.63-8.48 (2m, 2H), 7.94-7.80 (2m, 2H), 7.63-7.30 (series of m, 18H), 7.12-7.01 (m, 2H), 4.69-4.51 (2m, 2H), 3.60-3.41 (m, 4H), 2.21-2.12 (m, 2H), 2.04-1.92 (m, 4H), 1.85-1.73 (2m, 2H); LCMS (R$_t$=2.73 min, m/z (M−H)$^-$833.1, 835.2).

Following the procedure described in Example 230 and substituting the appropriate reagents, the following compounds were prepared:

| Example | Structure | HPLC (min/method*) | (M + H)$^+$ |
|---|---|---|---|
| 231 | 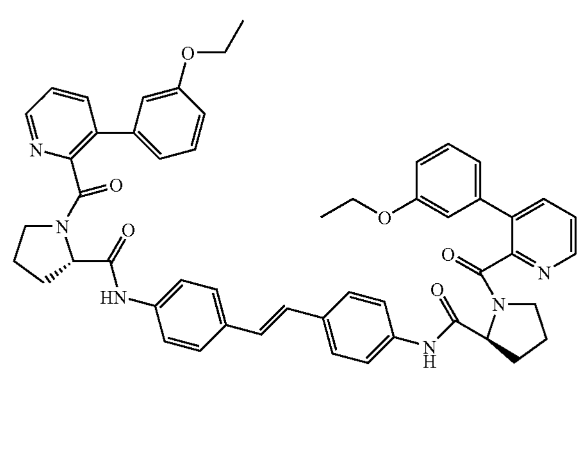 | 2.63/B | 855.5 |

-continued

| Example | Structure | HPLC (min/method*) | (M + H)+ |
|---|---|---|---|
| 232 | 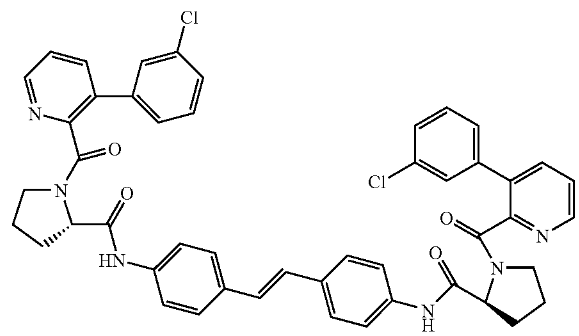 | 2.66/B | 835.2 |
| 233 | 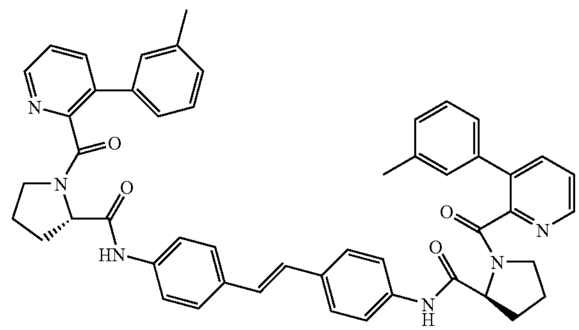 | 2.66/B | 795.4 |
| 234 | 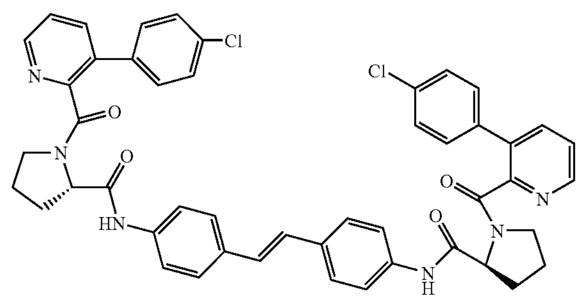 | 2.73/B | 833.1 |
| 235 | 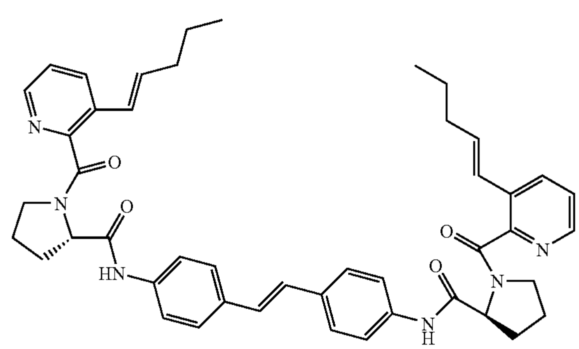 | 2.70/B | 751.5 |

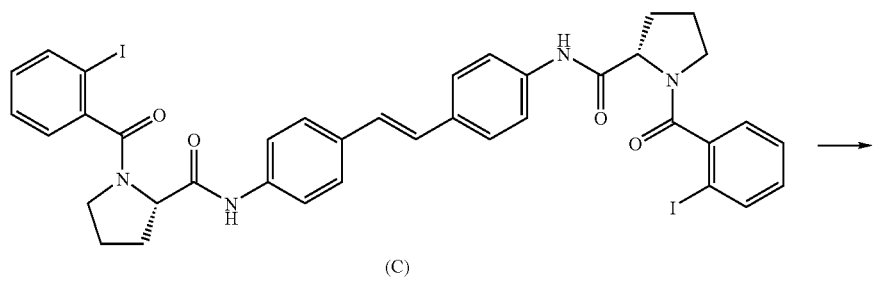

(C)

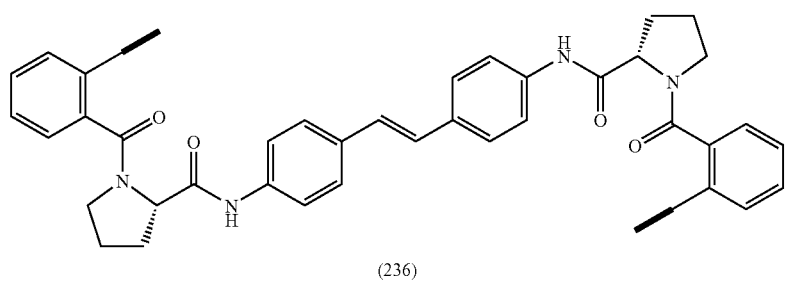

(236)

Example 236

Tetrakis(triphenylphosphine)palladium (0) (4 mg, 0.003 mmol) was added to compound (C) (prepared by substituting the appropriate reagents into Examples 23A and 23B, 75 mg, 0.087 mmol) in a 1 dram vial and the vial was purged with argon for 5 minutes before anhydrous DMF (1 mL) and ethynyl tributyltin (56 µL, 0.191 mmol) were added. The vial was sealed and the suspension was heated to 80° C. for 16 hours before it was cooled to room temperature and treated with a saturated solution of KF in water. The mixture was stirred vigorously for 2 hours at room temperature before it was diluted with ethyl acetate and saturated KF. The organic phase was separated, washed with water and brine, dried (MgSO$_4$), filtered, and concentrated. Purification of the residue by flash chromatography (gradient elution from 100% dichloromethane to 5% methanol in dichloromethane) afforded the desired product (18.4 mg, 32%) as a light orange solid: $^1$H NMR (CDCl$_3$, 500 MHz) δ 9.63 (s, 2H), 7.67-7.36 (series of m, 16H), 6.95 (s, 2H), 5.04-5.02 (m, 2H), 3.43-3.41 (m, 2H), 3.31-3.27 (m, 2H), 3.00 (s, 2H), 2.70-2.60 (m, 2H), 2.15-1.90 (serie of m, 6H); LCMS (R$_t$=1.80 min (2 min grad.), (M+H)$^+$ m/z 661.22).

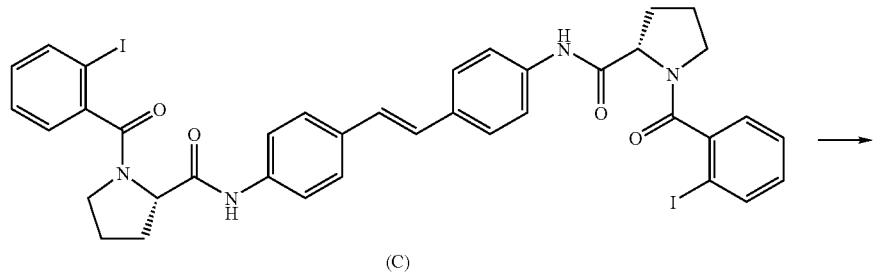

(C)

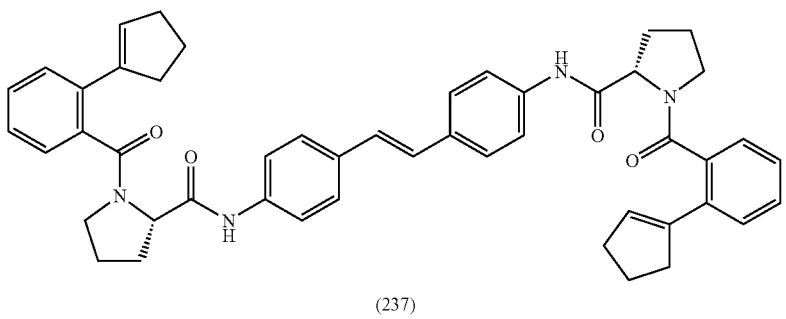

(237)

Example 237

Tetrakis(triphenylphosphine)palladium (0) (4 mg, 0.003 mmol) and cyclopenten-1-ylboronic acid (29 mg, 0.26 mmol) were added to compound (C) (prepared by substituting the appropriate reagents into Examples 23A and 23B, 75 mg, 0.087 mmol) in a 1 dram vial and the vial was purged with argon for 5 minutes before anhydrous DMF (0.7 mL) and 2M Na$_2$CO$_3$ (0.1 mL) were added. The vial was sealed and the mixture was heated to 80° C. for 16 hours before it was filtered through a nylon syringe filter and purified by HPLC using Method A* to provide the desired product (20.8 mg, 32%) as a white film; $^1$H NMR (CDCl$_3$, 500 MHz), δ 9.93 (s, 2H), 7.56-7.45 (m, 4H), 7.41-7.26 (series of m, 12H), 6.96 (s, 2H), 5.90 (s, 2H), 4.94-4.92 (m, 2H), 4.25 (s, 2H), 3.19-3.15 (m, 4H), 2.66-2.64 (m, 4H), 2.43-2.40 (m, 4H), 2.08-2.03 (m, 2H), 1.90-1.83 (m, 8H); LCMS (R$_t$=2.19 min (2 min grad.), (M+H)$^+$ m/z 745.39).

The following compounds were synthesized by coupling compound (C) (prepared by substituting the appropriate reagents into Examples 23A and 23B) with the appropriately substituted boron or tin reagent.

| Example | Structure | HPLC (min/method*) | (M + H)$^+$ |
|---|---|---|---|
| 238 | 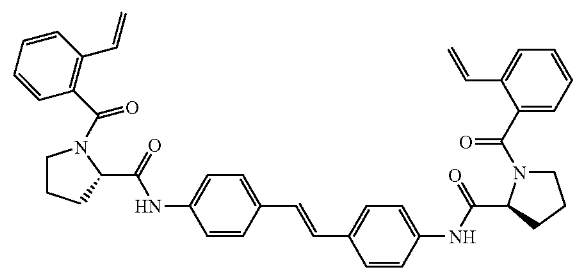 | 11.5/C | 665.2 |
| 239 | 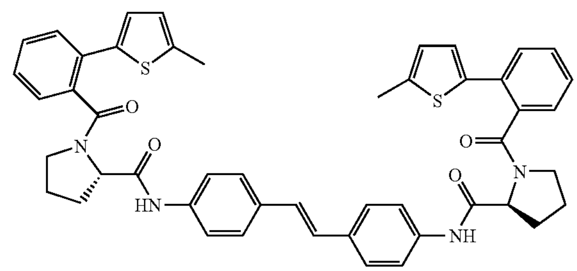 | 2.19/A | 805.4 |

Example 240A

Methanesulfonyl chloride (0.82 mL, 10.6 mmol) was added to a 0° C. mixture of Example 4 (3.0 g, 4.26 mmol) and triethylamine (0.60 mL, 10.6 mmol) in anhydrous dichloromethane (60 mL). The mixture was stirred for 1 hour at 0° C., diluted with dichloromethane, washed with 0.1N hydrochloric acid and brine, dried (MgSO$_4$), filtered, and concentrated to provide the desired product (3.55 g, 97%) as a tan solid: $^1$H NMR (DMSO-d$_6$, 500 MHz) δ 10.01 and 9.96 (2s, 2H), 7.60-7.53 (m, 8H), 7.41-7.15 (series of m, 10H), 7.13 (s, 2H), 5.29 (br s, 2H), 5.15-5.00 (2m, 4H), 4.50-4.46 (m, 2H), 3.95-3.89 (m, 2H), 3.69 (d, J=12.0 Hz, 2H), 3.19 and 3.18 (2s, 3H), 2.80-2.67 (m, 2H), 2.30-2.23 (m, 2H); LCMS (R$_t$=2.30 min, m/z 861.2).

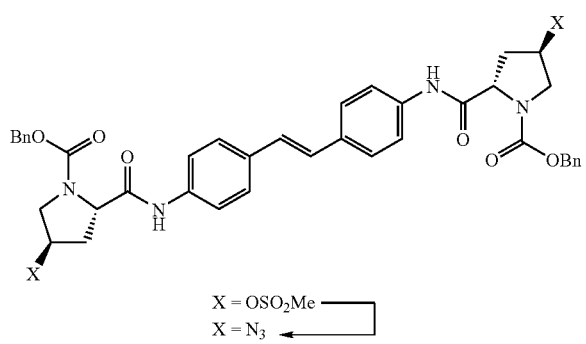

Example 240B

Sodium azide (0.46 g, 7.1 mmol) was added to a stirred solution of Example 240A (1.5 g, 1.74 mmol) in dry DMF (15 mL). The mixture was heated to 70° C. for 8 hours before the DMF was removed in vacuo. The residue was dissolved in ethyl acetate, washed sequentially with water, saturated sodium bicarbonate, and brine, dried (MgSO$_4$), filtered, and concentrated to provide the desired product. $^1$H NMR (DMSO-d$_6$, 500 MHz) δ 10.20 (s, 2H), 7.62-7.53 (m, 8H), 7.38-7.33 (m, 4H), 7.23-7.10 (m, 8H), 5.12-5.09 (m, 2H), 5.10-4.98 (2m, 2H), 4.47-4.43 (m, 4H), 3.70-3.65 (m, 2H), 3.56 (d, J=11.5 Hz, 2H), 2.40-2.35 (m, 2H), 2.24-2.20 (m, 2H); LCMS (R$_t$=2.68 min, m/z 755.3).

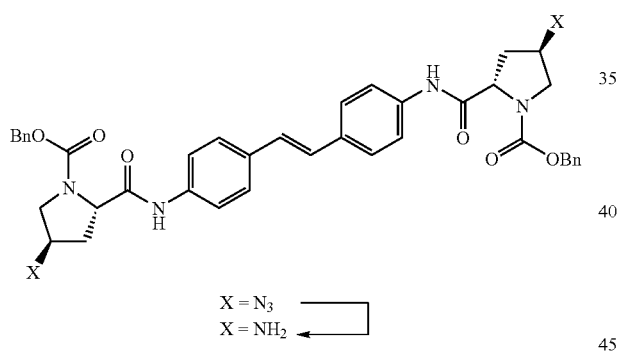

Example 240C

Tin (II) chloride dihydrate (0.81 g, 3.58 mmol) was added in one portion to a stirred solution of Example 240B (0.90 g, 1.19 mmol) in dry methanol (20 mL) at room temperature under nitrogen. The mixture was heated to 50° C. for 6 hours, diluted with ethyl acetate, washed with 1N sodium hydroxide and brine, dried (MgSO$_4$), filtered, and concentrated to provide the desired product. $^1$H NMR (DMSO-d$_6$, 500 MHz) δ 10.12 and 10.10 (2s, 2H), 7.62-7.53 (2m, 8H), 7.39-7.33 (2m, 5H), 7.24-7.10 (3m, 7H), 5.11-5.08 (m, 2H), 5.06-4.95 (2m, 2H), 4.51-4.48 (m, 1H), 4.46-4.43 (m, 1H), 3.63-3.58 (m, 4H), 3.29-3.22 (m, 2H), 2.10-2.01 (m, 4H); LCMS (R$_t$=2.00 min, m/z 702.8).

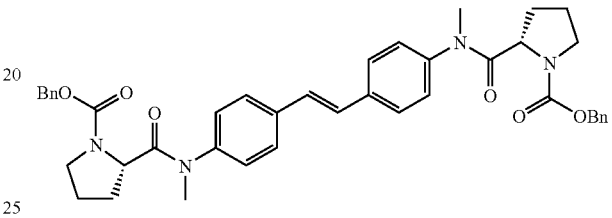

Example 244

To a solution of Example 2 (0.084 g, 0.12 mmol, 1.0 equiv) in 4 mL 1:1 DMF/THF was added NaH (60%, 0.0125 g, 0.31 mmol, 2.5 equiv) as a solid. After 10 minutes, methyl iodide (50 μL) was added by syringe. Aqueous workup followed by HPLC purification provided the desired product: $^1$H NMR (DMSO-d$_6$, 500 MHz) δ 7.53 (m, 2H), 7.52 (m, 2H), 7.46 (m, 2H), 7.35-7.46 (m, 14H), 6.90 (m, 2H), 5.06 (s, 2H), 5.05 (d, J=11.9 Hz, 2H), 4.94 (d, J=11.9 Hz, 2H), 4.42 (m, 4H), 3.17 (s, 3H), 3.07 (s, 3H), 1.69-1.91 (m, 8H). HPLC (method C) R$_t$=14.30 min.

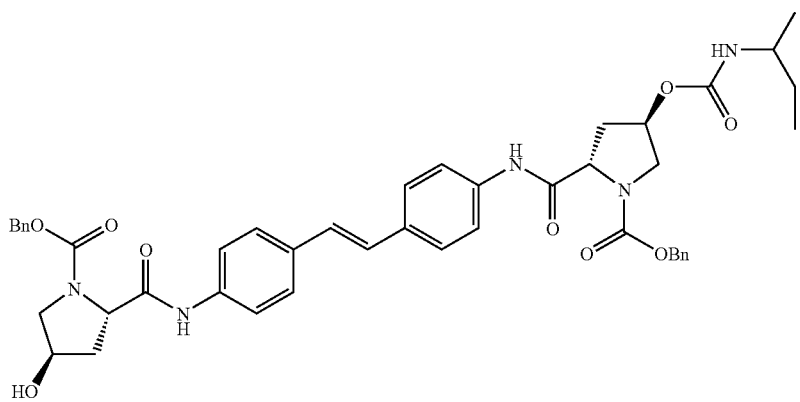

Example 245

A solution of Example 4 (0.050 g, 0.071 mmol, 1.0 equiv) in 1 mL DMF was treated with CuCl (0.014 g, 0.142 mmol, 2.0 equiv) followed by sec-butyl isocyanate (16 μL, 0.142 mmol, 2.0 equiv). The dark green solution gradually became homogeneous upon shaking at room temperature overnight. Purification by HPLC provided the desired product: $^1$H NMR (DMSO-$d_6$, 500 MHz) δ 10.19 and 10.14 (2s, 2H), 7.62 (m, 2H), 7.54 (m, 2H), 7.37 (m, 2H), 7.23 (m, 2H), 7.11 (m, 10H), 5.07 (m, 4H), 4.33-4.48 (m, 4H), 3.43-3.72 (m, 4H), 2.19 (m, 2H), 2.16 (m, 4H), 1.96 (m, 2H), 1.38 (m, 2H), 1.02 (m, 3H), 0.82 (m, 3H); LCMS ($R_t$=1.89 min, m/z 804.3).

Following the procedure described in Example 245 and substituting the appropriate reagents, the following compounds were prepared:

| Example | Structure |
|---------|-----------|
| 246 | 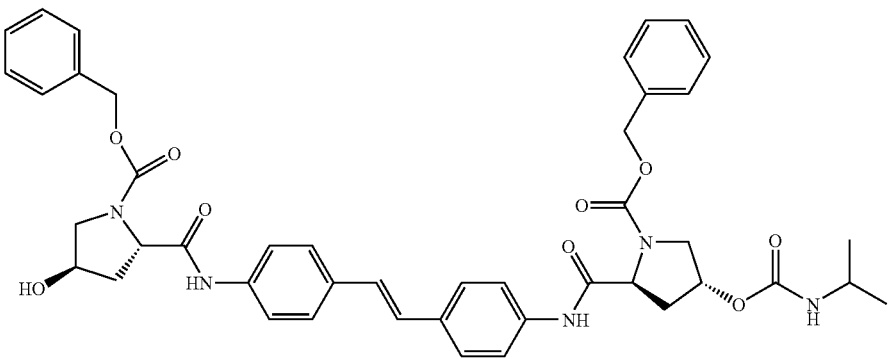 |
| 247 | 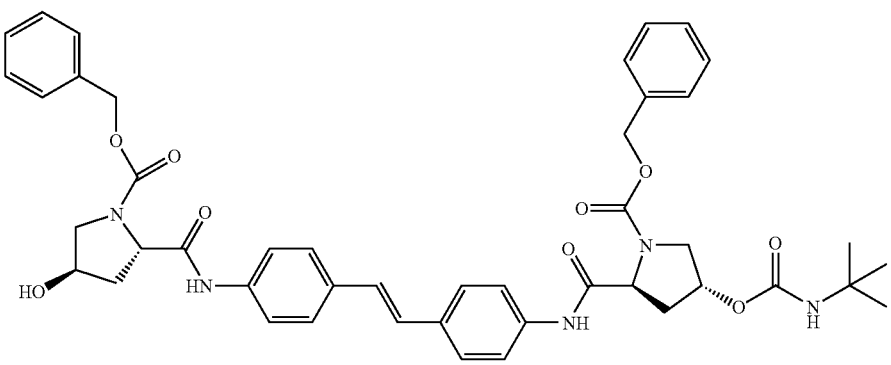 |
| 248 | 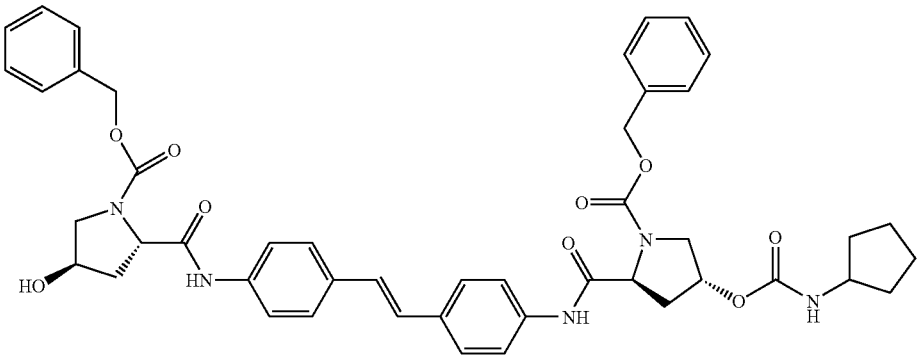 |

249

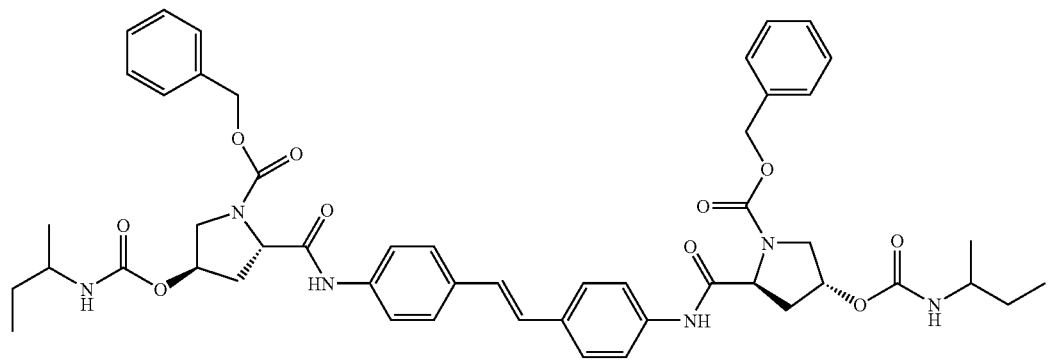

| Example | HPLC (min/method*) | (M + H)+ |
|---|---|---|
| 246 | 1.80/A | 661.2 |
| 247 | 11.5/C | 665.2 |
| 248 | 2.19/A | 745.4 |
| 249 | 2.19/A | 805.4 |

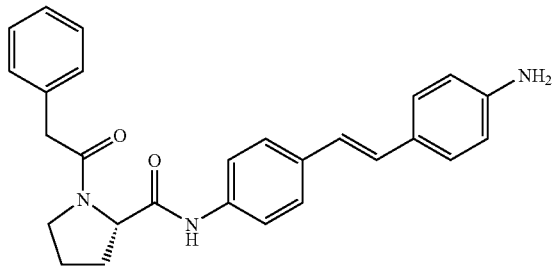

Example 250A

A solution of 4,4'-diaminostilbene (4.0 g, 19.0 mmol) in dry dimethylformamide (30 mL) was added to a stirred solution of N-phenylacetyl-L-proline (4.44 g, 19.0 mmol), diisopropylcarbodiimide (DIC, 2.3 g, 19.0 mmol) and 1-hydroxybenzotriazole (2.57 g, 19.0 mmol) in dry DMF (30 mL) under nitrogen at room temperature. The mixture was stirred for 20 hours at room temperature, diluted with ethyl acetate, washed with saturated sodium bicarbonate and brine, dried (MgSO$_4$), filtered, and concentrated. The residue was preabsorbed onto silica gel, eluted through a plug of silica gel (gradient elution from 30% dichloromethane in ethyl acetate to 70% dichloromethane in ethyl acetate), concentrated to ¼ of its original volume, and collected by filtration to provide a light tan solid. Three additional crops afforded an additional 4.06 g (50.2%) of the desired product. An analytically-pure sample was obtained after reverse-phase HPLC: $^1$H NMR (DMSO d$_6$, 400 MHz) δ 10.31 and 10.07 (rotomeric, 2s, 1H), 7.63-7.59 (m, 2H), 7.55-7.50 (m, 4H), 7.32-7.17 (series of m, 5H), 7.12-7.04 (m, 4H), 4.66 and 4.44 (rotomeric, 2dd, J=8.4, 2.8 Hz and 8.6, 3.9 Hz, 1H), 3.70 (s, 2H), 3.69-3.37 (m, 2H), 2.38-2.25 and 2.21-2.07 (2m, 1H), 2.06-1.81 (2m, 3H); LC/MS (R$_t$=1.69 min, m/z 426.3).

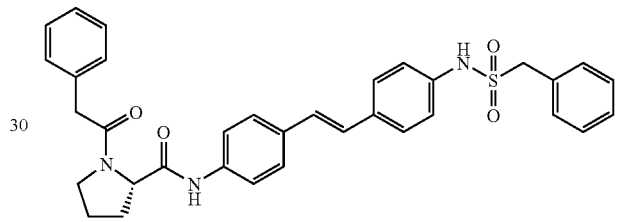

Example 250B

α-Toluenesulfonyl chloride (22.4 mg, 0.12 mmol) was added to a solution of Example 250A (50 mg, 0.12 mmol) and diisopropylethylamine (0.1 mL) in dry pyridine (1 mL) at room temperature under nitrogen. The mixture was stirred for 20 hours at room temperature and purified by HPLC to provide the desired product (31.9 mg, 47.0) as a tan solid: $^1$H NMR (DMSO-d$_6$, 400 MHz) δ 10.27 and 10.05 (2s, 1H), 9.91 and 9.90 (2s, 1H), 7.59-7.52 (m, 6H), 7.36-7.11 (series of m, 14H), 4.70-4.43 (2m, 1H), 4.48 (s, 2H), 3.71 (s, 2H), 3.70-3.45 (m, 2H), 2.20-1.90 (3m, 4H); LC/MS (R$_t$=2.46 min, m/z 580.4).

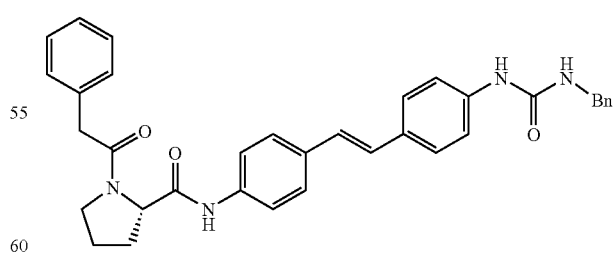

Example 250C

Benzyl isocyanate (14.4 μL, 0.12 mmol) was added to a solution of Example 250A (50 mg, 0.12 mmol in dry pyridine (1 mL) at room temperature under nitrogen. The mixture was

155 stirred for 20 hours at room temperature and collected by filtration to provide the desired product (31.4 mg, 47.8%) as an off-white solid: $^1$H NMR (DMSO-$d_6$, 400 MHz) δ 10.25 and 10.3 (2s, 1H), 8.64 (s, 1H), 7.62-7.17 (series of m, 18H), 7.09-7.00 (m, 2H), 6.65-6.62 (m, 1H), 4.67-4.44 (2m, 1H), 4.32 (d, J=5.9 Hz, 2H), 3.71 (s, 2H), 3.70-3.58 (m, 2H), 2.16-1.89 (3m, 4H); LC/MS ($R_t$=2.49 min, m/z 559.5).

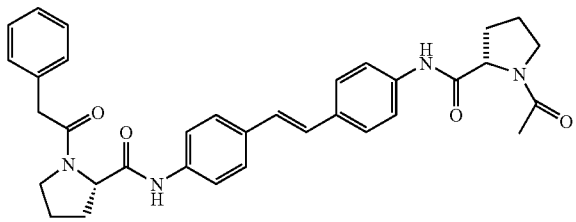

156

Example 251

A solution of Example 250A (0.050 g, 0.12 mmol, 1.0 equiv) in 1 mL of DMF was added to a premixed suspension of N-acetylproline (0.055 g, 0.36 mmol, 3.0 equiv) and DCC-resin (1.9 mmol/g, 0.18 g, 3.0 equiv) in 1 mL DMF. The mixture was stirred vigorously at room temperature for 20 hours then filtered to remove the resin. The filtrate was purified by reverse-phase preparative HPLC to provide the desired product (38.4 mg, 58%) as a tan solid: $^1$H NMR (DMSO-$d_6$, 400 MHz) δ 10.27, 10.20, 10.04 and 10.00 (rotomeric, 4s, 2H), 7.63-7.50 (m, 8H), 7.33-7.17 (m, 5H), 7.12-7.09 (m, 2H), 4.66-4.15 (rotomeric, 4m, 2H), 3.71 (s, 2H), 3.68-3.38 (m, 4H), 2.36-1.80 (series of m, 8H), 2.00 (s, 3H); LCMS ($R_t$=2.20 min, m/z 565.5).

Following the procedures described in Examples 250 and 251 and substituting the appropriate reagents, the following compounds were prepared. Example 252 was prepared using the BOC-protected proline. The BOC group was removed prior to HPLC purification using HCl in diethyl ether.

| Example | Structure | HPLC (min/method*) | (M + H)$^+$ |
|---|---|---|---|
| 252 | 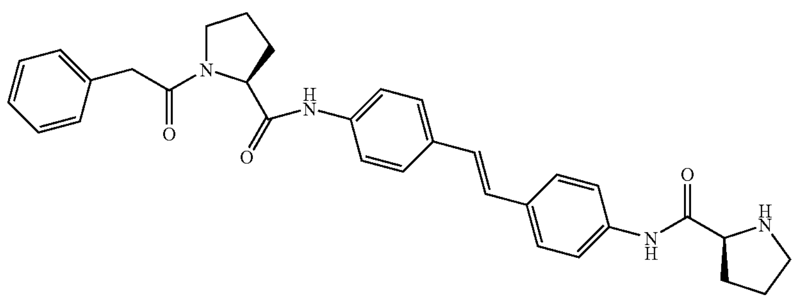 | 1.91/B | 523.3 |
| 253 | 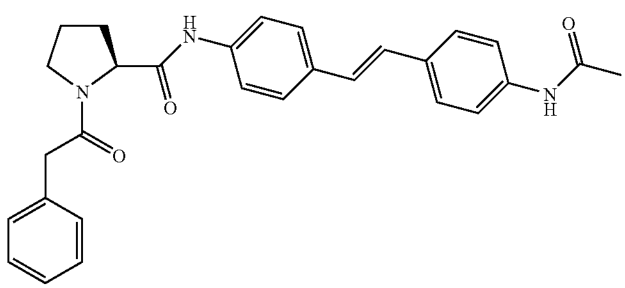 | 2.46/B | 469.3 |
| 254 | 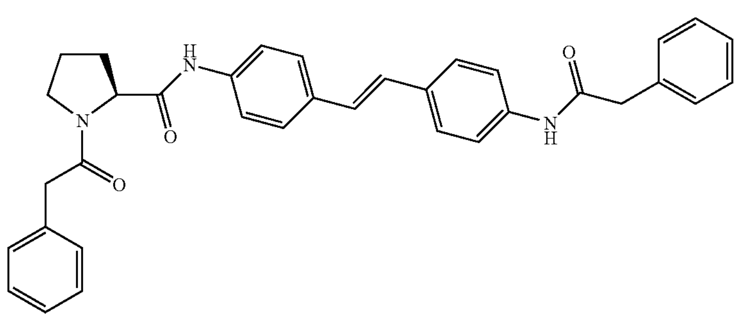 | 2.80/B | 544.4 |

| Example | Structure | HPLC (min/method*) | (M + H)+ |
|---|---|---|---|
| 255 | 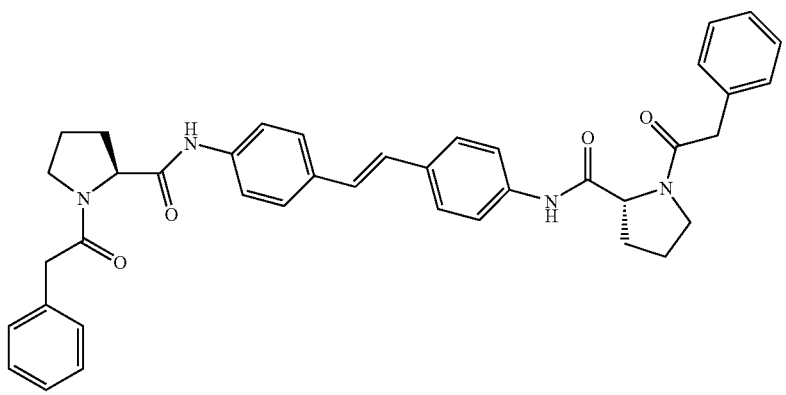 | 2.50/B | 641.4 |
| 256 | 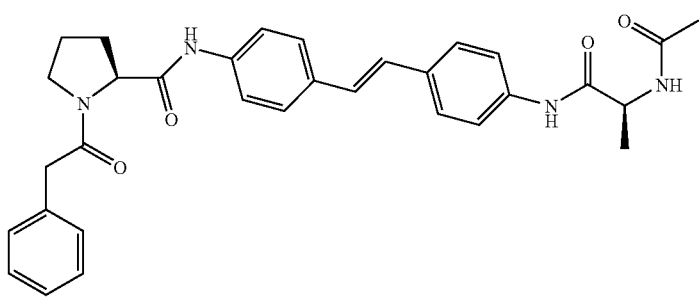 | 2.41/B | 539.4 |
| 257 | 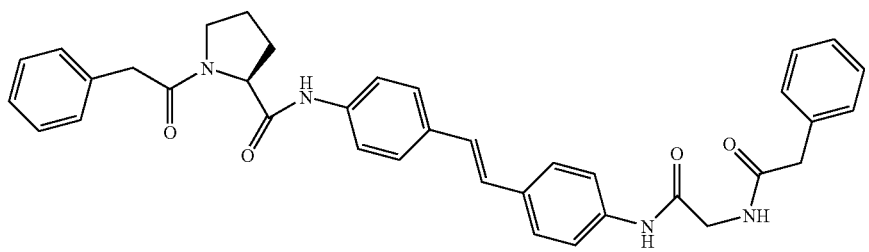 | 2.34/B | 601.5 |
| 258 | 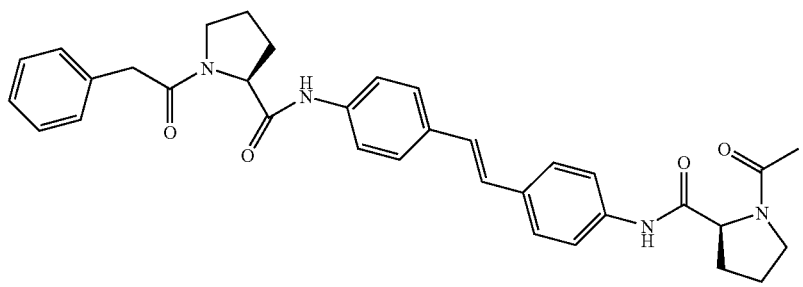 | 2.20/B | 565.5 |

| Example | Structure | HPLC (min/method*) | (M + H)+ |
|---|---|---|---|
| 259 | 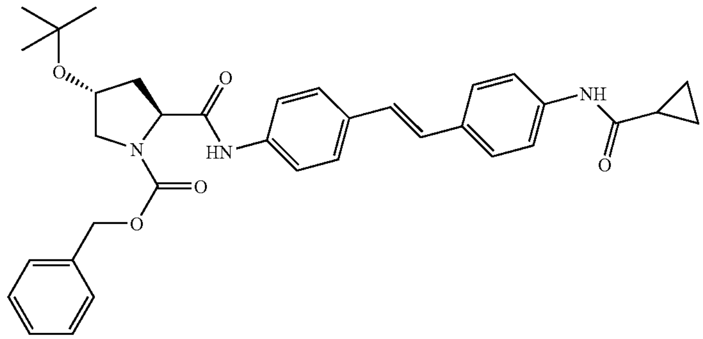 | 3.41 | 604.29 |
| 260 | 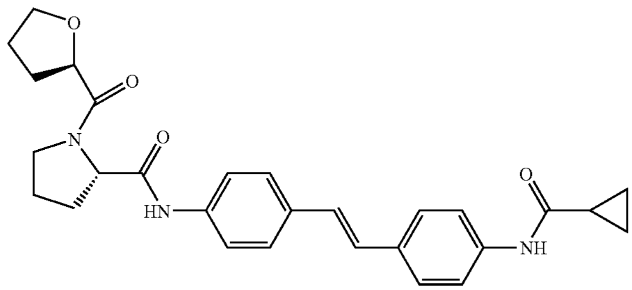 | 7.68/C | 474.2 |
| 261 | 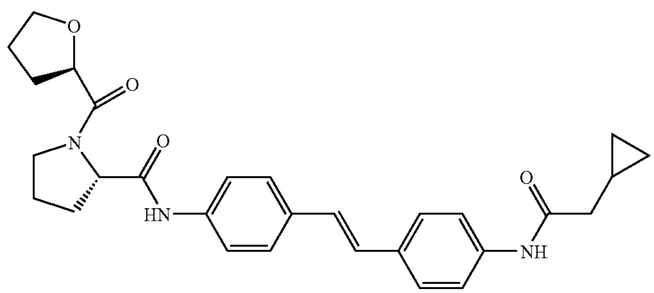 | 1.67/A | 488.2 |
| 262 | 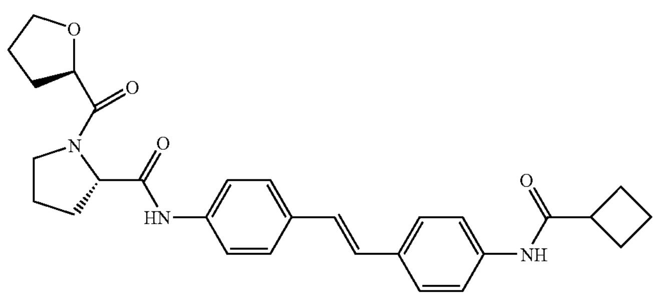 | 1.7/A | 488.1 |
| 263 | 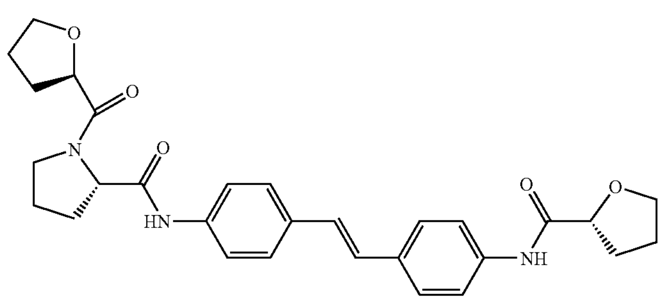 | 7.77/C | 504.2 |

-continued

| Example | Structure | HPLC (min/method*) | (M + H)+ |
|---|---|---|---|
| 264 | 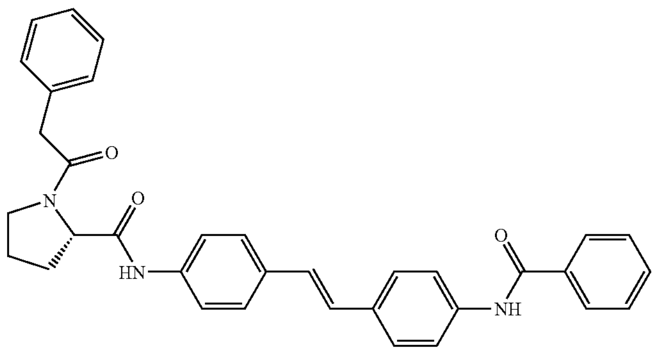 | 1.75/A | 530.2 |
| 265 | 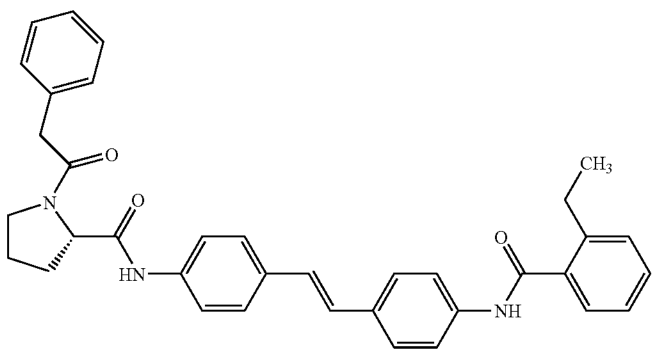 | 2.09/A | 558.2 |
| 266 | 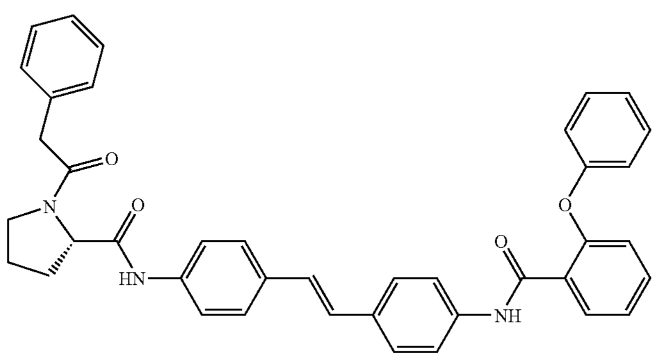 | 2.09/A | 622.2 |
| 267 | 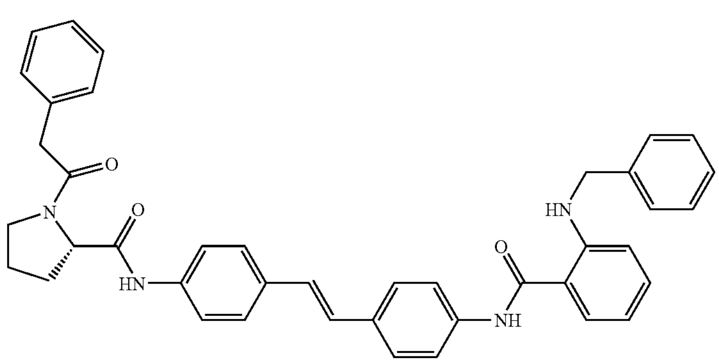 | 1.97/A | 635.4 |

| Example | Structure | HPLC (min/method*) | (M + H)+ |
|---|---|---|---|
| 268 | 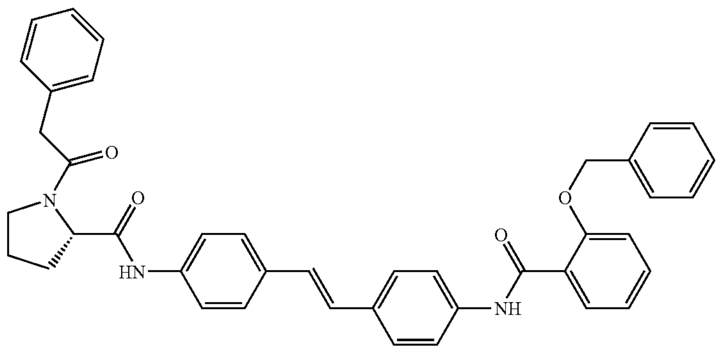 | 2.15/A | 636.2 |
| 269 | 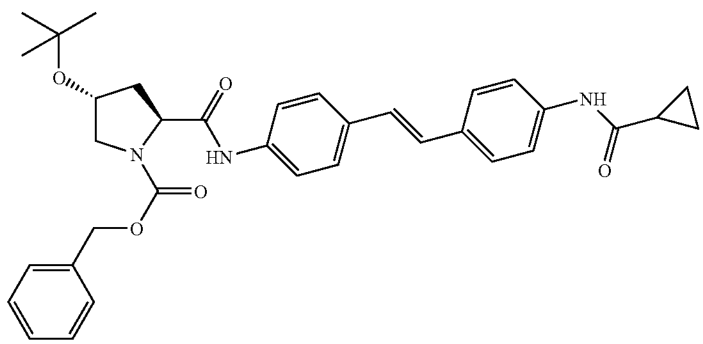 | 3.41/G | 604.29 |
| 270 | 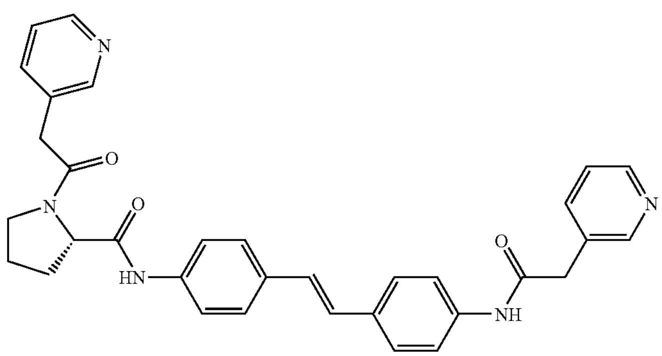 | 1.02/A | 546.3 |
| 271 | 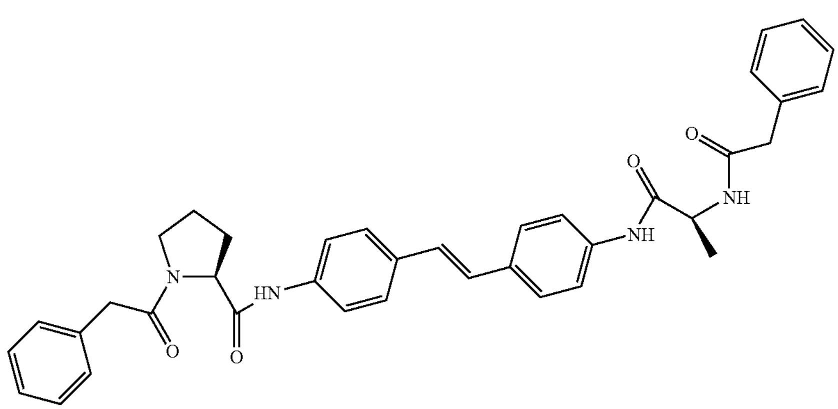 | 2.38/B | 615.4 |

-continued
| Example | Structure | HPLC (min/method*) | (M + H)+ |
|---|---|---|---|
| 272 | 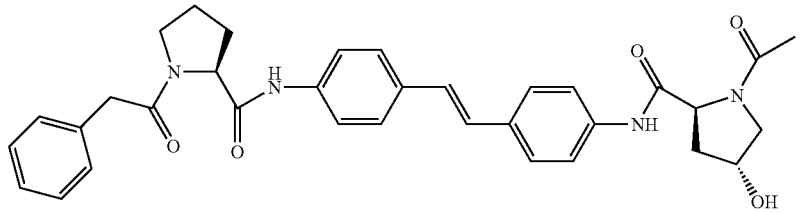 | 2.00/B | 581.4 |
| 273 | 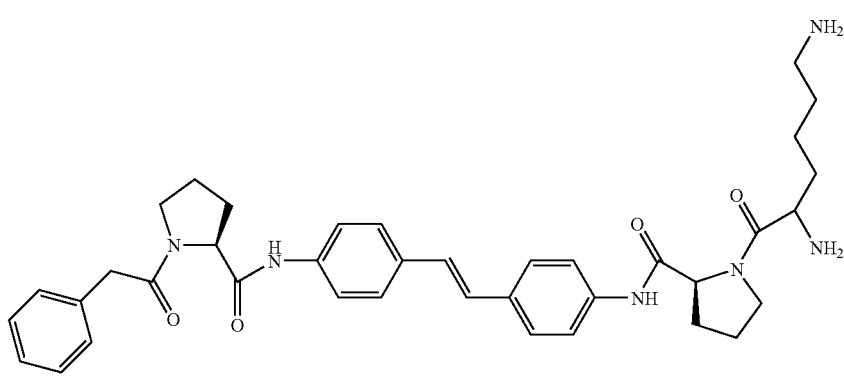 | 1.78/B | 651.4 |
| 274 | 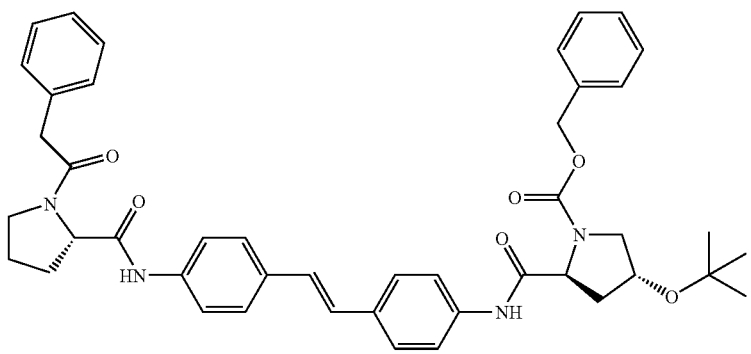 | 1.83/A | 729.4 |
| 275 | 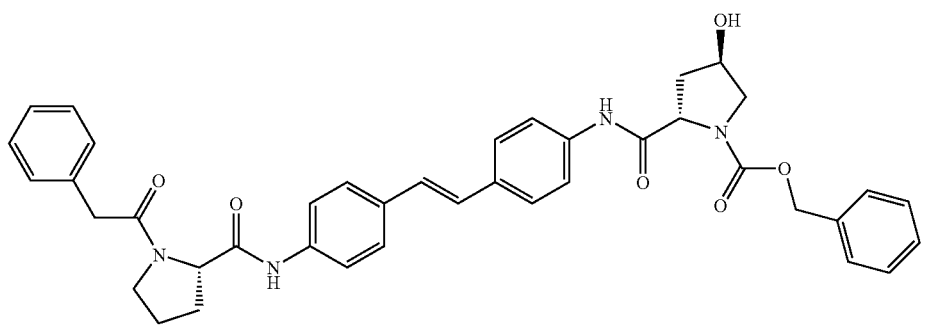 | 1.73/A | 673.3 |

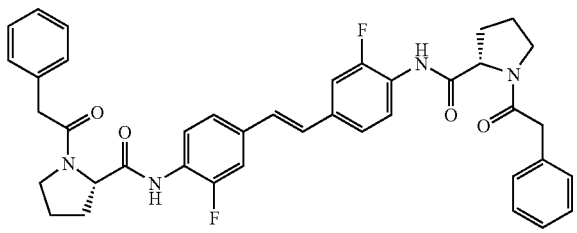

Example 276

4-Bromo-2-fluoroaniline (1.0 g, 5.3 mmol) was treated with N-phenylacetylproline (1.3 g, 5.52 mmol) and EEDQ as described in Example 1 to provide 2.1 g of N-(4-bromo-2-fluorophenyl)-1-(phenylacetyl)-L-prolinamide. A portion of this intermediate (0.51 g, 1.26 mmol) was suspended in 5 mL toluene and treated with 0.38 mL of trans-1,2-bis(tri-n-butyl-stannyl)ethylene (0.69 mmol, 0.55 equiv) followed by 0.029 g of $Pd(PPh_3)_4$. The reaction was sealed under nitrogen and heated to 100° C. for 2 hours. The mixture was then cooled to room temperature and stirred vigorously with an equal volume of aqueous saturated KF for 2 hours. Filtration through diatomaceous earth (Celite®) followed by extractive workup and HPLC purification provided the desired product. $^1$H NMR (DMSO-$d_6$, 500 MHz, mixture of rotamers) δ 10.10 and 9.86 (s, 1H), 7.94 and 7.81 (m, 1H), 7.52 (m, 1H), 7.20-7.35 (m, 16H), 4.82 and 4.64 (m, 2H), 3.65 (m, 4H), 1.94-2.11 (m, 8H); LCMS (Rt=1.76 min, m/z 677.34).

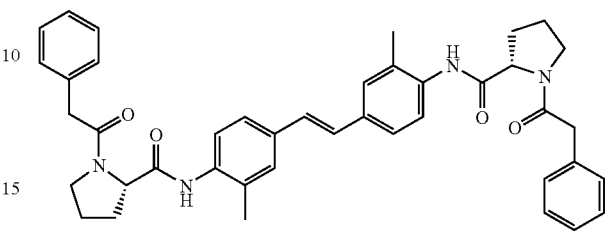

Example 277

The desired product was prepared by substituting 4-bromo-2-methylaniline for 4-bromo-2-fluoroaniline in Example 276: LCMS ($R_t$=1.71 min, m/z 669.3).

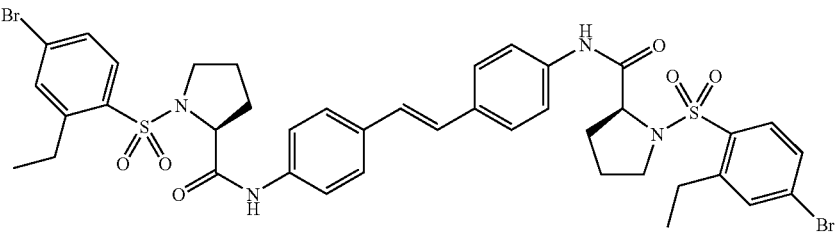

Example 278

To a solution of Example 23A (0.10 mmol; 0.05 g) in 3 mL DMF was added diisopropylethylamine (0.52 mmol; 0.91 mL) and 4-bromo-2-ethylbenzenesulfonyl chloride (0.26 mmol; 0.078 g). After three hours the reaction mixture was concentrated under reduced pressure providing a brown wax which was redissolved in 5 mL methanol and subjected to sonication. The resultant brown solid was collected by filtration and dried to provide 0.067 g of the desired product in 71% yield: $^1$H NMR (500 MHz, DMSO-$d_6$) δ 1.19 (t, J=7.48 Hz, 6H), 1.88 (m, 2H), 2.01 (m, 4H), 2.21 (m, 2H), 2.98 (m, 4H), 3.38 (m, 2H), 3.47 (m, 2H), 4.40 (dd, J=8.39, 3.81 Hz, 2H), 7.10 (s, 2H), 7.50 (m, 8H), 7.58 (dd, J=8.55, 2.14 Hz, 2H), 7.67 (d, J=2.14 Hz, 2H), 7.80 (d, J=8.24 Hz, 2H), 10.03 (s, 2H); LC/MS ($R_t$=10.41 min, m/z 897.2).

Following the procedure described in Example 280 and substituting the appropriate reagents, the following compounds were prepared:

| Example | Structure | HPLC (min/method*) | (M + H)$^+$ |
|---|---|---|---|
| 279 | 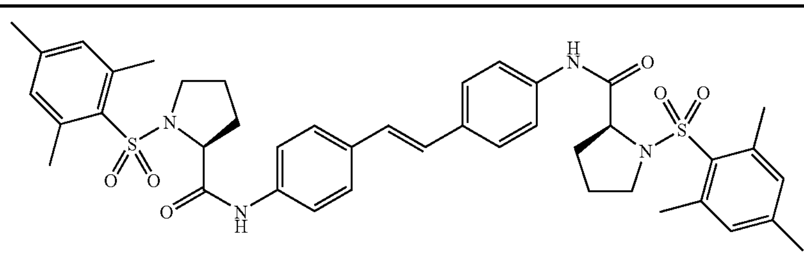 | 9.17/H | 769.5 |

-continued
| Example | Structure | HPLC (min/method*) | (M + H)+ |
|---|---|---|---|
| 280 | 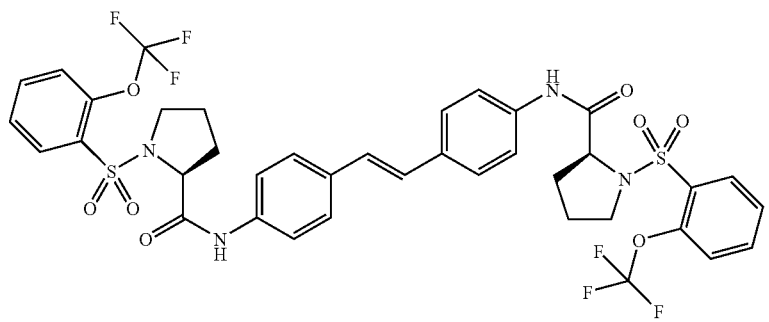 | 8.35/H | 853.3 |
| 281 | 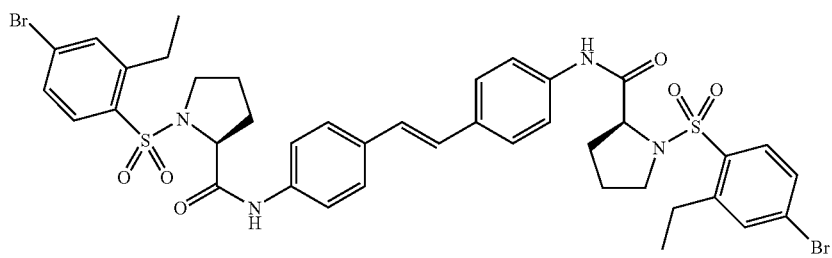 | 10.41/H | 897.2 |
| 282 | 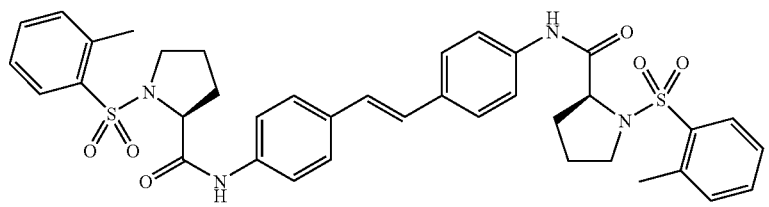 | 9.13/H | 713.3 |
| 283 | 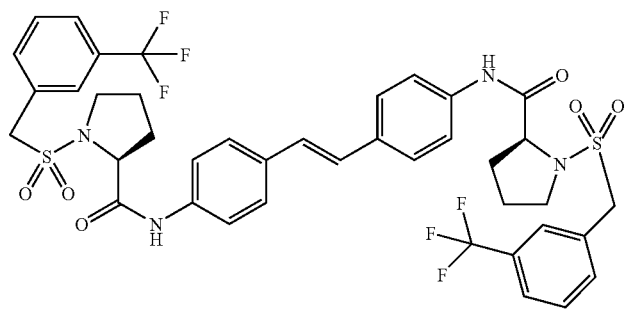 | 9.7/H | 849.4 |
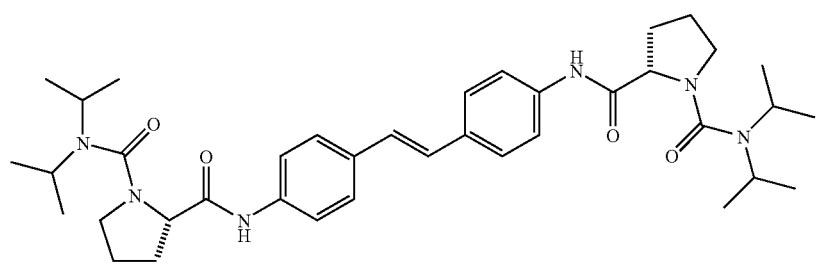

Example 284

A solution of Example 23A (80 mg) and diisopropylcarbamyl chloride (45 mg) were dissolved in dichloromethane (2 mL), treated slowly with triethylamine (164 µL), stirred for 16 hours, and concentrated. The concentrate was purified by HPLC to provide 11.9 mg of the desired product: MS m/z: 659.40 (HPLC retention time: 3.58 min). $^1$H NMR (CD$_3$OD): δ 9.57 (s, 2H), 7.36 (d, J=8.8, 4H), 7.17 (d, J=8.8, 4H), 6.75 (s, 2H), 4.74 (m, 2H), 3.71 (m, 4H), 3.57 (m, 2H), 3.37 (m, 2H), 2.11 (m, 6H), 1.89 (m, 2H), 1.30 (m, 24H).

Following the procedure described in Example 284 and substituting the appropriate reagents, the following compounds were prepared:

| Example | Structure | HPLC (min/method*) | (M + H)$^+$ |
|---|---|---|---|
| 285 | 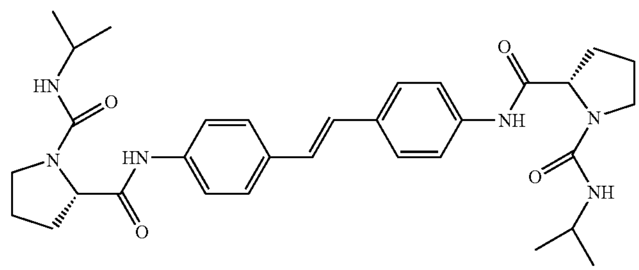 | 1.54 | 575.36 |
| 286 | 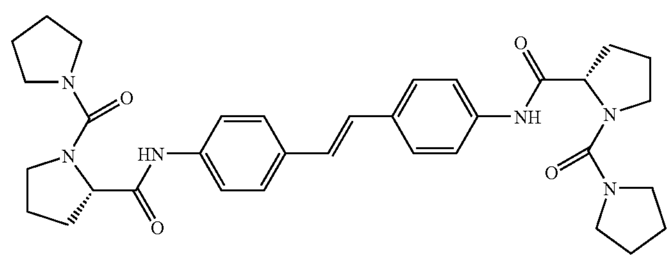 | 2.87/G | 599.36 |
| 287 | 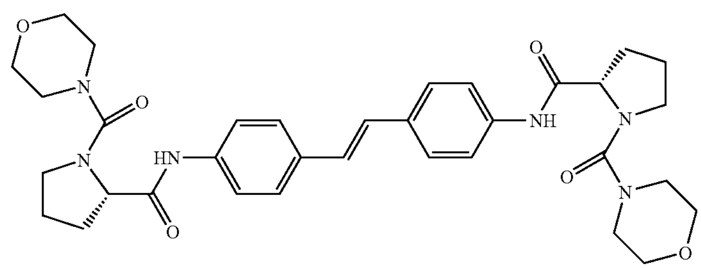 | 2.49/G | 631.32 |
| 288 | 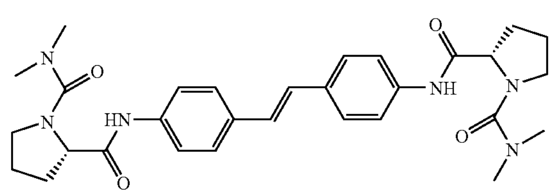 | 2.58/G | 547.31 |
| 289 | 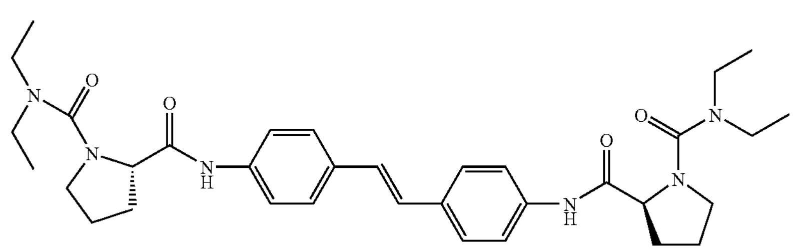 | 3.12/G | 603.39 |

| Example | Structure | HPLC (min/method*) | (M + H)+ |
|---|---|---|---|
| 290 | 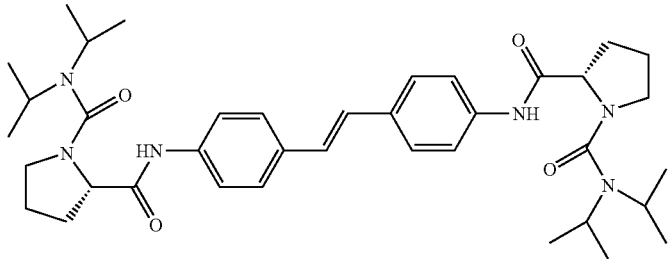 | 3.58/G | 659.40 |

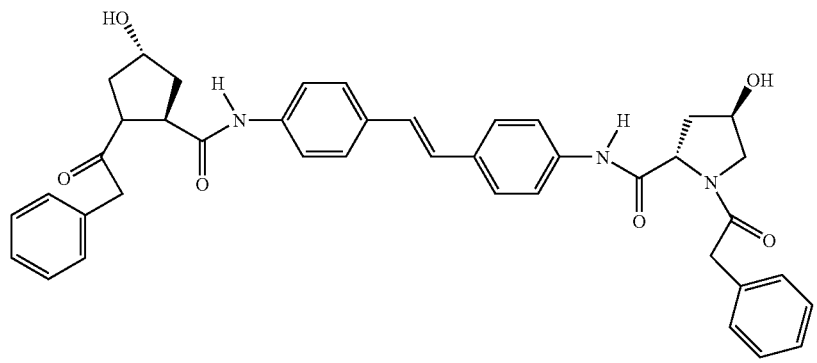

Example 291

A mixture of polystyrene based aldehyde resin (polymer labs, 3 g, 3.6 mmol), 4,4'-diaminostilbene (7.56 g, 36 mmol), sodium triacetoxyborohydride (7.63 g, 36 mmol), acetic acid (3 mL) in DMF (210 mL), and trimethylorthoformate (90 mL) was shaken at 200 rpm for 72 hours, filtered, washed with DMF (5 mL), methanol (5 mL), THF (50 mL), and dichloromethane (50 mL), and dried for 2 hours to give 3.76 g (99% loading) of diaminostilbene loaded resin 1.

To a solution of FMOC-4-O-tert-butyl-L-proline (1.928 g, 6 mmol) in dichloromethane was added oxalyl chloride in dichloromethane (3 mL, 2M solution) followed by DMF (0.1 mL). The mixture was shaken at 200 rpm for 30 minutes, treated with diisopropylethylamine (1.4 mL, 8 mmol), shaken for 5 minutes, atreated with 500 mg (0.6 mmol) of resin 1, and shaken for 48 hours. The mixture was filtered, washed with DMF (25 mL), methanol (25 mL), THF (25 mL), and dichloromethane (25 mL), and dried for 2 hours to give 864 mg of resin, which was shaken in dichloromethane/piperidine (4:1, 20 mL) solution for 6 hours. The mixture was filtered, washed with DMF (25 mL), methanol (25 mL), THF (25 mL), and dichloromethane (25 mL), and dried for 2 hours to give 645 mg of resin 2.

Resin-bound stilbene derivative 2 (645 mg, 0.6 mmol) in dichloromethane was shaken with phenylacetyl chloride (0.8 mL, 6 mmol) and diisopropylethylamine (1.4 mL, 8 mmol) for 24 hours, filtered, washed with DMF (25 mL), methanol (25 mL), THF (25 mL), and dichloromethane (25 mL), and dried for 2 hours to give 925 mg of resin 3. Resin 3 was shaken with 60% TFA in dichloromethane (4 mL) for 2 hours and filtered. The filtrate was concentrated and dissolved in 2 mL methanol and purified by prep. HPLC using water/methanol to provide 112 mg (30% yield) of the desired product as a white solid. MS (ESI) m/z=672.8 (MH+); HPLC rt: 2.1 min, Purity (>95%).

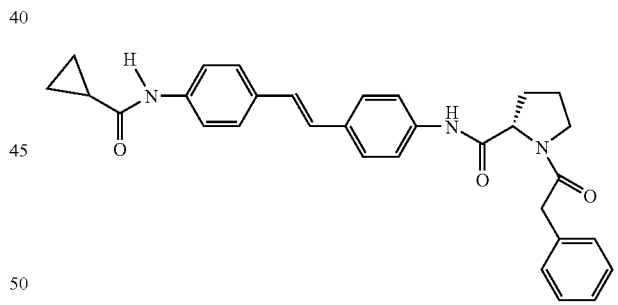

Example 292

A mixture of resin 1 from Example 291 (250 mg, 0.3 mmol), phenylacetyl-L-proline (350 mg, 1.5 mmol), PyBOP (780 mg, 1.5 mmol) and diisopropylethylamine (0.7 mL, 4 mmol) in dichloromethane was shaken for 48 hours and filtered. The resin was washed with DMF (25 mL), methanol (25 mL), THF (25 mL), and dichloromethane (25 mL) and dried for 2 hours to give 380 mg of resin 5. Resin 5 was shaken with cyclopropanecarbonyl chloride (0.2 mL, 2 mmol) and diisopropylethylamine (0.7 mL, 4 mmol) in dichloromethane for 24 hours, filtered, washed with DMF (25 mL), methanol (25 mL), THF (25 mL), and dichloromethane (25 mL) and dried for 2 hours to give 400 mg of resin 6. Resin 6 was shaken with TFA/dichloromethane (3:2, 3 mL) for 2 hours, and filtered. The filtrate was concentrated and purified by prep. HPLC to provide 23 mg (15% yield) of the desired product as a white solid. MS (ESI) m/z=493.60 (MH+); HPLC rt: 2.1 min, Purity (>95%). $^1$H NMR (DMSO-$d_6$) δ 9.83 (s, 1H), 9.75 (s, 1H), 7.50-7.10 (m, 13H), 6.90 (br s, 2H), 4.55 (m, 1H), 3.66 (m, 3H), 3.50 (m, 2H), 2.06 (m, 1H), 1.91 (m, 1H), 2.75 (m, 1H), 0.87 (m, 2H), 0.72 (m, 2H).

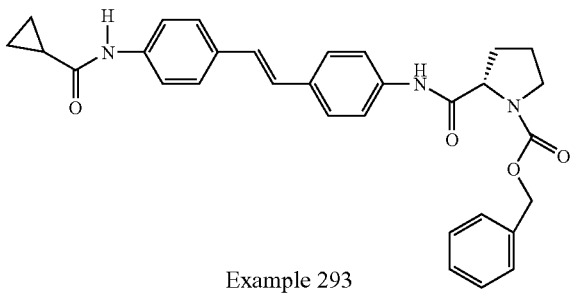

Example 293

CBZ-L-proline (375 mg, 1.5 mmol) was coupled to resin 1 from Example 291 (250 mg, 0.3 mmol) and then treated with cyclopropanecarbonyl chloride (0.2 mL, 2 mmol) as described above in the synthesis of Example 292 to provide 23 mg (15% yield) of the desired product as a white solid. MS (ESI) m/z=510.18 (MH+); HPLC rt: 2.2 min, Purity (>95%).

Example 294

To a stirred solution of 4,4'-diaminostilbene (0.21 g, 1 mmol), FMOC-4-O-tert-butyl-L-Proline (643 mg, 2 mmol) and diisopropylethylamine (0.7 mL, 4 mmol) in DMF was added HATU (1.71 g, 4.5 mmol). The mixture was stirred for 48 hours and concentrated under high vacuum. The residue was dissolved in dichloromethane (20 mL), treated with piperidine (4 mL), stirred for 24 hours, and concentrated. The residue was partitioned between water and dichloromethane (30 mL each). The organic layer was separated, dried (sodium sulfate), filtered, and triturated with diethyl ether (50 mL) until a precipitate formed. The precipitate was collected by filtration and dried to give 0.33 g (60% yield) of the intermediate which was dissolved in dichloromethane (10 mL) and stirred with benzyl chloroformate (0.29 mL, 2 mmol) and diisopropylethylamine at room temperature for 2 hours. The mixture was poured into saturated aqueous bicarbonate solution and stirred for 10 minutes. The organic layer was separated, dried (sodium sulfate), filtered, and concentrated to give 500 mg of crude product. The crude product was purified by preparative liquid chromatography using methanol/water to give 102 mg (12.5% yield) of the desired product as a white solid. MS (ESI) m/z=817.23 (MH+); HPLC rt: 2.30 min, Purity (>95%). $^1$H NMR (DMSO-$d_6$) δ 10.17 (s, 1H), 10.14 (s, 1H), 7.50-7.10 (m, 20H), 5.08 (m, 4H), 4.96 (m, 4H), 4.40 (m, 4H), 3.65 (m, 1H), 3.28 (m, 1H), 2.10 (m, 2H), 1.16 (s, 9H) and 1.14 (s, 9H).

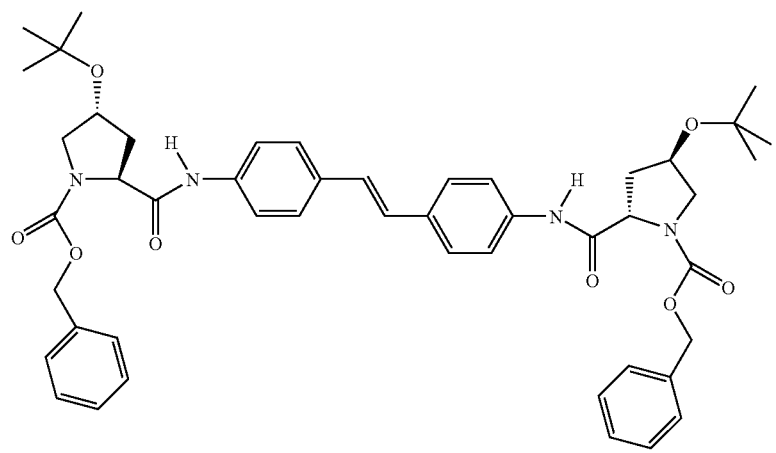

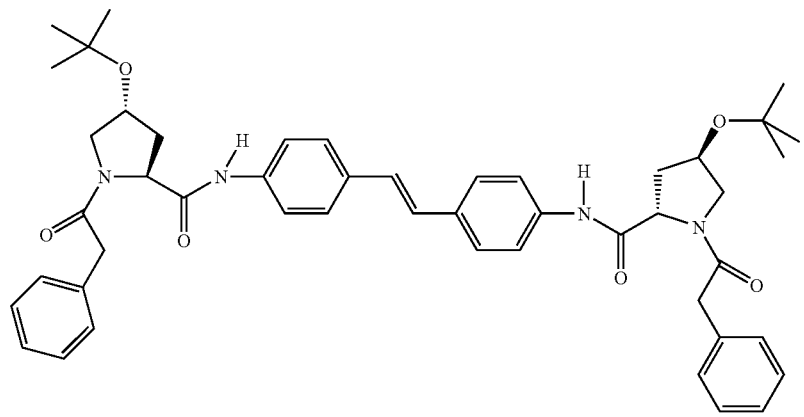

Example 295

4,4'-Diaminostilbene (0.21 g, 1 mmol) was treated with FMOC-4-O-tert-butyl-L-Proline and then with phenylacetyl-chloride as described in Example 294 to provide 94 mg (12% yield) of the desired product as a white solid. MS (ESI) m/z=785.26 (MH+); HPLC rt: 2.30 min, Purity (>95%)

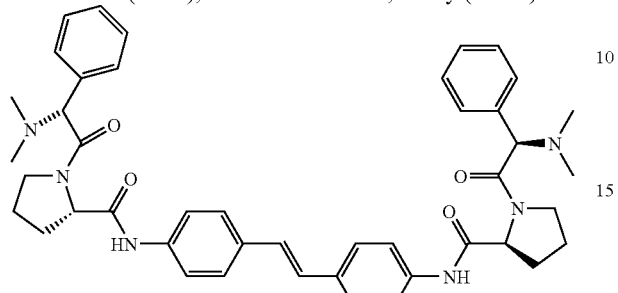

Example 296

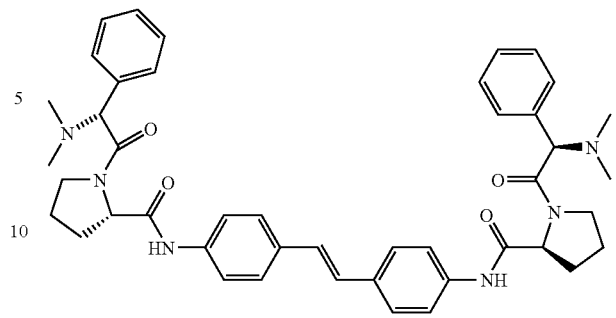

Example 296B

The desired product was prepared by substituting Example 296A for 2,5-dimethoxybenzoic acid in Example 23B. LCMS ($R_t$=1.67 min, m/z 727.26, 3 min grad, 0 to 100% B). Purity: 97.0%

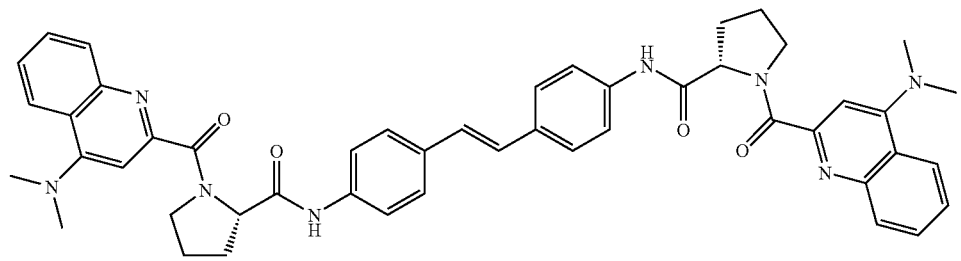

Example 297

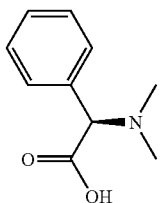

Example 296A

A suspension of 10% palladium on carbon (300 mg) in methanol (2 mL) was added to a solution of D-phenylgylcine (1.51 g, 10.0 mmol), 37% formalin (5 mL), and 1N hydrochloric acid (10 mL) in methanol (30 mL) at room temperature under nitrogen. The reaction vessel was then evacuated and charged with hydrogen using a balloon three times before the mixture was allowed to stir for 4 hours at room temperature. The mixture was filtered through diatomaceous earth (Celite®) and concentrated. The residue was dissolved in a minimal amount of methanol and triturated with diethyl ether to provide the desired product as a white solid (1.62 g, 75%) after filtration. $^1$H NMR (CH$_3$OH-d$_4$, 300 MHz) δ 7.55 (s, 5H), 5.14 (s, 1H), 3.08 (br s, 3H), 2.62 (br s, 3H); LCMS ($R_t$=0.54 min, m/z 180.1, 3 min grad, 0 to 50% B). $α_D$=−119.54° (c=10 mg/mL in H$_2$O, λ=589 nm, 50 mm cell).

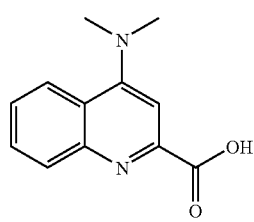

Example 297A

A mixture of 4-bromoquinoline-2-carboxylic acid (synthesized according to *Tetrahedron Lett.* 2001, 42, 4849-4852) (60 mg, 0.238 mmol), dimethylamine (5.25 mL, 40 wt % in water) and DMSO (1 mL) was microwaved at 100° C. for 2.5 hours. All volatile components were removed in vacuo and the residue was dissolved in methanol/DMF (2:1, 8 mL) and purified by preparative HPLC to provide the desired product as a yellow solid (54 mg, 100% yield). $^1$H NMR (DMSO-d$_6$, 500.03 MHz): δ 8.39 (d, 1H, J=8.5 Hz), 8.27 (d, 1H, J=7.6 Hz), 7.94 (t, 1H, J=7.2 Hz), 7.64 (t, 1H, J=7.2 Hz), 7.35 (s, 1H), 3.50 (s, 6H). LC/MS-Method B [$R_t$=0.70 min, m/z (M+H)$^+$=217.06].

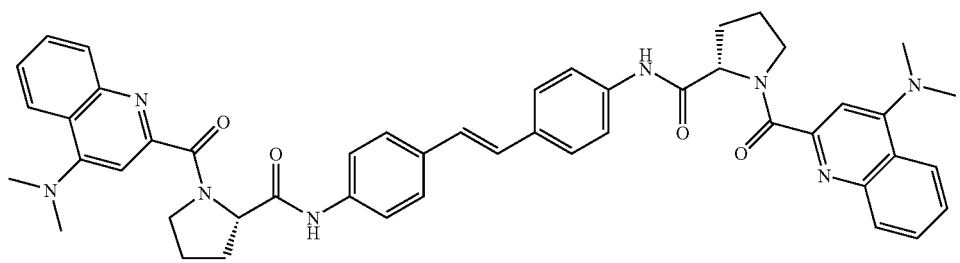

Example 297B

The desired product was prepared by substituting Example 297A for 2,5-dimethoxybenzoic acid in Example 23B. HPLC rt: 1.82 (method A); MS 801.46 (M+H)+.

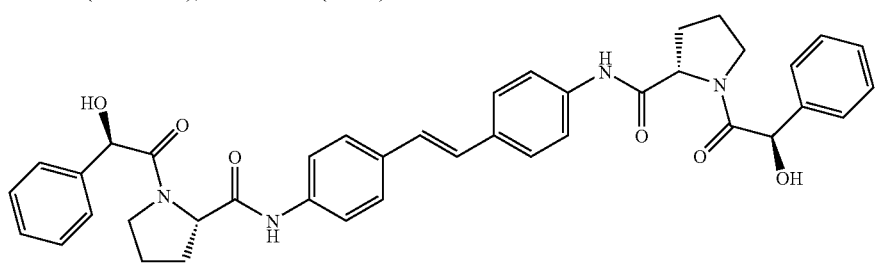

Example 298

The desired product was prepared by substituting (R)-(−)-mandelic acid for 2,5-dimethoxybenzoic acid in Example 23B. HPLC rt: 2.18 (method B); MS 673.316 (M+H)+.

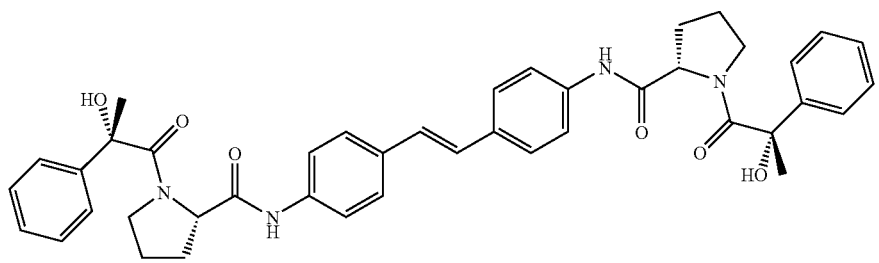

Example 299

The desired product was prepared by substituting (2S)-2-hydroxy-2-phenylpropanoic acid for 2,5-dimethoxybenzoic acid in Example 23B. HPLC rt: 2.55 (method B); MS 701.30 (M+H)+.

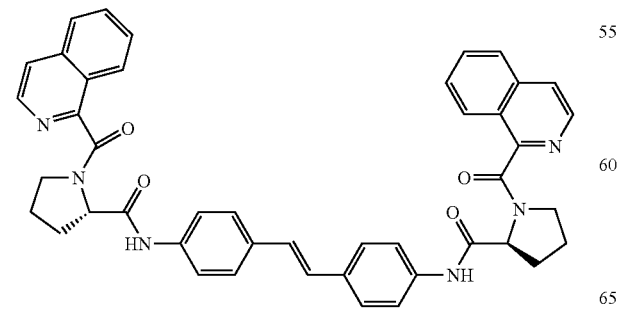

Example 300

The desired product was prepared by substituting 1-isoquinolinecarboxylic acid for 2,5-dimethoxybenzoic acid in Example 23B. HPLC rt: 2.38 (method B); MS 713.3 (M+H)+.

General HPLC Methods:

HPLC Method A: XTERRA 3.0×50 mm, 0 to 100% B over 2 min, 5 mL/min; A: 10% CH$_3$OH/water+0.1% TFA; B: 90% CH$_3$OH/water+0.1% TFA HPLC Method B: XTERRA 3.0×50 mm S7, 0 to 100% B over 3 min, 4 mL/min; A: 10% CH$_3$OH/water+0.1% TFA; B: 90% CH$_3$OH/water+0.1% TFA HPLC Method C: YMC 6.0×150 mm, 60 to 100% B over 15 min, 1.5 mL/min, A: 10% CH$_3$OH/water+0.1% TFA; B: 90% CH$_3$OH/water+0.1% TFA HPLC Method D: Waters Atlantis 2.1×150 mm, 25 to 100% B over 15 min, 0.35 mL/min, A: 2% ACN/water+5 mM NH$_4$OAc; B: 90% ACN/water+5 mM NH$_4$OAc HPLC Method E: Phenomenex Luna (C18) 4.6×150 mm S5 50 to 100% B over 20 min at 1 mL/min, A: 2% ACN/water+ 0.1% TFA; B: ACN+0.1% TFA HPLC Method F: J'Sphere ODS-H80 4.6×150 mm, S4, 50 to 100% B over 15 min, 1.5 mL/min, A: 2% ACN/water 10 mM NH$_4$OAc; B: 90% ACN/water+10 mM NH$_4$OAc HPLC Method G: XTERRA 3.0×50 mm, 0 to 100% B over 4 min, 4 mL/min, A: 10% CH$_3$OH/water+0.1% TFA; B: 90% CH$_3$OH/water+0.1% TFA HPLC Method H: XTERRA 4.6×50 mm, S5, 0 to 100% B over 11 min, 4 mL/min, A: 10% CH$_3$OH/water+2% H$_3$PO$_4$; B: 90% CH$_3$OH/water+0.1% TFA HPLC Method I: XTERRA 3.0×5 mm, S7, 0 to 100% B over 3 min, 5 mL/min, A: 10% CH$_3$OH/water+0.1% TFA; B: 90% CH$_3$OH/water+0.1% TFA

Bioligical Activity

An HCV Replion assay was utilized in the present invention, and was prepared, conducted and validated as follows:

HCV Replicon Cell Line Preparation

The HCV replicon cell line was isolated from colonies as described by Lohman, et. al. (*Science* 1999, 285, 110-113, expressly incorporated by reference in its entirety) and used for all experiments. The HCV replicon has the nucleic acid sequence set forth in EMBL Accession No.: AJ242652, the coding sequence of which is from nt 1801 to 7758.

The coding sequence of the published HCV replicon was synthesized by Operon Technologies, Inc. (Alameda, Calif.), and the fall-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions.

To generate cell lines, 4×10$^6$ Huh-7 cells (kindly provided by R. Bartenschlager and available from Health Science Research Resources Bank, Japan Health Sciences Foundation) were electroporated (GenePulser System, Bio-Rad) with 10 micrograms("μg") of RNA transcript and plated into 100-mm dishes. After 24 hours, selective media containing 1.0 milligrams/milliliter ("mg/mL") G418 was added and media was changed every 3 to 5 days. Approximately 4 weeks after electroporation, small colonies were visible which were isolated and expanded for further analysis. These cell lines were maintained at 37° C., 5% CO$_2$, 100% relative humidity in DMEM (Cat#11965-084) Gibco-BRL, Rockville, Md., with 10% heat inactivated calf serum (Sigma), 10 mL of 100× penicillin/streptomycin (Cat#15140-122) Gibco-BRL, Rockville, Md., Geneticin (Cat#10131-027) Gibco-BRL, Rockville, Md. at 1 mg/mL. One of the cell lines (deposited as ATCC Accession No. PTA-4583 in the American Type Culture Collection) which had approximately 3,000 copies of HCV replicon RNA/cell was used for development of the assay (HCV 1b-377-neo replicon cells).

BVDV Replicon Cell Line Preparation

To generate a BVDV replicon (termed BVDV-bu), the SphI/BgIII fragment from 153E-2 (see *J Virol.* 2003, 77 (12), 6753-60) was ligated with the SphI/BssHII fragment from 166A-4 (see *J Virol.* 2003, 77 (12), 6753-60), a BssHII/SacII fragment from ubiquitin and a SacII/BgIII digested PCR fragment which was the BVDV NS3 region amplified to incorporate the C-terminus of ubiquitin onto the 5' end of NS3. A firefly luciferase gene was then amplified by standard PCR methods to add BssHII sites at each end and cloned into BVDV-bu at a BssHII site at nt 740 by nondirectional cloning to generate BVDV-Luc. The neomycin gene and EMC IRES were PCR amplified from the HCV genotype 1b replicon plasmid and ligated into BVDV-Luc to generate the final clone (BVDV-Luc-neo) consisting of the BVDV 5' UTR followed by the gene for firefly luciferase, a ubiquitin monomer, the neomycin phosphotransferase gene, the EMCV IRES, BVDV NS3-5B and the BVDV 3' UTR. Stable BVDV-Luc-neo cell lines were generated and maintained as described above using 0.5 mg/mL G418 selection. BVDV RNA levels in these cell lines were examined directly using quantitative Taqman RT/PCR and BVDV proteins were confirmed by Western blot. In addition, the BVDV luciferase assay was validated in these cell lines by examining luciferase levels in the presence and absence of compound-1453, a specific inhibitor of BVDV replication (see *J. Virol.* 2003, 77 (12), 6753-60). As determined by luciferase, the EC$_{50}$ of compound-1453 was ~1 μM, which is comparable to previous results obtained with BVDV virus (see *J. Virol.* 2003, 77 (12), 6753-60).

FRET Assay

To perform the HCV FRET screening assay, 96-well cell culture plates were used. The FRET peptide (Anaspec, Inc., San Jose, Calif.) (Taliani et al., *Anal. Biochem.* 1996, 240, 60-67, hereby incorporated by reference in its entirety) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The assay reagent was made as follows: 5X luciferase cell culture lysis (Cat#E153A, Promega, Madison, Wis.) diluted to 1X with dH$_2$O, NaCl added to 150 millimoles ("m") final, the FRET peptide diluted to 20 micromolar ("μM") final from a 2 mM stock. HCV 1b-377-neo replicon cells were trypsinized, placed into each well of a 96-well plate and allowed to attach overnight. The next day, the test compounds were added to columns 1 through 10; column 11 was media plus DMSO only, and column 12 contained a titration of interferon or an HCV specific inhibitor as a control (1000 units for A12, B12, 100 units for C12, D12, 10 units for E12, F12 and 1 unit for G12, H12). Table 2 shows the layout for the HTS of the replicon cells in 96-well plates. In addition, naïve Huh-7 cells could also be used to replace wells A12 and B12 as a background control.

At subsequent various times (typically 72 hours), 10% final volume Alamar blue (Cat#00-100, Trek Diagnostics, Cleveland, Ohio) was added to each well. The plates were returned to the incubator for 5 hours and then read in the Cytoflour (PE Biosystems) to determine Alamar blue conversion in each well as a measure of cellular toxicity. After reading the Alamar blue fluorescence following the manufacturers directions, plates were rinsed 2× with PBS and then used for FRET assay by the addition of 30 µl of the FRET peptide assay reagent (described above) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least threefold.

Compound analysis depended upon the quantification of the relative HCV replicon inhibition and the relative cytotoxicity values. To calculate cytotoxicity values, the average alamar blue fluorescence signals from the control wells in row 11 were set as 100% non-toxic. The individual signals in each of the compound test wells were then divided by the average control signal and multiplied by 100% to determine percent cytotoxicity. To calculate the HCV replicon inhibition values, an average background value FRET signal was obtained from the two wells containing the highest amount of interferon or an HCV specific inhibitor at the end of the assay period. These numbers were similar to those obtained from naïve Huh-7 cells (results not shown). The background numbers were then subtracted from the average FRET signal obtained from the control wells in row 11 and this number was used as 100% activity. The individual signals in each of the compound test wells were then divided by the averaged control values after background subtraction and multiplied by 100% to determine percent activity. $EC_{50}$ values for an interferon titration were calculated as the concentration which caused a 50% reduction in FRET activity. The two numbers generated for the compound plate, percent cytotoxicity and percent activity, were used to determine compounds of interest for further analysis.

The assay was further adapted to accommodate titrations of compounds to determine $EC_{50}$ and $CC_{50}$ values. Briefly the plates were set-up with controls as before in columns 11 and 12, but the first 10 columns were used for titration of compounds in duplicate starting at the highest concentration in row A to the most dilute in row H. The amount of compound which yielded a 50% reduction in HCV FRET activity determined the $EC_{50}$ while the amount which caused a 50% reduction in Alamar blue conversion was used for $CC_{50}$.

$EC_{50}$ values were confirmed by HCV RNA detection using RT-PCR, according to the manufacturer's instructions, with a Platinum Quantitative RT-PCR Thermoscript One-Step Kit (Cat#11731-015) on a Perkin-Elmer ABI Prism Model 7700 sequence detector. The primers and probe used for TaqMan amplify the HCV 5'UTR from nucleotides 131 to 231 as previously described (Antimicrobial Agents and Chemotherapy 2005, 49 (4), 1346-1353). RNA-s were purified from 96-wells using the RNAeasy 96 kit (Cat#74181) Qiagen, Valencia, Calif.

$EC_{50}$ values were also determined by Western analysis performed according to the instructions for Chemiluminescence Immunology Kit (Cat#NEL105) Amersham, Arlington Heights, Ill. using a Molecular Dynamics Storm 860 phosphoimager and associated software. Experiments were done in duplicate. The primary and secondary antibody dilutions were at 1 to 5,000. Antisera was generated by immunizing rabbits with purified NS3 protease made from an E. Coli expression vector encoding the first 181 amino acids of HCV 1a NS3 with subsequent boosts. Bleeds were tested weekly and boosts continued until a positive signal on a control western was seen. Secondary antibody was a BioR$^a$ d (#170-6515) Goat anti-Rabbit IgG HRP Conjugate (Cat#170-6515) BioRad, Hercules, Calif. The protein samples for Western analysis were from the same wells used for the FRET assay and were prepared by the addition of an equal volume of 2×SDS-PAGE buffer to the FRET assay mixture, heating and loading on a 10% gel for SDS-PAGE. Interferon alpha (Cat#I-4276) Sigma, St. Louis, Mo. (IFN-α) was obtained and stored as recommended.

Results of Western, FRET and RT-PCR assays indicate $EC_{50}$ values (in units of IFN-α per milliliter) of 1.9 for the Western, 2.9 for the FRET and 5.3 for RT-PCR. These values are within 3-fold of one another and indicate equivalency between the assay methods. This demonstrates the utility of the FRET assay method for inhibitor titration and provides a comparison of a HTS format to the standard qRT-PCR method of HCV quantification.

TABLE 2

| Diagram of 96-Well Plate Layout for HCV Replicon HTS | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | Screen | Screen | Screen | Screen | Screen | Screen | Screen | Screen | Screen | Screen | 1-HCV | Inhibited |
| B | Screen | Screen | Screen | Screen | Screen | Screen | Screen | Screen | Screen | Screen | 1-HCV | Inhibited |
| C | Screen | Screen | Screen | Screen | Screen | Screen | Screen | Screen | Screen | Screen | 1-HCV | Titration |
| D | Screen | Screen | Screen | Screen | Screen | Screen | Screen | Screen | Screen | Screen | 1-HCV | Titration |
| E | Screen | Screen | Screen | Screen | Screen | Screen | Screen | Screen | Screen | Screen | 1-HCV | Titration |
| F | Screen | Screen | Screen | Screen | Screen | Screen | Screen | Screen | Screen | Screen | 1-HCV | Titration |
| G | Screen | Screen | Screen | Screen | Screen | Screen | Screen | Screen | Screen | Screen | 1-HCV | Titration |
| H | Screen | Screen | Screen | Screen | Screen | Screen | Screen | Screen | Screen | Screen | 1-HCV | Titration |

In Table 2, "Screen" indicates wells with test compound, "1-HCV" denotes control replicon wells (100% activity), "Inhibited" contains the highest amount of a control inhibitor (100% inhibited) and is used to determine background on each plate, and "titration" indicates the titration of interferon and is used as a sensitivity control. Units of interferon from the top of row 12 in duplicate are 1000, 100, 10, and 1.

Isolation of Resistant Replicons

HCV 1b-377-neo replicon cells were plated in 100-mm plates with ~25% confluence after 24 hour seeding. Compound A (prepared by the procedure described in WO04/014852, published Feb. 19, 2004) was added at the final concentrations of 5, 10 and 20 μM in the presence of G418. Wild type replicon cells 15 in the absence of the compound were used as a control. After 5-6 weeks, both wt replicon cells and selected cells were tested for their sensitivity to Compound A. In addition, cell lines derived from individual colonies from different concentrations of selective Compound A were also isolated, expanded and tested. In the initial test, approximately 60-fold resistance, judged by the FRET assay, was observed between wt replicon cells and selected replicon cells (designated as Compound A-r replicon cells).

Compound A

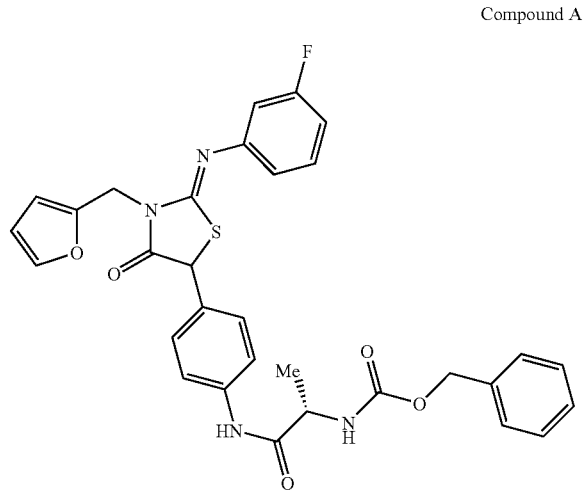

Target Mapping

Materials and Methods cDNA Cloning: To generate Compound A resistant cDNA, total RNA was isolated from Compound A-r replicon cells using Trizol (Cat#15596-026) Gibco-BRL, Rockville, Md. and precipitated with isopropanol. As a control, RNA was isolated in parallel from wild-type replicon cells. The entire HCV ORF was generated and amplified in a single fragment using the SuperScript One-Step RT-PCR for Long Templates (Cat#11922-028) Gibco-BRL, Rockville, Md. and primers targeting the EMC IRES and 3' UTR. Reaction products were gel purified and cloned directly into pCR2.1-TOPO using a TOPO TA cloning kit (Cat#45-0641) Invitrogen, Carlsbad, Calif. The DNA sequence of the entire HCV nonstructural coding region was determined for multiple clones.

Plasmid Construction: To put the Y2065H and Y2065C substitutions into the HCV 1b-377-neo replicon, cDNAs containing these changes were digested with EcoRI and HpaI, the correct size fragments were gel purified, and ligated into similarly digested HCV 1b-377-neo DNA. Clones containing the correct sequence were identified by restriction digestion and confirmed by sequence analysis.

Results

Mapping of Compound A Resistance: To determine the target gene of Compound A, sequencing was performed on the HCV nonstructural proteins NS3-NS5B from the resistant cells. Eight different cDNA clones were generated from 3 independently isolated resistant cell lines (cell lines B, C and D, all derived from 5 uM selection) and one from a wild-type cell line. All three clones from cell line B had a T-to-C substitution at nt 4943, resulting in an amino acid substitution of Tyr2065-to-His in NS5A. Likewise, all 4 clones from cell line C had an A-to-G substitution at nt 4944, resulting in an amino acid substitution of Tyr2065-to-Cys. The one clone from cell line D had the wild-type sequence at both of these nucleotide positions as did the clones generated from the wild-type cell line. Although cell line D was resistant to Compound A, finding the wild-type sequence in the one clone examined suggests that it is a heterogeneous population.

To determine if the Y2065H change was necessary and sufficient to confer resistance to Compound A, the single mutation was generated in the HCV 1b-377-neo replicon. RNA transcripts of this clone, in parallel with the wild-type replicon clone, were transfected into Huh-7 cells and colony formation was examined after 3 weeks of G418-selection in the presence or absence of 2 μM Compound A. As shown in Table 3, cells transfected with the wild-type replicon RNA had a 95% reduction in colony number in the presence of Compound A. In contrast, similar numbers of colonies were observed for the Y2065H clone regardless of whether or not Compound A was present, suggesting the substitution conferred resistance to this compound. To further verify this, colonies formed in the absence of Compound A were isolated and expanded for both the wild-type and Y2065H clones. Sensitivity of these cells to Compound A was then examined using the FRET assay. On the wild-type cells, Compound A had an $EC_{50}$ of 1.5 μM (Table 4) while the Y2065H cell line showed no inhibition up to 5 μM, the highest concentration tested. Further testing with Example 3 showed there was more than a 100-fold window of resistance in the Y2065H cells as compared to wild-type cells.

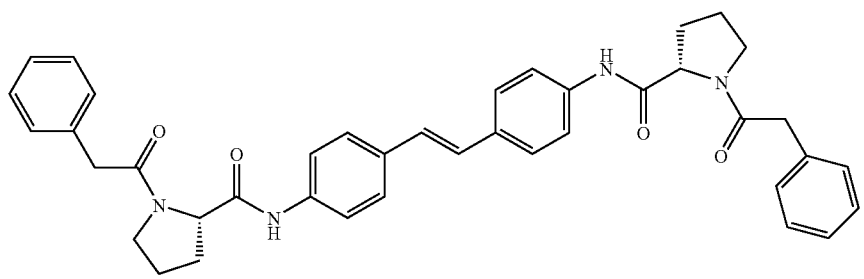

Example 3

Taken together, these data demonstrate that the Y2065H/C mutation in NS5A is sufficient and necessary to confer resistance to the Compound A chemotype. Thus, the compounds of the invention can be effective to inhibit the function of the HCV NS5A protein. Further, the compounds of the invention can be effective against the HCV 1b genotype. It should be understood that the compounds of the present invention can inhibit the HCV virus by mechanisms in addition to or other than NS5A inhibition.

TABLE 3

Colony Formation in the Presence and Absence of Compound A

| RNA transfected | Number of colonies | |
|---|---|---|
| | No compound | 2 µM Compound A |
| Wild-type | 60 | 3 |
| Y > H | 15 | 10 |

TABLE 4

Compound Testing on Wild-Type and Y > H Replicon Cells

| | Compound A | | Example 3 | |
|---|---|---|---|---|
| Cell Line | $EC_{50}$ µM | $CC_{50}$ µM | $EC_{50}$ µM | $CC_{50}$ µM |
| Wild-type | 1.5 | >5 | <0.050 | >5 |
| Y > H | >5 | >5 | >5 | >5 |

Combination Studies

Since clinical drug resistance often develops in viral infections following single-agent therapies, there is a need to assess the additive, antagonistic, or synergistic properties of combination therapies. The HCV replicon system was used to assess the potential use of a representative compound of the invention in combination therapies with Intron A and inhibitors targeting other HCV proteins. Three HCV antivirals, a protease inhibitor (example 901 in WO 00/09543), replicase inhibitors (cmpd 2006 of WO 03/010141, and des fluoro analog of example 289 of EP 1162196A) as well as Intron A, were tested in combination with Example 3 herein, an inhibitor of HCV NS5A. Drugs were tested at eleven concentrations each, diluted in DMSO by 3-fold dilutions. The highest concentration used for the four HCV inhibitors was 0.1 µM for Example 3 and 20 µM for the three other HCV antivirals. The highest concentration for Intron A was 5,000 IU/mL. The drugs were tested as monotherapies and in combination with Example 3 at various concentration ratios. Cells were exposed to compounds for 72 hours and the amount of HCV inhibition was then determined using the FRET assay. The potential cytotoxicities of these combined agents were also analyzed in parallel by Alamar blue staining. The degree of antagonism or synergy was determined over a range of drug concentrations, and the combination response curves were fit to assess the antiviral effects of the drug treatment combinations. The concentration ratios were analyzed using the method of Chou. Table 5 reports the combination indices (CI) and the asymptotic confidence intervals at the different concentration ratios. All combination indices were tested for departure from additivity using isobologram methods. In general, CIs near 1 indicate additive effects, while values less than 1 or much greater than 1 suggest synergy or antagonism, respectively.

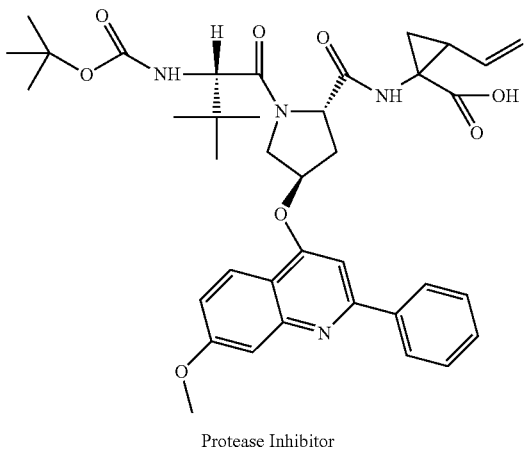

Protease Inhibitor

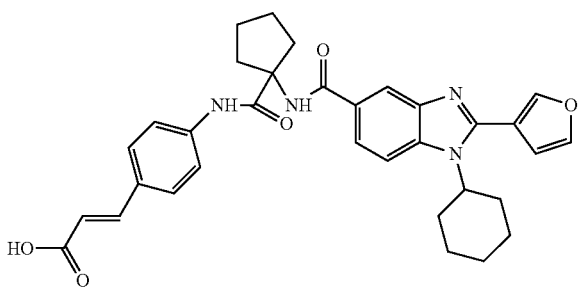

Replicase Inhibitor
cmpd 2006 of WO 03/010141

-continued

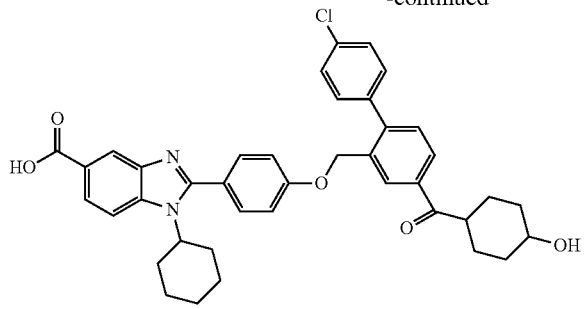

Replicase Inhibitor
des fluoro analog of Example 289
of EP 1162196A

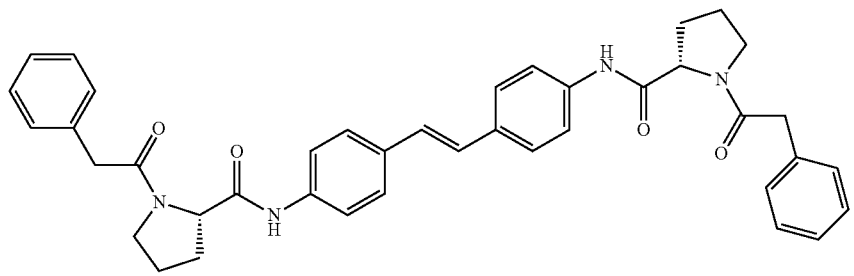

NS5A Inhibitor
Example 3

The EC$_{50}$s of these drugs in monotherapy were <50 nM for Example 3, 330 nM for the protease inhibitor, 2.6 µM for compound 2006, 0.9 µM for the des fluoro analog of Example 289, and 2 U/mL for Intron A, in agreement with published values (herein, WO 00/09543 as well as U.S. Pat. No. 6,268,207 B1, WO 03/010141, EP 1162196A, and Gu et al., *J. Virol.* 2003, 77, 5352-5359, respectively). Combining the protease inhibitor with Example 3 yielded an additive response and a CI near 1 with all the drug ratios (Table 5), except at the 1:2.5 drug ratio, where the CIs were significantly below 1 at both the 50 and 75% effective levels, suggesting a synergistic response. Likewise, the des fluoro analog of Example 289 in combination with Example 3 also showed a synergistic response for the 1:2.5 ratio at the 75% and 90% effective levels and an additive anti-HCV effect at the remaining drug ratios and different effective levels (Table 5). Combining Example 2006 with Example 3 yielded an additive response overall with CIs near 1 at all drug ratios and effective levels. Importantly, no significant drug antagonism was observed when Example 3 was combined with any of the three HCV inhibitors. Intron A in combination with Example 3 also showed additivity at both the 50 and 75% effective levels, and at the 2.5:1 drug ratio, the CI was significantly below 1 for the 75% effective level, suggesting a synergistic response (Table 5). At the 90% and 95% effective levels, synergism was observed for all drug ratios.

These results demonstrate that combination treatment of replicon cells with HCV NS5A inhibitors and either Intron A, or inhibitors targeting the HCV protease or polymerase, yields additive to synergistic antiviral effects. The ability to use these NS5A inhibitors in combination therapy can provide major advantages over single drug therapy for the treatment of HCV.

TABLE 5

Two Drug Combinations

| Drug combined with Example 3 | Molar ratio* | CI at HCV inhibition of: | | | | Overall Result |
| --- | --- | --- | --- | --- | --- | --- |
| | | 50% | 75% | 90% | 95% | |
| Protease Inhibitor | 1:1 | 1.05 +/− 0.29 | 0.96 +/− 0.38 | 0.91 +/− 0.55 | 0.88 +/− 0.69 | Additive |
| | 2.5:1 | 0.97 +/− 0.22 | 0.88 +/− 0.27 | 0.81 +/− 0.40 | 0.77 +/− 0.49 | Additive |
| | 1:2.5 | 0.82 +/− 0.17 | 0.78 +/− 0.22 | 0.76 +/− 0.33 | 0.75 +/− 0.43 | Synergistic/Additive |
| Compound 2006 | 1:1 | 1.25 +/− 0.32 | 1.19 +/− 0.44 | 1.15 +/− 0.66 | 1.14 +/− 0.82 | Additive |
| | 2.5:1 | 1.21 +/− 0.22 | 1.13 +/− 0.28 | 1.06 +/− 0.41 | 1.01 +/− 0.52 | Additive |
| | 1:2.5 | 0.83 +/− 0.19 | 0.79 +/− 0.24 | 0.76 +/− 0.37 | 0.74 +/− 0.47 | Additive |
| Example 289 des fluoro | 1:1 | 1.24 +/− 0.29 | 1.12 +/− 0.36 | 1.06 +/− 0.55 | 1.07 +/− 0.70 | Additive |
| | 2.5:1 | 1.24 +/− 0.29 | 1.04 +/− 0.34 | 0.9 +/− 0.47 | 0.84 +/− 0.55 | Additive |
| | 1:2.5 | 0.96 +/− 0.16 | 0.81 +/− 0.19 | 0.73 +/− 0.25 | 0.71 +/− 0.30 | Additive/Synergistic |
| Intron A | 1:1 | 1.09 +/− 0.13 | 0.88 +/− 0.15 | 0.72 +/− 0.20 | 0.64 +/− 0.22 | Additive/Synergistic |
| | 2.5:1 | 0.99 +/− 0.13 | 0.82 +/− 0.16 | 0.71 +/− 0.22 | 0.66 +/− 0.26 | Additive/Synergistic |

*The first number in each ratio represents Example 3.

Table 6 shows the EC50 ranges for the compounds of the present invention.

TABLE 6

EC$_{50}$ Values for Compounds of Present Invention

| Example | Activity (EC50)** |
|---|---|
| 1 | B |
| 2 | C |
| 3 | C |
| 4 | C |
| 5 | C |
| 6 | C |
| 7 | C |
| 8 | B |
| 9 | C |
| 10 | A |
| 11 | A |
| 12 | A |
| 13 | A |
| 14 | A |
| 15 | C |
| 16 | A |
| 17 | A |
| 18 | A |
| 19 | C |
| 20 | B |
| 21 | B |
| 22 | A |
| 23 | B |
| 24 | B |
| 25 | B |
| 26 | C |
| 27 | B |
| 28 | B |
| 29 | B |
| 30 | B |
| 31 | C |
| 32 | C |
| 33 | B |
| 34 | C |
| 35 | C |
| 36 | C |
| 37 | C |
| 38 | B |
| 39 | B |
| 40 | B |
| 41 | C |
| 42 | A |
| 43 | B |
| 44 | C |
| 45 | B |
| 46 | B |
| 47 | B |
| 48 | B |
| 49 | C |
| 50 | C |
| 51 | B |
| 52 | B |
| 53 | C |
| 54 | B |
| 55 | B |
| 56 | B |
| 57 | B |
| 58 | C |
| 59 | B |
| 60 | A |
| 61 | B |
| 62 | B |
| 63 | C |
| 64 | C |
| 65 | C |
| 66 | C |
| 67 | B |
| 68 | C |
| 69 | C |
| 70 | C |
| 71 | B |
| 72 | B |
| 73 | B |
| 74 | B |
| 75 | B |
| 76 | B |
| 77 | C |
| 78 | B |
| 79 | C |
| 80 | B |
| 81 | C |
| 82 | A |
| 83 | B |
| 84 | C |
| 85 | C |
| 86 | C |
| 87 | C |
| 88 | C |
| 89 | C |
| 90 | C |
| 91 | B |
| 92 | C |
| 93 | B |
| 94 | C |
| 95 | C |
| 96 | C |
| 97 | C |
| 98 | C |
| 99 | C |
| 100 | C |
| 101 | C |
| 102 | C |
| 103 | C |
| 104 | B |
| 105 | C |
| 106 | C |
| 107 | B |
| 108 | B |
| 109 | C |
| 110 | C |
| 111 | B |
| 112 | B |
| 113 | A |
| 114 | B |
| 115 | A |
| 116 | A |
| 117 | C |
| 118 | C |
| 119 | A |
| 120 | C |
| 121 | C |
| 122 | B |
| 123 | C |
| 124 | A |
| 125 | B |
| 126 | C |
| 127 | B |
| 128 | C |
| 129 | B |
| 130 | C |
| 131 | C |
| 132 | B |
| 133 | A |
| 134 | A |
| 135 | A |
| 136 | A |
| 137 | A |
| 138 | A |
| 139 | B |
| 140 | B |
| 141 | A |
| 142 | B |
| 143 | B |
| 144 | A |
| 145 | B |
| 146 | A |

TABLE 6-continued

EC$_{50}$ Values for Compounds of Present Invention

| Example | Activity (EC50)** |
|---|---|
| 147 | B |
| 148 | A |
| 149 | B |
| 150 | A |
| 151 | B |
| 152 | B |
| 153 | A |
| 154 | A |
| 155 | C |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | B |
| 170 | B |
| 171 | B |
| 172 | A |
| 173 | A |
| 174 | B |
| 175 | A |
| 176 | A |
| 177 | A |
| 178 | A |
| 179 | A |
| 180 | A |
| 181 | B |
| 182 | B |
| 183 | A |
| 184 | B |
| 185 | A |
| 186 | B |
| 187 | C |
| 188 | B |
| 189 | A |
| 190 | B |
| 191 | A |
| 192 | B |
| 193 | A |
| 194 | B |
| 195 | A |
| 196 | A |
| 197 | B |
| 198 | B |
| 199 | C |
| 200 | B |
| 201 | C |
| 202 | B |
| 203 | B |
| 204 | C |
| 205 | A |
| 206 | A |
| 207 | B |
| 208 | A |
| 209 | B |
| 210 | A |
| 211 | C |
| 212 | C |
| 213 | A |
| 214 | C |
| 215 | C |
| 216 | C |
| 217 | C |
| 218 | C |
| 219 | C |
| 220 | A |
| 221 | B |
| 223 | C |
| 224 | A |
| 225 | C |
| 226 | B |
| 227 | A |
| 228 | A |
| 229 | A |
| 230 | B |
| 231 | A |
| 232 | A |
| 233 | A |
| 234 | B |
| 235 | A |
| 236 | A |
| 237 | A |
| 238 | A |
| 239 | A |
| 240A | C |
| 240B | A |
| 240C | A |
| 244 | A |
| 245 | A |
| 246 | A |
| 247 | A |
| 248 | A |
| 249 | A |
| 250A | A |
| 250B | B |
| 250C | A |
| 251 | C |
| 252 | A |
| 253 | A |
| 254 | B |
| 255 | B |
| 256 | B |
| 257 | B |
| 258 | C |
| 259 | B |
| 260 | B |
| 261 | A |
| 262 | B |
| 263 | A |
| 264 | C |
| 265 | B |
| 266 | A |
| 267 | B |
| 268 | A |
| 269 | B |
| 270 | C |
| 271 | C |
| 272 | B |
| 273 | A |
| 274 | C |
| 275 | C |
| 276 | C |
| 277 | C |
| 278 | A |
| 279 | B |
| 280 | A |
| 281 | A |
| 282 | A |
| 283 | A |
| 284 | C |
| 285 | B |
| 286 | B |
| 287 | C |
| 288 | B |
| 289 | C |
| 290 | C |
| 291 | C |
| 292 | B |
| 293 | B |
| 294 | B |
| 295 | A |
| 296 | C |

TABLE 6-continued

EC50 Values for Compounds of Present Invention

| Example | Activity (EC50)** |
|---------|-------------------|
| 297 | C |
| 298 | C |
| 299 | C |
| 300 | C |

**Compound Activity: A: 1-10 µM  B: 0.1-1 µM  C: 0.1 nM-0.09 µM

The compounds of the invention may inhibit HCV by mechanisms in addition to or other than NS5A inhibition. Preferably the compounds of the invention inhibit HCV replicon and more preferably the compounds of the invention inhibit NS5A. Compounds of the present invention preferably inhibit multiple genotypes of HCV.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of formula (I)

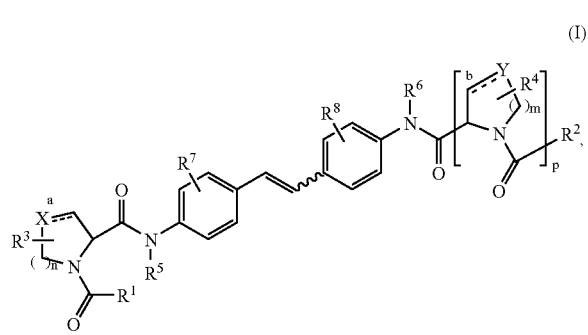

(I)

or a pharmaceutically acceptable salt thereof, wherein
- ----a---- is a single or double bond;
- ----b---- is a single or double bond;
- when ----a---- is a single bond, X is selected from the group consisting of O, $CH_2$, and $CHR^3$;
- when ----a---- is a double bond, X is selected from the group consisting of CH and $CR^3$;
- when ----b---- is a single bond, Y is selected from the group consisting of O, $CH_2$, and $CHR^4$;
- when ----b---- is a double bond, Y is selected from the group consisting of CH and $CR^4$;
- n and m are independently 1, 2, or 3;
- p is 1;
- $R^1$ and $R^2$ are independently selected from the group consisting of alkoxy, alkoxyalkoxyalkyl, alkoxyalkyl, alkyl, alkylsulfenylalkyl, alkylsulfinylalkyl, alkylsulfonylalkyl, aryl, arylalkoxy, arylalkoxyalkyl, arylalkyl, arylcarbonyl, aryloxy, aryloxyalkyl, arylsulfenylalkyl, arylsulfinylalkyl, arylsulfonylalkyl, carboxyalkyl, cycloalkenyl, cycloalkenylalkyl, cycloalkyl, cycloalkylalkyl, heterocyclyl, heterocyclylalkoxy, heterocyclylalkoxyalkyl, heterocyclylalkyl, heterocyclylcarbonyl, heterocyclyloxy, heterocyclyloxyalkyl, $-NR^aR^b$, and $(NR^aR^b)$alkyl;
- $R^3$ and $R^4$ are independently selected from the group consisting of hydrogen, alkenyl, alkoxy, alkoxycarbonyloxy, alkyl, alkylsulfonyl, alkylsulfonyloxy, aryl, arylalkyl, azido, hydroxy, $-NR^aR^b$, $(NR^aR^b)$alkyl, and $(NR^aR^b)$carbonyloxy; wherein the alkenyl and the alkyl can optionally form a saturated or unsaturated cyclic structure, respectively, with an adjacent carbon atom;
- $R^5$ and $R^6$ are independently selected from the group consisting of hydrogen, alkenyl, alkoxycarbonyl, alkyl, alkylcarbonyl, aryl, arylalkyl, heterocyclylalkylcarbonyl, and heterocyclylcarbonyl;
- $R^7$ and $R^8$ are independently selected from the group consisting of hydrogen, alkenyl, alkoxy, alkyl, halo, and haloalkyl; and
- $R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

2. A compound of formula (II)

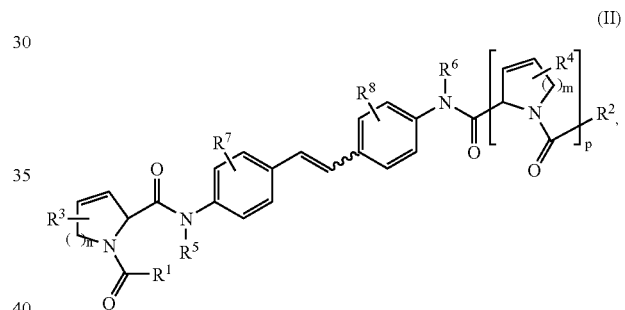

(II)

or a pharmaceutically acceptable salt thereof, wherein
- n and m are independently 1 or 2;
- p is 1;
- $R^1$ and $R^2$ are independently selected from the group consisting of alkoxy, alkoxyalkoxyalkyl, alkoxyalkyl, alkyl, alkylsulfenylalkyl, alkylsulfinylalkyl, alkylsulfonylalkyl, aryl, arylalkoxy, arylalkoxyalkyl, arylalkyl, arylcarbonyl, aryloxy, aryloxyalkyl, arylsulfenylalkyl, arylsulfinylalkyl, arylsulfonylalkyl, carboxyalkyl, cycloalkenyl, cycloalkenylalkyl, cycloalkyl, cycloalkylalkyl, heterocyclyl, heterocyclylalkoxy, heterocyclylalkoxyalkyl, heterocyclylalkyl, heterocyclylcarbonyl, heterocyclyloxy, heterocyclyloxyalkyl, $-NR^aR^b$, and $(NR^aR^b)$alkyl;
- $R^3$ and $R^4$ are independently selected from the group consisting of hydrogen, alkenyl, alkoxy, alkoxycarbonyloxy, alkyl, alkylsulfonyl, alkylsulfonyloxy, aryl, arylalkyl, azido, hydroxy, $-NR^aR^b$, $(NR^aR^b)$alkyl, $(NR^aR^b)$carbonyloxy; wherein the alkenyl and the alkyl can optionally form a saturated or unsaturated cyclic structure, respectively, with an adjacent carbon atom;
- $R^5$ and $R^6$ are independently selected from the group consisting of hydrogen, alkenyl, alkoxycarbonyl, alkyl, alkylcarbonyl, aryl, arylalkyl, heterocyclylalkylcarbonyl, and heterocyclylcarbonyl;

R[7] and R[8] are independently selected from the group consisting of hydrogen, alkenyl, alkoxy, alkyl, halo, and haloalkyl; and R[a] and R[b] are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

3. The compound of claim 2, wherein
n and m are independently 1 or 2;
p is 1;
R[1] and R[2] are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —NR[a]R[b], and (NR[a]R[b])alkyl;
R[3] and R[4] are independently selected from the group consisting of hydrogen, alkoxy, alkylsulfonyloxy, azido, hydroxy, —NR[a]R[b], (NR[a]R[b])carbonyloxy;
R[5] and R[6] are independently selected from the group consisting of hydrogen, alkoxycarbonyl, alkyl, and heterocyclylcarbonyl;
R[7] and R[8] are independently selected from the group consisting of hydrogen, alkyl, and halo; and
R[a] and R[b] are independently selected from the group consisting of hydrogen, alkyl, alkylcarbonyl, arylalkyl, arylalkylcarbonyl, and cycloalkyl.

4. The compound of claim 2, wherein
n and m are 1;
p is 1;
R[1] and R[2] are independently selected from the group consisting of alkyl, aryl, arylalkyl, cycloalkyl, cycloalkylalkyl, heterocyclyl, and heterocyclylalkyl; and
R[3], R[4], R[5], R[6], R[7], and R[8] are hydrogen.

5. The compound of claim 2, wherein
n and m are 1;
p is 1;
R[1] and R[2] are independently selected from the group consisting of alkyl, cycloalkyl, and heterocyclylalkyl; and
R[3], R[4], R[5], R[6], R[7], and R[8] are hydrogen.

6. A compound of formula (III)

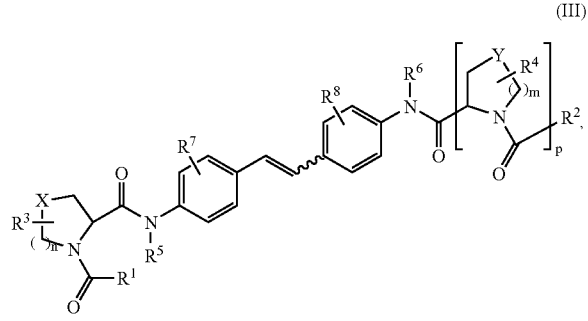

(III)

or a pharmaceutically acceptable salt thereof, wherein
X is selected from the group consisting of O, $CH_2$, and $CHR^3$;
Y is selected from the group consisting of O, $CH_2$, and $CHR^4$;
n and m are independently 1 or 2;
p is 1;
R[1] and R[2] are independently selected from the group consisting of alkoxy, alkoxyalkoxyalkyl, alkoxyalkyl, alkyl, alkylsulfenylalkyl, alkylsulfinylalkyl, alkylsulfonylalkyl, aryl, arylalkoxy, arylalkoxyalkyl, arylalkyl, arylcarbonyl, aryloxy, aryloxyalkyl, arylsulfenylalkyl, arylsulfinylalkyl, arylsulfonylalkyl, carboxyalkyl, cycloalkenyl, cycloalkenylalkyl, cycloalkyl, cycloalkylalkyl, heterocyclyl, heterocyclylalkoxy, heterocyclylalkoxyalkyl, heterocyclylalkyl, heterocyclylcarbonyl, heterocyclyloxy, heterocyclyloxyalkyl, —NR[a]R[b], and (NR[a]R[b])alkyl;
R[3] and R[4] are independently selected from the group consisting of hydrogen, alkenyl, alkoxy, alkoxycarbonyloxy, alkyl, alkylsulfonyl, alkylsulfonyloxy, aryl, arylalkyl, azido, hydroxy, —NR[a]R[b], (NR[a]R[b])alkyl, and (NR[a]R[b])carbonyloxy; wherein the alkenyl and the alkyl can optionally form a saturated or unsaturated cyclic structure, respectively, with an adjacent carbon atom;
R[5] and R[6] are independently selected from the group consisting of hydrogen, alkenyl, alkoxycarbonyl, alkyl, alkylcarbonyl, aryl, arylalkyl, heterocyclylalkylcarbonyl, and heterocyclylcarbonyl;
R[7] and R[8] are independently selected from the group consisting of hydrogen, alkenyl, alkoxy, alkyl, halo, and haloalkyl; and
R[a] and R[b] are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl.

7. The compound of claim 6, wherein
X is selected from the group consisting of O, $CH_2$, and $CHR^3$;
Y is selected from the group consisting of O, $CH_2$, and $CHR^4$;
n and m are independently 1 or 2;
p is 1;
R[1] and R[2] are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —NR[a]R[b], and (NR[a]R[b])alkyl;
R[3] and R[4] are independently selected from the group consisting of hydrogen, alkenyl, alkoxy, alkylsulfonyloxy, azido, hydroxy, —NR[a]R[b], (NR[a]R[b])carbonyloxy;
wherein the alkenyl can optionally form an unsaturated cyclic structure with an adjacent carbon atom;
R[5] and R[6] are independently selected from the group consisting of hydrogen, alkoxycarbonyl, alkyl, and heterocyclylcarbonyl;
R[7] and R[8] are independently selected from the group consisting of hydrogen, alkyl, and halo; and
R[a] and R[b] are independently selected from the group consisting of hydrogen, alkyl, alkylcarbonyl, arylalkyl, arylalkylcarbonyl, and cycloalkyl.

8. The compound of claim 6, wherein
X is $CHR^3$;
Y is $CHR^4$;
n and m are 1;
p is 1;
R[1] and R[2] are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —NR[a]R[b], and (NR[a]R[b])alkyl;
R[3] and R[4] are independently selected from the group consisting of hydrogen, alkenyl, alkoxy, alkylsulfonyloxy, azido, hydroxy, —NR[a]R[b], (NR[a]R[b])carbonyloxy;
wherein the alkenyl can optionally form an unsaturated cyclic structure with an adjacent carbon atom;

R⁵ and R⁶ are independently selected from the group consisting of hydrogen, alkoxycarbonyl, alkyl, and heterocyclylcarbonyl;
R⁷ and R⁸ are independently selected from the group consisting of hydrogen, alkyl, and halo; and
$R^a$ and $R^b$ are independently selected from the group consisting of hydrogen, alkyl, alkylcarbonyl, arylalkyl, arylalkylcarbonyl, and cycloalkyl.

9. The compound of claim 6, wherein
X is $CHR^3$;
Y is $CHR^4$;
n and m are 1;
p is 1;
$R^1$ and $R^2$ are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —$NR^aR^b$, and ($NR^aR^b$)alkyl;
$R^3$ and $R^4$ are independently selected from the group consisting of hydrogen, alkenyl, alkoxy, alkylsulfonyloxy, azido, hydroxy, —$NR^aR^b$, ($NR^aR^b$)carbonyloxy;
wherein the alkenyl can optionally form an unsaturated cyclic structure with an adjacent carbon atom;

R⁵ and R⁶ are independently selected from the group consisting of hydrogen, alkoxycarbonyl, alkyl, and heterocyclylcarbonyl;
R⁷ and R⁸ are independently selected from the group consisting of hydrogen, alkyl, and halo; and
$R^a$ and $R^b$ are independently selected from the group consisting of hydrogen, alkyl, alkylcarbonyl, arylalkyl, arylalkylcarbonyl, and cycloalkyl.

10. The compound of claim 6, wherein
X is $CH_2$;
Y is $CH_2$;
n and m are 1;
p is 1;
$R^1$ and $R^2$ are independently selected from the group consisting of alkoxy, alkoxyalkoxyalkyl, alkoxyalkyl, alkyl, alkylsulfenylalkyl, aryl, arylalkoxy, arylalkyl, aryloxyalkyl, carboxyalkyl, cycloalkyl, cycloalkylalkyl, heterocyclyl, heterocyclylalkyl, —$NR^aR^b$, and ($NR^aR^b$)alkyl;
$R^5$, $R^6$, $R^7$, and $R^8$ are hydrogen; and
$R^a$ and $R^b$ are independently selected from the group consisting of hydrogen, alkyl, alkylcarbonyl, arylalkyl, arylalkylcarbonyl, and cycloalkyl.

11. A compound selected from the group consisting of

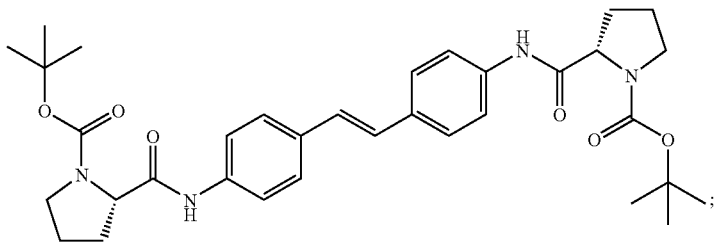

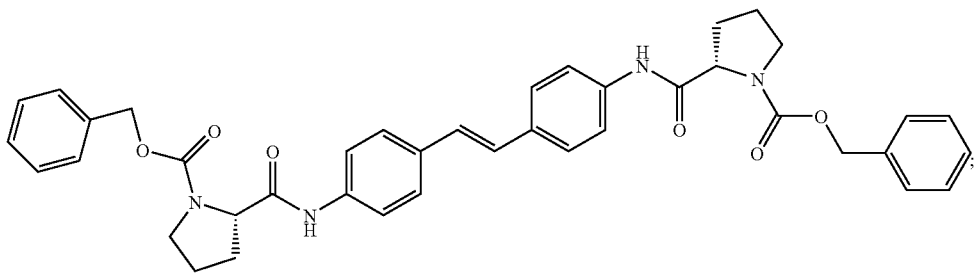

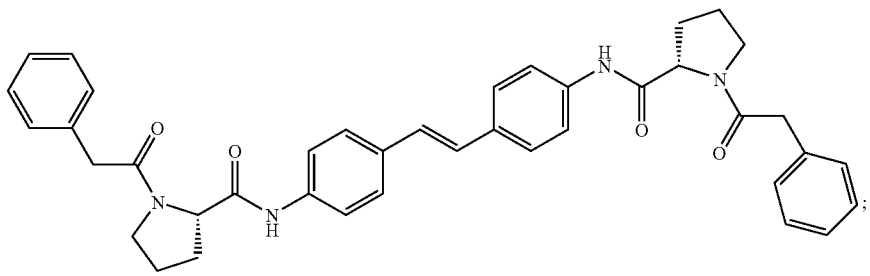

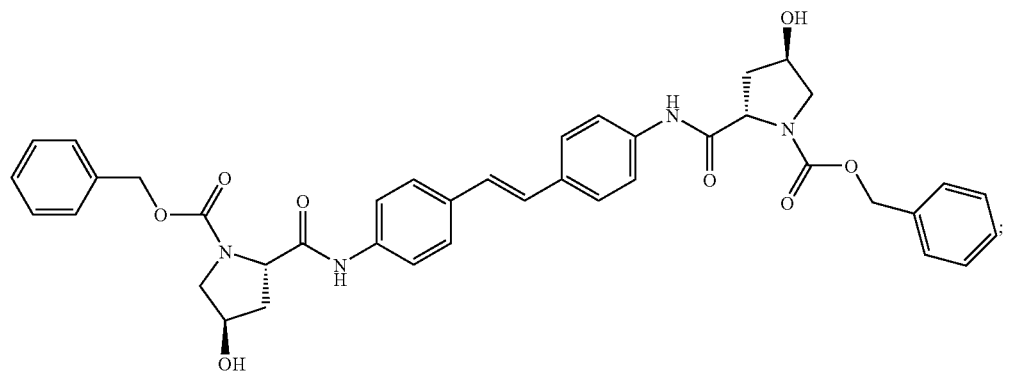
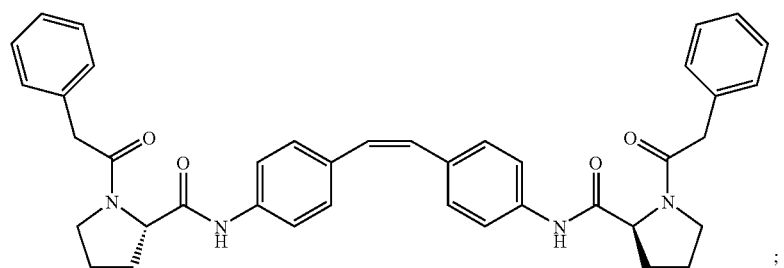
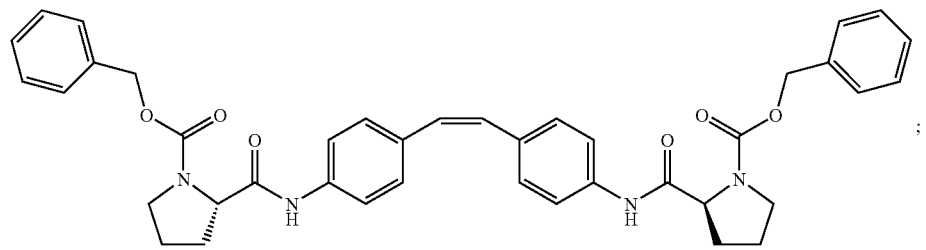
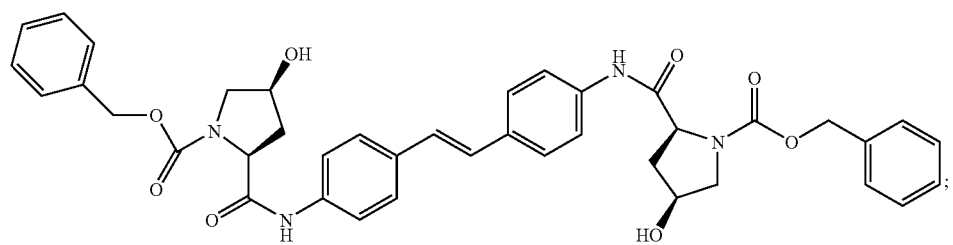
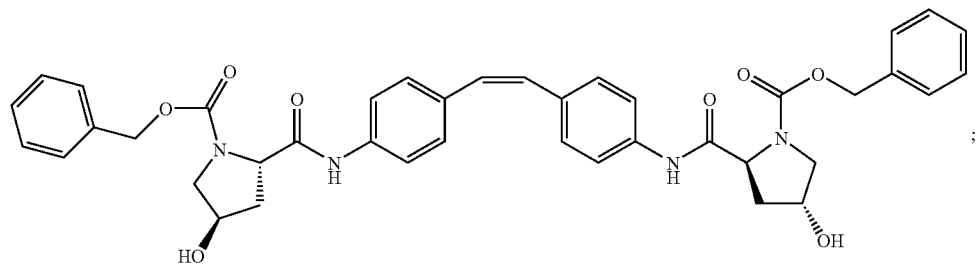

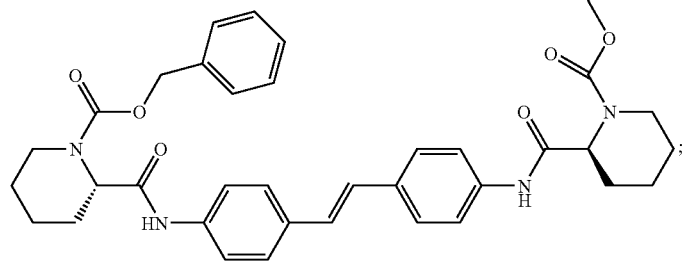
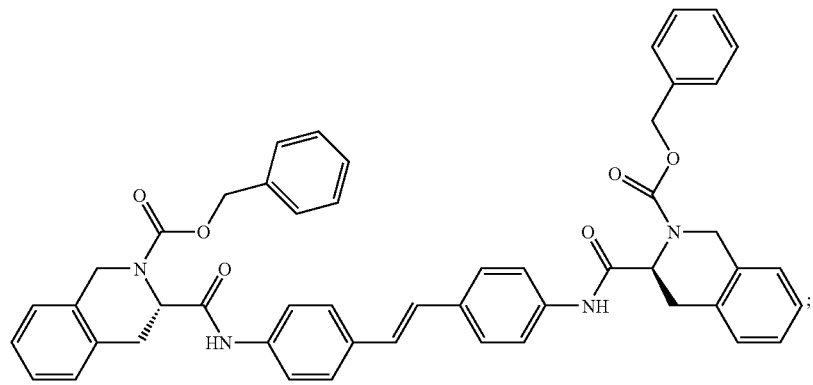
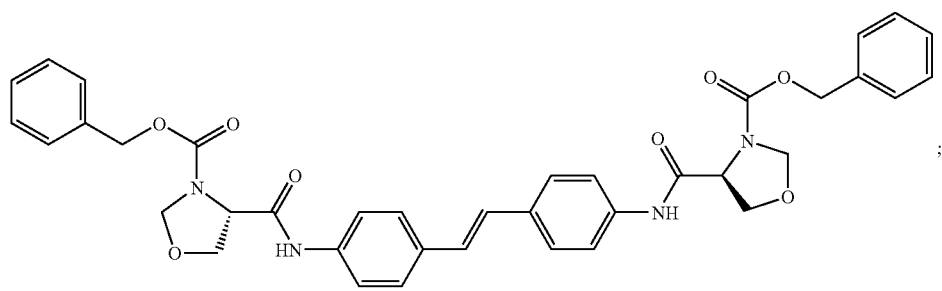
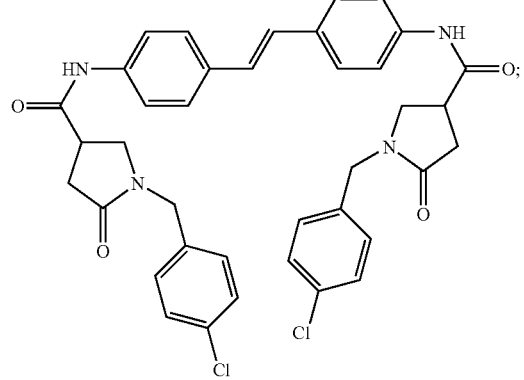
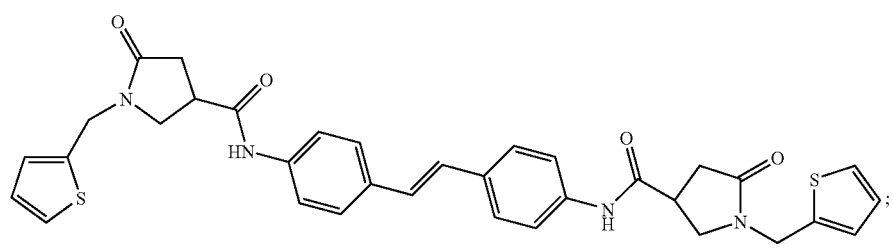

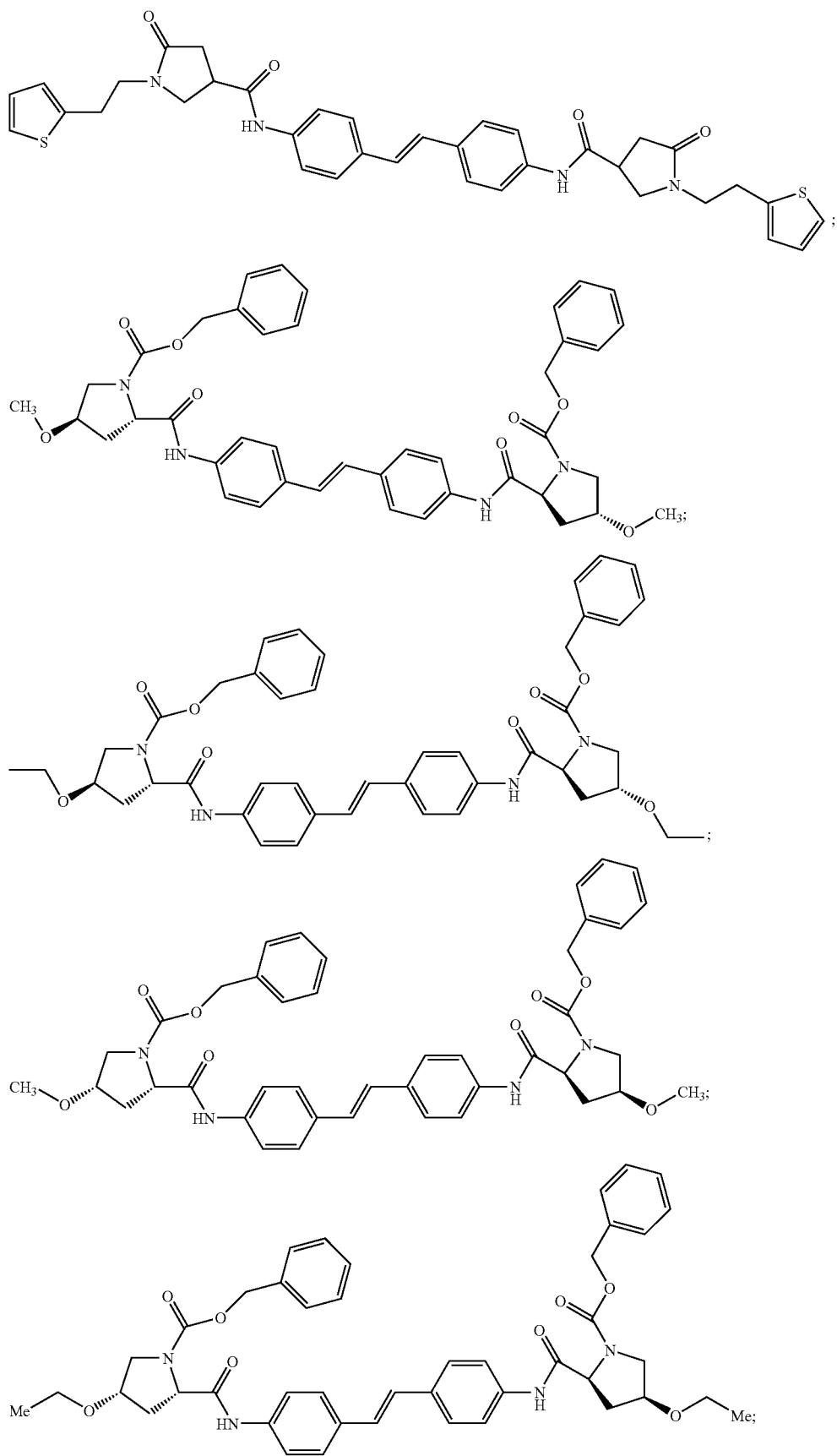

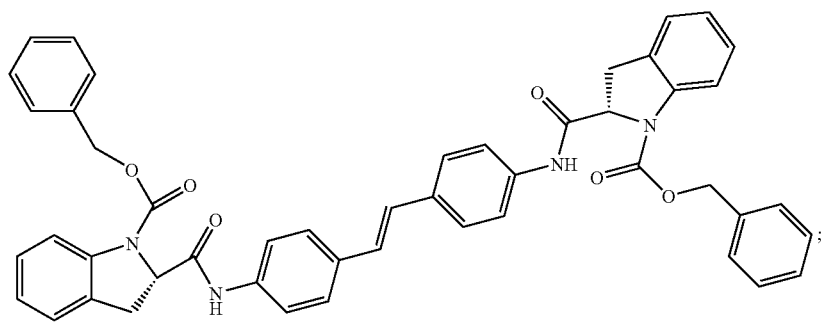
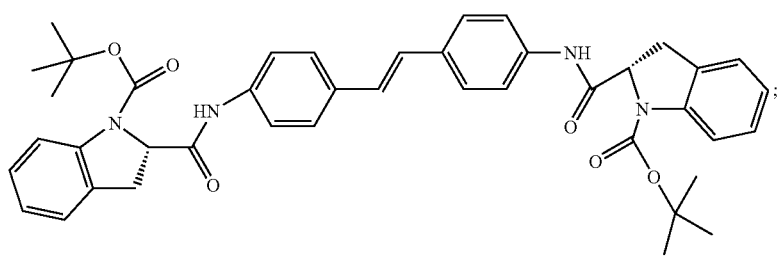
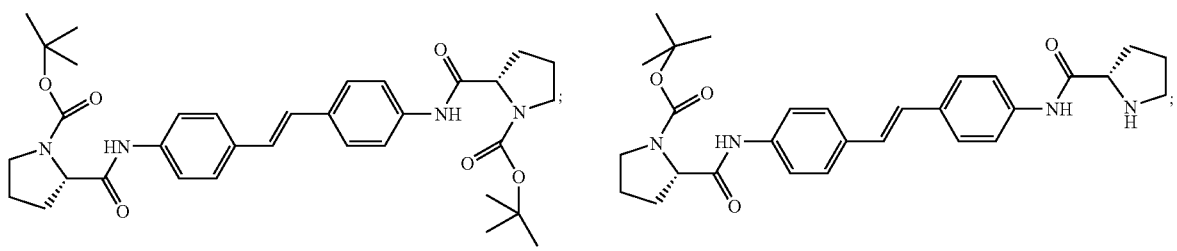
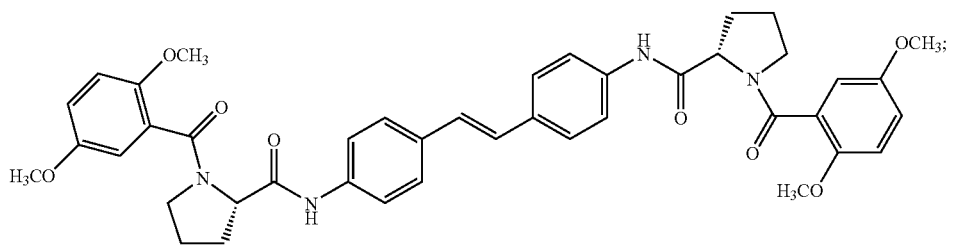
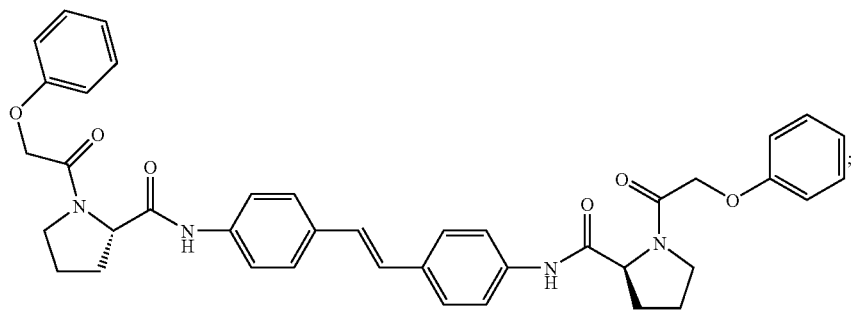

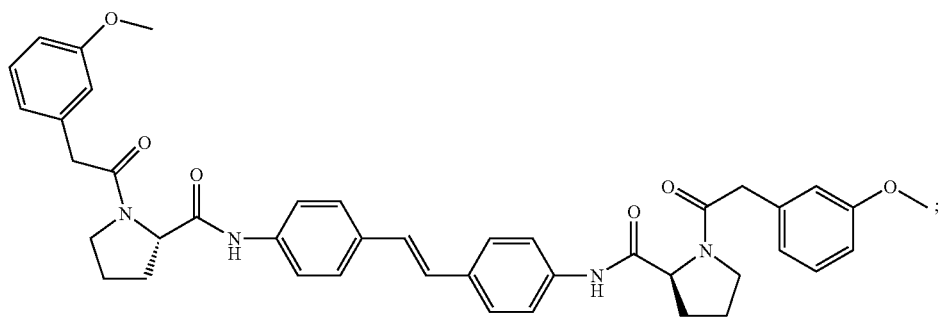
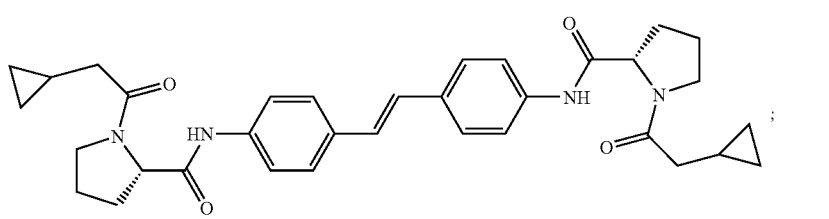
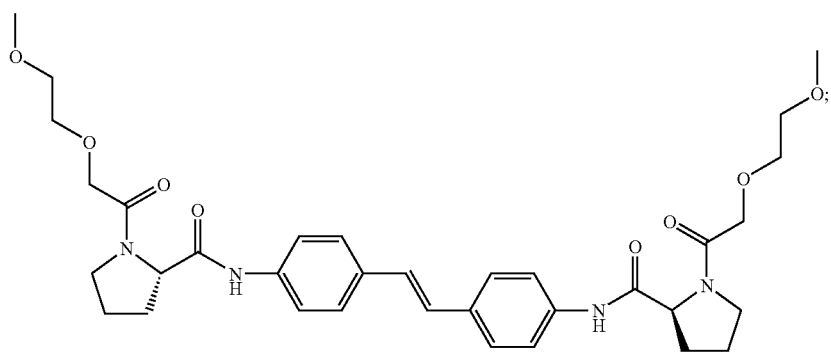
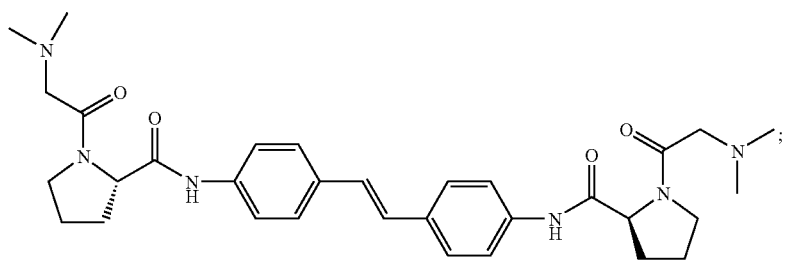
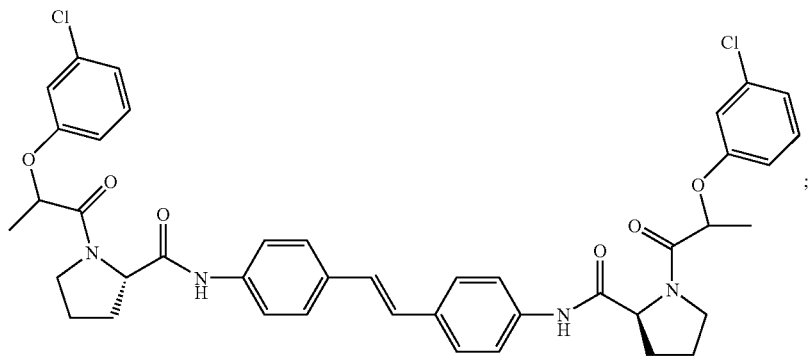

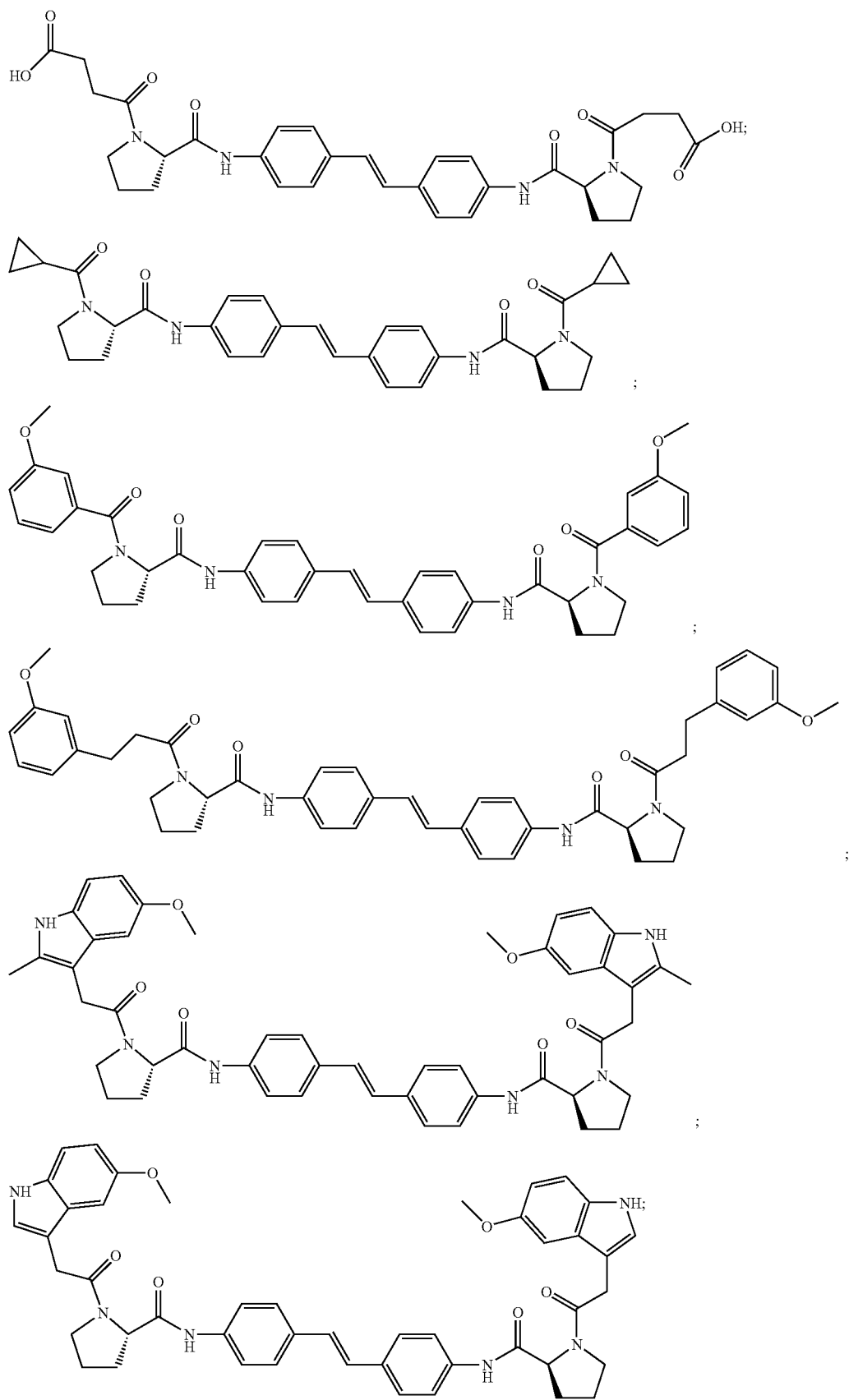

-continued
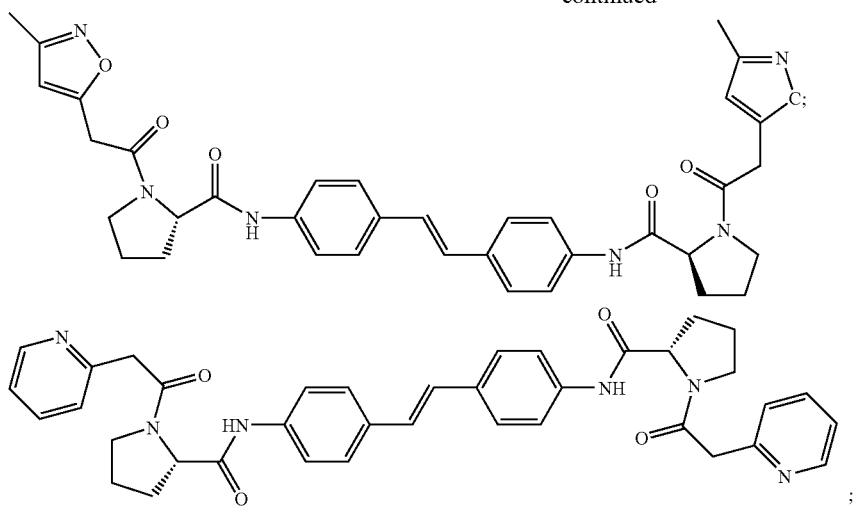
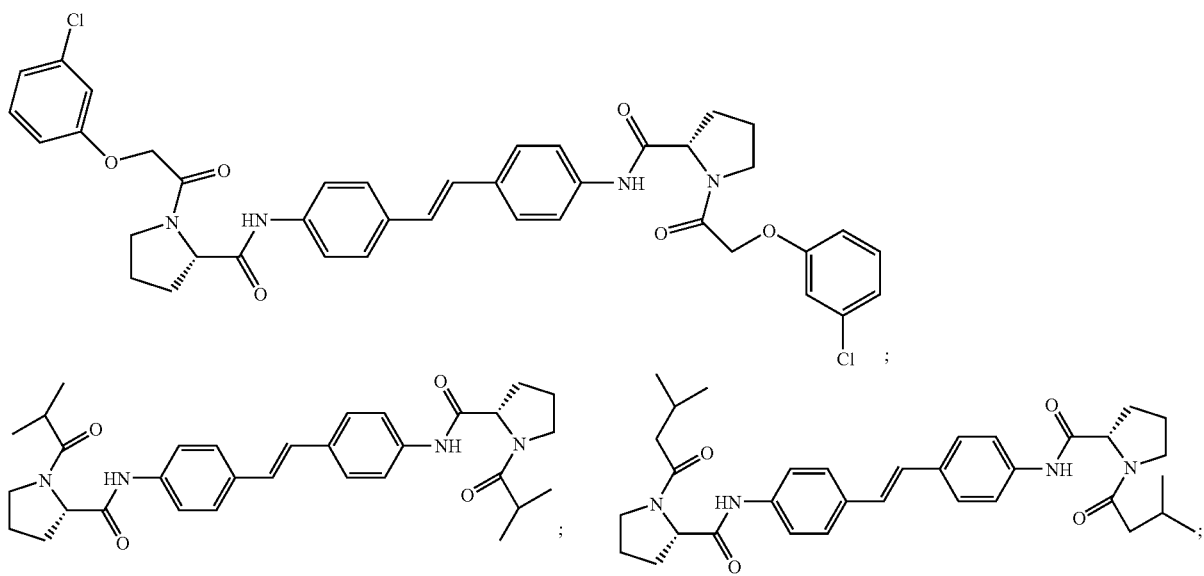
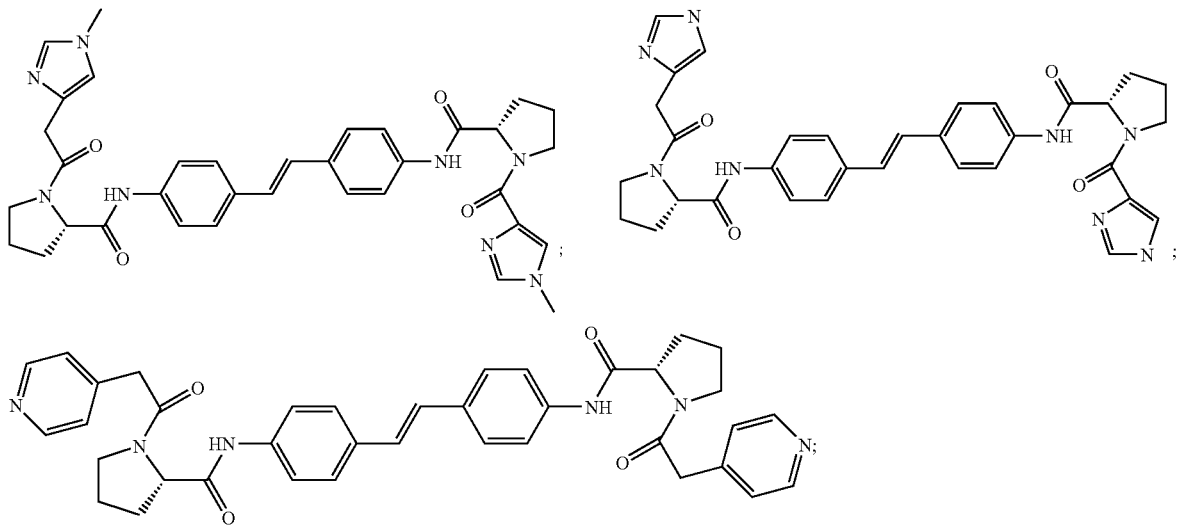

-continued
215
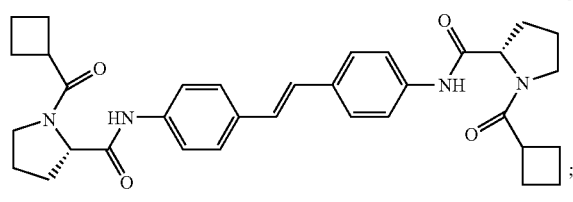
216
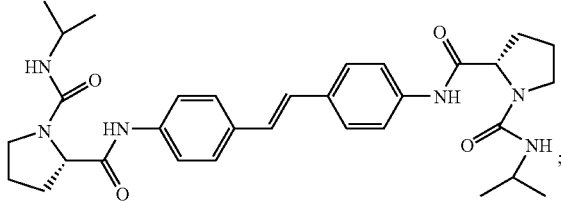
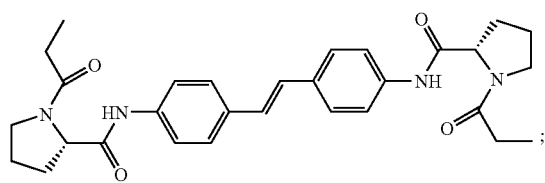
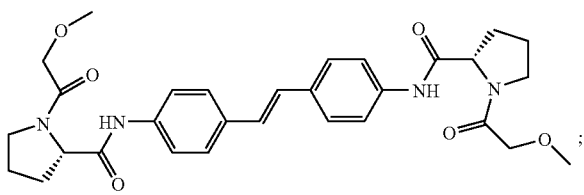
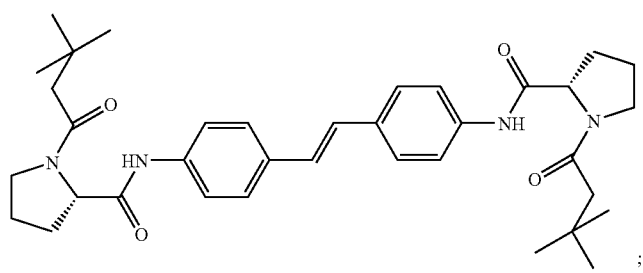
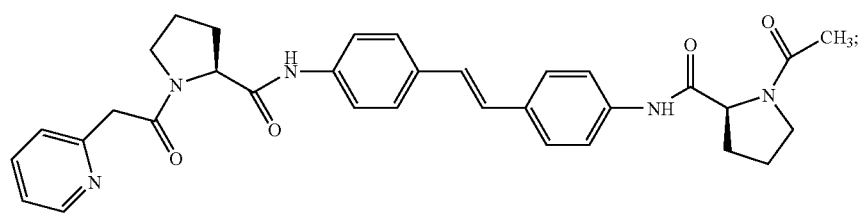
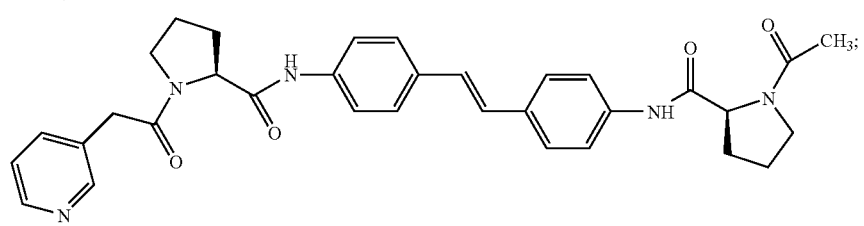
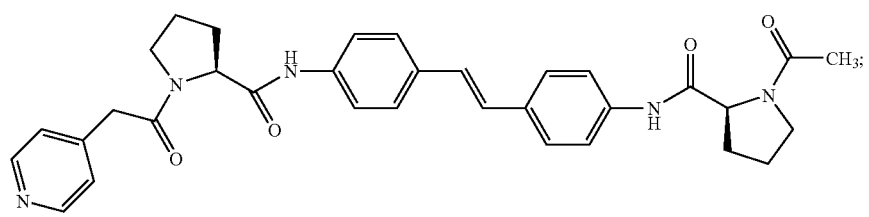
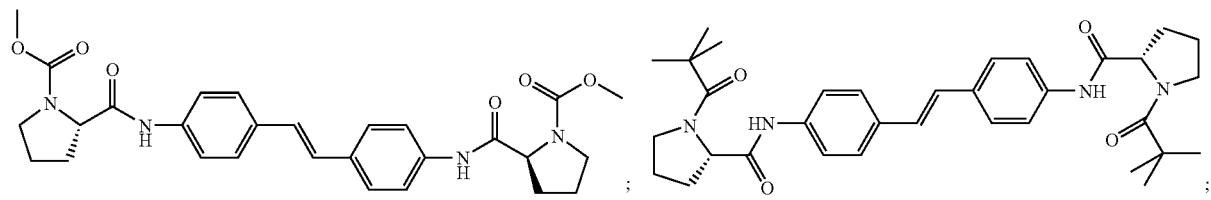
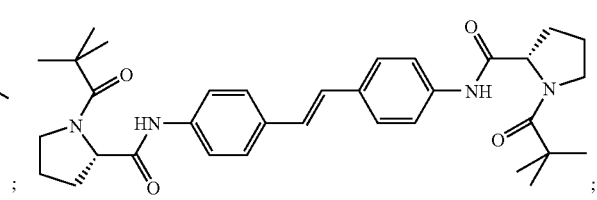

-continued
217
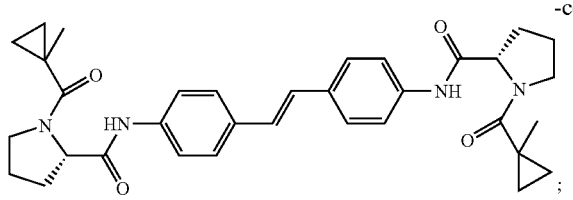
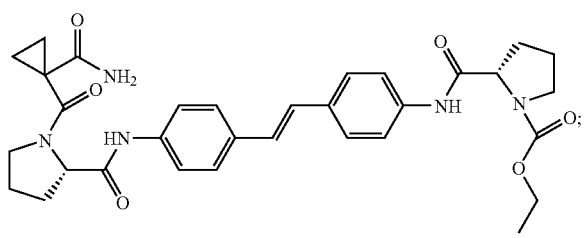
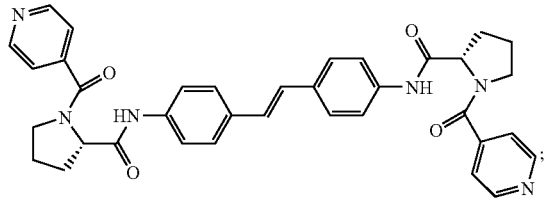
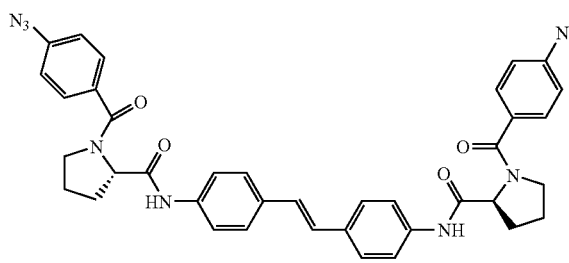
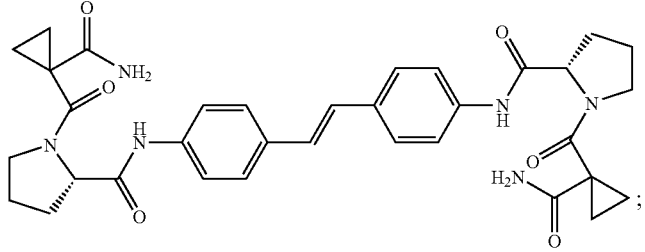
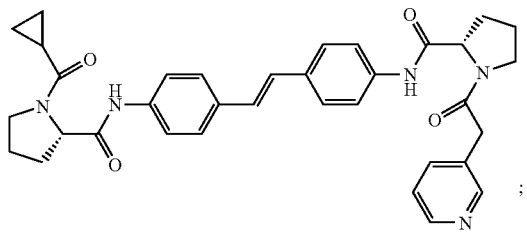
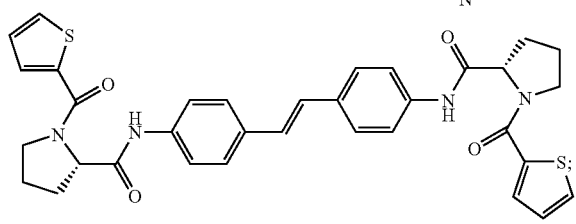
218
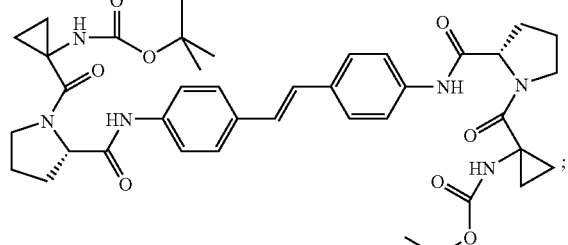
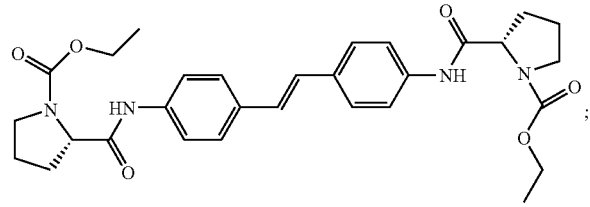
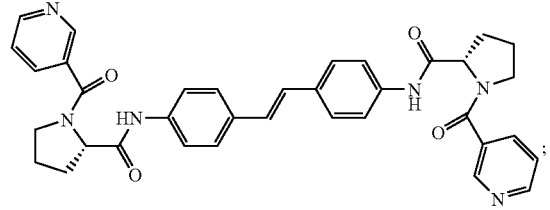
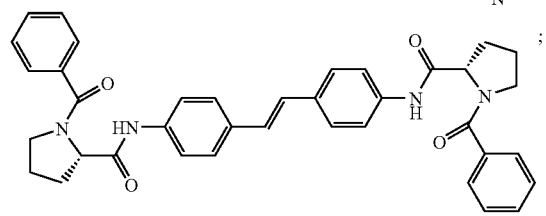
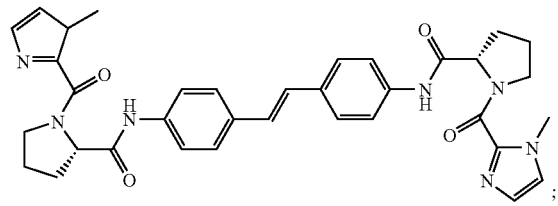
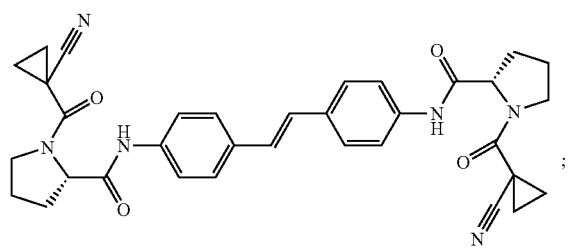

219
220
-continued
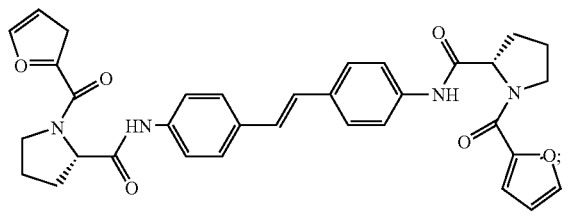
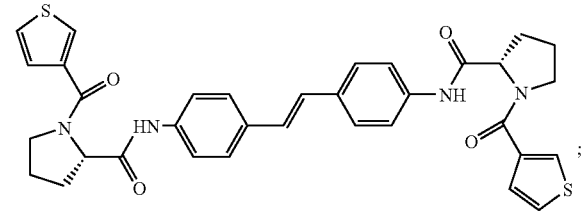
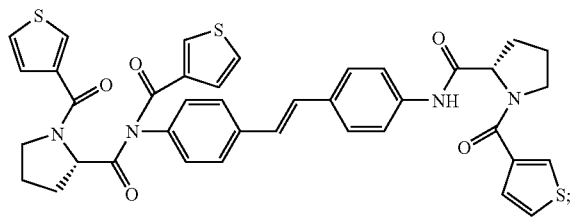
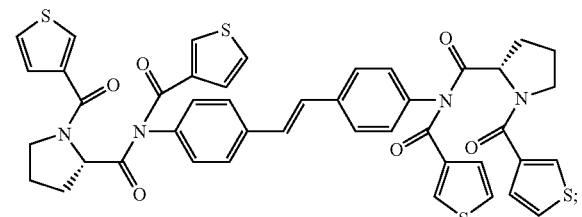
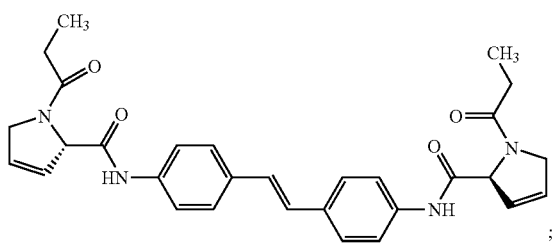
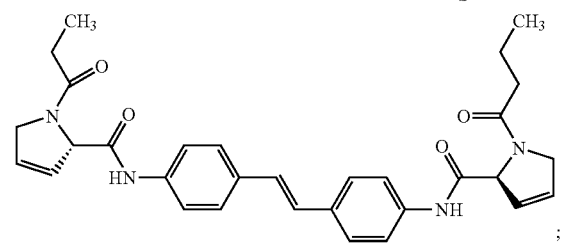
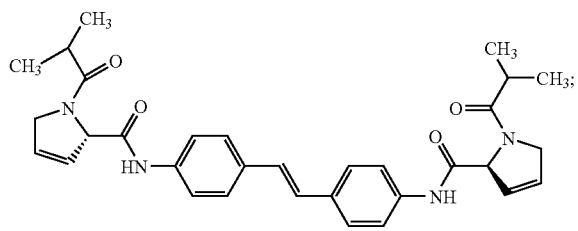
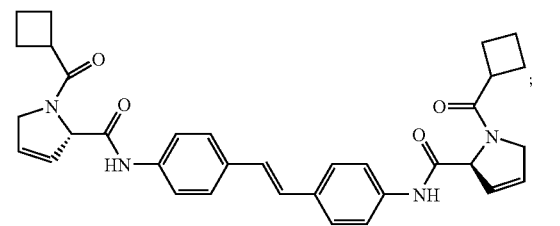
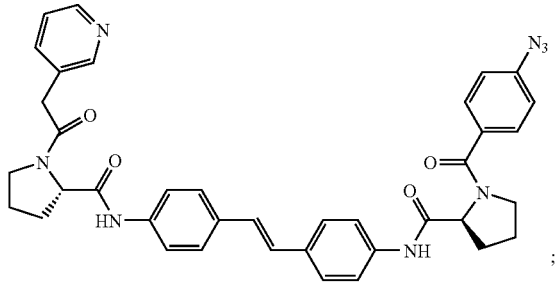
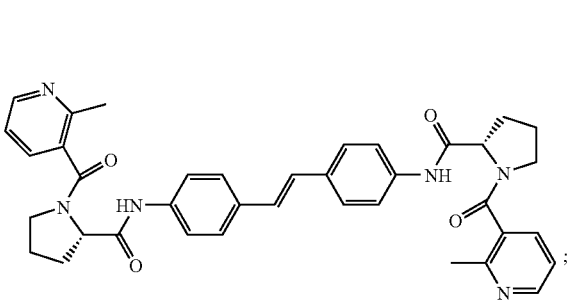
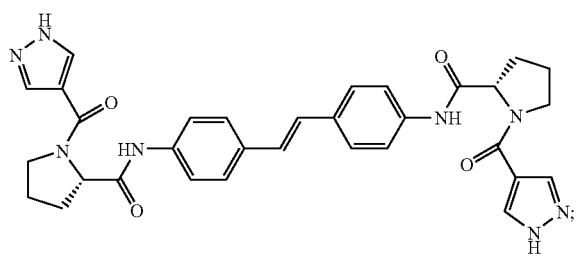
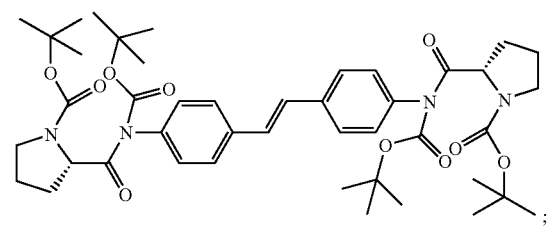
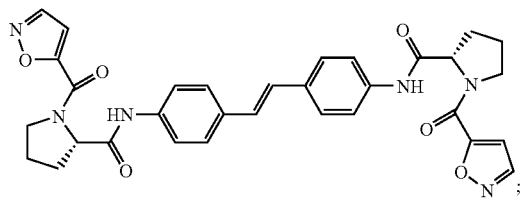
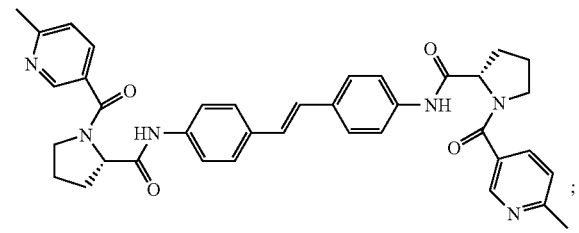

-continued
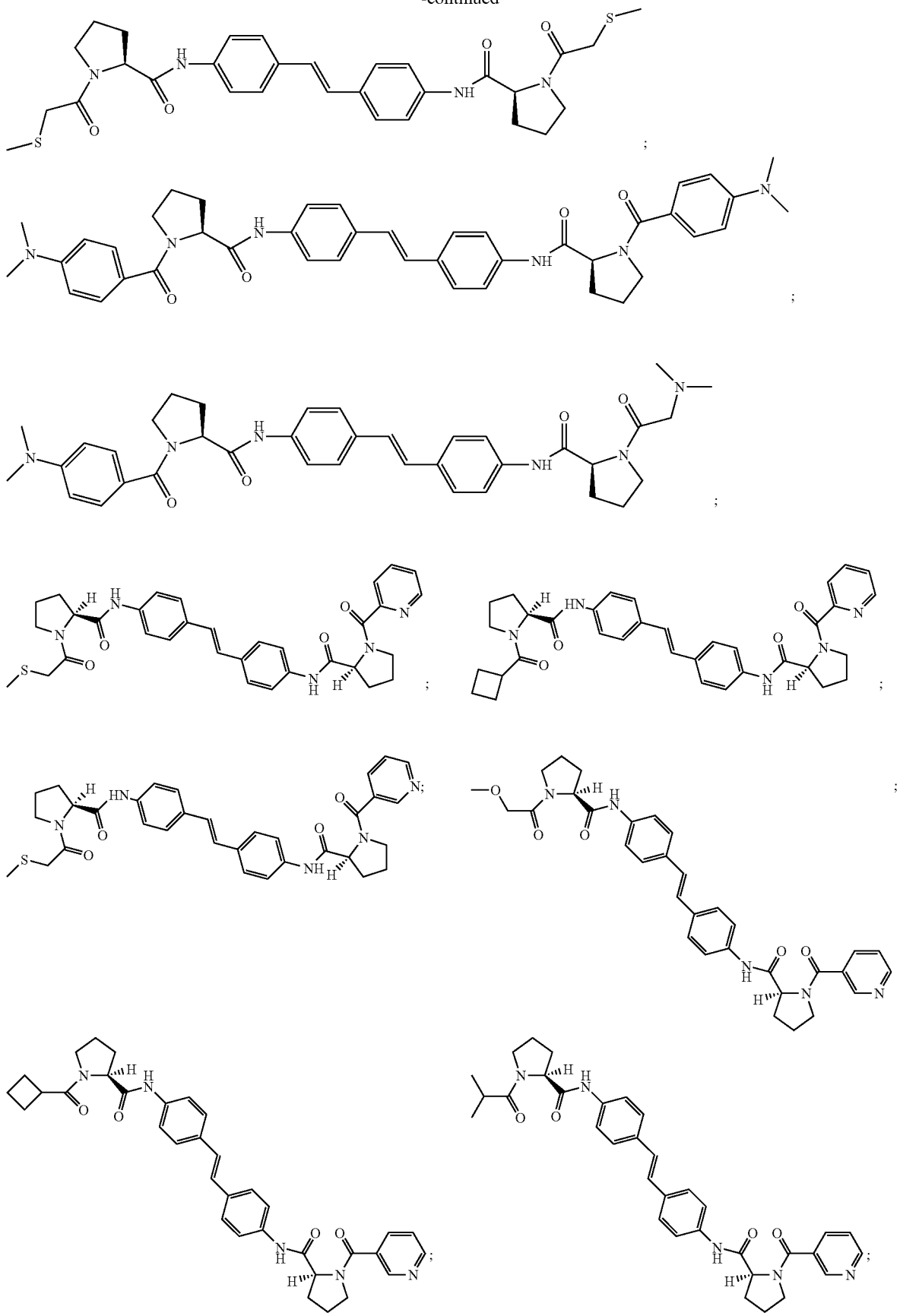

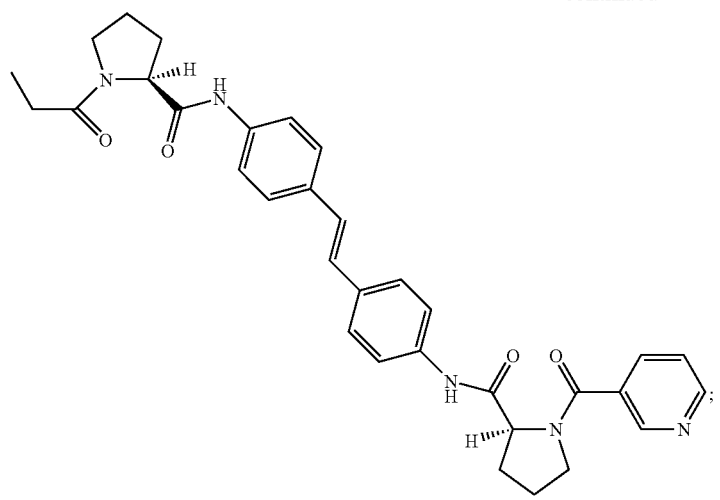
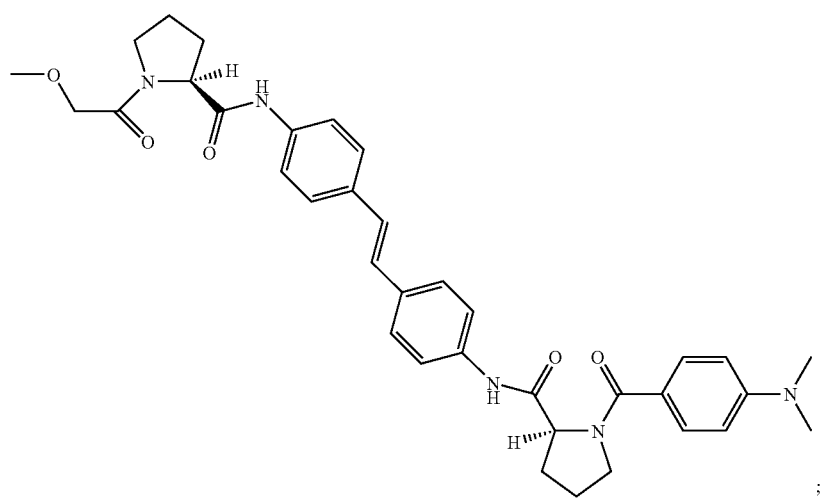
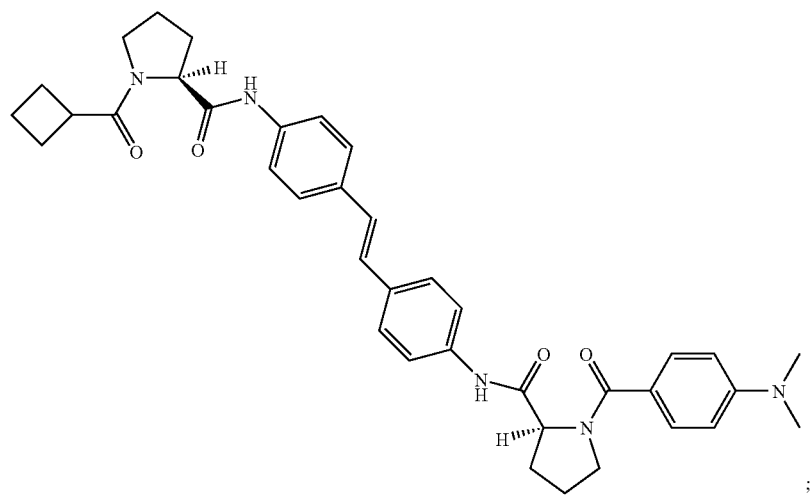

-continued
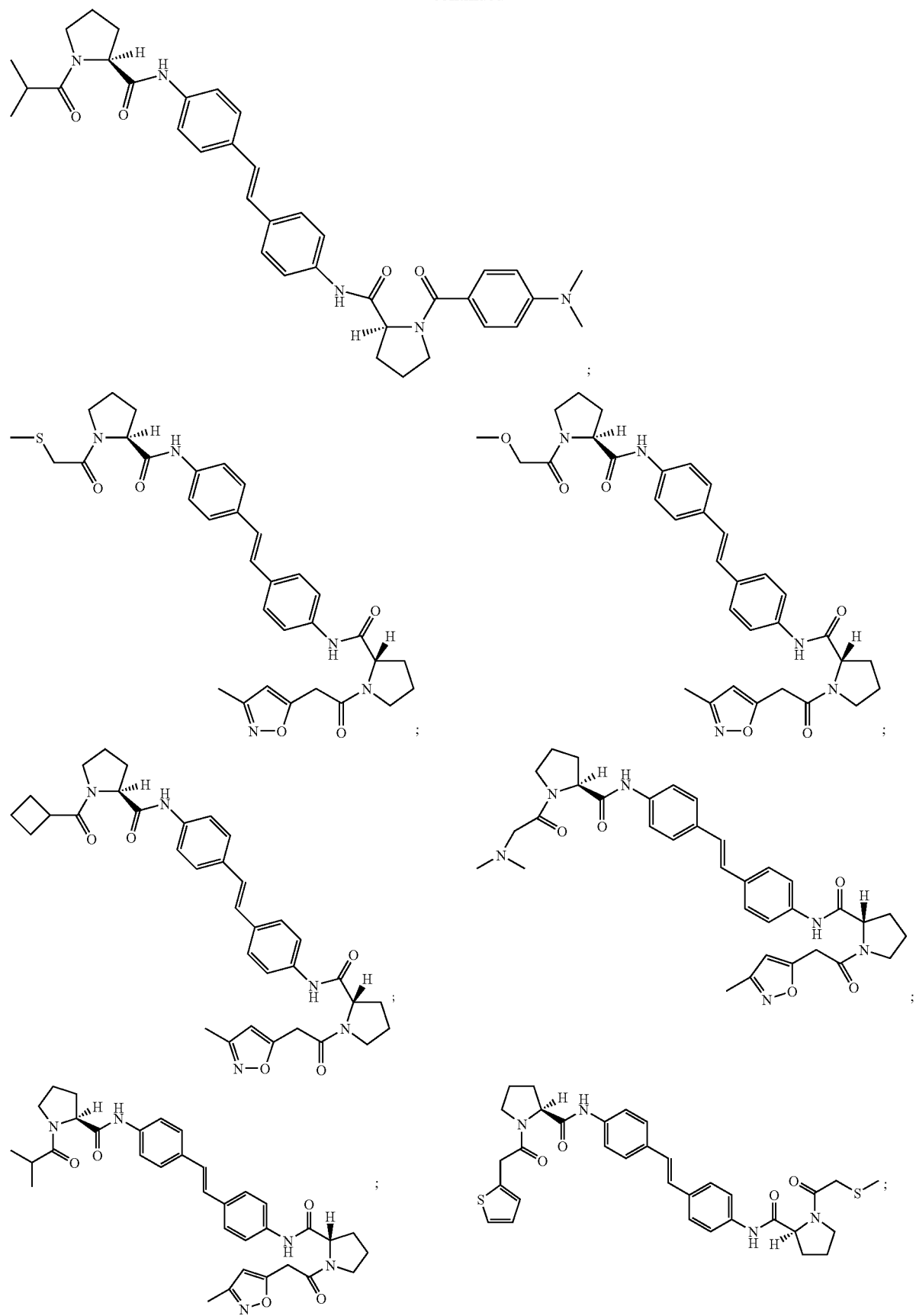

227 228
-continued
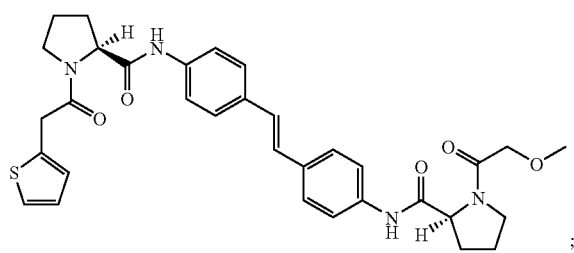
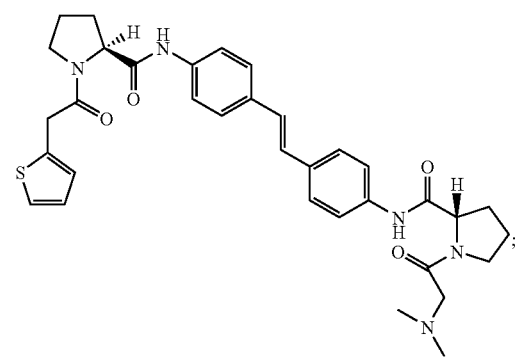
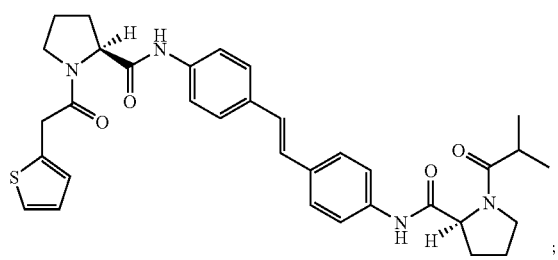
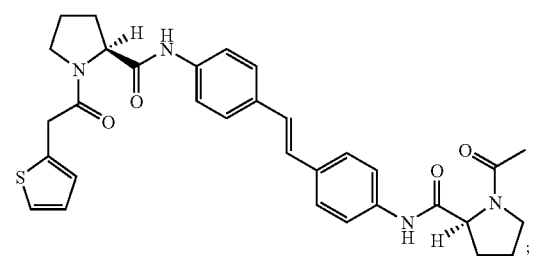
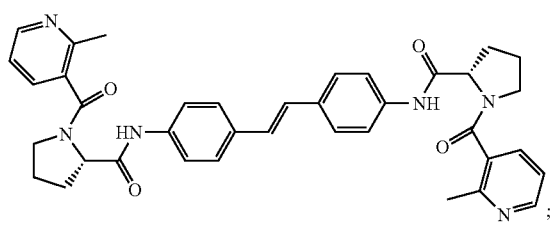
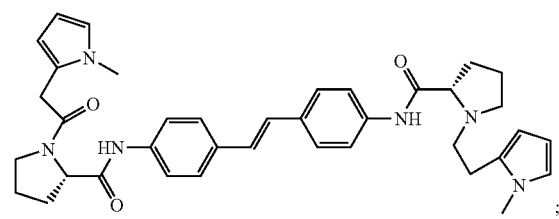
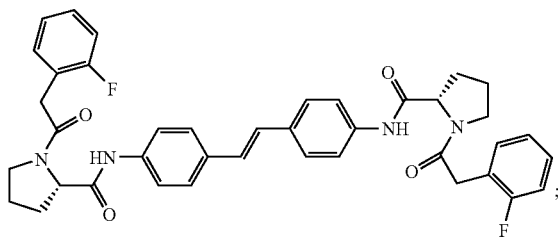
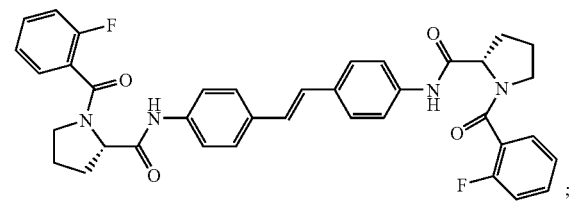
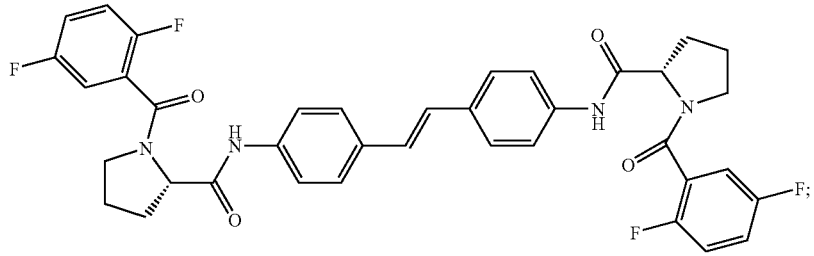
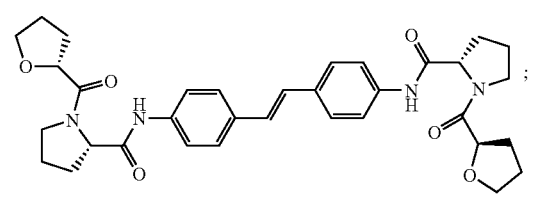
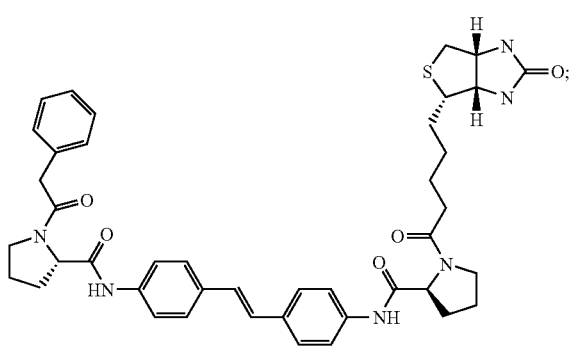

-continued
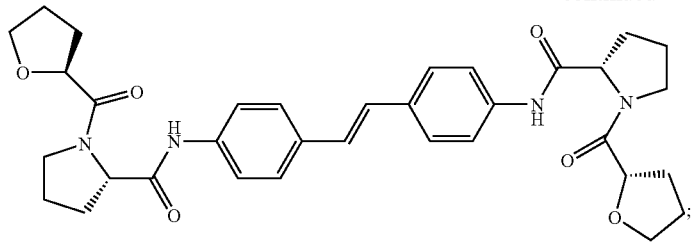
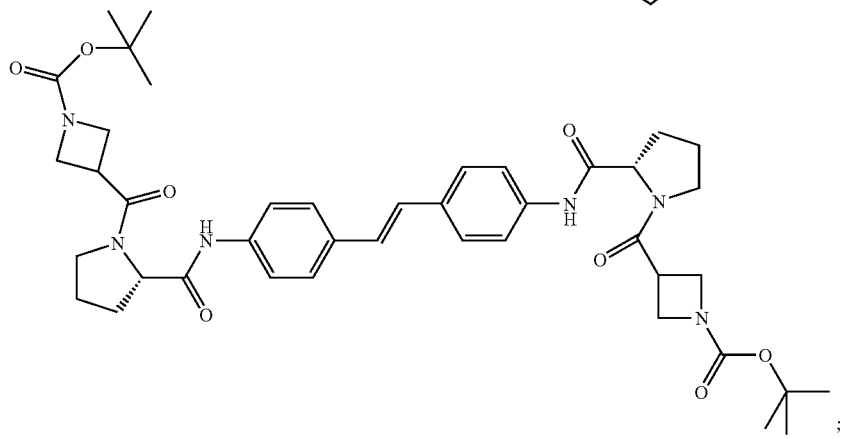
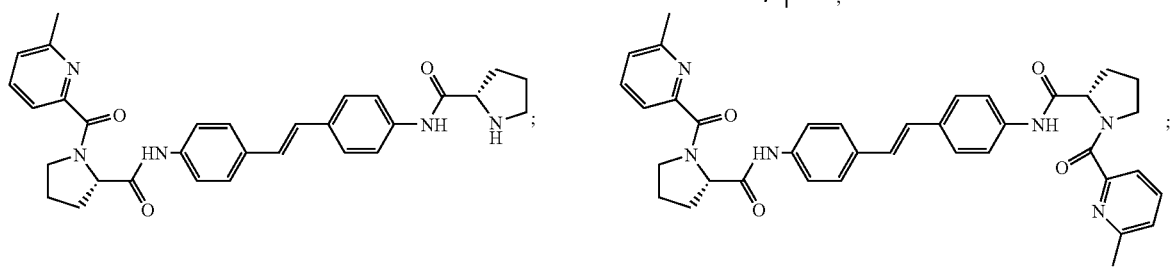
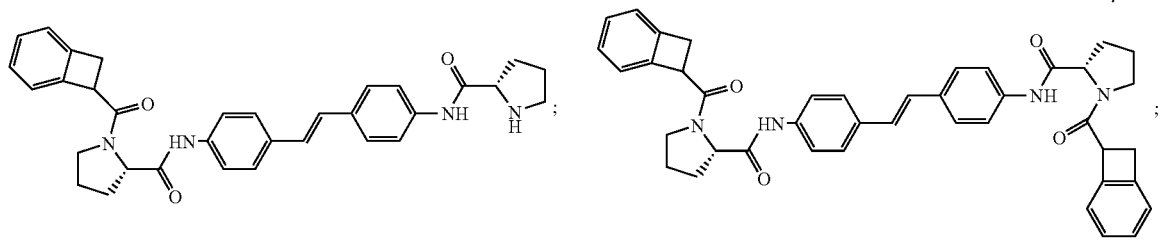
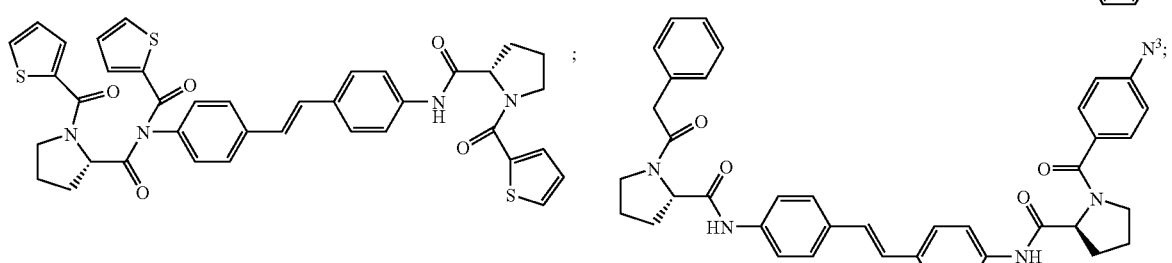
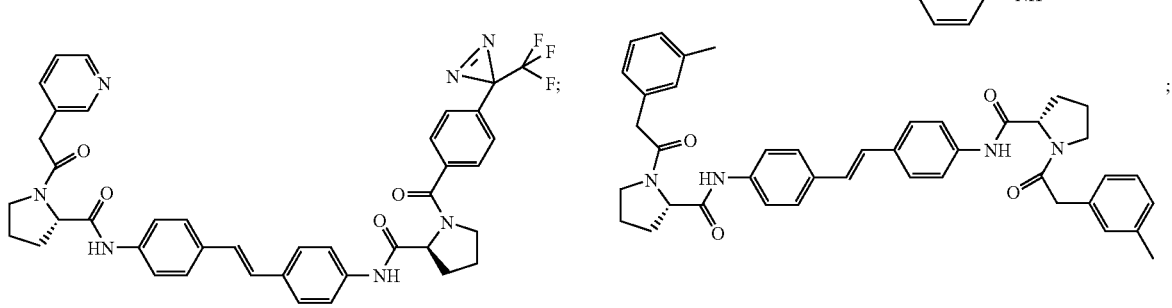

-continued
231
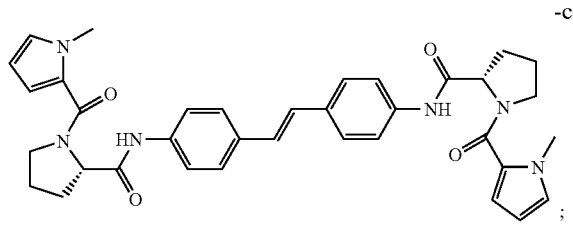
232
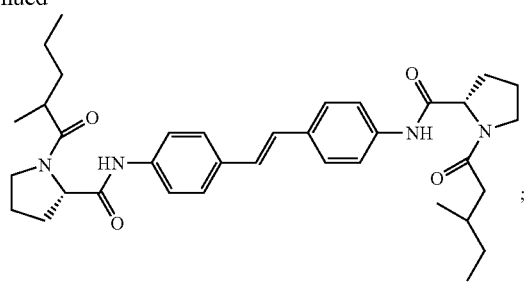
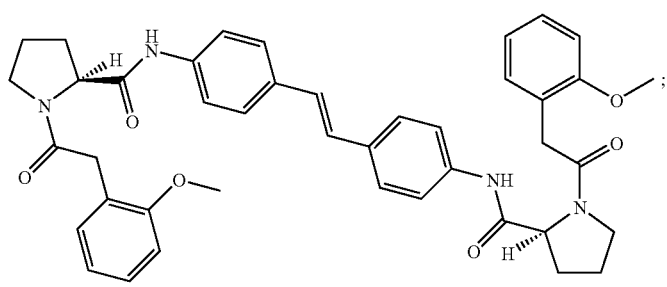
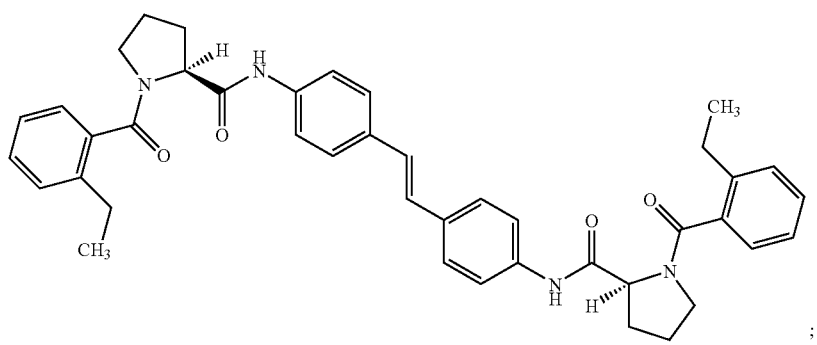
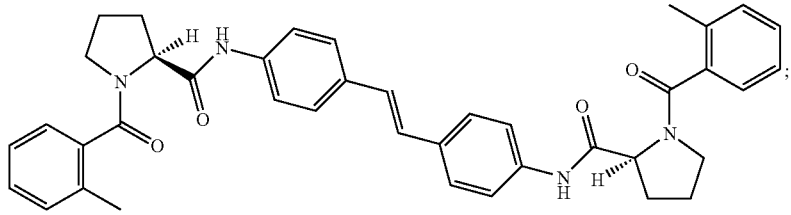
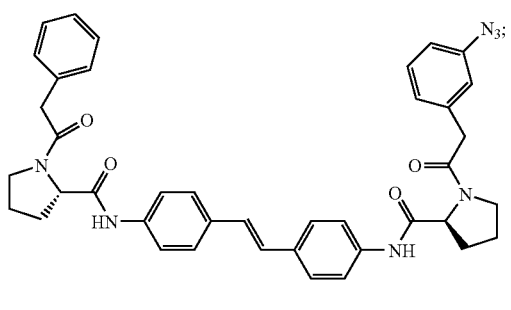
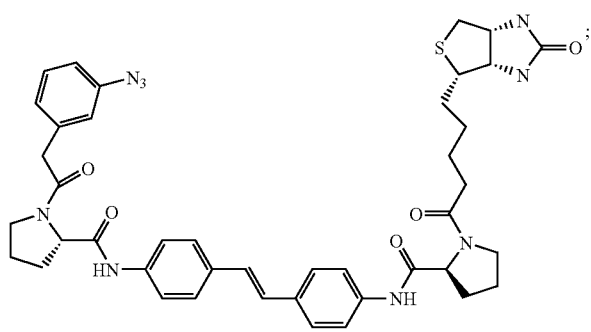

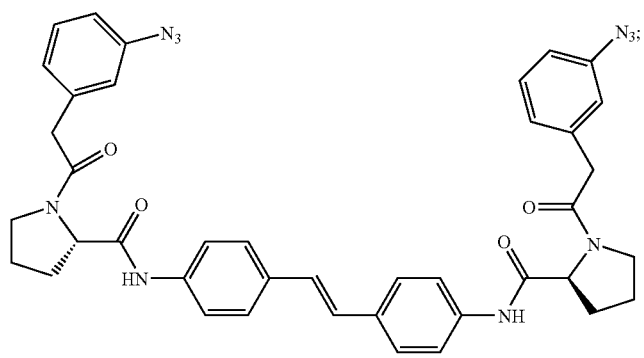
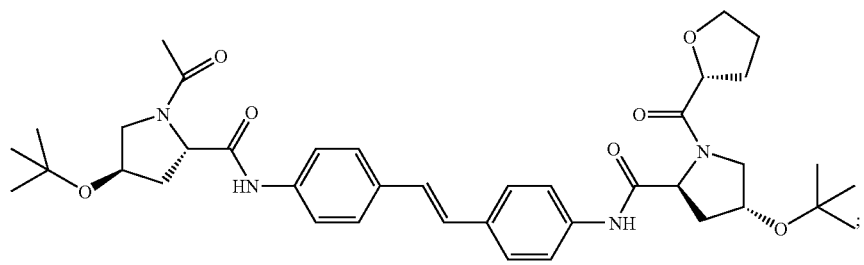
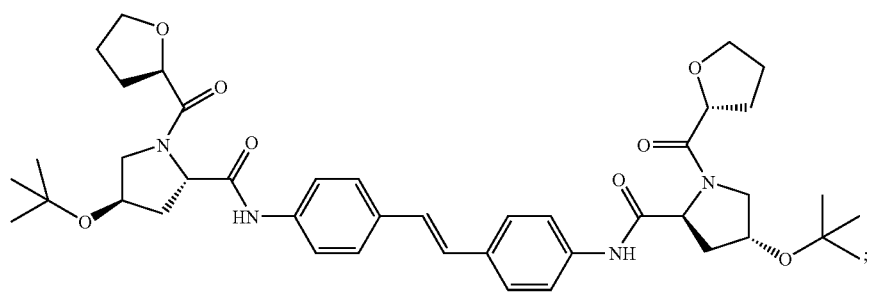
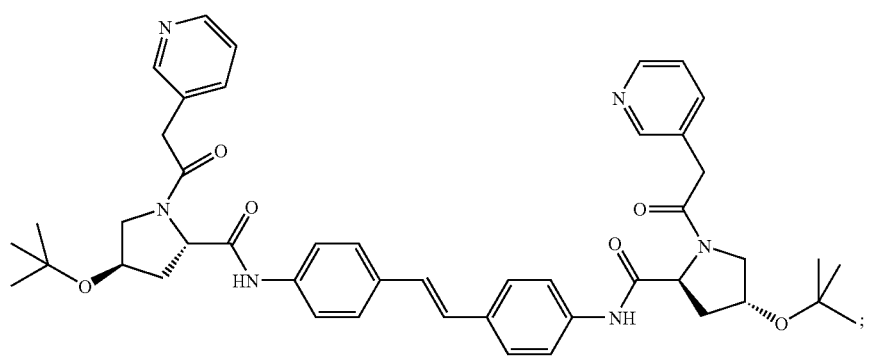
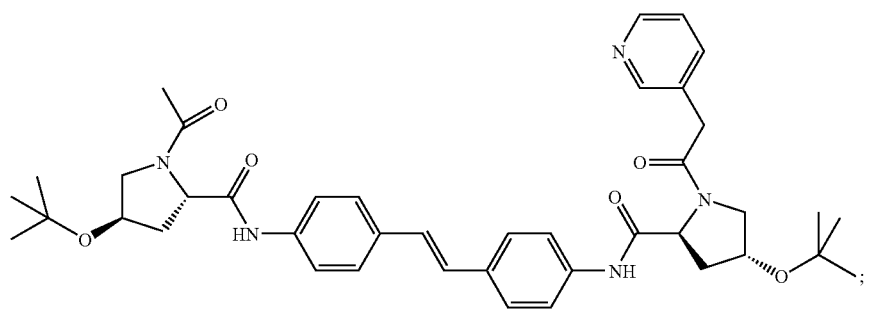

-continued
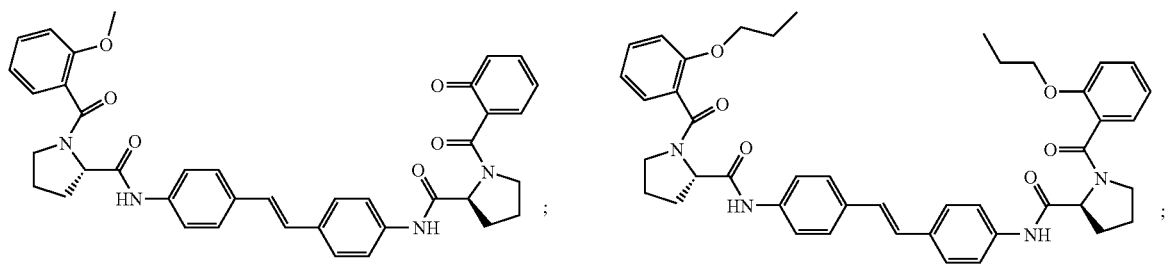
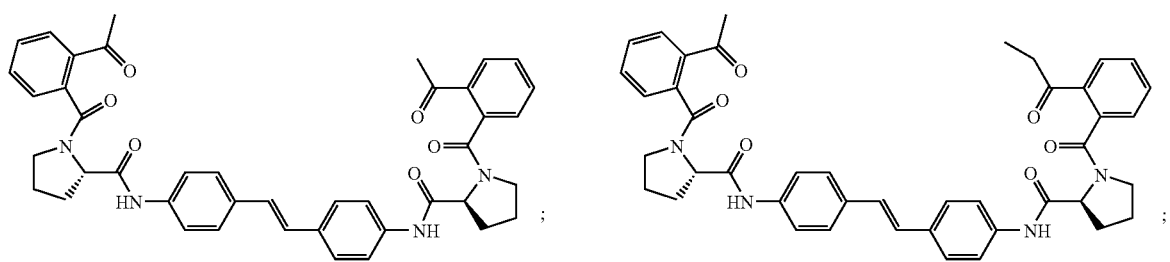
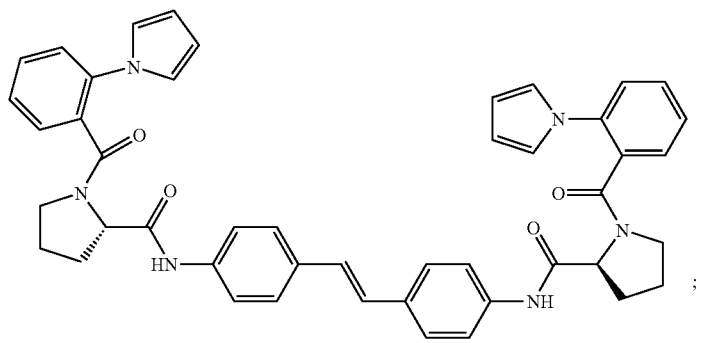
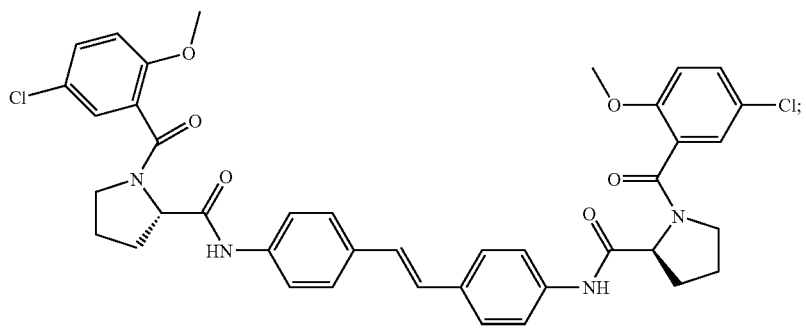
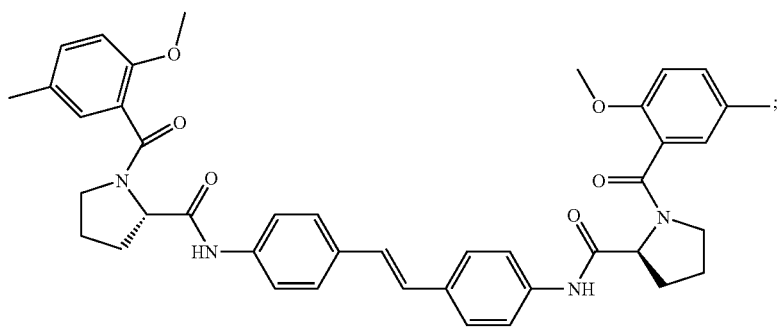

-continued
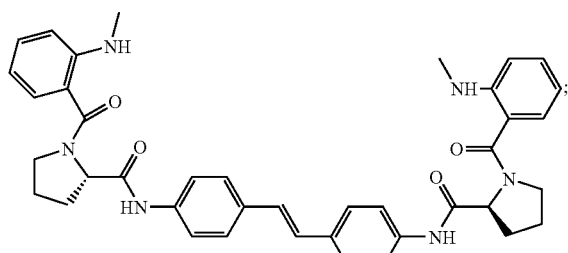
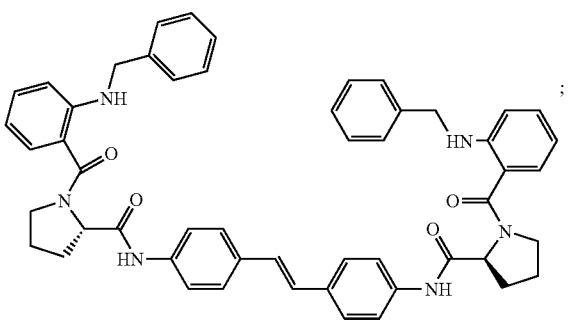
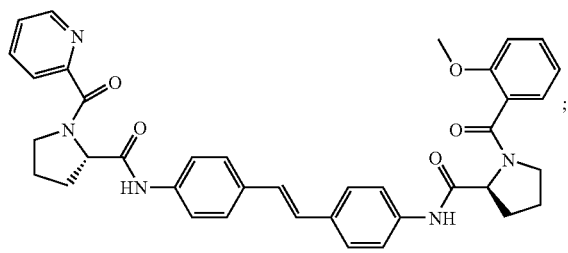
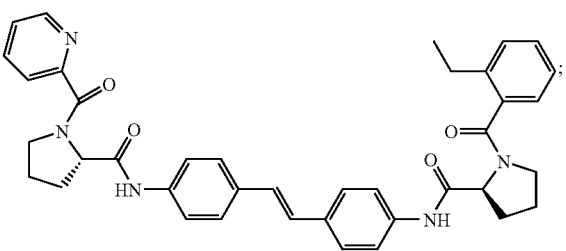
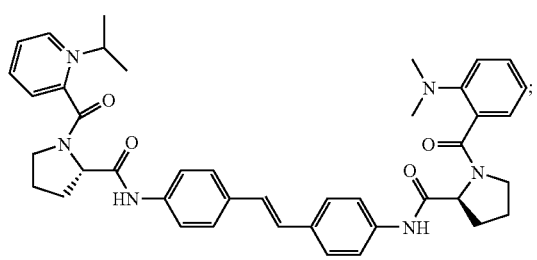
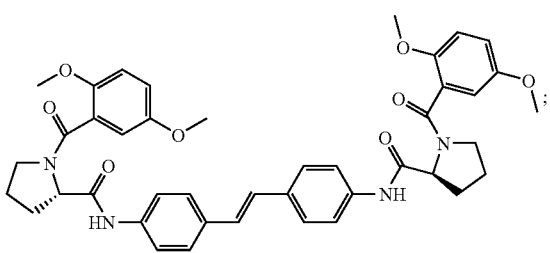
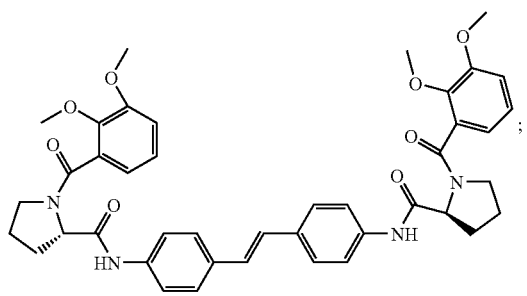
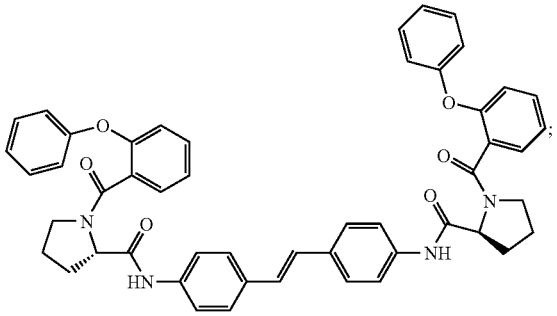
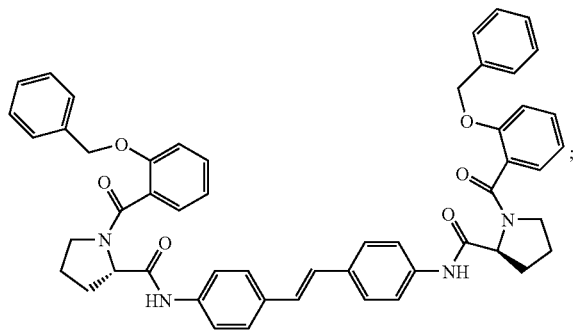
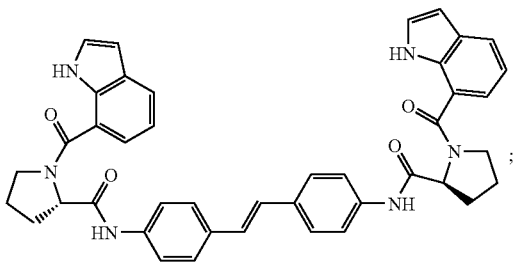

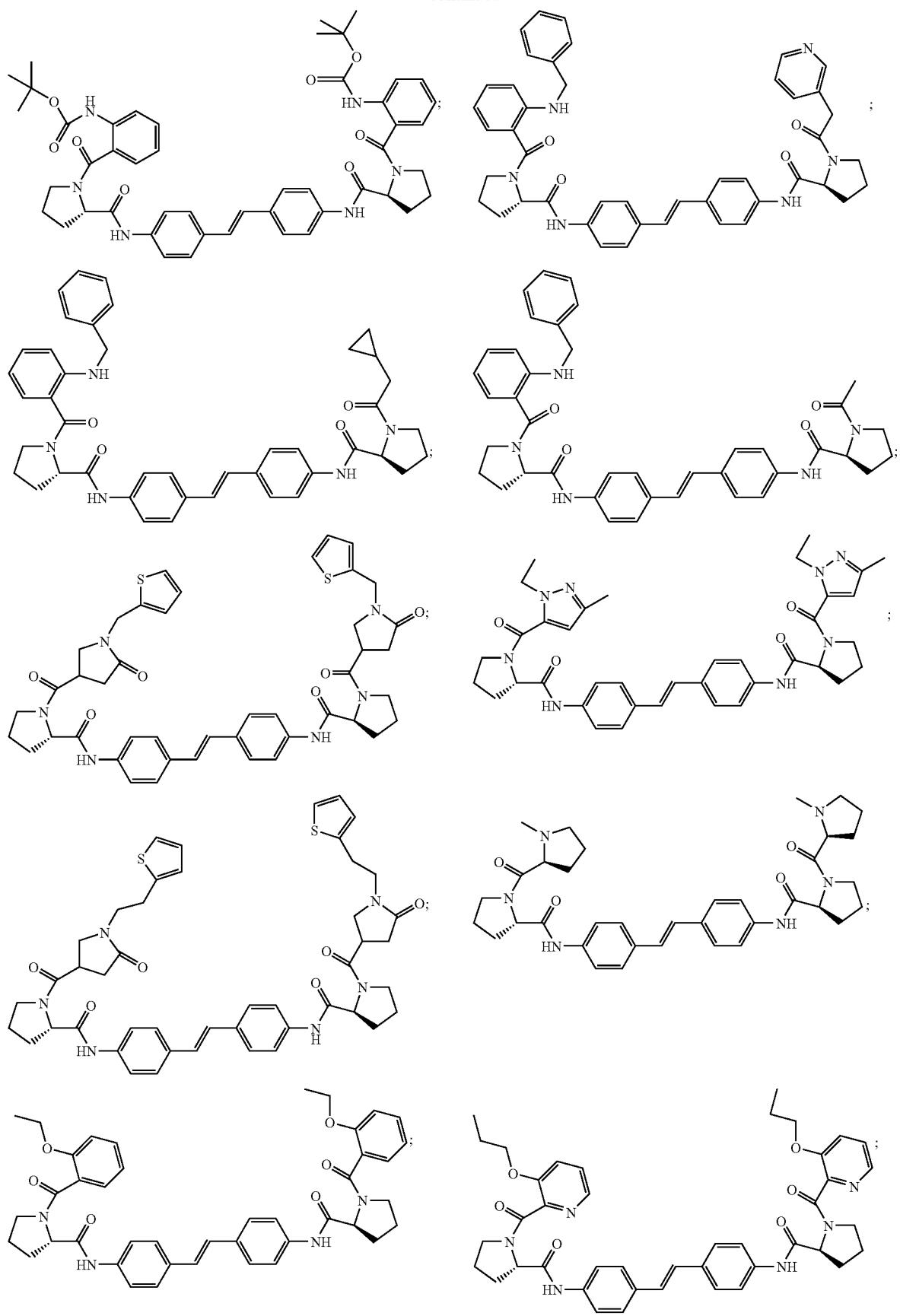

241
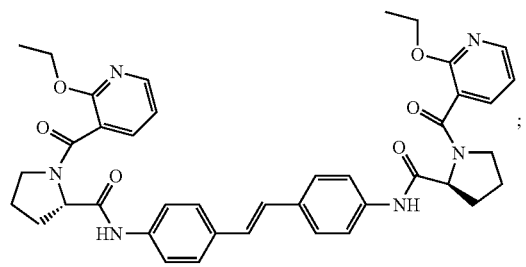
242
-continued
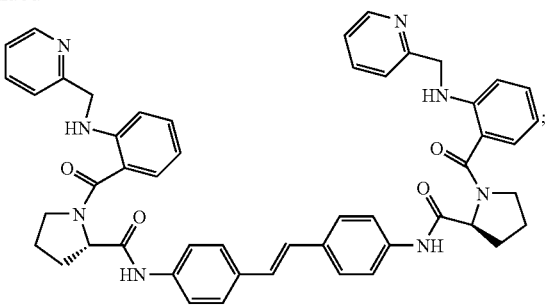
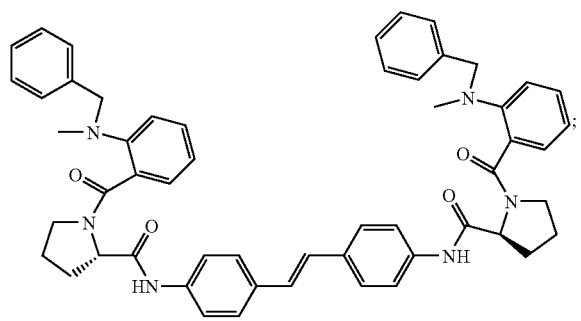
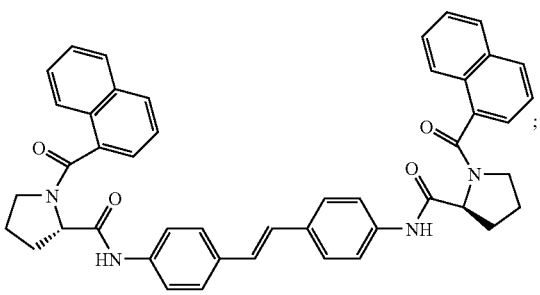
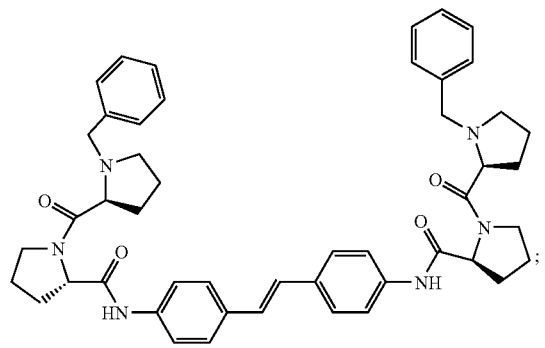
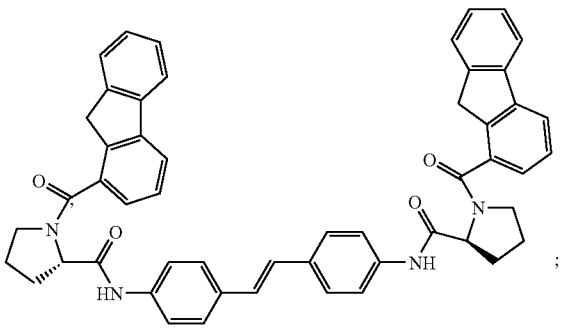
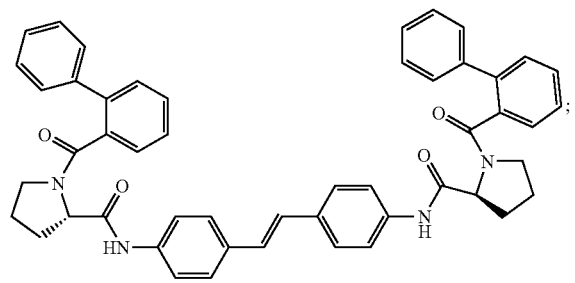
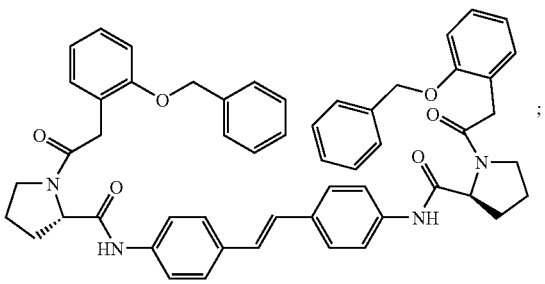
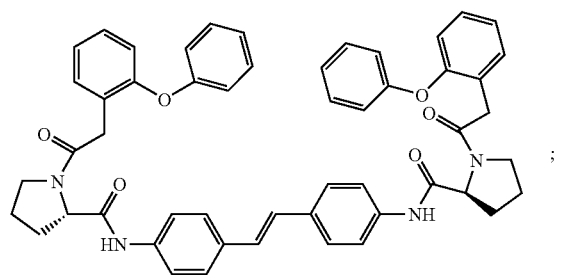
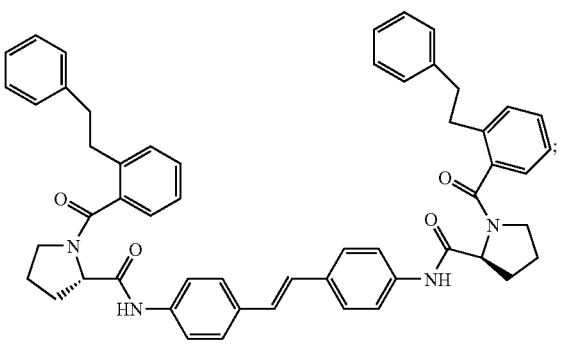

243
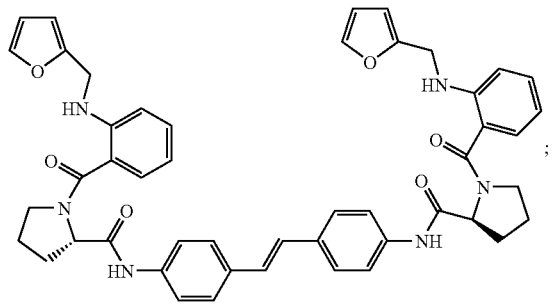
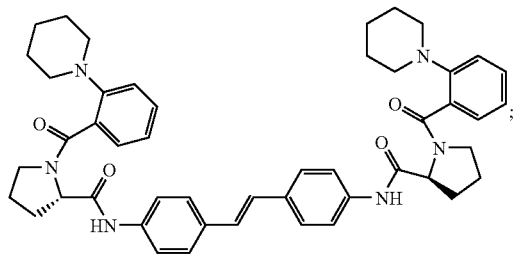
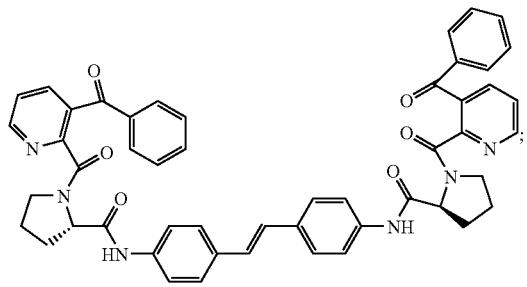
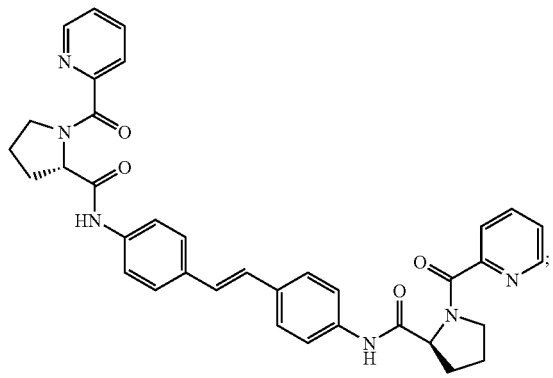
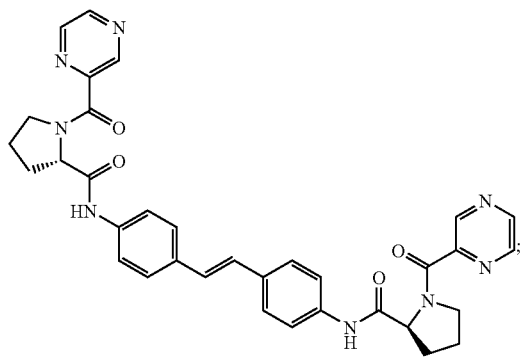
244
-continued
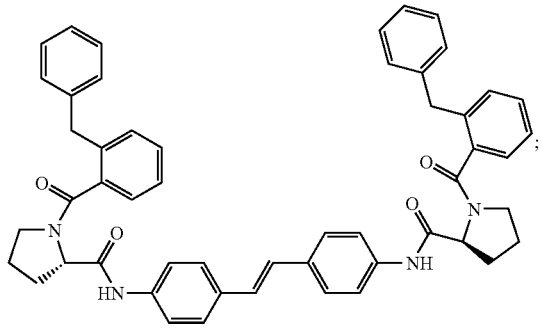
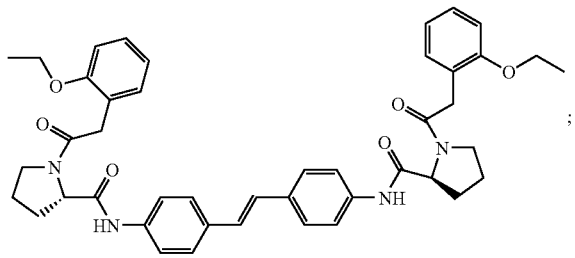
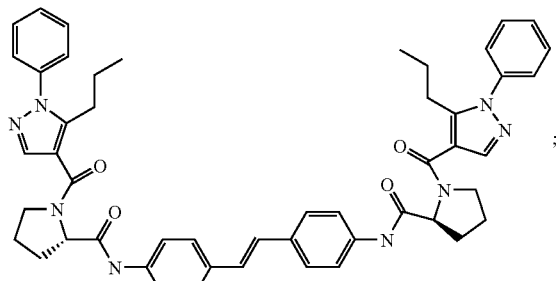
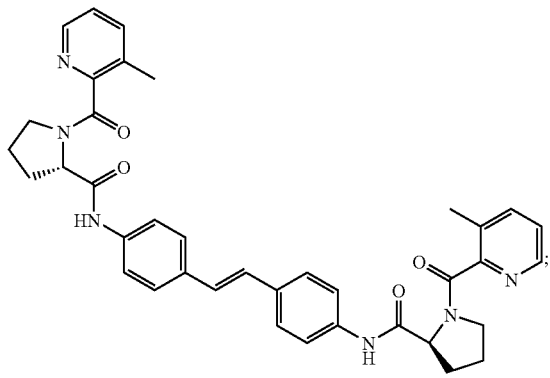
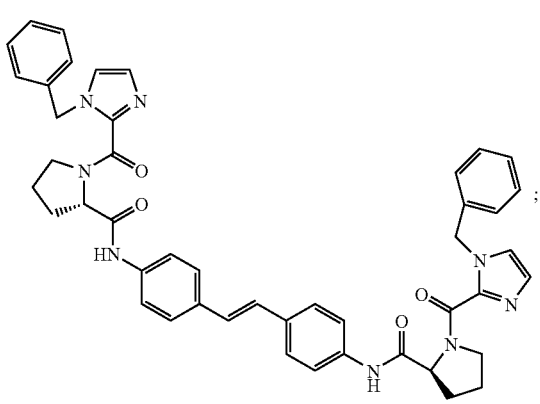

245
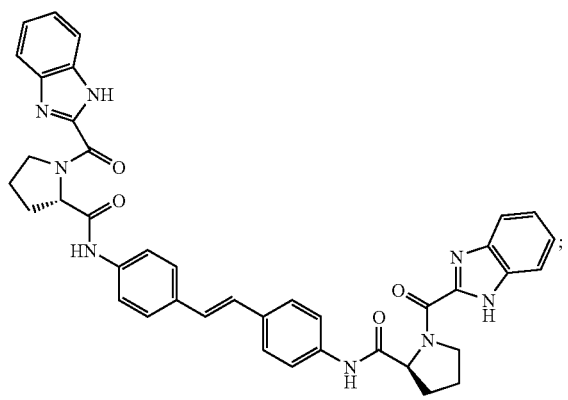
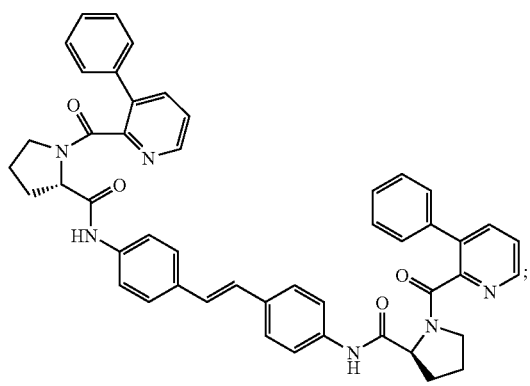
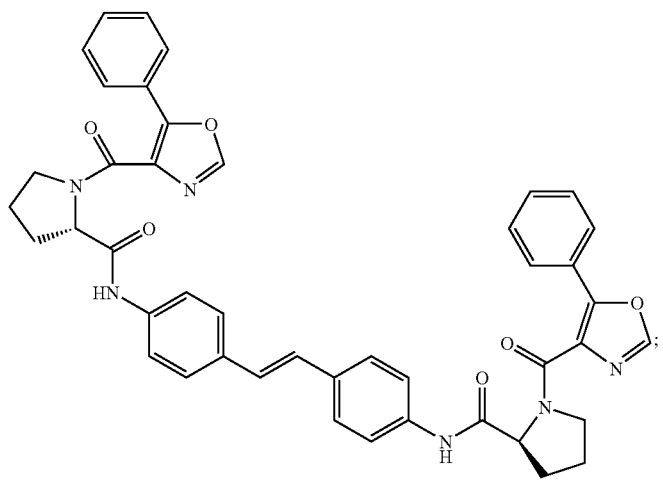
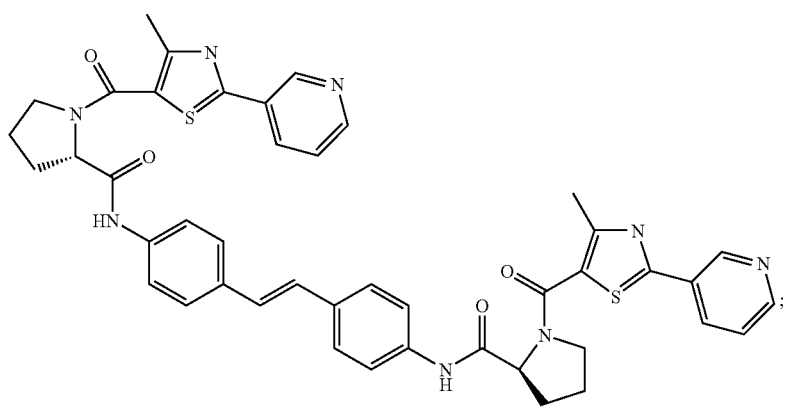
246
-continued
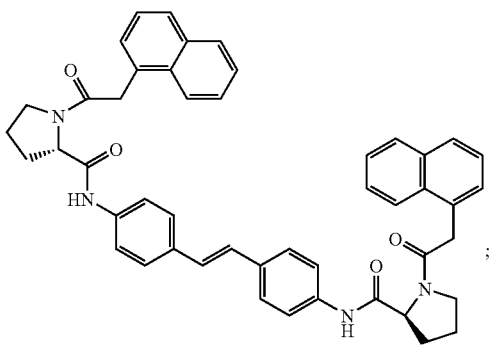
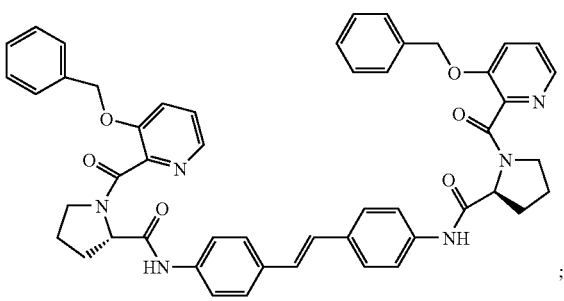

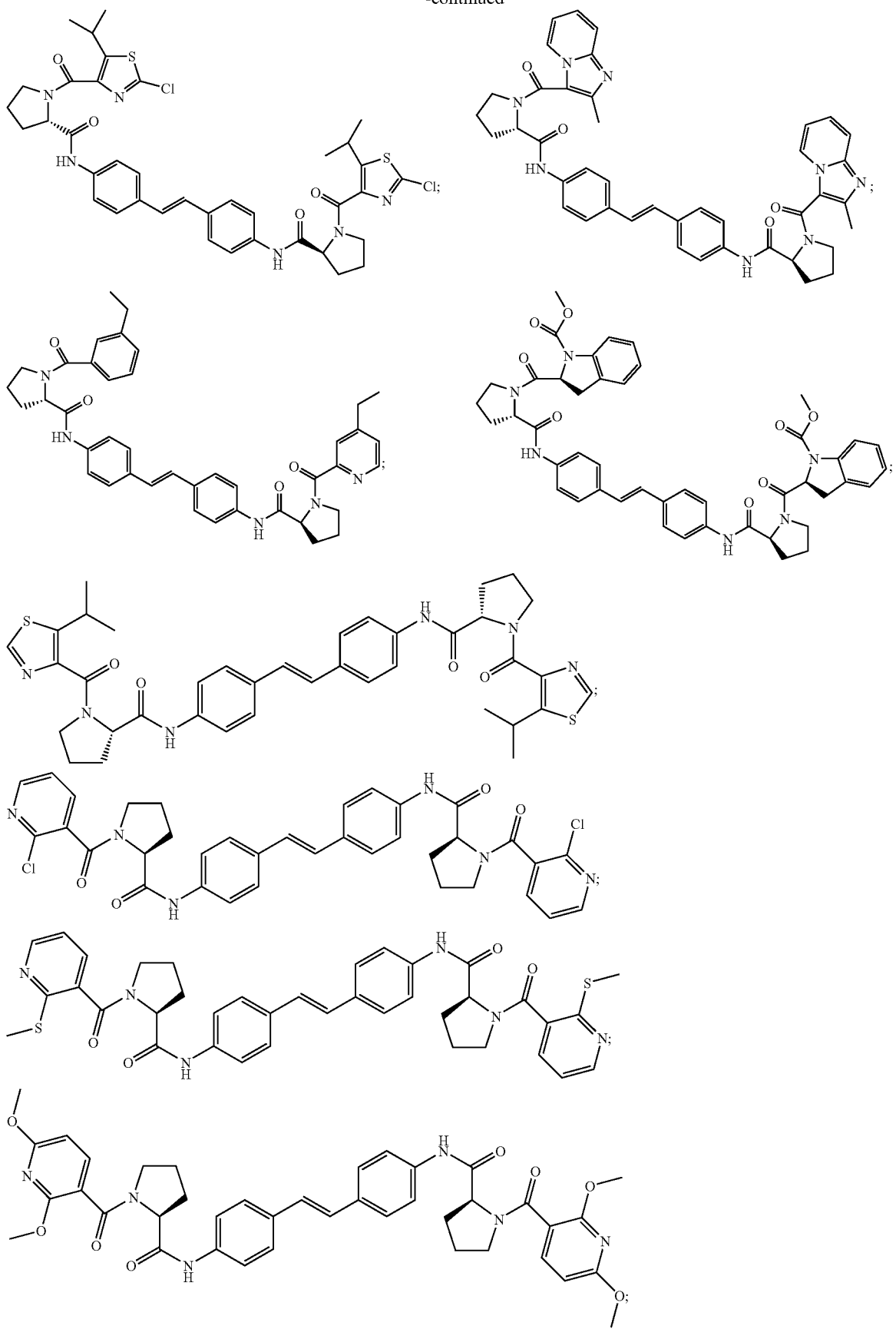

-continued
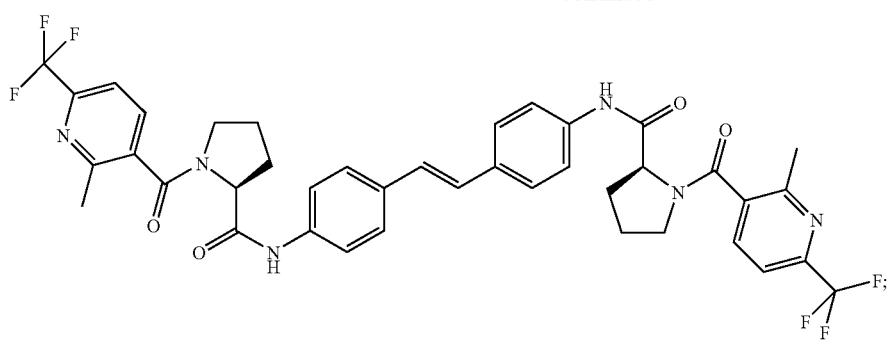
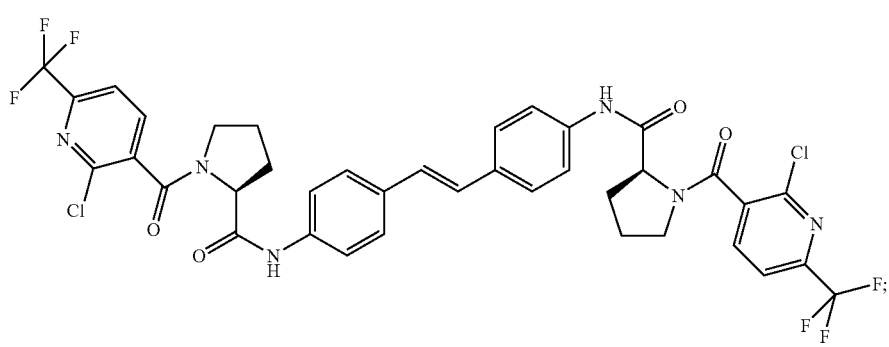
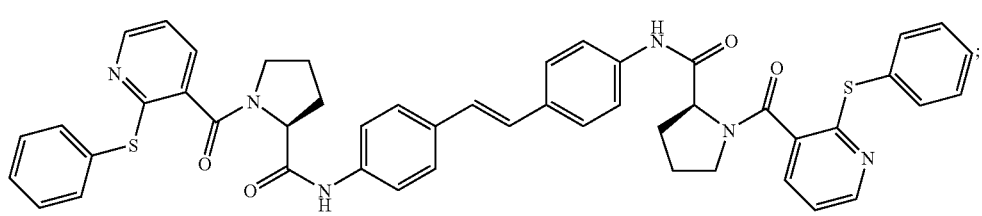
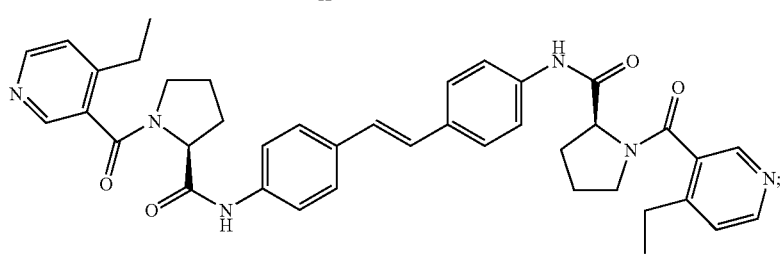
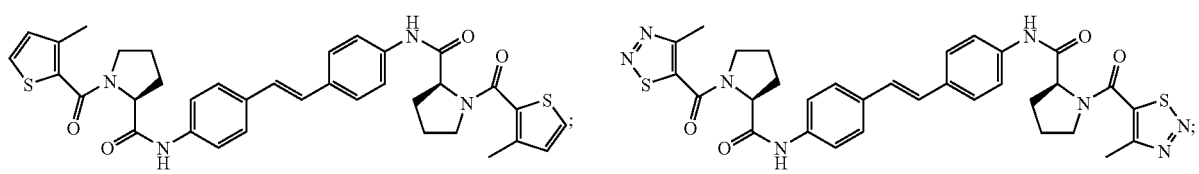
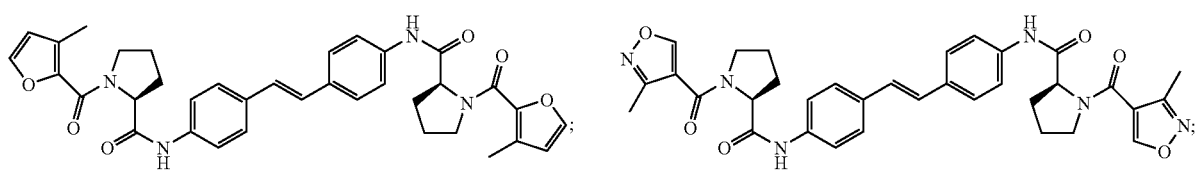
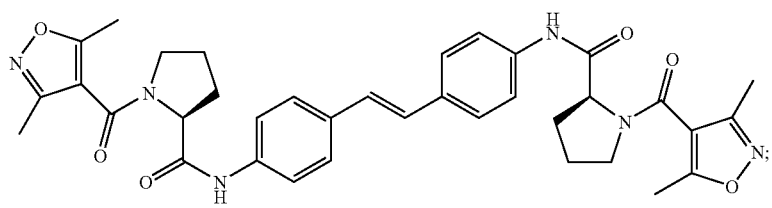

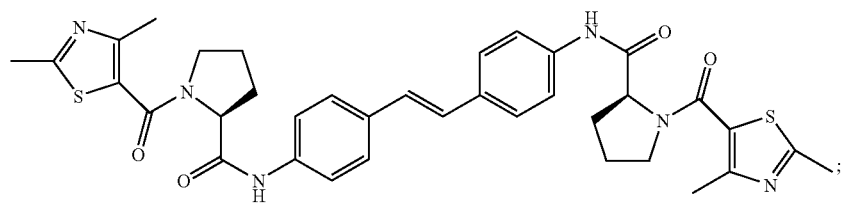
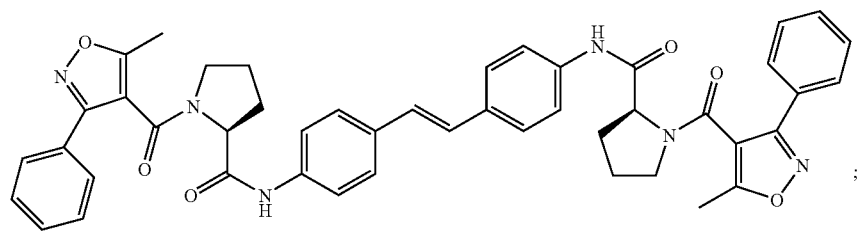
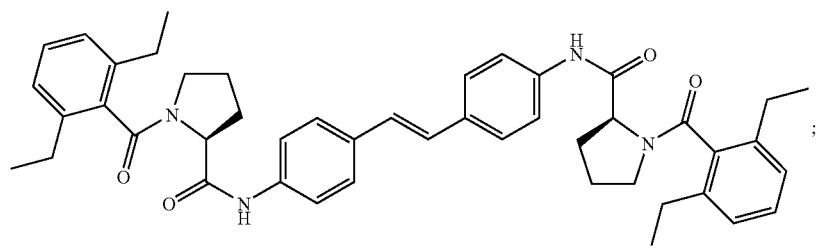
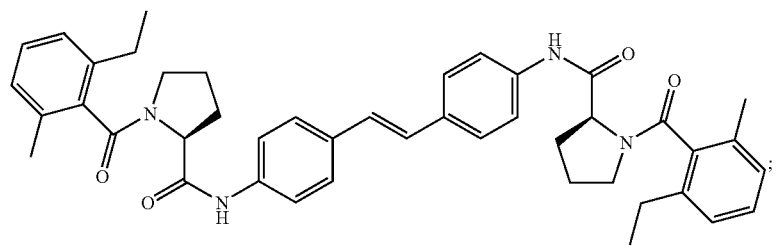
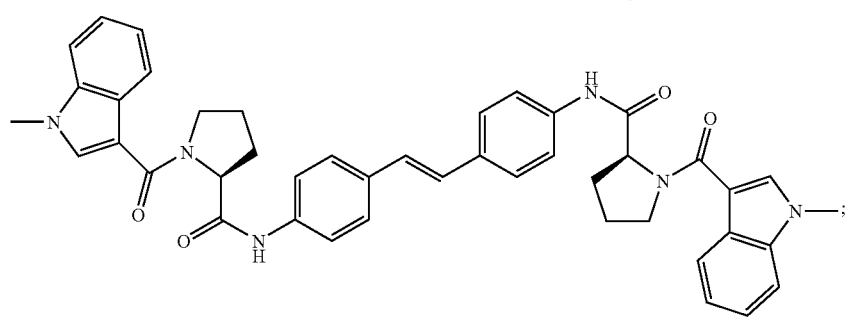
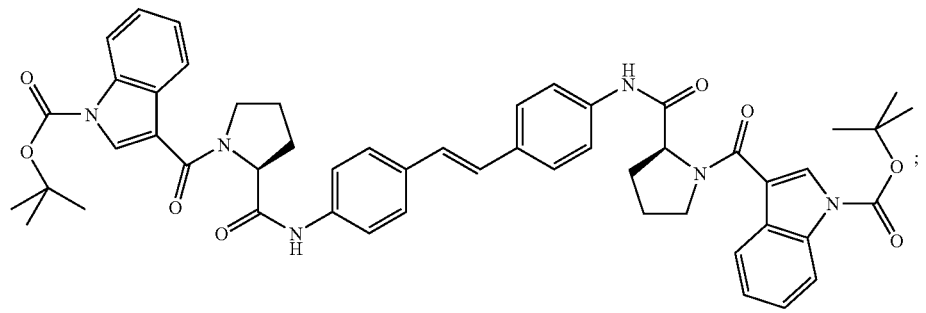

-continued
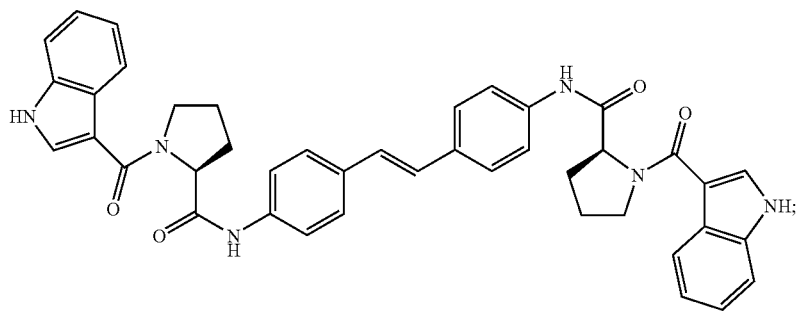
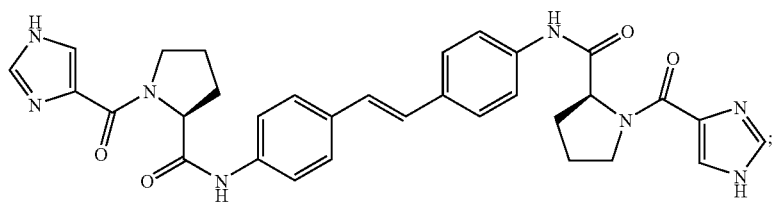
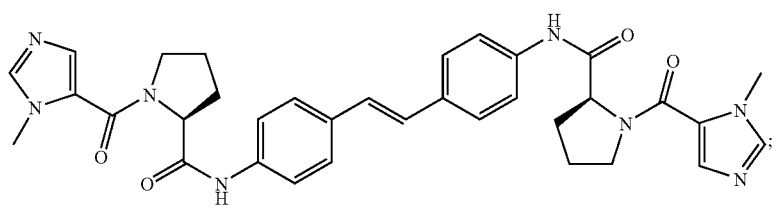
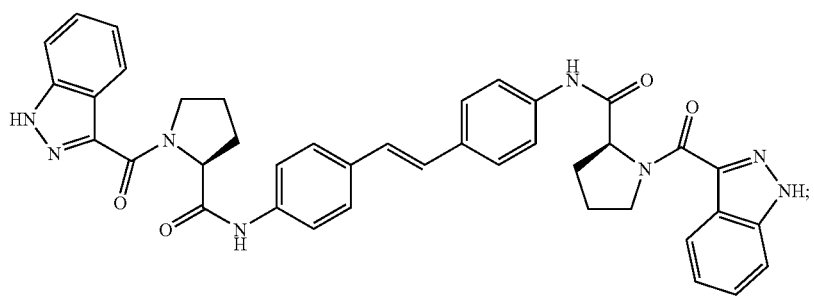
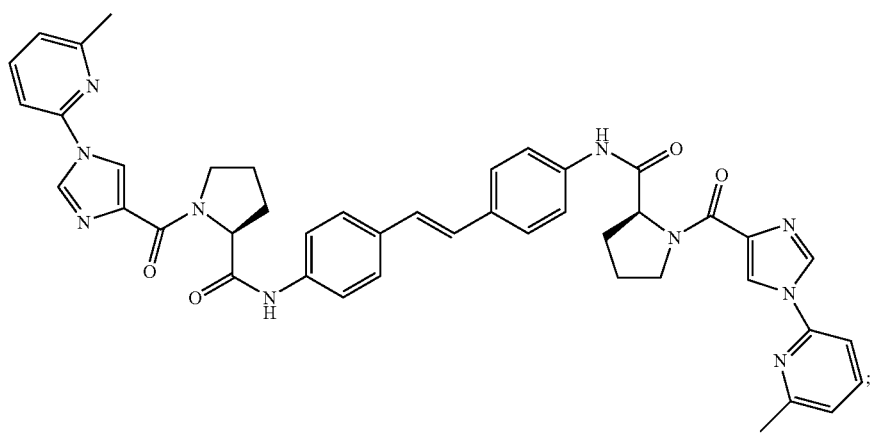
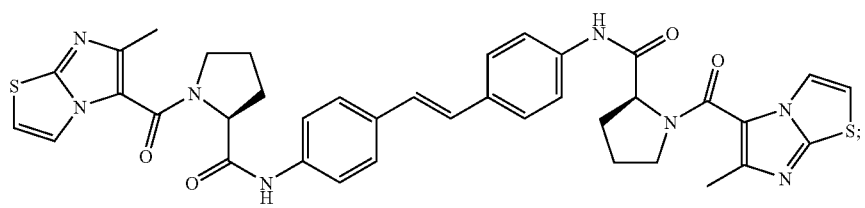

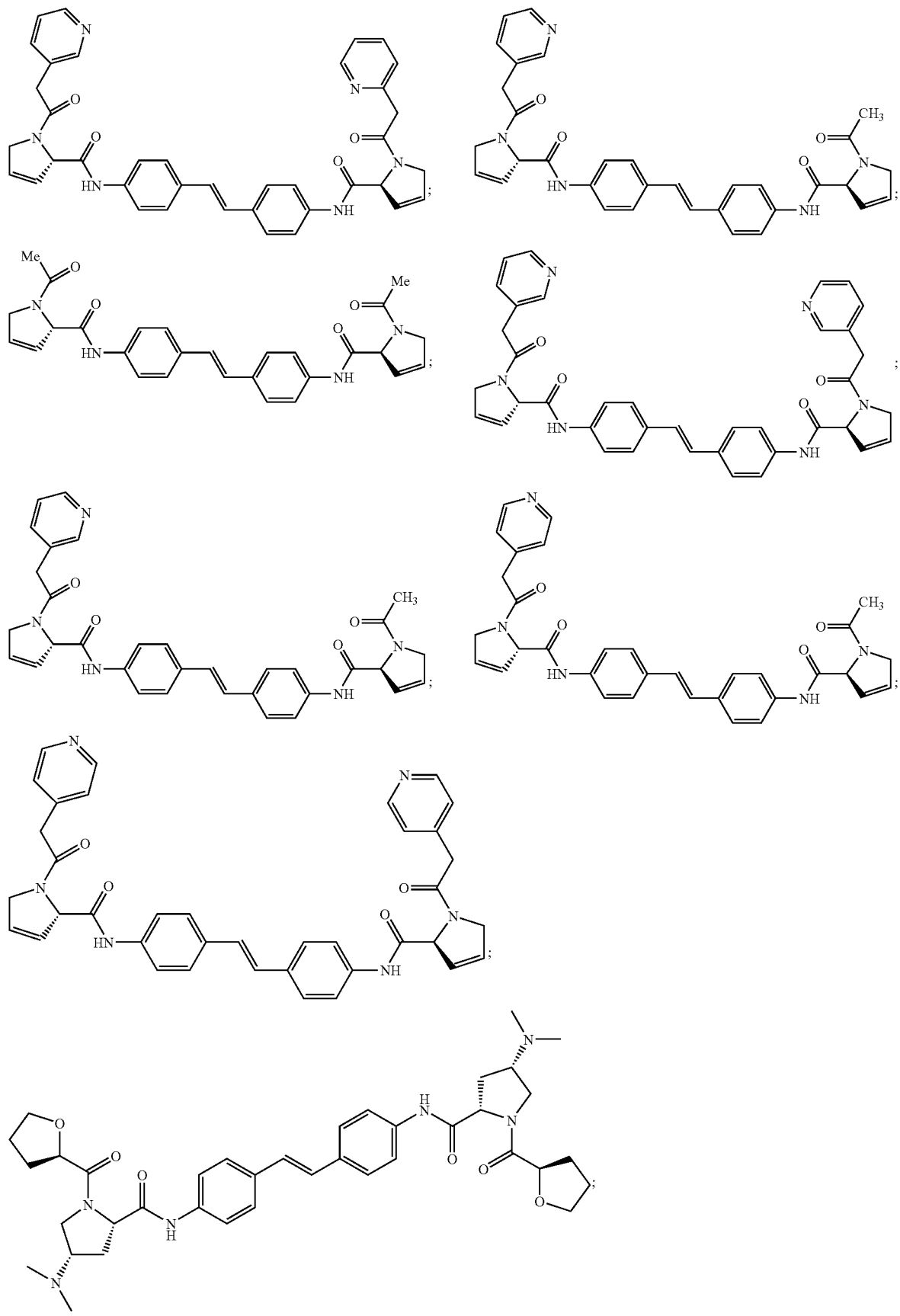

-continued
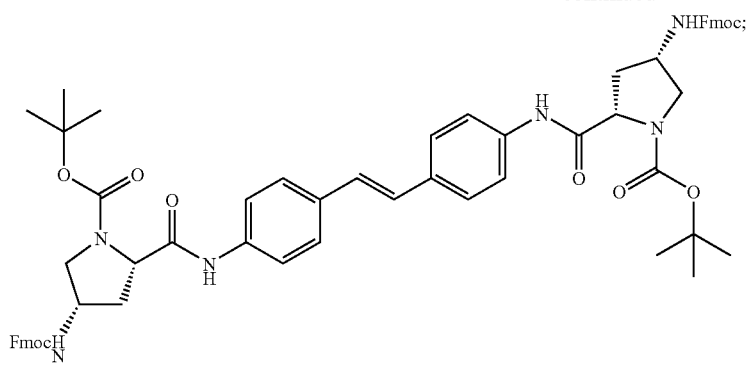
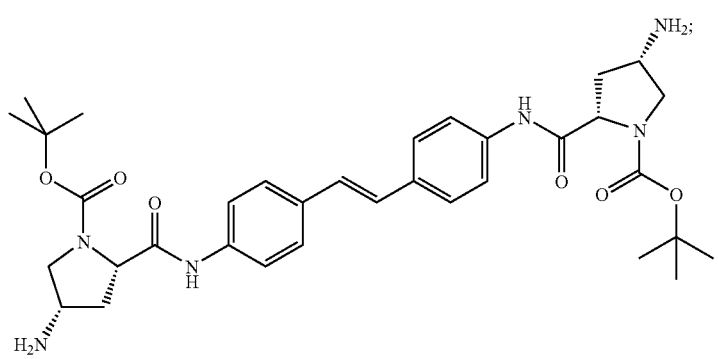
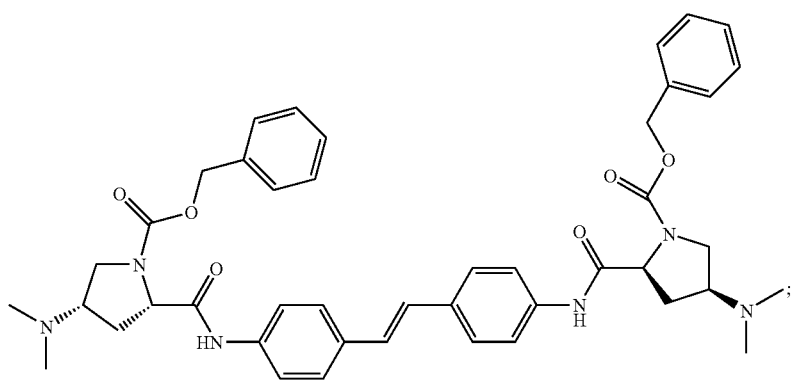
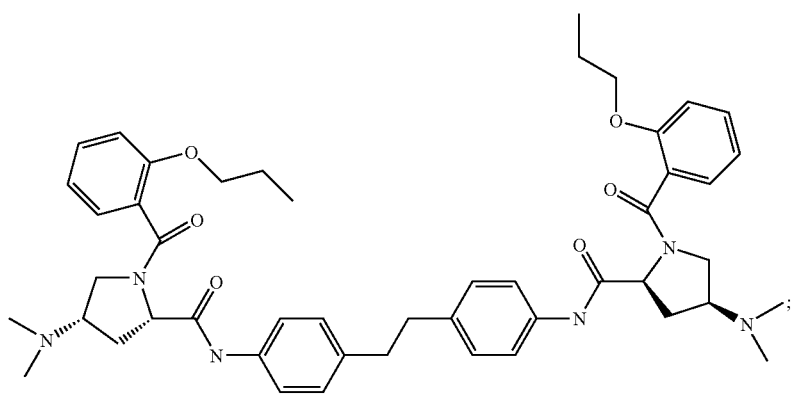

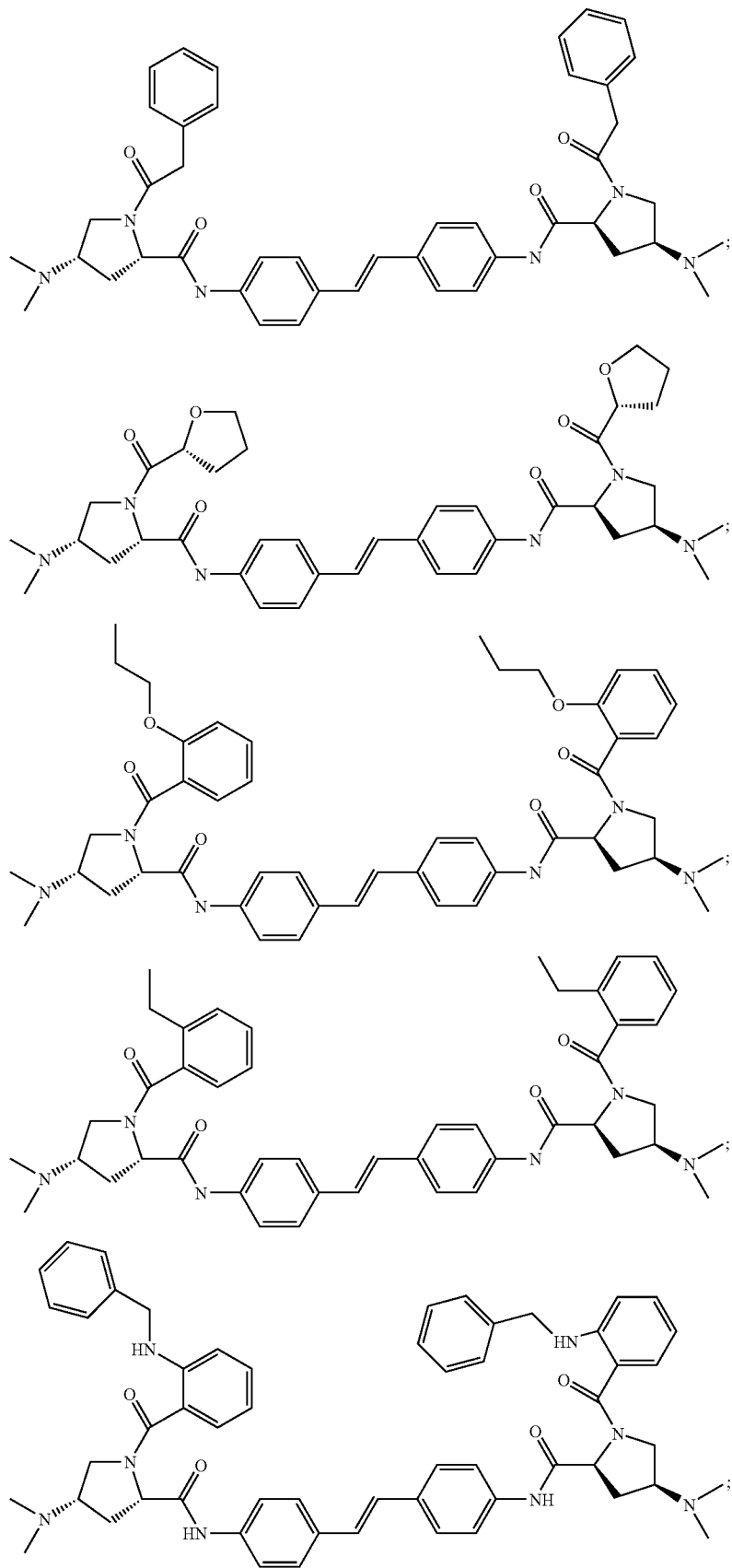

261                                                                                    262
-continued
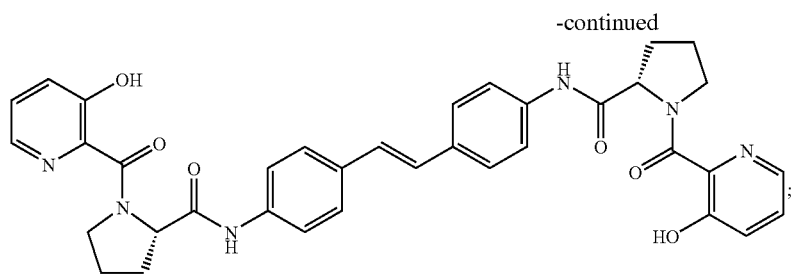
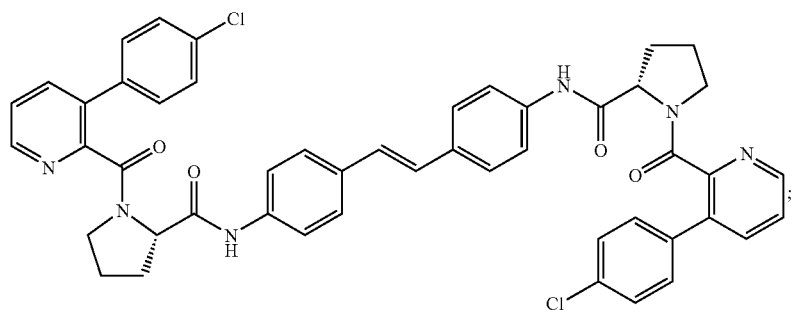
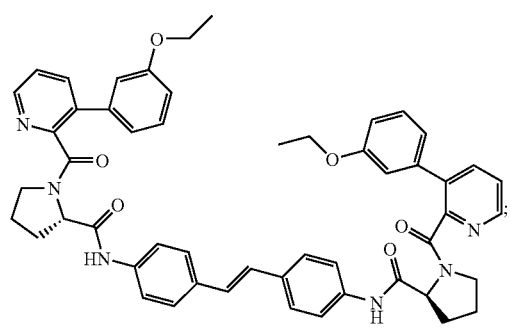
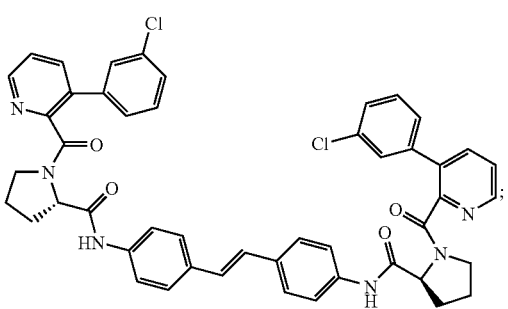
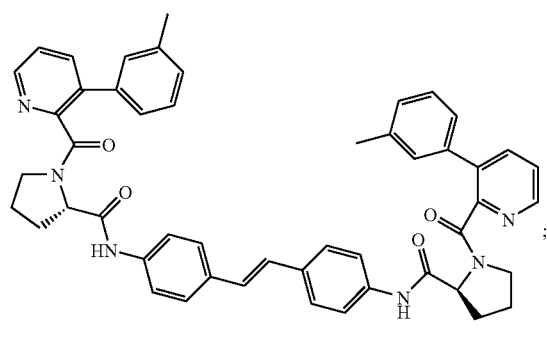
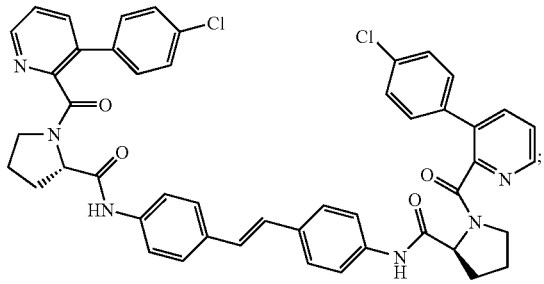
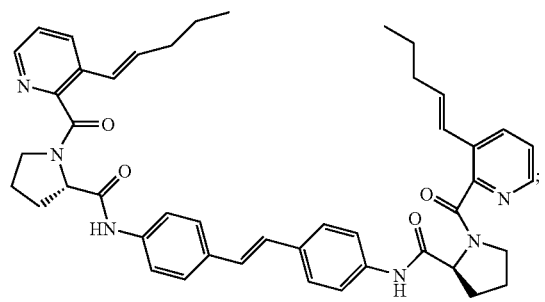
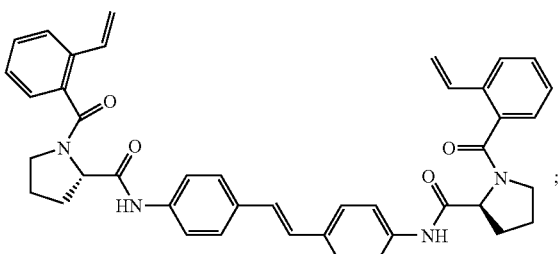

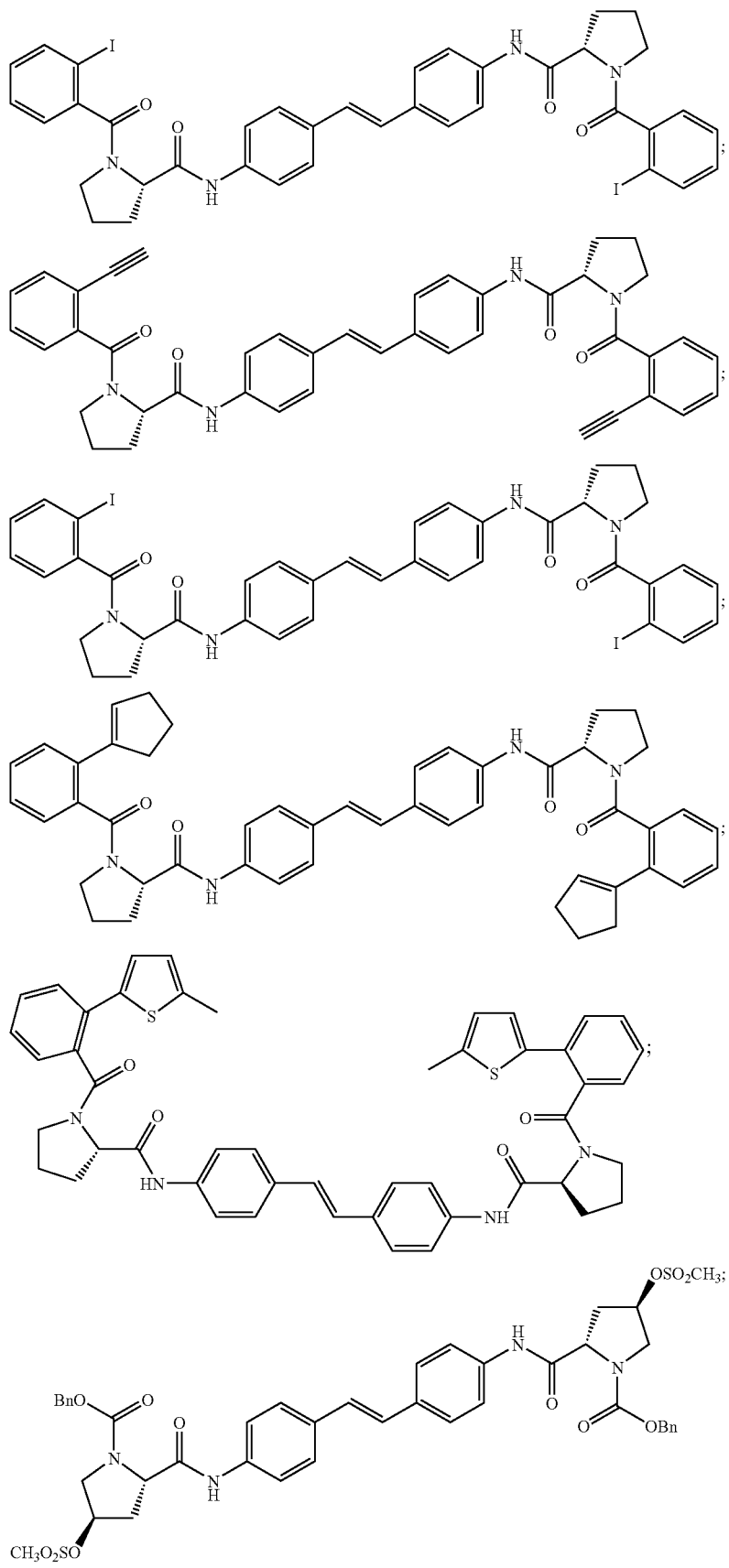

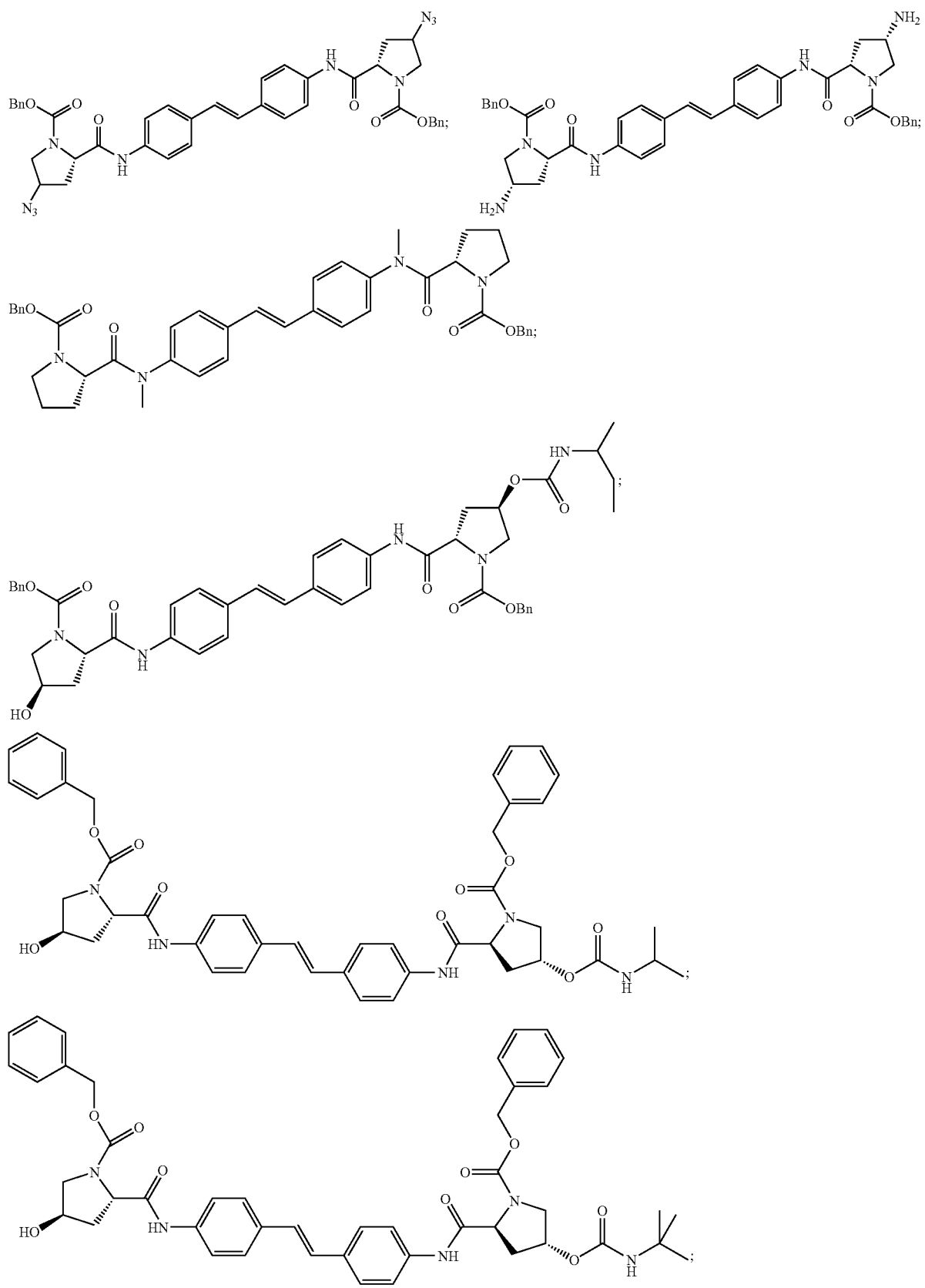

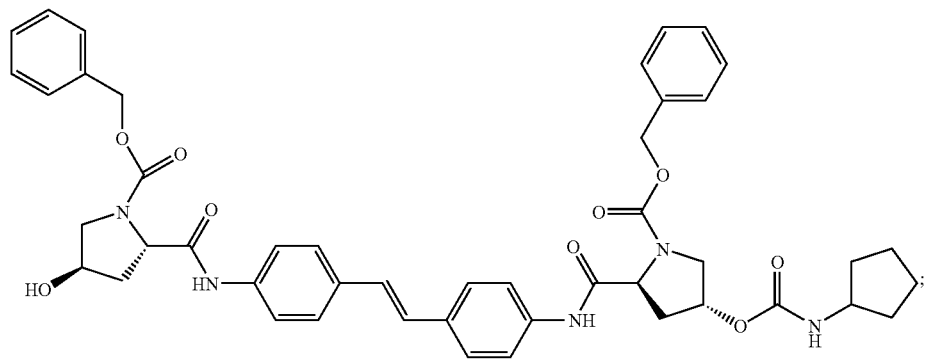
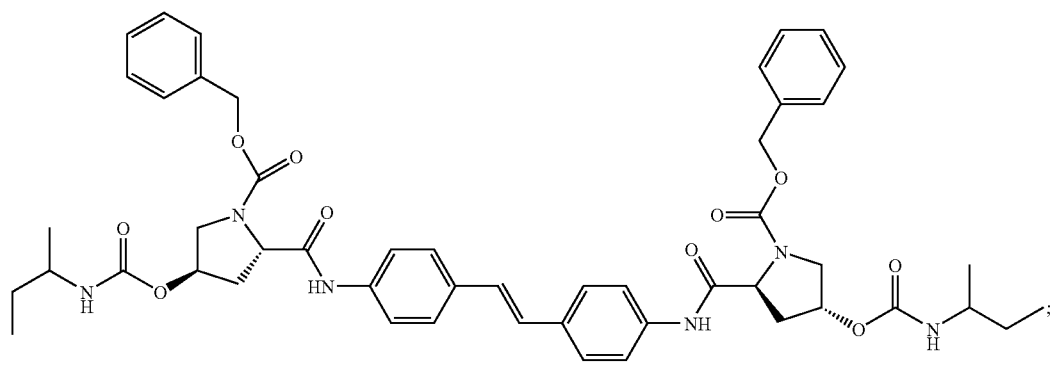
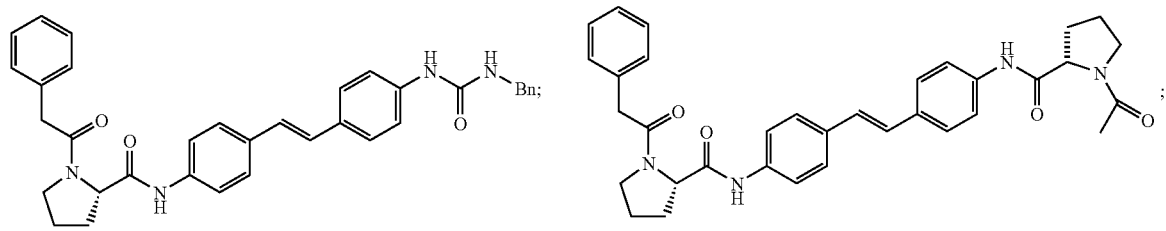
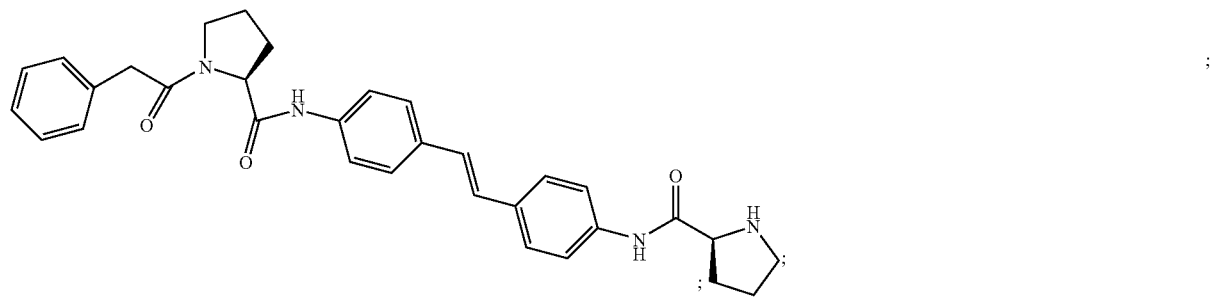
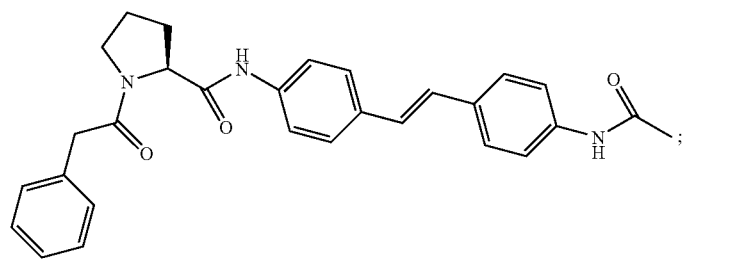

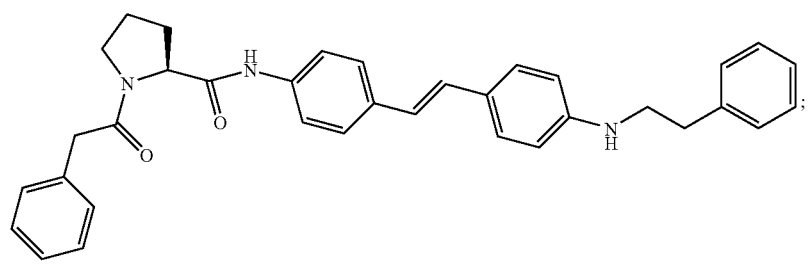
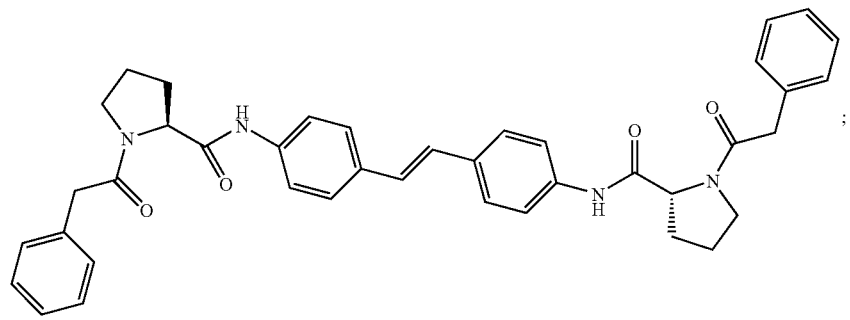
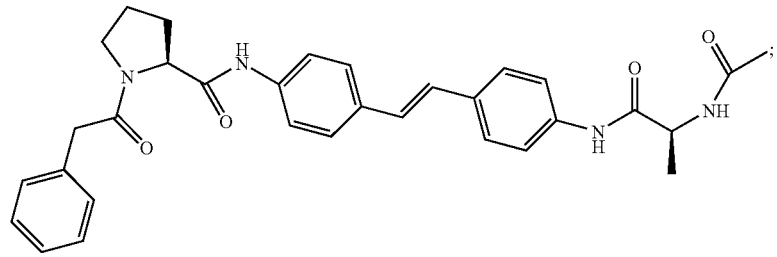
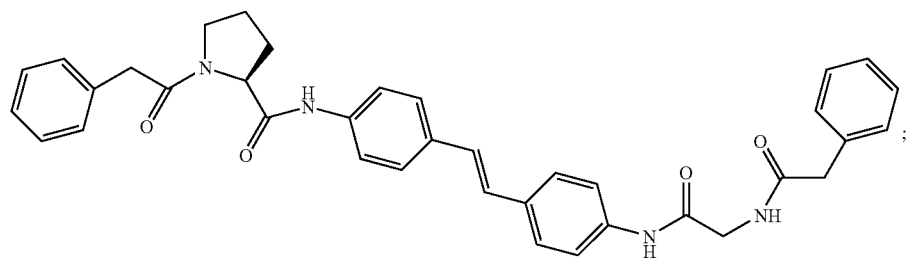
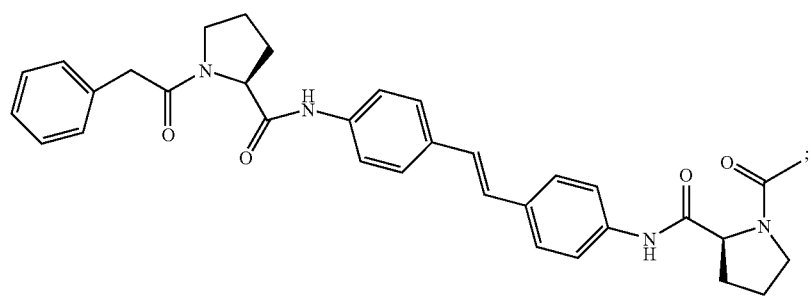
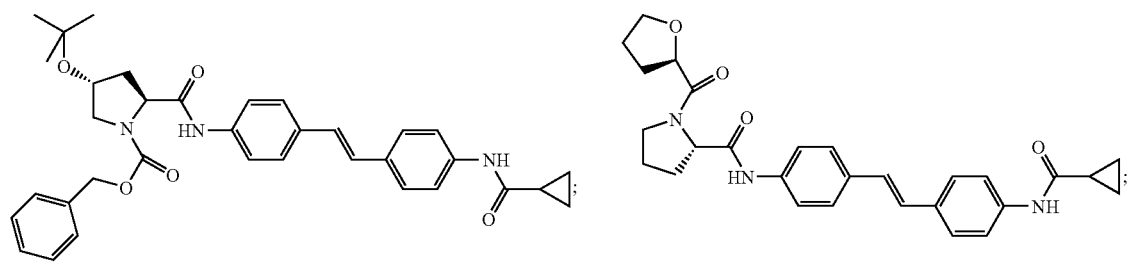

-continued
271
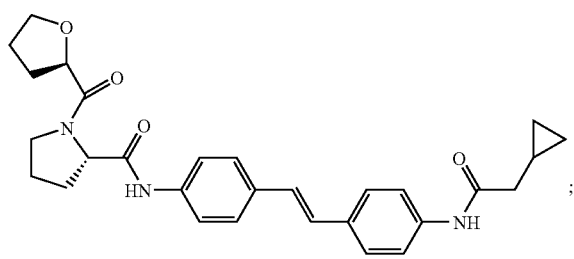
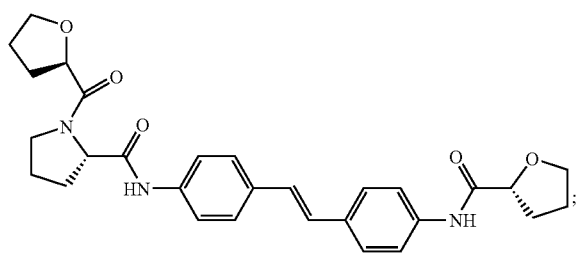
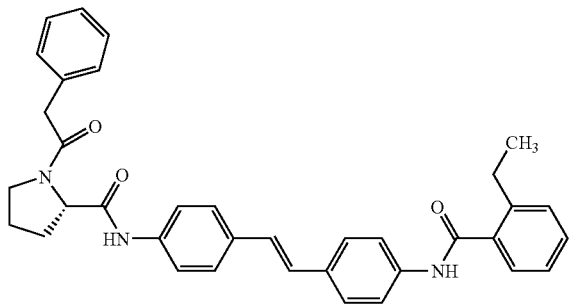
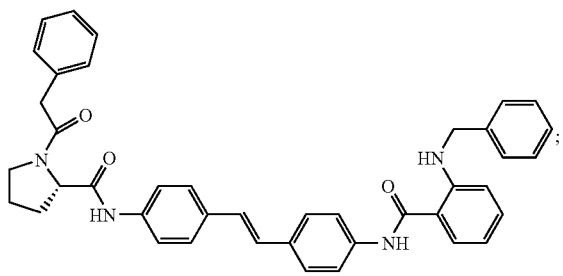
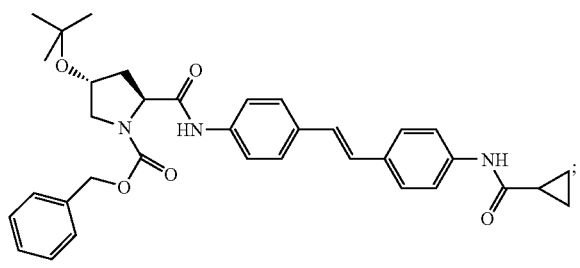
272
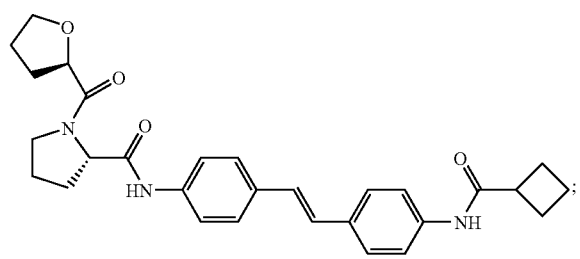
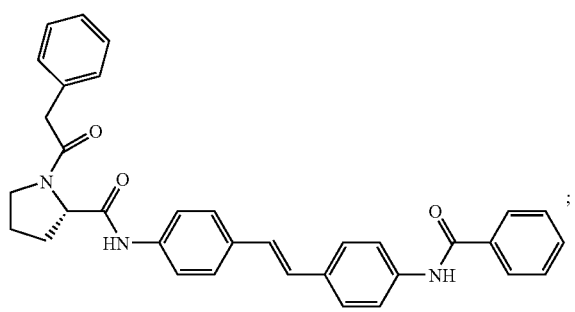
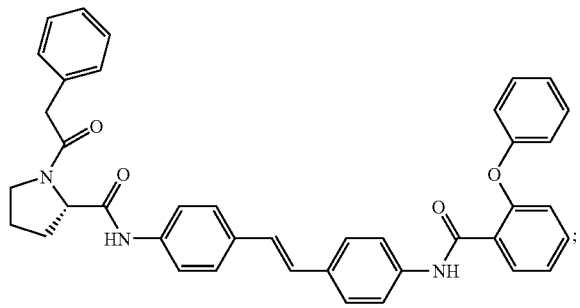
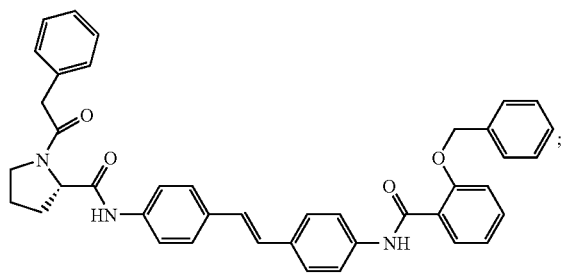
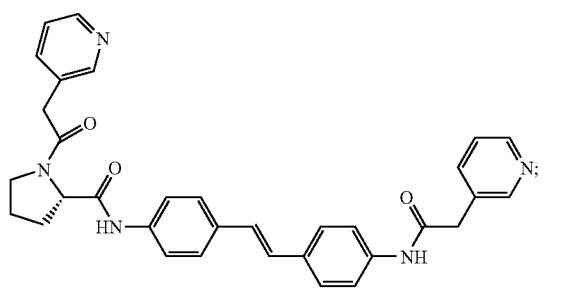

-continued
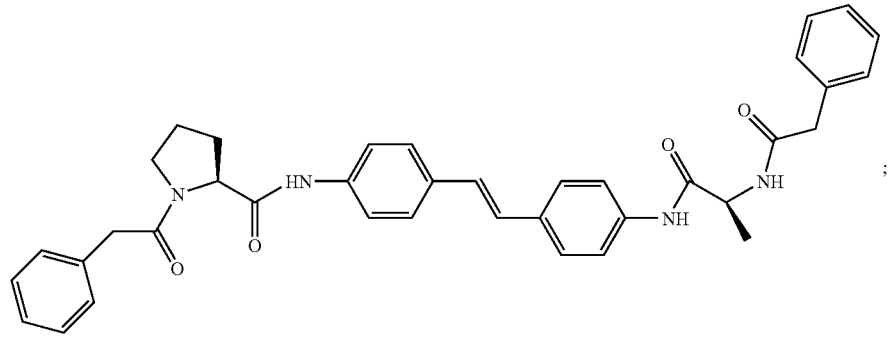
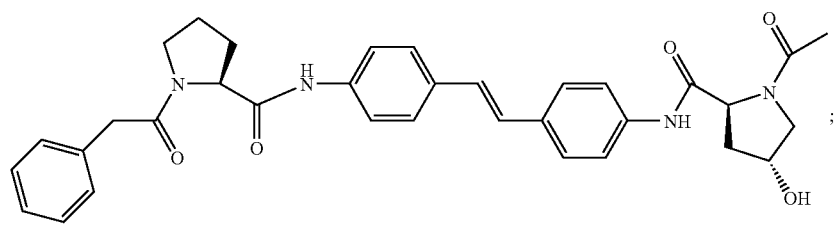
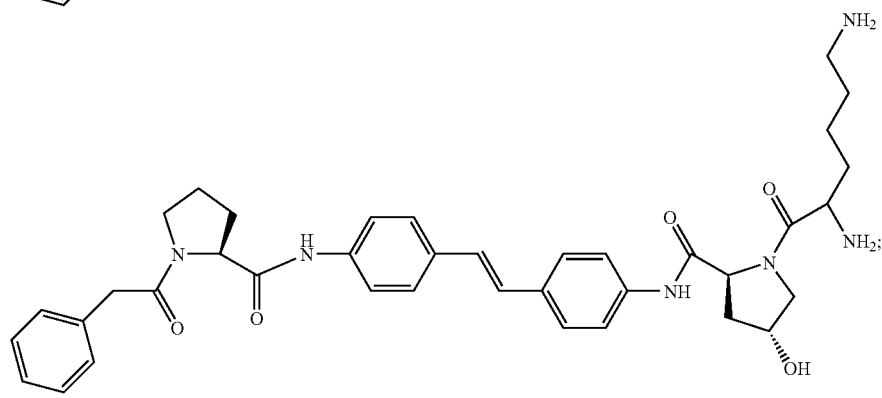
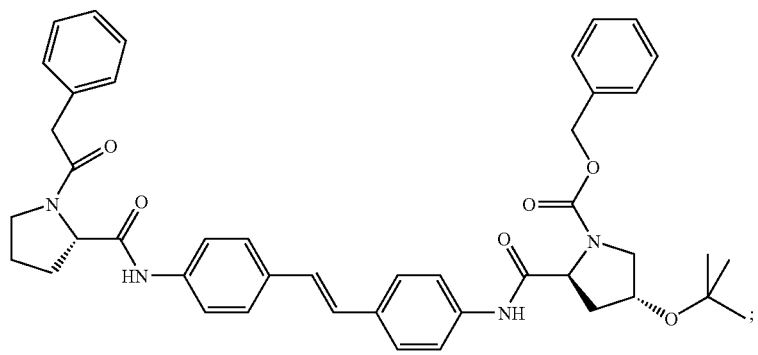
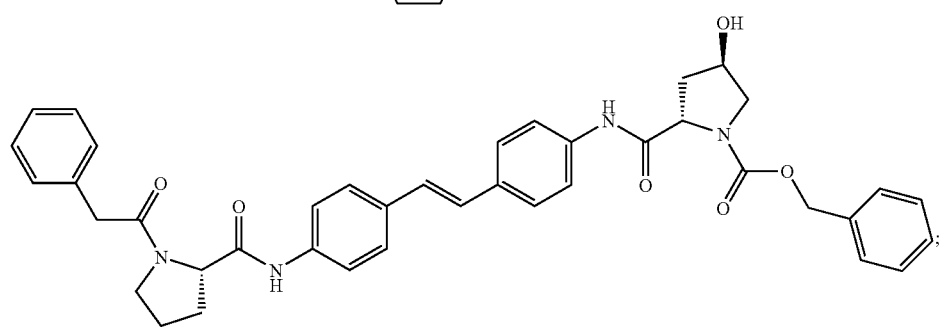

275 276
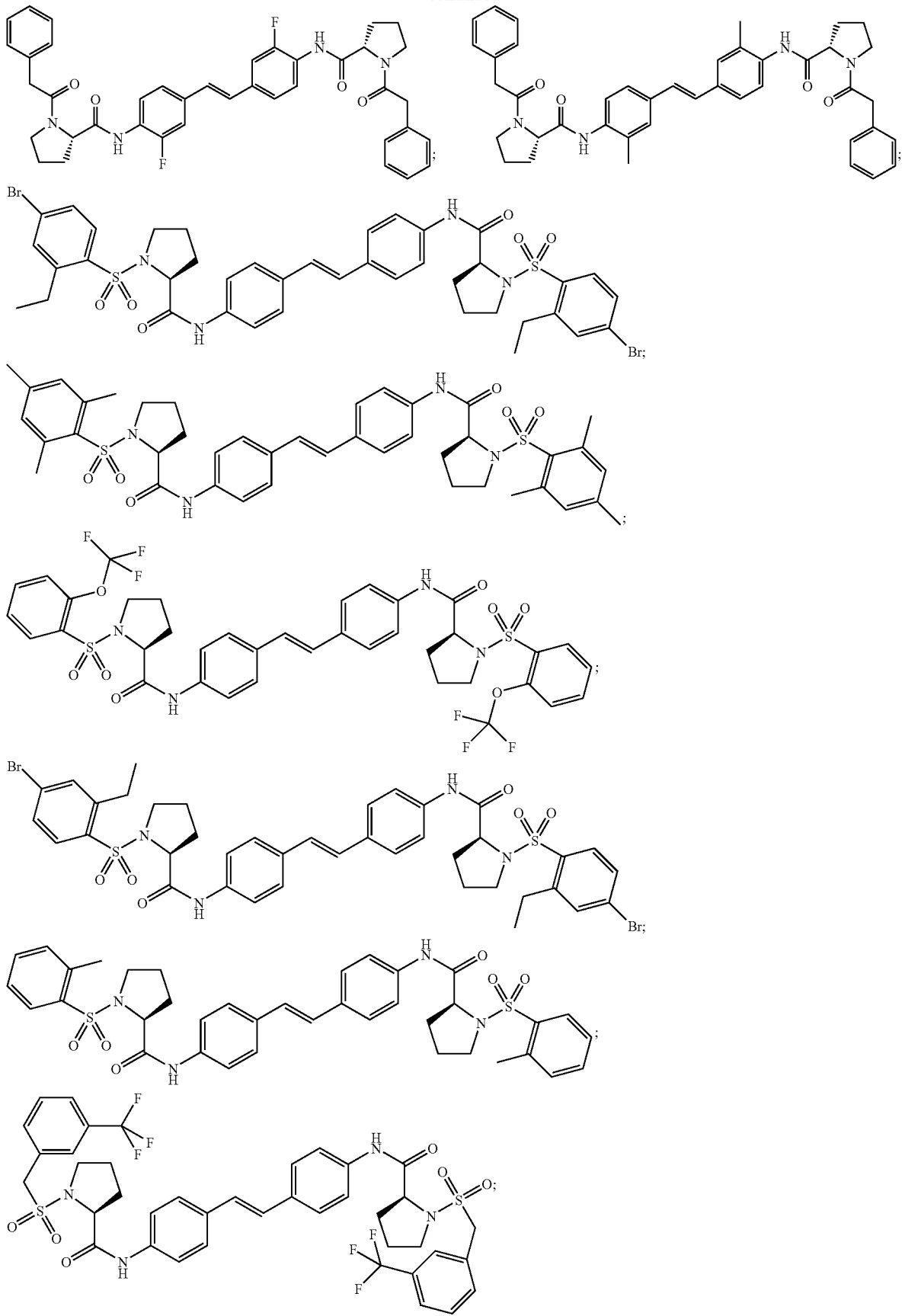
-continued

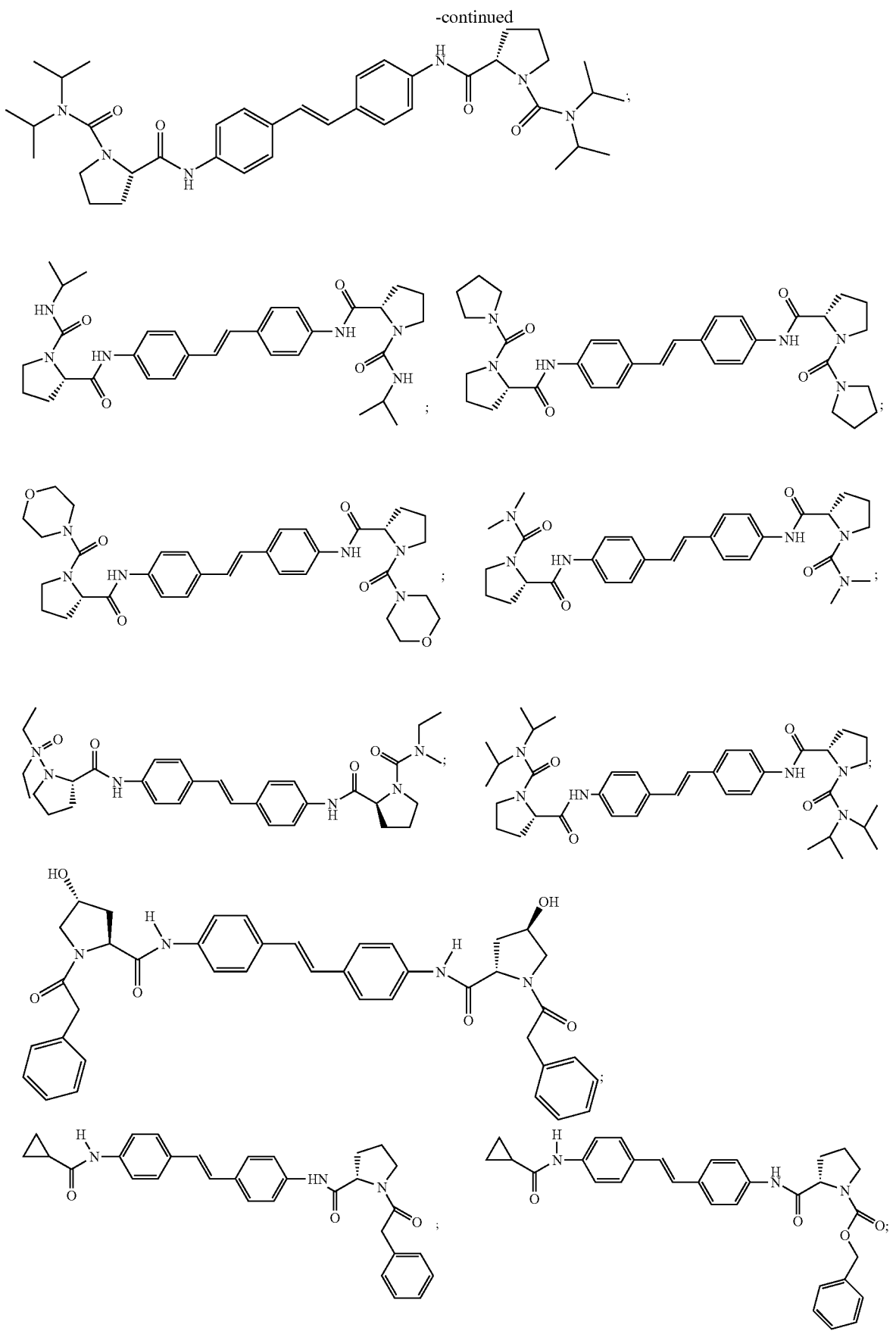

-continued
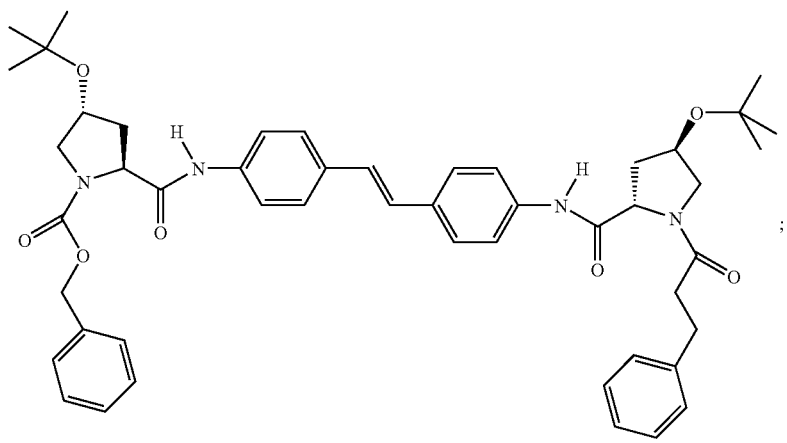
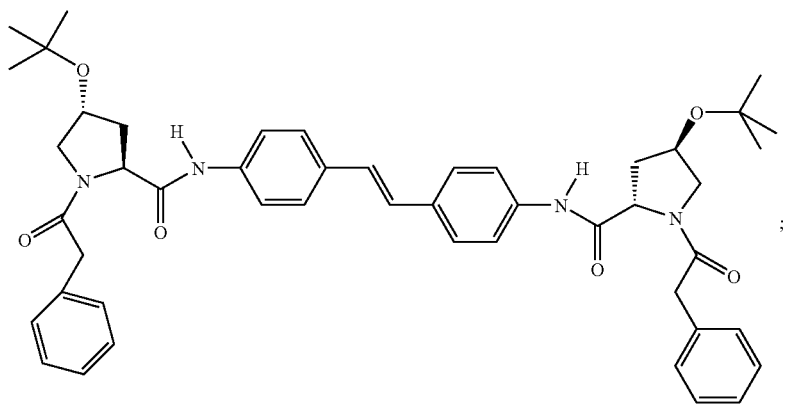
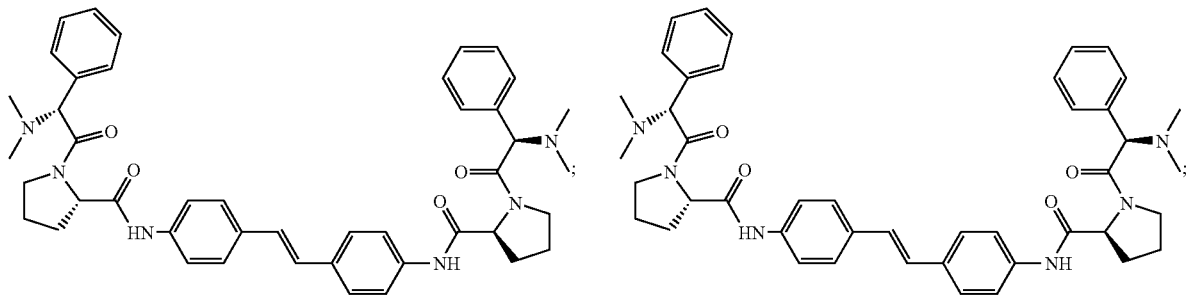
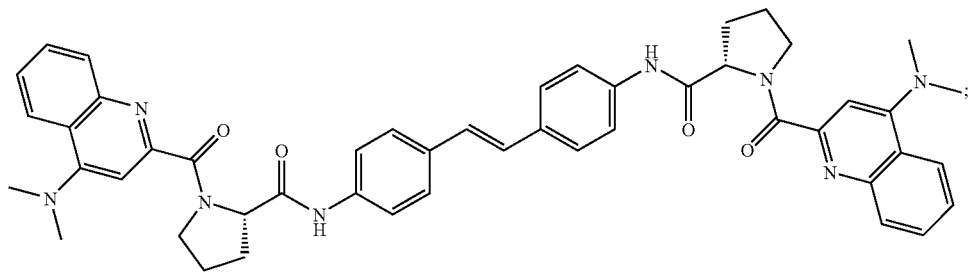
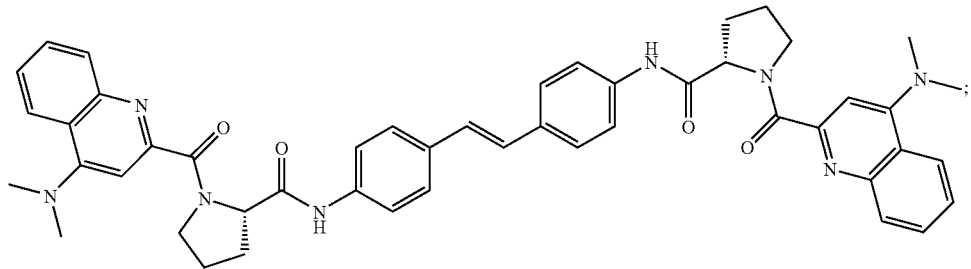

-continued
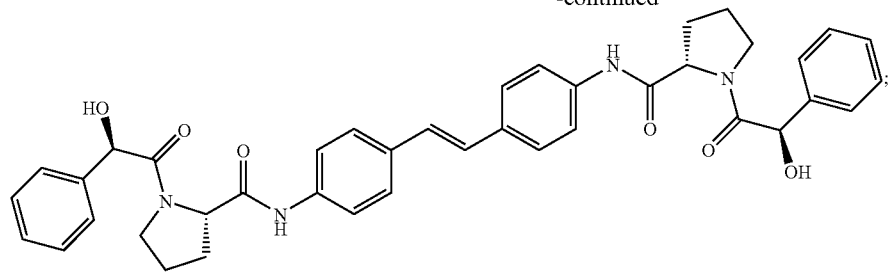
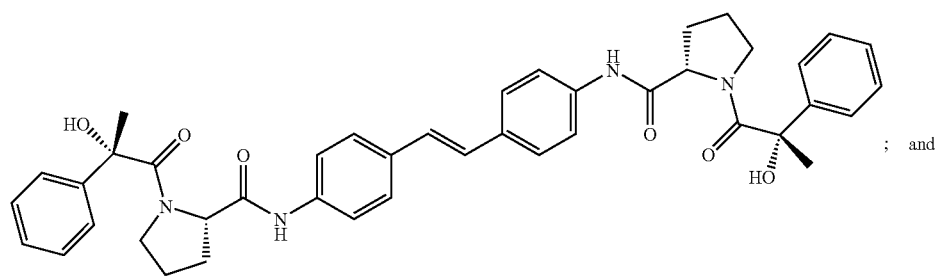; and
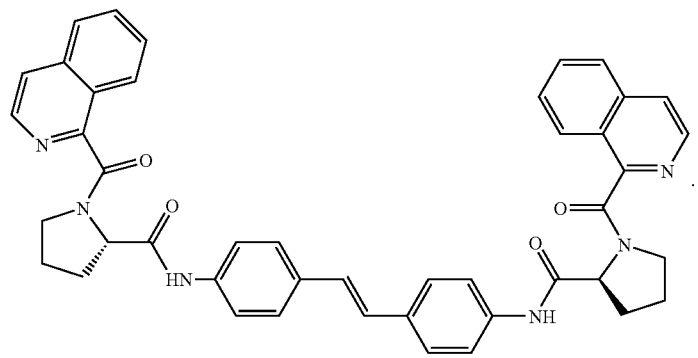.
12. A compound selected from the group consisting of
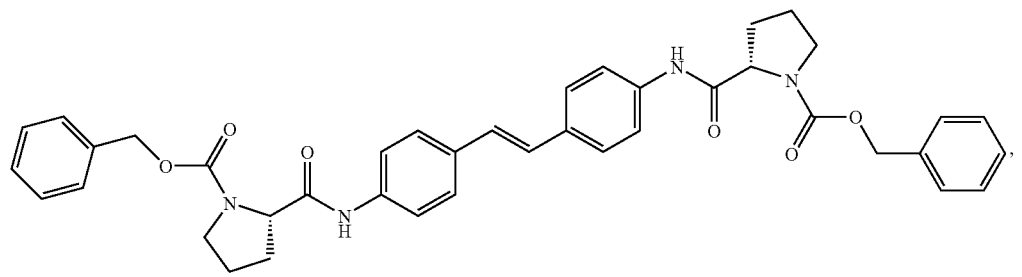,
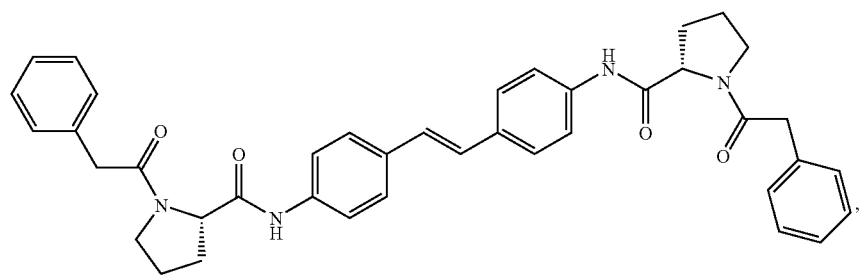,

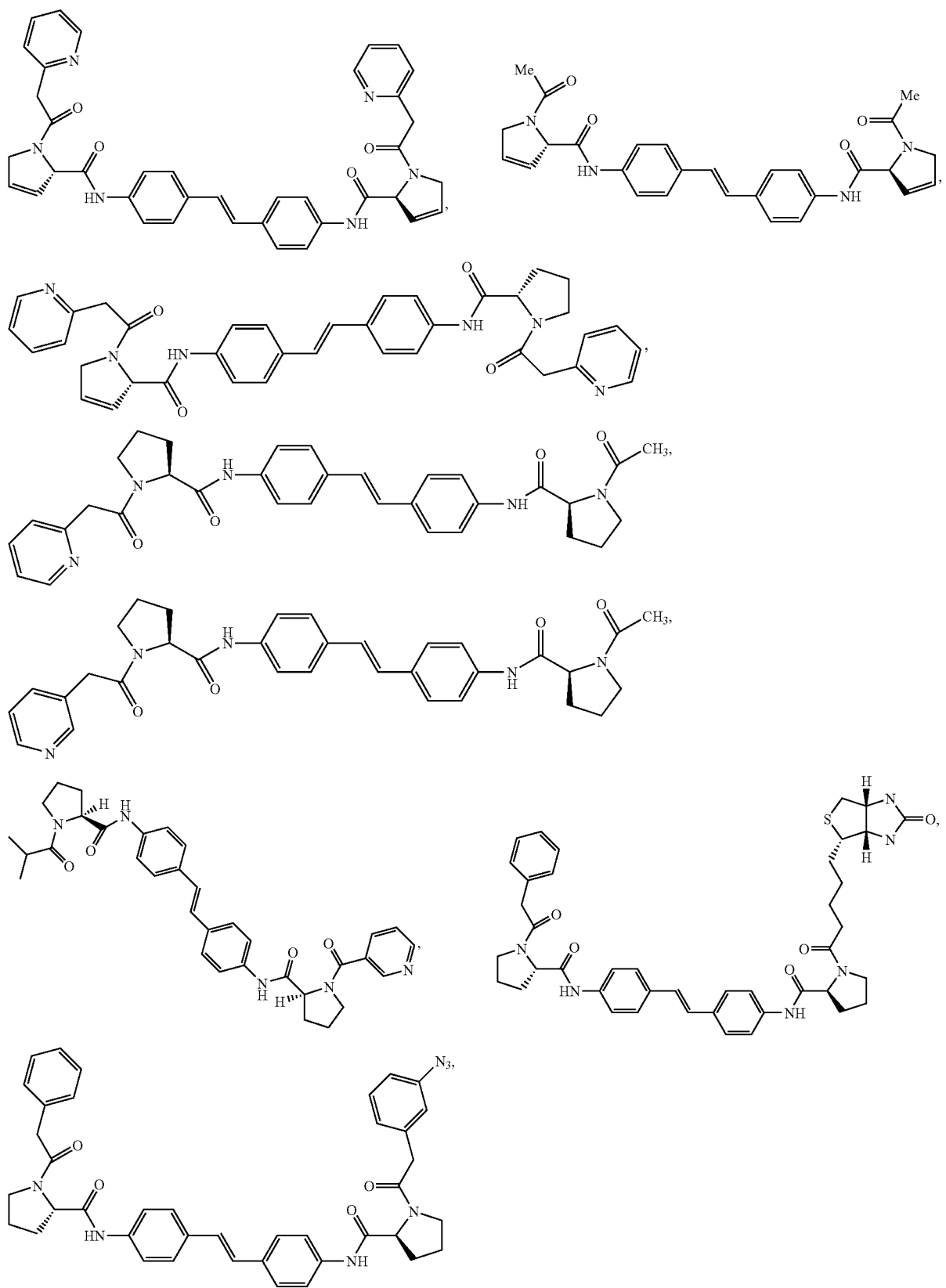

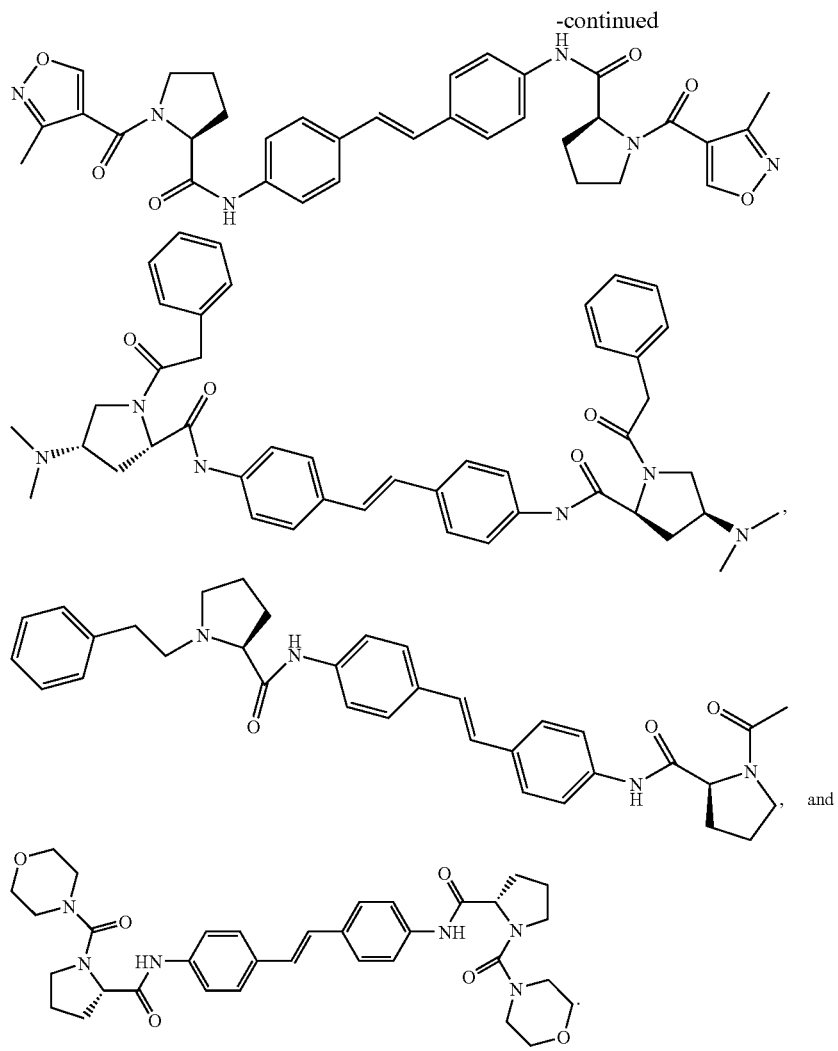

13. A composition comprising the compound of claim 1 and a pharmaceutically acceptable carrier.

14. The composition of claim 13 further comprising an interferon and ribavirin.

15. The composition of claim 13 further comprising a second compound having anti-HCV activity.

16. The composition of claim 15 wherein the second compound having anti-HCV activity is an interferon.

17. The composition of claim 16 wherein the interferon is selected from the group consisting of interferon alpha 2B, pegylated interferon alpha, consensus interferon, interferon alpha 2A, and lymphoblastoid interferon tau.

18. The composition of claim 15 wherein the second compound having anti-HCV activity is a cyclosporin.

19. The composition of claim 18 wherein the cyclosporin is cyclosporin A.

20. The composition of claim 15 wherein the second compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

21. A compound of formula (I)

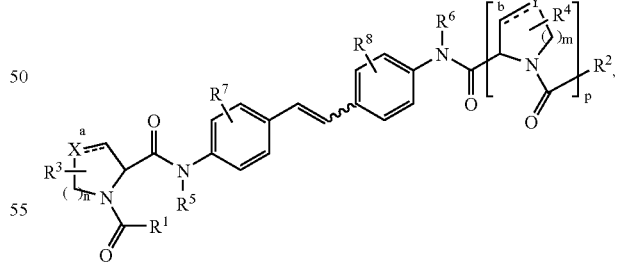

or a pharmaceutically acceptable salt thereof, wherein

- - - - -$\overset{a}{}$is a single or double bond;

- - - - -$\overset{b}{}$is a single or double bond;

when - - - - -$\overset{a}{}$is a single bond, X is selected from the group consisting of O, $CH_2$, and $CHR^3$;

when - - - - -$\overset{a}{}$is a double bond, X is selected from the group consisting of CH and $CR^3$;

when $\overset{b}{\text{-----}}$ is a single bond, Y is selected from the group consisting of O, CH$_2$, and CHR$^4$;

when $\overset{b}{\text{-----}}$ is a double bond, Y is selected from the group consisting of CH and CR$^4$;

n and m are independently 1, 2, or 3;

p is 1;

R$^1$ and R$^2$ are independently selected from the group consisting of alkoxy, alkoxyalkoxyalkyl, alkoxyalkyl, alkyl, alkylsulfenylalkyl, alkylsulfinylalkyl, alkylsulfonylalkyl, aryl, arylalkoxy, arylalkoxyalkyl, arylalkyl, arylcarbonyl, aryloxy, aryloxyalkyl, arylsulfenylalkyl, arylsulfinylalkyl, arylsulfonylalkyl, carboxyalkyl, cycloalkenyl, cycloalkenylalkyl, cycloalkyl, cycloalkylalkyl, heterocyclyl, heterocyclylalkoxy, heterocyclylalkoxyalkyl, heterocyclylalkyl, heterocyclylcarbonyl, heterocyclyloxy, heterocyclyloxyalkyl, —NR$^a$R$^b$, and (NR$^a$R$^b$)alkyl;

one of R$^3$ and R$^4$ is selected from —NR$^a$R$^b$, (NR$^a$R$^b$)alkyl, (NR$^a$R$^b$)carbonyloxy, and oxo; and the other is selected from the group consisting of hydrogen, alkenyl, alkoxy, alkoxycarbonyloxy, alkyl, alkylsulfonyl, alkylsulfonyloxy, aryl, arylalkyl, azido, hydroxy, —NR$^a$R$^b$, (NR$^a$R$^b$)alkyl, (NR$^a$R$^b$)carbonyloxy, and oxo; wherein the alkenyl and the alkyl can optionally form a saturated or unsaturated cyclic structure, respectively, with an adjacent carbon atom;

R$^5$ and R$^6$ are independently selected from the group consisting of hydrogen, alkenyl, alkoxycarbonyl, alkyl, alkylcarbonyl, aryl, arylalkyl, heterocyclylalkylcarbonyl, and heterocyclylcarbonyl;

R$^7$ and R$^8$ are independently selected from the group consisting of hydrogen, alkenyl, alkoxy, alkyl, halo, and haloalkyl;

one of R$^a$ and R$^b$ is arylalkoxycarbonyl and the other is selected from the group consisting of hydrogen, alkenyl, alkyl, alkylcarbonyl, aryl, arylalkoxycarbonyl, arylalkyl, arylalkylcarbonyl, cycloalkyl, cycloalkylalkyl, heterocyclyl, and heterocyclylalkyl.

\* \* \* \* \*

UNITED STATES PATENT AND TRADEMARK OFFICE
CERTIFICATE OF CORRECTION

PATENT NO. : 8,143,288 B2
APPLICATION NO. : 11/446788
DATED : March 27, 2012
INVENTOR(S) : Michael Serrano-Wu et al.

It is certified that error appears in the above-identified patent and that said Letters Patent is hereby corrected as shown below:

In the Specification:

Column 22, line 67, change "Imiqimod" to -- Imiquimod --.

Column 23, line 1, change "5′-monophospate" to -- 5′-monophosphate --.

In the Claims:

Claim 1:

Column 195, line 57, change "0" to -- O --.

Claim 6:

Column 197, line 58, change "0" to -- O --.

Column 197, line 60, change "0" to -- O --.

Claim 11:

Column 218, fifth structure, change

" 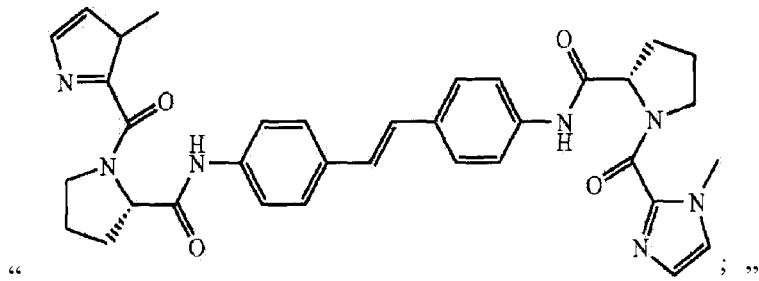 ; "

to

Signed and Sealed this
Twentieth Day of August, 2013

Teresa Stanek Rea
*Acting Director of the United States Patent and Trademark Office*

CERTIFICATE OF CORRECTION (continued)
U.S. Pat. No. 8,143,288 B2

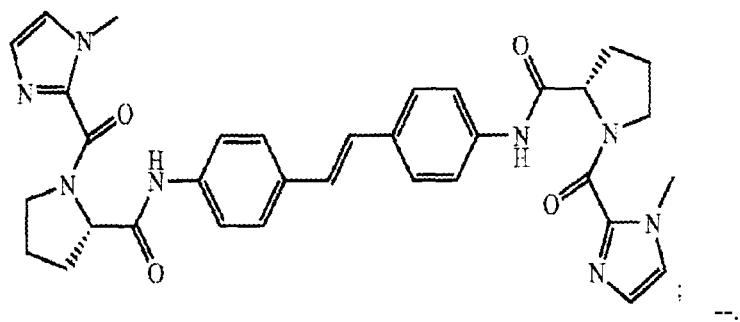
--    --.

Claim 11 (continued):

Column 228, third structure, change

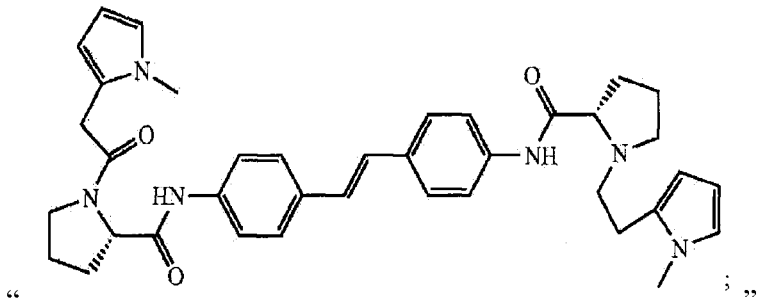
"    ; "

to

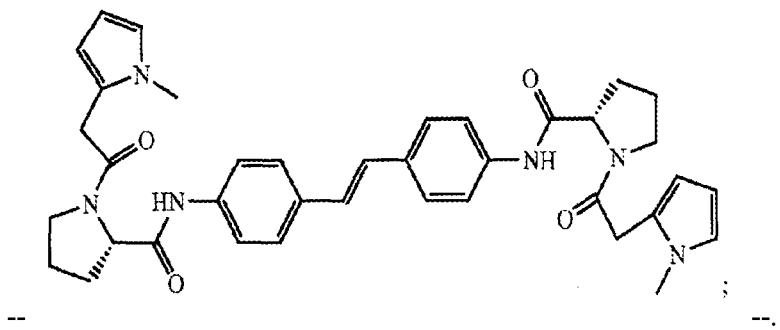
--    --.

Claim 11 (continued):

Columns 269 and 270, first structure, change

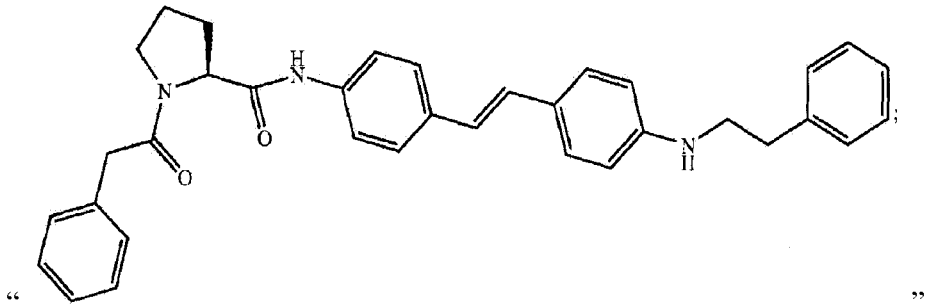
"    "

to

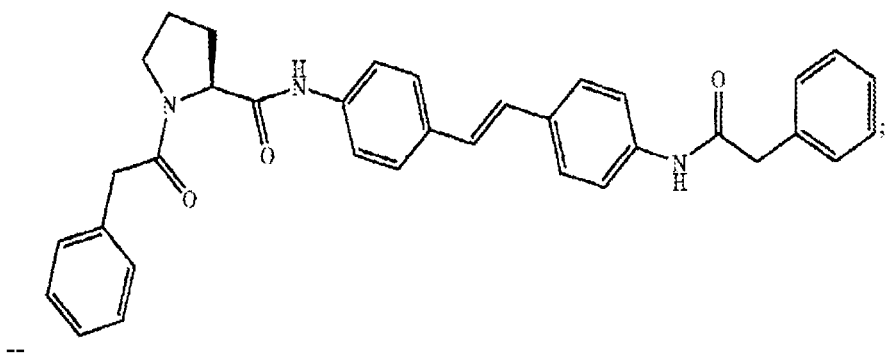
--
Claim 11 (continued):
Columns 273 and 274, third structure, change
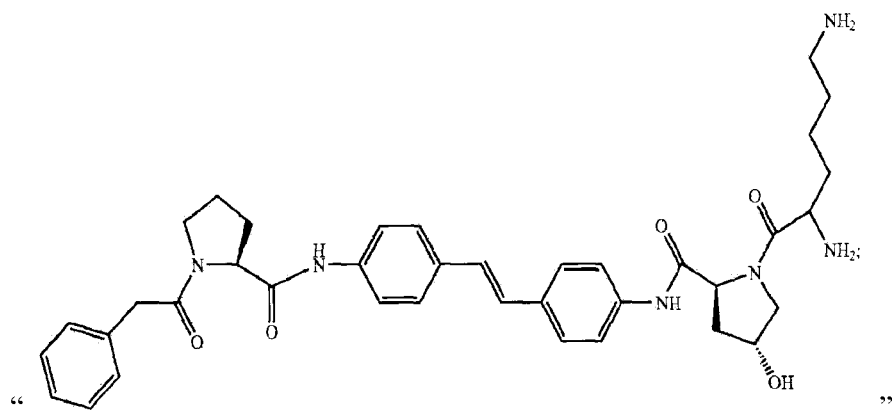
"  "
to
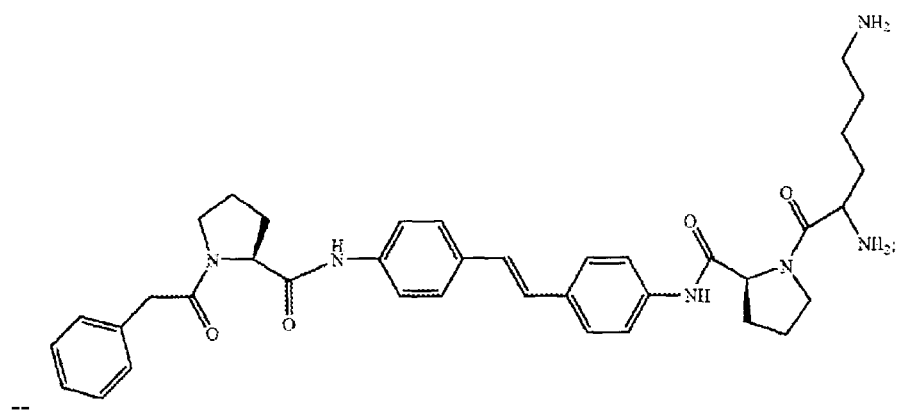
--

Claim 12:
Columns 285 and 286, third structure, change
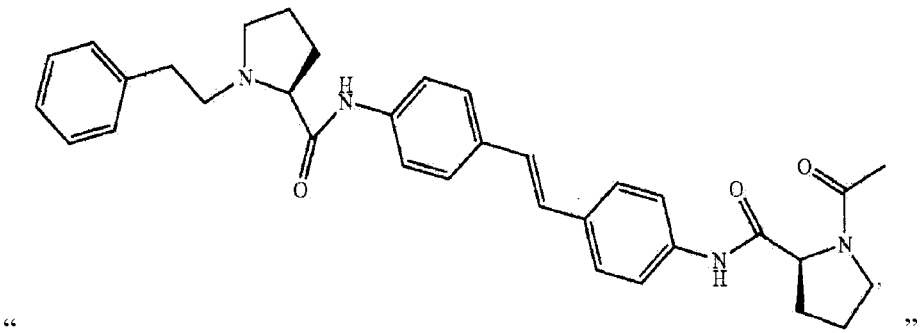
"
to
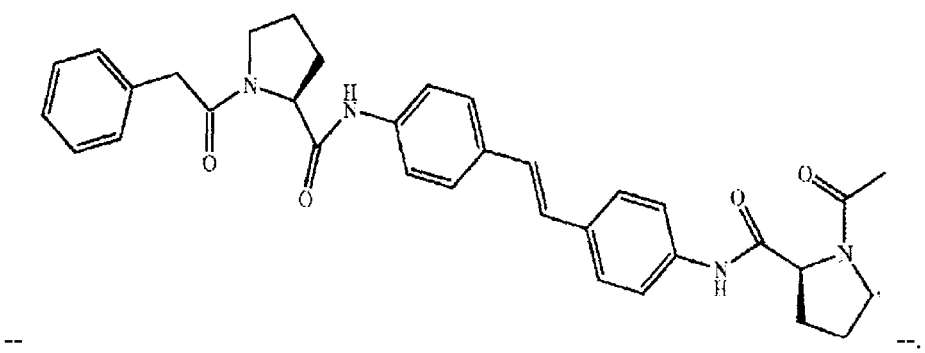
--                                                                                                  --.
Claim 20:
Column 285, line 65, change "Imiqimod" to -- Imiquimod --.
Column 285, line 66, change "5'-monophospate" to -- 5'-monophosphate --.
Claim 21:
Column 287, line 1, after "is", delete "s".